United States Patent
DeWitte et al.

(10) Patent No.: US 10,557,835 B2
(45) Date of Patent: Feb. 11, 2020

(54) AUTOMATED SYSTEM FOR SAMPLE PREPARATION AND ANALYSIS

(71) Applicant: Thermo Fisher Scientific Oy, Vantaa (FI)

(72) Inventors: Robert DeWitte, Burlington (CA); Juhani Siidorov, Vantaa (FI); Vesa Nuotio, Espoo (FI); Raimo Salminen, Helsinki (FI); Jarmo Vehkomaki, Veikkola (FI); Jukka Saukkonen, Espoo (FI); Bill Ostman, Helsinki (FI); Joseph M. Senteno, San Jose, CA (US); John Edward Brann, III, Shrewsbury, MA (US); Joseph L. Herman, West Chester, PA (US); Jeffrey A. Zonderman, Westwood, MA (US); Terry N. Olney, Tracy, CA (US)

(73) Assignee: THERMO FISHER SCIENTIFIC OY, Vantaa (FI)

( * ) Notice: Subject to any disclaimer, the term of this patent is extended or adjusted under 35 U.S.C. 154(b) by 483 days.

(21) Appl. No.: 14/753,272

(22) Filed: Jun. 29, 2015

(65) Prior Publication Data
US 2015/0301002 A1 Oct. 22, 2015

Related U.S. Application Data

(62) Division of application No. 13/882,393, filed as application No. PCT/US2011/058452 on Oct. 28, 2011, now Pat. No. 10,088,460.

(Continued)

(51) Int. Cl.
*G01N 30/72* (2006.01)
*G01N 35/00* (2006.01)
(Continued)

(52) U.S. Cl.
CPC ......... *G01N 30/7233* (2013.01); *G01N 27/62* (2013.01); *G01N 30/06* (2013.01);
(Continued)

(58) Field of Classification Search
None
See application file for complete search history.

(56) References Cited

U.S. PATENT DOCUMENTS 3,540,856 A 11/1970 Hoffa
3,645,690 A 2/1972 Rochte
(Continued)

FOREIGN PATENT DOCUMENTS

CN 101275962 10/2008
EP 0345782 A2 12/1989
(Continued)

OTHER PUBLICATIONS

Japanese Patent Office, Official Action in Japanese Patent Application No. 2013-536895, dated May 23, 2016, with English Translation (7 pages).
(Continued)

*Primary Examiner* — Kathryn Wright
(74) *Attorney, Agent, or Firm* — Thompson Hine LLP

(57) ABSTRACT

A sample preparation and analysis system. The system includes a sample preparation system and a sample analysis system. The sample preparation system prepares samples in accordance with an assay that is selected from a database containing a plurality of unique assays. The sample analysis system includes an analyzer that is dynamically reconfigurable based on the selected assay so as to analyze the prepared sample in accordance with that selected assay. A data communication link communicates data from the
(Continued)

sample preparation system to the sample analysis system to reconfigure the analyzer in accordance with the selected assay.

6 Claims, 58 Drawing Sheets

Related U.S. Application Data

(60) Provisional application No. 61/408,180, filed on Oct. 29, 2010.

(51) Int. Cl.

| | | |
|---|---|---|
| *G01N 35/08* | (2006.01) | |
| *H01J 49/26* | (2006.01) | |
| *G01N 30/06* | (2006.01) | |
| *G01N 30/86* | (2006.01) | |
| *G01N 35/02* | (2006.01) | |
| *G01N 27/62* | (2006.01) | |
| *H01J 49/04* | (2006.01) | |
| *H01J 49/00* | (2006.01) | |
| *H01J 49/10* | (2006.01) | |
| *G01N 30/88* | (2006.01) | |
| *G01N 30/16* | (2006.01) | |
| *G06F 19/00* | (2018.01) | |
| *G01N 30/02* | (2006.01) | |
| *G01N 30/62* | (2006.01) | |

(52) U.S. Cl.
CPC ............. *G01N 30/16* (2013.01); *G01N 30/72* (2013.01); *G01N 30/8658* (2013.01); *G01N 30/88* (2013.01); *G01N 35/0092* (2013.01); *G01N 35/00871* (2013.01); *G01N 35/026* (2013.01); *G01N 35/08* (2013.01); *G06F 19/00* (2013.01); *H01J 49/0031* (2013.01); *H01J 49/0413* (2013.01); *H01J 49/0431* (2013.01); *H01J 49/10* (2013.01); *G01N 2030/027* (2013.01); *G01N 2030/067* (2013.01); *G01N 2030/628* (2013.01); *G01N 2030/8804* (2013.01); *G01N 2030/8813* (2013.01); *H01J 49/00* (2013.01); *H01J 49/0409* (2013.01); *Y10T 436/24* (2015.01)

(56) References Cited

U.S. PATENT DOCUMENTS

| | | | |
|---|---|---|---|
| 4,570,068 A | | 2/1986 | Sakairi et al. |
| 4,754,414 A | | 6/1988 | Gocho |
| 4,854,181 A | | 8/1989 | Gerstel |
| 4,883,504 A | | 11/1989 | Gerstel |
| 5,065,614 A | | 11/1991 | Hartman et al. |
| 5,301,261 A | | 4/1994 | Poole et al. |
| 5,313,061 A | | 5/1994 | Drew et al. |
| 5,314,825 A | | 5/1994 | Weyrauch |
| 5,366,896 A | | 11/1994 | Margrey et al. |
| 5,576,215 A | * | 11/1996 | Burns ................ G01N 35/0092 422/116 |
| 5,789,746 A | | 8/1998 | Kato et al. |
| 5,988,857 A | * | 11/1999 | Ozawa ............ G01N 35/00732 198/346.1 |
| 6,054,683 A | | 4/2000 | Bremer et al. |
| 6,055,845 A | | 5/2000 | Gerstel et al. |
| 6,134,945 A | | 10/2000 | Gerstel et al. |
| 6,180,410 B1 | | 1/2001 | Gerstel et al. |
| 6,245,298 B1 | | 6/2001 | Bremer et al. |
| 6,354,136 B1 | | 3/2002 | Bremer et al. |
| 6,360,588 B1 | | 3/2002 | Ross et al. |
| 6,447,575 B2 | | 9/2002 | Bremer et al. |
| 6,475,437 B1 | | 11/2002 | Gerstel et al. |
| 6,730,517 B1 | | 5/2004 | Koster et al. |
| 6,743,397 B1 | | 6/2004 | Zesiger |
| 6,761,056 B2 | | 7/2004 | Schram et al. |
| 6,815,216 B2 | | 11/2004 | Sandra et al. |
| 6,858,435 B2 | | 2/2005 | Chervet et al. |
| 6,907,796 B2 | | 6/2005 | Bremer et al. |
| 6,973,846 B2 | | 12/2005 | Bremer et al. |
| 7,127,956 B2 | | 10/2006 | Bremer et al. |
| 7,157,055 B2 | | 1/2007 | Rose |
| 7,178,414 B1 | | 2/2007 | Kokosa |
| 7,530,258 B2 | | 5/2009 | Bremer et al. |
| 7,584,019 B2 | | 9/2009 | Feingold et al. |
| 7,603,201 B2 | | 10/2009 | Feingold et al. |
| 7,712,385 B2 | | 5/2010 | Bremer et al. |
| 7,939,310 B2 | | 5/2011 | Ginns et al. |
| 2001/0019826 A1 | | 9/2001 | Ammann |
| 2002/0001544 A1 | | 1/2002 | Hess et al. |
| 2002/0084222 A1 | | 7/2002 | Brann |
| 2002/0098594 A1 | | 7/2002 | Sandra et al. |
| 2002/0137194 A1 | | 9/2002 | Ammann et al. |
| 2002/0155587 A1 | | 10/2002 | Opalsky et al. |
| 2003/0068825 A1 | | 4/2003 | Washburn et al. |
| 2003/0124539 A1 | | 7/2003 | Warrington et al. |
| 2003/0180185 A1 | | 9/2003 | Rose |
| 2003/0233893 A1 | | 12/2003 | Bremer et al. |
| 2004/0158433 A1 | | 8/2004 | Wimschneider et al. |
| 2004/0159167 A1 | | 8/2004 | Bremer et al. |
| 2004/0171171 A1 | | 9/2004 | Appoldt et al. |
| 2005/0032237 A1 | | 2/2005 | Sandra et al. |
| 2005/0074360 A1 | | 4/2005 | DeWalch |
| 2005/0194318 A1 | | 9/2005 | Ozbal et al. |
| 2005/0220669 A1 | | 10/2005 | Malyarov et al. |
| 2005/0229723 A1 | | 10/2005 | Bremer et al. |
| 2005/0288183 A1 | | 12/2005 | Sandra et al. |
| 2006/0226358 A1 | | 10/2006 | Ishikawa et al. |
| 2007/0137320 A1 | | 6/2007 | Bremer et al. |
| 2007/0140904 A1 | | 6/2007 | Bremer et al. |
| 2007/0233518 A1 | | 10/2007 | Tanaka et al. |
| 2008/0089809 A1 | | 4/2008 | Gerstel et al. |
| 2008/0118932 A1 | | 5/2008 | Toler et al. |
| 2008/0241957 A1 | | 10/2008 | Shibata et al. |
| 2008/0314129 A1 | | 12/2008 | Schultz et al. |
| 2009/0138207 A1 | | 5/2009 | Cosentino et al. |
| 2009/0247417 A1 | | 10/2009 | Haas et al. |
| 2009/0305392 A1 | * | 12/2009 | Alfredsson ....... G01N 35/00712 435/286.1 |
| 2009/0325279 A1 | | 12/2009 | Hornauer |
| 2011/0046910 A1 | * | 2/2011 | Haas ................ G01N 35/00871 702/108 |
| 2011/0157580 A1 | | 6/2011 | Nogami et al. |
| 2013/0056631 A1 | | 3/2013 | Tomany et al. |

FOREIGN PATENT DOCUMENTS

| | | |
|---|---|---|
| EP | 2 207 030 | 7/2010 |
| JP | H01174965 A | 7/1989 |
| JP | H02280053 A | 11/1990 |
| JP | H03273162 A | 12/1991 |
| JP | H09-061420 | 3/1997 |
| JP | H09-178735 | 7/1997 |
| JP | H09-329604 | 12/1997 |
| JP | 3134775 B2 | 2/2001 |
| JP | 2003532117 A | 10/2003 |
| JP | 2004053445 A | 2/2004 |
| JP | 2004174331 A | 6/2004 |
| JP | 2004212355 A | 7/2004 |
| JP | 2004-226402 | 8/2004 |
| JP | 2004-347604 | 12/2004 |
| JP | 2004-354221 | 12/2004 |
| JP | 2005283344 A | 10/2005 |
| JP | 2008-547030 | 12/2008 |
| WO | 9960372 | 11/1999 |
| WO | 0045929 A1 | 8/2000 |
| WO | 0184143 A1 | 11/2001 |
| WO | 02/19171 A1 | 3/2002 |
| WO | 02/097446 | 12/2002 |
| WO | 03049831 A2 | 6/2003 |
| WO | 2005009202 A2 | 2/2005 |
| WO | 2006038014 A1 | 4/2006 |

(56) References Cited

FOREIGN PATENT DOCUMENTS

| WO | 2006089103 A1 | 8/2006 | |
|---|---|---|---|
| WO | WO-2006108263 A1 * | 10/2006 | ....... G01N 35/00871 |
| WO | 2007/003343 | 1/2007 | |
| WO | 2008/012104 A2 | 1/2008 | |
| WO | 2008/140742 | 11/2008 | |
| WO | 2009/100653 A1 | 8/2009 | |

OTHER PUBLICATIONS

Gerstel, Maestro Software, product brochure, date unknown (4 pages).

International Property Office of Singapore, Singapore Search Report and Written Opinion in related patent application No. 201303312-1, dated Jul. 21, 2014 (20 pages).

International Searching Authority, International Search Report and Written Opinion in corresponding Application No. PCT/US2011/058452, dated Mar. 23, 2012 (26 pages).

International Searching Authority, Preliminary Report on Patentability and Written Opinion in corresponding Application No. PCT/US2011/058452, dated Apr. 30, 2013 (15 pages).

International Searching Authority, Preliminary Report on Patentability and Written Opinion in related Application No. PCT/US2011/058323, dated Apr. 30, 2013 (18 pages).

International Property Office of Singapore, Singapore Search Report and Written Opinion in related patent application No. 201303300-6, dated Apr. 4, 2015 (12 pages).

State Intellectual Property Office of China, First Office Action and Search Report for related Chinese Application No. 201180063460.3 (English Translation) dated May 1, 2015, 12 pages.

Muhlberger F. et al.: "A Mobile Mass Spectrometer for Comprehensive On-Line Analysis of Trace and Bulk Components of Complex Gas Mixtures: Parallel Application of the Laser-Based Ionization Methods VUV Single-Photon Ionization, Resonant Multiphoton Ionization, and Laser-Induced Electron Impact Ionization", Analytical Chemistry, American Chemical Society, vol. 73, No. 15, pp. 3590-3604 (Aug. 1, 2001).

Extended European Search Report and Opinion issued in European Patent Application No. 17150253.7 (dated May 26, 2017, 10 pages).

JP, Notice of Reasons for Rejection with English translation; issued in corresponding Japanese patent application No. 2016-240146 (dated Sep. 25, 2017).

European Patent Office, Examining Division, Examination Repot issued in corresponding European Patent Application No. 11785837.5, dated Jul. 7, 2016 (3 pages).

AU, Examination Report No. 2 issued in Australian Patent Application No. 2015261711 (dated Sep. 16, 2017, 6 pages).

U.S. Non-Final Office Action; U.S. Appl. No. 13/882,393, 12 pages (dated Aug. 10, 2017).

CN, Office Action and Search Report with English translation, Chinese Application No. 201610227246.1 (dated Nov. 16, 2017).

CN, First Office Action and Search Report with English translation, Chinese Application No. 201710103232.3, 15 pages (dated Jan. 31, 2018).

U.S. Final Office Action, U.S. Appl. No. 13/882,393, 16 pages (dated Feb. 8, 2018).

JP, Notice of Reasons for Rejection with English translation; Japanese Application No. 2016-240146, 9 pages (dated Apr. 9, 2018).

CN, Second Office Action (with English translation), Chinese Divisional Patent Application No. 201610227246.1, 5 pages, dated Jun. 21, 2018.

U.S. Notice of Allowance, U.S. Appl. No. 13/882,393, 9 pages, dated Jun. 26, 2018.

U.S. Office Action, U.S. Appl. No. 15/363,127, 21 pages, dated Jul. 24, 2018.

Lovrien, R. et al, "Selective Precipitation of Proteins," *Current Protocols in Protein Science*, vol. 7, No. 1, pp. 4.5.1-4.5.36, May 2001.

RANDOX RX daytona; "A compact benchtop solution for clinical chemistry testing"; pp. 1-16 (at least as early as Aug. 25, 2016).

RANDOX Evidence Evolution; "Multiplexing . . . Proven, Perfected, Evolved The World's First Random Access Biochip Testing Platform"; pp. 1.16 (at least as early as Sep. 7, 2015).

Van Staden, J., "Analytical Continuous Flow Systems. Where Two Worlds Collide! From Gravimetry and Test Tubes to Flow Systems to FIA to SIA to PAT and from ORSAT to Control Room to PAT to TAP"; *Revue Roumaine de Chimie*; 60(5-6), pp. 403-414 (2015).

Peterson, H.E. et al.; "The History of the AutoChemist®: From Vision to Reality"; *IMIA Yearbook of Medical Informatics*; pp. 235-243 (2014).

Hawker, C. et al.; "Automation in the Clinical Laboratory"; *ResearchGate*; Chapter 26, pp. 370-370.e24 (Feb. 27, 2017).

The American Association for Clinical Chemistry (AACC); "Clinical Laboratory Analyzer Archive"; located at https://www.aacc.org/community/divisions/history-of-clinical-chemistry/clinical-laboratory-analyzer-archive (at least as early as Aug. 21, 2016).

U.S. Non-Final Office Action; U.S. Appl. No. 15/363,127, 31 pages (dated Jan. 18, 2019).

* cited by examiner

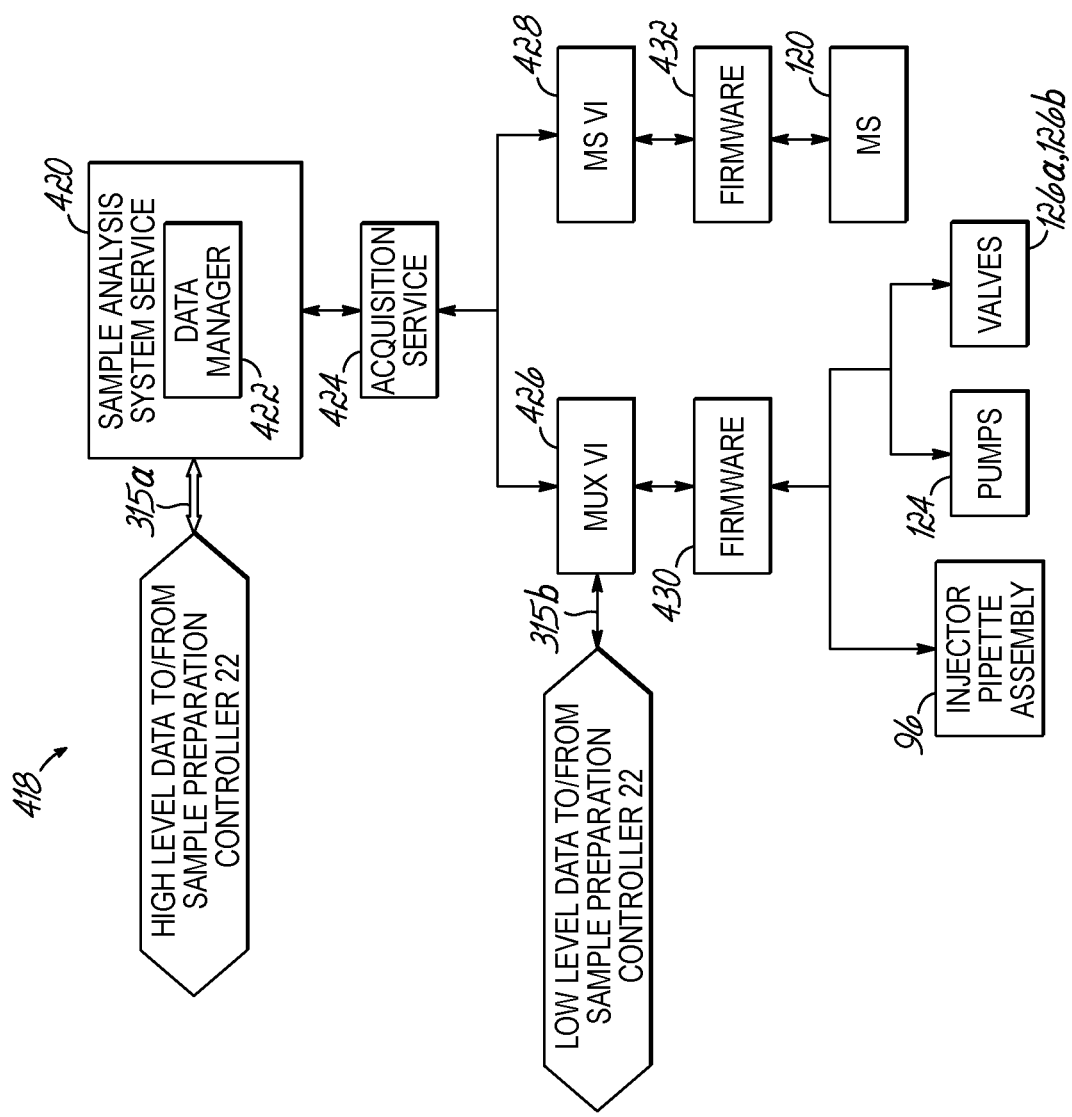

| Setup Single Test Sample | | |
|---|---|---|
| Sample Name: | Test Sample | |
| Assay Type: | hydrocortisone | |
| Time to Result: | ⟨ ⟩ min ☐ Priority | |
| Dilution Factor: | ⟨ ⟩ 1.000 | |
| Volume: | ⟨ ⟩ 10.0 ml | |
| Submitter: | User | |
| | OK | Cancel |

Sample 2 Raw Data Fraction 1
| Sample/Assay Identifier | Analyte | RT | AA | AH | TIC |
|---|---|---|---|---|---|
|  |  |  |  |  |  |
|  |  |  |  |  |  |
|  |  |  |  |  |  |
|  |  |  |  |  |  |
FIG. 39B
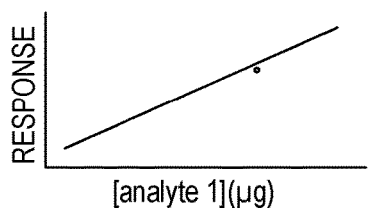
FIG. 39C
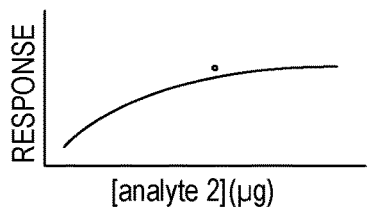
FIG. 39D
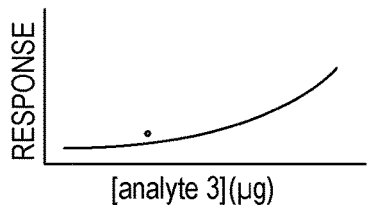
FIG. 39E
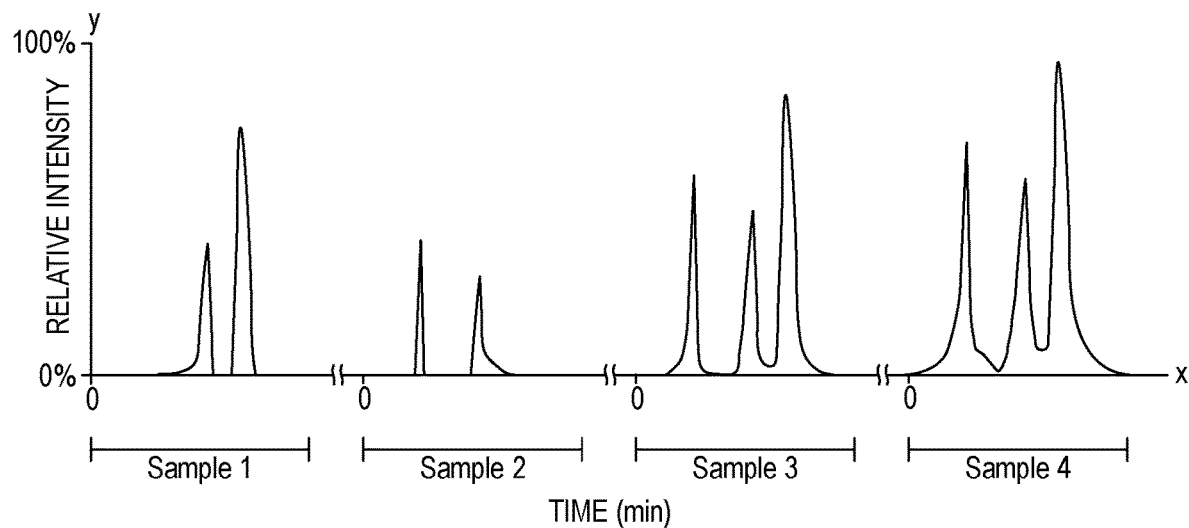
FIG. 40

AUTOMATED SYSTEM FOR SAMPLE PREPARATION AND ANALYSIS

CROSS REFERENCE TO RELATED APPLICATIONS

This application is a divisional of co-pending U.S. application Ser. No. 13/882,393, filed Jul. 17, 2013, which is a submission under 35 U.S.C. § 371 of International Application No. PCT/US2011/058452, filed Oct. 28, 2011, which claims the benefit of U.S. Provisional Application Ser. No. 61/408,180, filed Oct. 29, 2010, the disclosures of which are hereby expressly incorporated by reference herein in their entireties.

FIELD OF THE INVENTION

The present invention relates generally to the field of sample preparation and analysis and, more particularly, to sample preparation systems and sample analysis systems for preparing and analyzing samples according to a variety of different analyte assays.

BACKGROUND OF THE INVENTION

Liquid chromatography mass spectrometry ("LCMS") is a powerful analyte detection and measurement technique that has become the preferred method of detecting small molecule, amino acid, protein, peptide, nucleic acid, lipid, and carbohydrate analytes to a high accuracy for diagnostic purposes. However, the instrumentation required for LCMS is technically complex and not well suited to the typical hospital clinical lab or medical lab technician. These clinical labs have not adopted LCMS diagnostics and, instead, generally use alternative diagnostic techniques, including automated immunoassay. Alternatively, the clinical labs may send the samples out to a central reference laboratory for analysis.

Current LCMS methods require careful selection of the appropriate liquid chromatography column and mobile phases for each analyte assay, as well as complex calibration of the mass spectrometer to isolate and identify the analyte of interest. Moreover, in order to analyze a different analyte or different class of analyte on the same instrument, one or more of the column, the mobile phases, the liquid chromatography settings, and/or the mass spectrometer settings must be changed and optimized by the LCMS technologist. Often, individual hardware components, such as the ion source of the mass spectrometer, must be manually reconfigured in order to accommodate a different mode of analysis for a particular analyte. Such complicated equipment and sophisticated scientific techniques require very sophisticated LCMS specialist technologists, and heretofore only the large centrally located reference laboratories have been able to use such LCMS equipment for clinical diagnostics.

At each such reference laboratory, because of the time and technical complexity of such equipment adjustments, patient specimens that utilize the same type of assay are generally grouped into large batches and processed serially, in order to avoid the necessity of making manual adjustments that are time consuming and may be prone to produce errors. While this batch mode automation approach may reduce the amount of LCMS technologist intervention, it significantly increases the "time to result" for each specimen. Thus, non-urgent specimens may not be processed for several hours or even days prior to analysis. For time sensitive specimens, for example, for emergency department patients or transplant patients requiring short turnaround time results for immediate treatment decisions, such delays are unacceptable.

Still further, some specimens have a limited shelf-life due to deterioration of one or more analytes or evaporation which distorts the concentration of the analyte. Therefore, there is a set of complex factors that determine how long a specimen of a particular type may be delayed behind other specimens of a higher priority.

For a typical hospital lab, an LCMS system is a very large capital investment. As such, it is often impractical for a hospital lab to purchase multiple systems for different dedicated analyses. Thus, it is impractical for a hospital, even a large one, to use batch mode automation for clinical LCMS application, as it does not have the scale of a central reference laboratory and may be forced to make frequent changes to the LCMS hardware and complex setting, as it switches the testing from one type or class of analytes to another. Faced with the large economic and technical challenges, such clinical labs have been unable to reap the technical benefit of LCMS technologies for routine patient specimens, but have been forced to send patient samples on to the central reference labs.

Therefore, there is a need for sample preparation and sample analysis systems that are more flexible for handling different types of analyte assays. There is also a need for sample preparation and sample analysis systems that are less complex to configure and use for preparing samples and conducting a variety of different analyte assays, without requiring the expertise of LCMS technologists, or the massive scale of a reference laboratory. There is yet also a need for a sample preparation and sample analysis systems that improve the efficiency of the time to result for a variety of different analyte assays.

SUMMARY OF THE INVENTION

The present invention overcomes the foregoing problems and other shortcomings, drawbacks, and challenges of conventional sample preparation and sample analysis systems. While the invention will be described in connection with certain embodiments, it will be understood that the invention is not limited to these embodiments. To the contrary, this invention includes all alternatives, modifications, and equivalents as may be included within the spirit and scope of the present invention.

In accordance with one embodiment of the present invention, a sample preparation and analysis system includes a sample preparation system and a sample analysis system. The sample preparation system prepares samples in accordance with an assay that is selected from a database containing a plurality of unique assays. The sample analysis system includes an analyzer that is dynamically reconfigurable based on the selected assay so as to analyze the prepared sample in accordance with that selected assay. A data communication link communicates data from the sample preparation system to the sample analysis system to reconfigure the analyzer in accordance with the selected assay.

According to another embodiment of the present invention, a method of preparing and analyzing a sample includes preparing a sample with a sample preparation system and analyzing the prepared sample with a sample analysis system. The sample is taken from a specimen in accordance with an assay that is selected from a database containing a plurality of unique assays. The sample analysis system includes an analyzer, which is dynamically reconfigured in response to the selected assay and analyzes the prepared sample in that regard. Data to dynamically reconfigure the analyzer is communicated between the sample preparation system and the sample analysis system over a data communication link.

Another embodiment of the present invention is directed to a sample preparation and analysis system that includes a sample preparation station and a sample analysis station. The sample preparation system prepares samples in accordance with an assay that is selected from a database containing a plurality of unique assays. The sample analysis system includes an analyzer that is dynamically reconfigurable based on the selected assay so as to analyze the prepared sample in accordance with that selected assay. A transport mechanism transports the prepared sample from the sample preparation system to the sample analysis system.

Still another embodiment of the present invention is directed to a method to prepare and analyze a sample by a sample preparation system and sample analysis system, respectively. The sample is taken from a specimen in accordance with an assay that is selected from a database containing a plurality of unique assays. The sample analysis system includes an analyzer, which is dynamically reconfigured in response to the selected assay and analyzes the prepared sample in that regard. A transport mechanism transports the prepared sample from the sample preparation system to the sample analysis system.

In accordance with another embodiment of the present invention, an encapsulated sample preparation and analysis system having a sample preparation system and a sample analysis system includes a controller. The controller controls the operation the sample preparation system as well as the operation of a portion of the sample analysis system. Operation of the sample preparation system and the portion of the sample analysis system are in accordance with an assay, which is selected from a database containing a plurality of unique assays.

According to another embodiment of the present invention, an encapsulated sample preparation and analysis system includes a controller. The controller is configured to dynamically and automatically vary one or more parameters of a sample preparation system in order to prepare samples in accordance with respective assays. The assays are selected from a database containing a plurality of unique assays.

Yet another embodiment of the present invention is directed to an automated sample preparation and analysis system that includes a sample preparation system and a sample analysis system. The sample preparation station prepares a sample, taken from a specimen, in accordance with an assay that is selected from a plurality of unique assays. The sample analysis system is configured to analyze the prepared sample according to the selected assay. Sequencing of the preparation of the samples in the sample preparation system and analysis by the sample analysis system is controlled by a controller.

Still another embodiment of the present invention includes a method of preparing and analyzing samples taken from specimens. The method includes sequencing the samples for preparation, which is in accordance with respective assays selected from a database containing a plurality of unique assays. The method further includes sequencing the analysis of the prepared samples, which is also in accordance with the respective assays.

In accordance with another embodiment of the present invention, an automated sample preparation and analysis system includes a sample preparation system and a sample analysis system. The sample preparation system prepares a sample taken from a specimen in accordance with an assay, which is selected from a database containing a plurality of unique assays. The sample analysis system is configured to analyze the prepared sample in accordance with the selected assay. A controller dynamically sequences the prepared sample for analysis by the sample analysis system.

Another embodiment of the present invention is directed to a method of preparing and analyzing samples taken from specimens. The method includes dynamically sequencing the analysis of the prepared samples according to respective assays selected from a database containing a plurality of unique assays.

Another embodiment of the present invention is directed to a method of preparing and analyzing samples. The method includes querying a first controller with a second controller to determine a plurality of unique assays that may be performed by the sample analysis station. A human perceptible indication of the plurality of unique assays is provided.

Yet another embodiment of the present invention is directed to a method of preparing a sample by receiving a specimen and automatically determining a test to be performed on the sample. The test is in accordance with an assay selected from a database containing a plurality of unique assays. A plurality of preparation steps is determined in response to the selection of the assay. The preparation steps prepare the sample for analysis.

Still another embodiment of the present invention is directed to a method of preparing a sample. The method includes receiving a specimen and then, automatically, determining a target time to prepare a sample from the specimen. The target time to prepare is indicative of a time at which preparation of the sample should be complete.

In accordance with another embodiment of the present invention, a method of analyzing a sample includes receiving a specimen. The sample is prepared from the specimen and then, automatically, determining a target time to result. The target time to result is indicative of a time at which the analysis of the prepared sample is returned.

In accordance with yet another embodiment of the present invention, a method of multiplexing the operation of a sample preparation and analysis system include preparing first and second prepared samples with a sample preparation station. The first prepared sample is prepared in accordance with a first assay, and the second prepared sample is prepared in accordance with a second assay. The first and second assays are selected from a database containing a plurality of unique assays. The first and second prepared samples are transported, separately, to a sample analysis station having first and second separation channels and an analyzer. The first prepared sample is analyzed in accordance with the first selected assay. While analyzing the first prepared sample, the second prepared sample is being separated with the second separation channel and in accordance with the second selected assay.

According to still another embodiment of the present invention, a method of multiplexing a sample preparation and analysis system having a sample preparation system and a sample analysis system includes determining a sample analysis system readiness. The sample analysis system is configured to analyze a plurality of prepared samples with a mass spectrometer. The injection of the plurality of prepared samples into one a plurality of injection ports is sequenced.

Each of the plurality of injection ports is coupled to a respective separation channel. The sequencing is in accordance with information associated with the respective one of the plurality of prepared samples and the sample analysis system readiness.

According to another embodiment of the present invention, a method of multiplexing a sample preparation and analysis system having a sample preparation system and a sample analysis system includes receiving a specimen at the sample preparation system. An indication of an assay associated with the specimen is automatically determined such that an assay corresponding to the indication of the assay is selected from a database containing a plurality of unique assays. A sample is taken from the specimen in accordance with the selected assay with the sample preparation system. A mass spectrometer and/or a separation channel of the sample analysis system are dynamically reconfigured according to the selected assay. The reconfigured sample analysis system processes the prepared sample according to the selected assay.

One embodiment of the present invention is directed to a sample preparation and analysis system that is configured to inhibit evaporation of volatile liquids used therein. The sample preparation and analysis system includes a sample preparation system that is configured to receive a plurality of openable sample vessels, wherein each of the openable sample vessels is configured to be opened and to receive a sample and/or a volatile liquid therein. The openable sample vessel is then closed to inhibit evaporation of the volatile liquid.

Another embodiment of the present invention is directed to a sample preparation and analysis system. That includes a sample preparation station and a sample analysis station. The sample preparation station prepares a sample taken from a specimen for analysis in accordance with an assay. The assay is selected from a database containing a plurality of unique assays. The sample preparation system includes a first controller to control at least a portion of the operation of the sample preparation system. The sample analysis system analyzes the prepared sample using an analyzer configured in accordance with the selected assay. The sample analysis system further includes a second controller to control at least a portion of the operation of the sample analysis system. A software data communication link and a hardware data communication link each communicate data between the first and second controllers.

Still another embodiment of the present invention is directed to a method of preparing and analyzing a sample. The method includes preparing a sample for analysis by mass spectrometry by a sample preparation system. The sample is prepared in accordance with an assay selected from a database containing a plurality of unique assays. The sample preparation system includes a first controller to control at least a portion of the operation of the sample preparation system. A mass spectrometer analyzes the prepared sample in accordance with the selected assay and includes a second controller to control at least a portion of the operation of the mass spectrometer. Data associated with the prepare sample is communicated between the first and second controllers via at least a portion of a data communication link, which includes a software data link and a hardware data link.

Yet another embodiment of the present invention is directed to an automated sample preparation and analysis system having a sample preparation system and a sample analysis system. The sample preparation system prepares a sample for an assay, which is selected from a database comprising a plurality of unique assays. The sample analysis system includes a mass spectrometer for analyzing the prepared sample in accordance with the selected assay. First and second controllers are configured to control at least a portion of the sample preparation system and the sample analysis system, respectively. The second controller is further configured to send result data to the first controller.

In accordance with another embodiment of the present invention, a method to prepare and analyze a sample includes preparing a sample for an assay with a sample preparation system. The assay is selected from a database containing a plurality of unique assays. A sample analysis system, which includes a mass spectrometer, analyzes the prepared sample according to the selected assay. Data with respect to at least one of a result of the analysis and an identification of the prepared sample is communicated from the sample analysis system to the sample preparation system.

According to another embodiment of the present invention, an automated sample preparation and analysis system includes a sample analysis system and a sample preparation system. The sample analysis system includes a mass spectrometer and is configured to analyze a plurality of samples according to respective assays selected from a database containing a plurality of unique assays. The sample preparation system includes a controller for sequencing the samples for analysis by the sample analysis system. The sequence of the sample analysis is dependent on the order of arrival to the automated sample preparation and analysis system, the priority status of each sample, and at least one of a target time to result for a sample, a target time to result for a selected assay, a remaining target time to result for a selected assay, a number of samples on-board, the number of samples awaiting analysis in accordance with the same selected assay, or mass spectrometer reconfiguration necessary for selected assays that precede and follow a selected assay for a particular sample.

In accordance with another embodiment of the present invention, an automated biological specimen preparation and mass spectrometry analysis system for analyzing a plurality of biological specimens according to a selected assay from a database containing a plurality of unique assays includes a sample preparation system and a sample analysis system. The sample preparation system prepares samples taken from at least one of the plurality of biological specimens. The sample analysis system, with a mass spectrometer, quantifies one or more analytes for one or more prepared samples. A specimen dock receives a plurality of containers, each containing a respective biological specimen. A reagent station receives a plurality of containers containing a reagent liquid. A sample station transfers a predetermined biological specimen and one or more predetermined reagent liquids to a sample vessel. An analysis staging station stores one or more sample vessels, each is containing a respective prepared sample. A transport mechanism transfers the prepared samples from one of the sample vessels to the sample analysis system.

Still another embodiment of the present invention is directed to a method of entering an idle state for a sample preparation and analysis system. The sample preparation and analysis system includes a sample preparation system and a sample analysis system. To enter the idle state, the sample preparation and analysis system receives an idle state command. A plurality of blank samples is prepared by the sample preparation system in accordance with an assay that is selected from a database containing a plurality of unique assays. The blank samples do not include a sample of a specimen. First and second ones of the plurality of blank samples are analyzed with the sample analysis system in accordance with the selected assay. Other ones of the plurality of blank samples are analyzed with the sample analysis system in accordance with the selected assay until a wake up command is received.

Another embodiment of the present invention is directed to a method of entering a standby state for a sample preparation and analysis system. The sample preparation and analysis system includes a sample preparation system and a sample analysis system. To enter the standby state, the sample preparation and analysis system receives a standby state command. A standby sample is prepared by the sample preparation system in accordance with an assay that is selected from a database containing a plurality of unique assays and does not include a sample of a specimen. The standby sample is analyzed with the sample analysis system in accordance with the selected assay. At least one component of the sample preparation and analysis system is then powered down. The at least one component is selected from a group comprising a chromatography column heater, a gas flow, a temperature of an ionization source of a mass spectrometer, at least one vacuum pump, at least one fluid pump, a robotic device, a pipette assembly, a mixing station, an incubation station, a matrix interference removal station, a cooling system, and a heating system.

The above and other objects and advantages of the present invention shall be made apparent from the accompanying drawings and the descriptions thereof.

BRIEF DESCRIPTION OF THE FIGURES

The accompanying drawings, which are incorporated in and constitute a part of this specification, illustrate embodiments of the invention and, together with the general description given above and the detailed description of the embodiments given below, serve to explain the principles of the present invention. In the figures, corresponding or like numbers or characters indicate corresponding or like structures.

FIG. 15 a diagrammatic view of a plurality of modules for a sample analysis controller and in accordance with one embodiment of the present invention.

FIGS. 16A-16G are exemplary screenshots provided by a sample preparation controller in accordance with one embodiment of the present invention.

FIG. 39B is exemplary raw data acquired from an automated sample preparation and analysis system, shown in a tabular format.

FIG. 39C is an exemplary linear response of an ion detector for a first analyte analyzed by an automated sample preparation and analysis system in accordance with one embodiment of the present invention.

FIG. 39D is an exemplary negative exponential response of an ion detector fit to the response of an ion detector for a second analyte analyzed by an automated sample preparation and analysis system in accordance with one embodiment of the present invention.

FIG. 39E is an exemplary positive exponential response of an ion detector fit to the response of an ion detector for a third analyte analyzed by an automated sample preparation and analysis system in accordance with one embodiment of the present invention.

FIG. 40 is an exemplary graphical view of a total ion current for various m/z values measured at an ion detector of an automated sample preparation and analysis system in accordance with one embodiment of the present invention.

DETAILED DESCRIPTION OF THE INVENTION

Figure 1A:
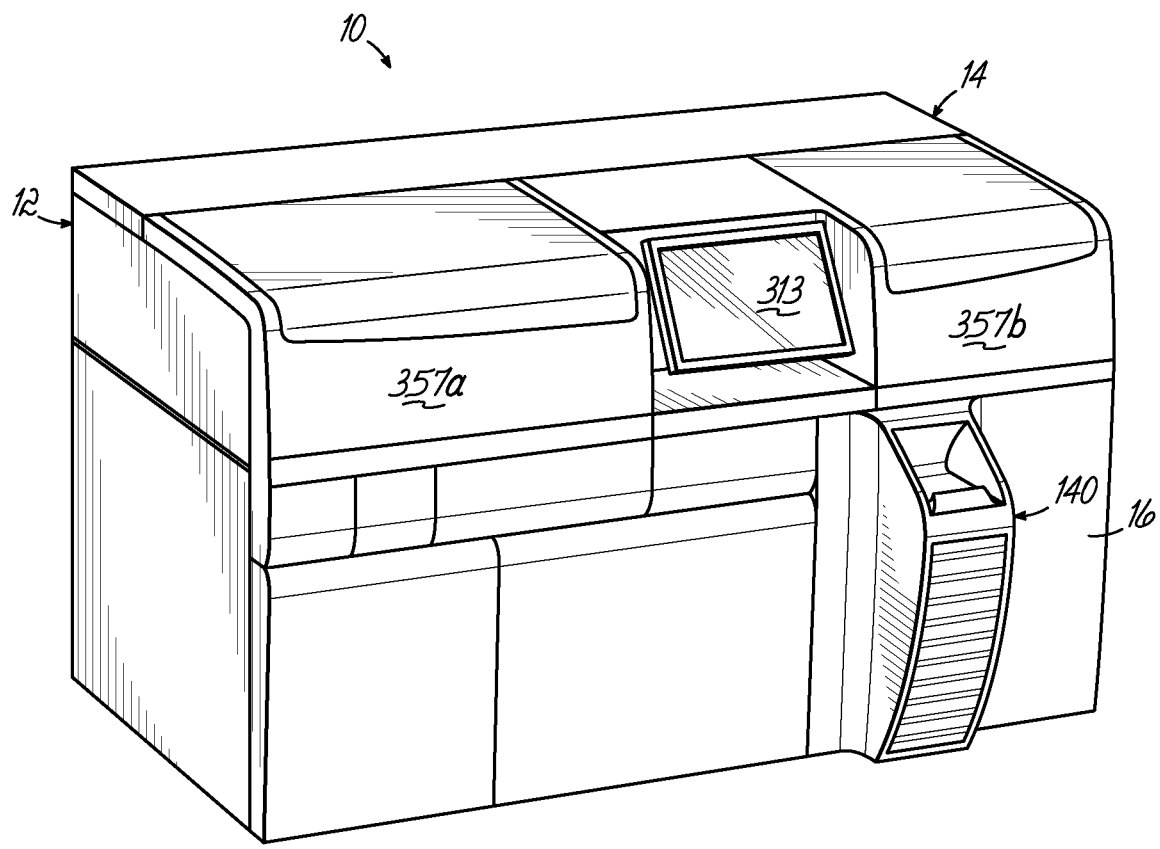
FIG. 1A is a perspective view of an automated sample preparation and analysis system in accordance with one embodiment of the present invention.

FIG. 1A is a perspective illustration of an automated sample preparation and analysis system 10 according to one exemplary embodiment of the present invention (referred to hereinafter as "system" 10). The system 10 is designed to automatically prepare a sample from a specimen for analysis and to analyze the prepared sample according to a predetermined analyte assay selected from a variety of different or unique analyte assays. As will be described in greater detail below, the exemplary system 10 is particularly designed to perform two distinct laboratory functions, i.e., sample preparation and sample analysis, in combination in an automated system.

Figure 1B:
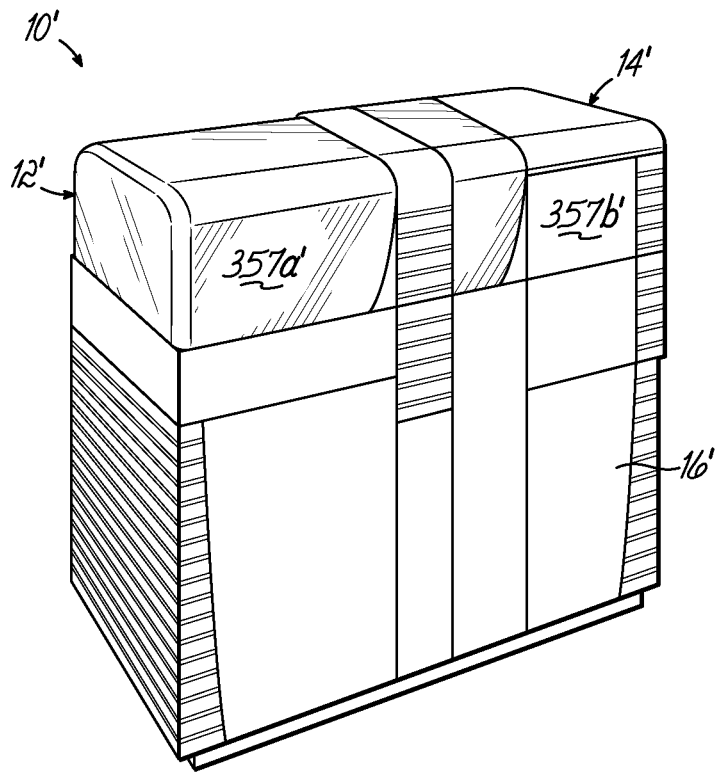
FIG. 1B is a perspective view of an automated sample preparation and analysis system in accordance with another embodiment of the present invention.

FIG. 1B, like FIG. 1A, is a perspective illustration of an automated sample preparation and analysis system 10' and where similar numbers with primes refer to similar features.

In one embodiment, the system 10 includes a sample preparation system 12 for preparing various samples and a sample analysis system 14, which includes a suitable analyzer, such as a liquid chromatography mass spectrometer ("LCMS"), a gas chromatography mass spectrometer ("GCMS"), a surface desorption/ionizer directly coupled to a mass spectrometer; a liquid chromatography ultra-violet spectrometer ("LC/UV-VIS"), or a fluorescence spectrometer, for example, for analyzing the prepared samples according to selected analyte assays. The sample preparation system 12 and the sample analysis system 14 are interconnected in an automated manner as will be described in detail below and may, in fact, be enclosed within a unitary cover 16.

Figure 2:
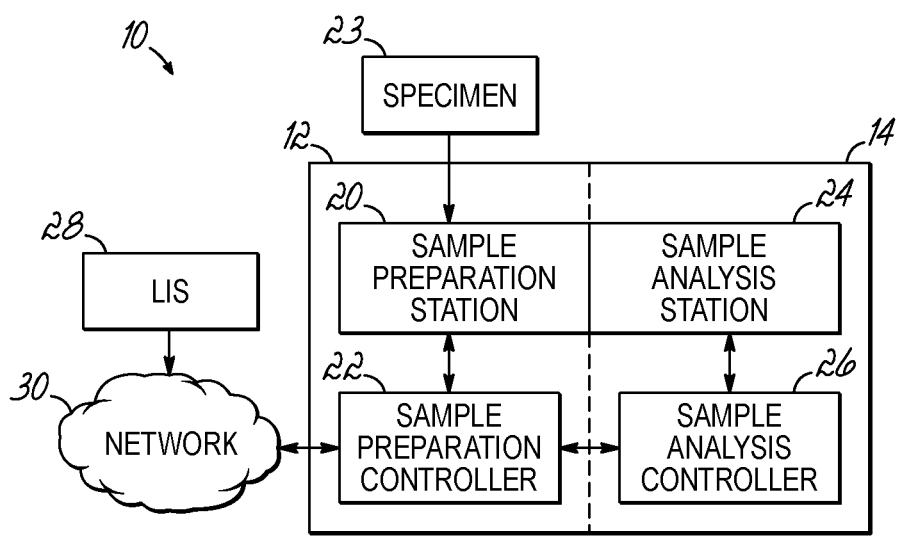
FIG. 2 is a diagrammatic view of the automated sample preparation and analysis system of FIG. 1A.

FIG. 2 is a diagrammatic illustration of various components of the system 10. The sample preparation system 12 includes a sample preparation station 20 and a sample preparation controller 22 that controls selected functions or operations of the sample preparation station 20. The sample preparation station 20 is configured to receive one or more specimens 23, to sample the specimens 23 to prepare the samples for analysis according to a variety of preselected analyte assays, and to transport the prepared samples for analysis to the sample analysis system 14. In some embodiments, the sample preparation station 20 is configured to prepare the sample such that the prepared sample is chemically compatible with the sample analysis system 14 according to the selected analyte assay to be performed by the sample analysis station 14.

Further referring to FIG. 2, in one embodiment the sample analysis system 14 includes a sample analysis station 24 and a sample analysis controller 26 that controls selected functions or operations of the sample analysis station 24. The sample analysis station 24 is configured to receive the prepared sample from the sample preparation station 20 via a transport mechanism described in greater detail below. The sample analysis station 24 then analyzes the prepared sample according to a selected analyte assay to obtain a result for that sample. The sample result is transmitted to the sample preparation controller 22, which may validate the results. If the result is valid, the result may be transmitted to a laboratory information system 28 (illustrated as, and referred to hereinafter, as "LIS" 28) via at least one network 30.

It will be readily appreciated that while FIG. 2 seems to indicate that the sample preparation station 20 and the sample analysis station 24 comprise two opposing sides of the system 10, the systems may encompass the same area or footprint. Indeed, in accordance with the present invention, in some embodiments the sample preparation station 20 and the sample analysis station 24 need not be encompassed within the same housing or unit.

Turning now to FIGS. 3A-3D, the details of two embodiments of layouts of the sample preparation station 20 and the sample analysis stations 24 associated with the systems 10, 10' of FIGS. 1A and 1B are shown and briefly described below. Additional features are described in detail in International Application No. PCT/US0211/58323, entitled "System Layout for an Automated System for Sample Preparation and Analysis," filed on even date herewith, and incorporated herein by reference in its entirety. It would be understood that, for the convenience of discussion, the like reference numerals referring to like features with primes are included herein, though each is not necessary provided explicitly. The sample preparation station 20 includes a specimen dock 40 having one or more specimen racks 42. Each specimen rack 42 includes one or more specimen rack positions capable of holding a specimen container 45 (see, FIG. 3A). The specimen containers 45 are configured to contain the acquired biological or environmental specimens, which may be any specimen containing or suspected of containing an analyte of interest. Patient specimens may include blood, serum, plasma, urine, stool, sputum, brochial lavage, nasopharangeal lavage, perspiration, tears, extracts of solid tissue, swabs (from all bodily sites, including skin), cerebrospinal fluid, or saliva, for example. Environmental samples may include, for example, food, water, or environmental surface samples. These patient specimens or environmental samples may be analyzed for one or more analytes, which may include, but are not limited to, drugs, pro-drugs, metabolites of drugs, metabolites of normal biochemical activity, peptides, proteins, antibiotics, metabolites of antibiotics, toxins, microorganisms (including bacteria, fungi, and parasites), and infectious agents (including viruses and prions). Further, any of the foregoing samples, alone or in combination, may be suspended in an appropriate media, for example, within a blood culture or a screening booth. The specimen container 45, itself, may include any suitable labware, such as a vessel, a vial, a test tube, a plate, or any other suitable container known in the art. One or more of the specimen racks 42 may be designated, or otherwise labeled (e.g., by placement of the rack 42 within the sample preparation station 20 or with a barcode or an RFID antenna), as priority racks 42a, or STAT, for introducing specimen containers 45 having urgent specimens. Alternatively, urgent specimens may be introduced into a specimen rack 42 and identified as priority or STAT samples by pressing a priority button (not shown) on the instrument or by setting the sample priority using a touch screen display 313, which is described in greater detail below. Urgent specimens may include, for example, emergency department patient specimens or patient specimens containing toxicants or immunosuppressants. The manner by which specimens within the priority rack 42a are prepared and tested is described in greater detail below.

The specimen dock 40 may be configured to accommodate an on-line accession station 47 (see, FIGS. 3C and 3D) for receiving the specimen vessels 45 from an off-line automated laboratory track system (not shown).

The sample preparation station 20 further includes a reagent station 46 containing multiple reagent racks 48. Each reagent rack 48 includes one or more reagent rack positions capable of holding one or more reagent containers 52 (see, FIG. 5A) that contain solvents and/or reagents, some of which may be comprised of a volatile liquid. While not necessary, the illustrative embodiment of the specimen racks 42 of the sample dock 40 and the reagent racks 48 of the reagent station 46 have similar construction. In other embodiments, it may be advantageous to include reagent racks 48 having a different structure as compared to the specimen racks 42 such that racks 42 containing biological specimens are not inadvertently inserted into the reagent station 46. In still other embodiments, reagent racks 48 may include distinct labeling, e.g., a barcode or an RFID antenna, as compared with the specimen racks 42.

Figure 5A:
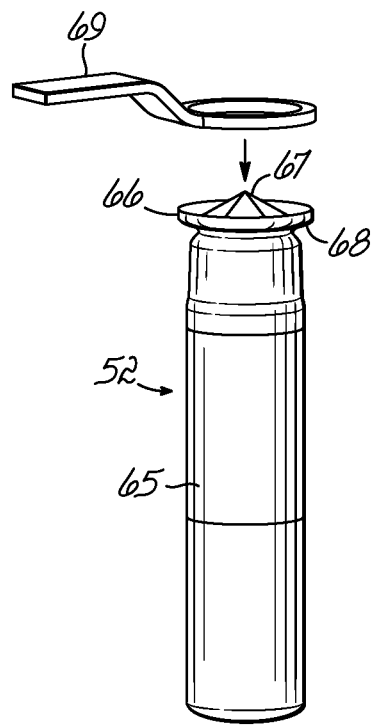
FIGS. 5A and 5B are side elevational views of a reagent container in accordance with one embodiment of the present invention, shown in closed and open states, respectively.
Figure 5B:
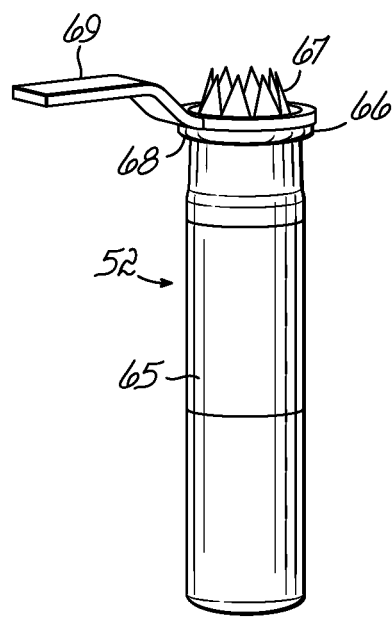

The reagent station 46 may include a cooling station 53 coupled to a thermostat (not shown) and chiller (not shown) to maintain the temperature of the reagent station 46 at a constant, cooled temperature, for example, between about 4° C. and about 10° C. This may aid in reducing the loss of reagent through evaporation and thereby extend the lifetime and activity of the reagents contained therein. The reagent container 52 may be similar to the reagent containers that are described in detail in U.S. Provisional Application No. 61/552,470, entitled "Reagent Bottle, System, Method, and Apparatus for Handling Closure Caps and Like," naming inventors YY, ZZ, and filed on even date herewith, the disclosure of which is incorporated herein by reference in its entirety. Alternatively, the reagent container 52 may be similar to the reagent containers that are described in detail in U.S. Application Publication No. 2008/0093364, the disclosure of which is incorporated herein by reference in its entirety. Briefly, and as shown in FIG. 5A, each reagent container 52 may include a body 65 and a top wall 66 having six or more flaps 67 (formed by three or more radially extending incisions) extending radially inward and a flange 68 extending radially outward. At rest, the flaps 67 are angularly extended inward to form a seal that reduces evaporation of the reagent contained within the volume of the body 65. According to one embodiment, the flaps 67 are opened by directing a ring-shaped actuator 69, operable by way of one or more robotics, which forces the ring-shaped actuator 69 downwardly over the top wall 66 and engages the flange 68. Continued downward movement of the ring-shaped actuator 69 lowers the flange 68 and biases the flaps 67 upwardly and outwardly, as shown in FIG. 5B.

Returning to FIGS. 3A-3D, various reagents may reside within the reagent station 46, including all reagents necessary for the plurality of assay types that are capable of being performed by the system 10. For example, the reagents may include protein precipitation reagents (e.g., acetonitrile, methanol, or perchloric acid), cell lysis reagents (e.g., zinc sulfate, a strong acid, an enzyme digestion with lysozymes, cellulases, proteases, detergents including, without limitation, non-ionic, zwitterionic, anionic, and cationic detergents, protein digestion reagents (e.g., serine proteases such as trypsin, threonine, cysteine, lysine, arginine, or aspartate proteases, metalloproteases, chymotrypsin, glutamic acid proteases, lys-c, glu-c, and chemotrypsin), internal standards (e.g., stabile isotope labeled analytes, heavy isotope labeled peptides, non-native peptides or analytes, structurally similar analogs, chemically similar analogs), antibiotics (for microbiological antibiotic susceptibility testing, or "AST"), protein stabilization agents, including buffers, chaotropic agents, or denaturants, calibration standards, and controls. According to various embodiments, one or more of the reagents may be pre-mixed to form a combined reagent mixture specific for a particular assay or panel of assays.

The reagent station 46 may further include an information acquisition device 54 which, for example, may be a bar code reader or an RFID receiver. The information acquisition device 54, in turn, may receive information associated with a reagent of the particular reagent container 52 or information associated with the particular reagent container 52 itself. A bar code or RFID antenna is imprinted or positioned on a reagent container 52. The bar code or RFID antenna may be configured to provide information associated with the particular reagent or it may contain an identification (such as an identifier) that is cross-referenced with a Look-Up Table ("LUT") (not shown) accessible by the sample preparation controller 22 (FIG. 2) (e.g., on the sample preparation controller 22 or on the LIS 28 and accessible by the sample preparation controller 22) and having detailed information regarding the reagent contained therein. The information obtained may be used to identify and/or monitor a respective reagent container 52 and/or the reagent therein. For example, the information may be used to identify the reagent within the reagent container 52, identify the location of the reagent container 52 within the reagent station 46, identify and/or monitor the quantity of reagent remaining in the reagent container 52, and/or identify the expiration date of the reagent within the reagent container 52. Though not specifically shown, the information acquisition device 54 may be mounted onto a track system (not shown) that spans between the specimen dock 40 and the reagent station 46, and by way of one or more motors (e.g., a stepper motor or like device) the information acquisition device 54 may be translated to a position within the specimen dock 40 or the reagent station 46 for receiving a specimen rack 42 or a reagent rack 48. In this way, the information acquisition device 54 may scan the barcode and/or RFID antenna as the specimen containers 45 and/or reagent containers 52 are loaded into the sample preparation station 20. Further, it would be understood that while only one information acquisition device 54 is shown, additional information acquisition devices, in like manner or having an alternate structure, may be included in other portions of the system 10 for tracking samples and the associated tests.

Figure 6A:
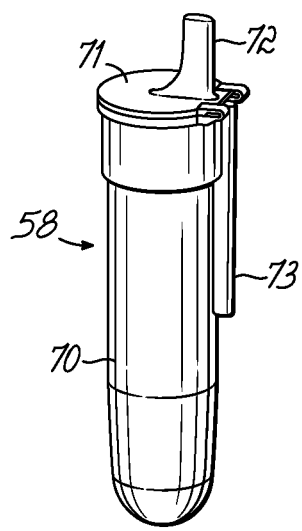
FIGS. 6A and 6B are side elevational view of a sample vessel in accordance with one embodiment of the present invention, shown in closed and open states, respectively.
Figure 6B:
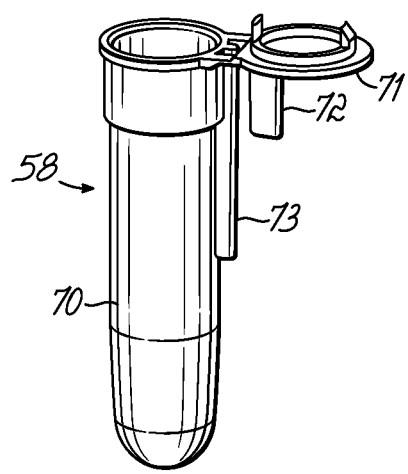

Turning now to an illustrative method of sample preparation, a patient sample (referred to hereinafter as "sample"), or a portion of a particular specimen contained within a specimen container 45 is transferred to an open-top sample vessel 58 (also known as a reaction vessel, but referred to hereinafter as "vessel" 58) to be prepared for analysis. Suitable vessels 58 may include, for example, open-top vessels, vessels having a screw-top cap, vessels having integrated flip-top caps, and vessels having tops with piercable septa. One exemplary embodiment of a vessel 58 for use with the sample preparation station 20 is described in detail in U.S. Provisional Application No. 61/408,059, entitled "A Reaction Vessel and Apparatus and Method for Opening and Closing a Reaction Vessel,", naming inventors Nuotio, Siidorov, and Kukkonen, filed on Oct. 29, 2010, and International Application No. PCT/FI2011/050950, entitled "A Reaction Vessel and Apparatus and Method for Opening and Closing a Reaction Vessel," filed on even date herewith, the disclosures which are incorporated herein by reference in their entirety. Briefly, the vessel 58 of the co-pending application is shown in FIGS. 6A and 6B and includes a body 70 for containing one or more of a sample, a reagent, a solvent, and a standard (calibration, control, or internal); and a hinged lid 71 having a guide rod 72 extending upwardly therefrom. At least one rib 73 may be included external to the body 70 for properly aligning the vessel 58 in various ones of the components within the sample preparation station 20. Accordingly, the vessel 58 has an open state (FIG. 6B) to receive one or more of the sample, reagents, solvents, and standards and a closed state (FIG. 6A) to seal the body 70 and to reduce the evaporation of volatile liquids therefrom. One manner of opening and closing the vessel is described in greater detail below.

Again, returning to FIGS. 3A-3D, the vessels 58 may be stored within, and introduced from, a storage station 59 (FIG. 3D) of the sample preparation station 20. Within the storage station 59, the vessels 58 may reside in plates 57 or other appropriate mass storage containers. As various ones of the vessels 58 are transferred and periodically leaving empty plates 57, the plates 57 may be discarded through a waste chute 55 from the sample preparation station 20.

When a specimen 23 (FIG. 2) is sampled, one or more vessels 58 are transferred to a sampling station 56 from the storage station 59 (FIG. 3D) by way of a transport assembly 60. The transport assembly 60 may include a robot assembly operating on one or more tracks 50 and configured to move in at least one of an x-y direction, an x-y-z direction, or a rotary direction. An exemplary track system and associated transport bases are described in detail in U.S. Pat. No. 6,520,313, entitled "Arrangement and Method for Handling Test Tubes in a Laboratory," naming inventors Kaarakainen, Korhonen, Makela, and which is hereby incorporated herein by reference in its entirety.

While not shown, the transport assembly 60 may further include a gripper, or other like device, to capture and release the vessel 58 or a transport handle 63 (FIG. 3B) associated with a vessel rack 84 (FIG. 3B) to simultaneously transport two or more vessels 58 within the system 10. An exemplary gripper for use on the transport assembly 60 is described in detail in U.S. Provisional Application No. 61/408,051, entitled "Method and Assembly for Transporting Single and Multiple Reaction Vessels," naming inventor Nuotio, filed on Oct. 29, 2010, and International Application No. PCT/FI2011/050949, entitled "Method and Assembly for Transporting Single and Multiple Reaction Vessels," filed on even date herewith, the disclosures of which are incorporated herein by reference in their entirety.

In another embodiment, not shown, the transport assembly 60 may include a robot assembly configured to move in at least one of an x-y direction, an x-y-z direction, or a rotary direction and which may include an automated liquid handler. According to this embodiment, the automated liquid handler may aspirate and dispense a volume of a liquid between two or more vessels 58 within the system 10 to transport the liquid between two or more stations 20, 24, 40, 46, 47 within the system 10.

In still other embodiments, the transport assembly 60 may further include carousels, i.e., a circular revolving disc, or autosamplers having multiple vessel positions therein to provide transport function and allow for a temporary, intermediate vessel storage function. In other embodiments, the transport assembly 60 may further include an information acquisition device (not shown). This information acquisition device may operate in a manner similar to the information acquisition device 54 and be used to identify the vessels 58 as they are moved throughout the sample preparation station 20.

Figure 3A:
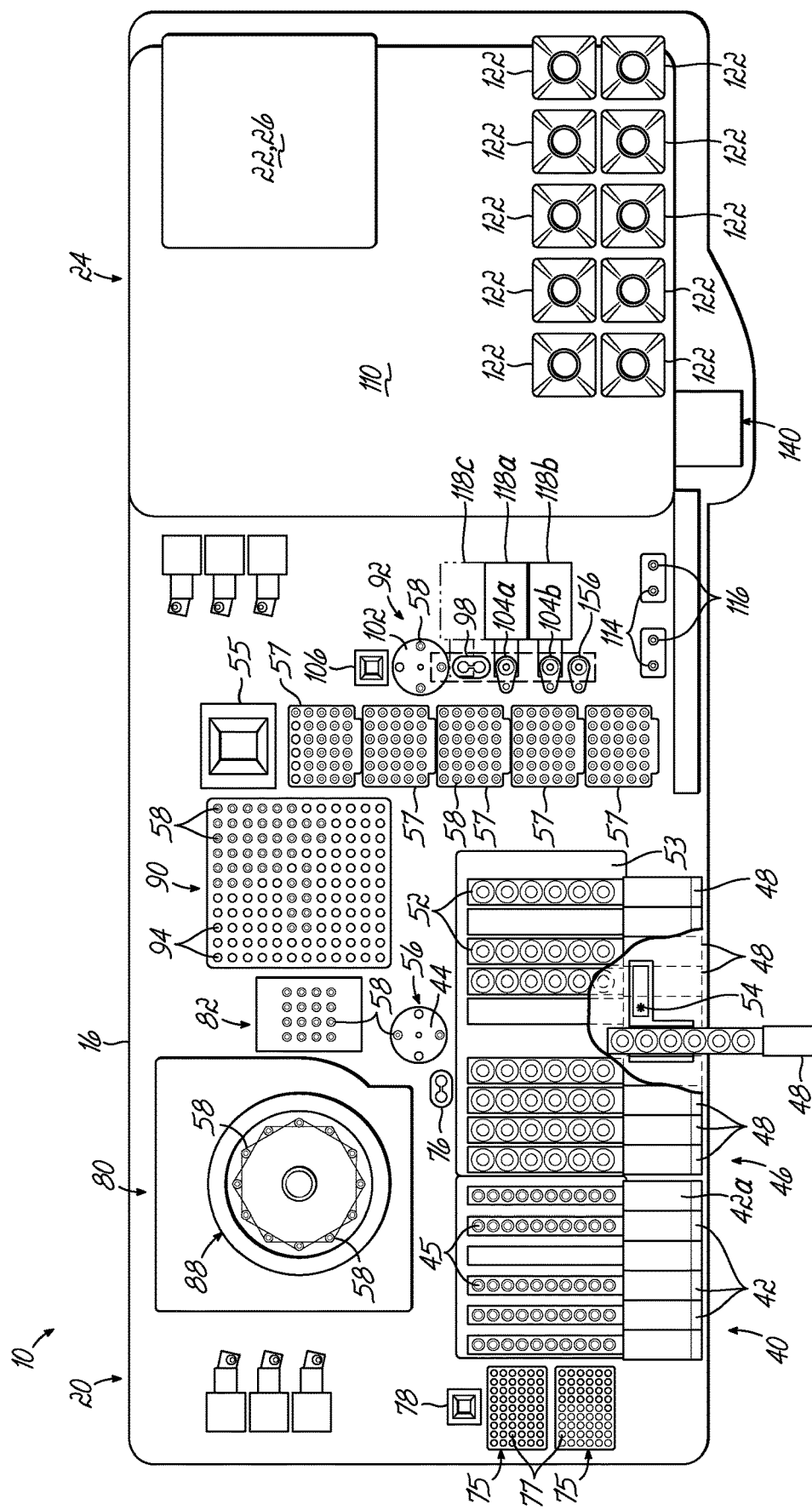
FIG. 3A is a top view of the automated sample preparation and analysis system of FIG. 1A and according to one embodiment of the present invention.
Figure 3B:
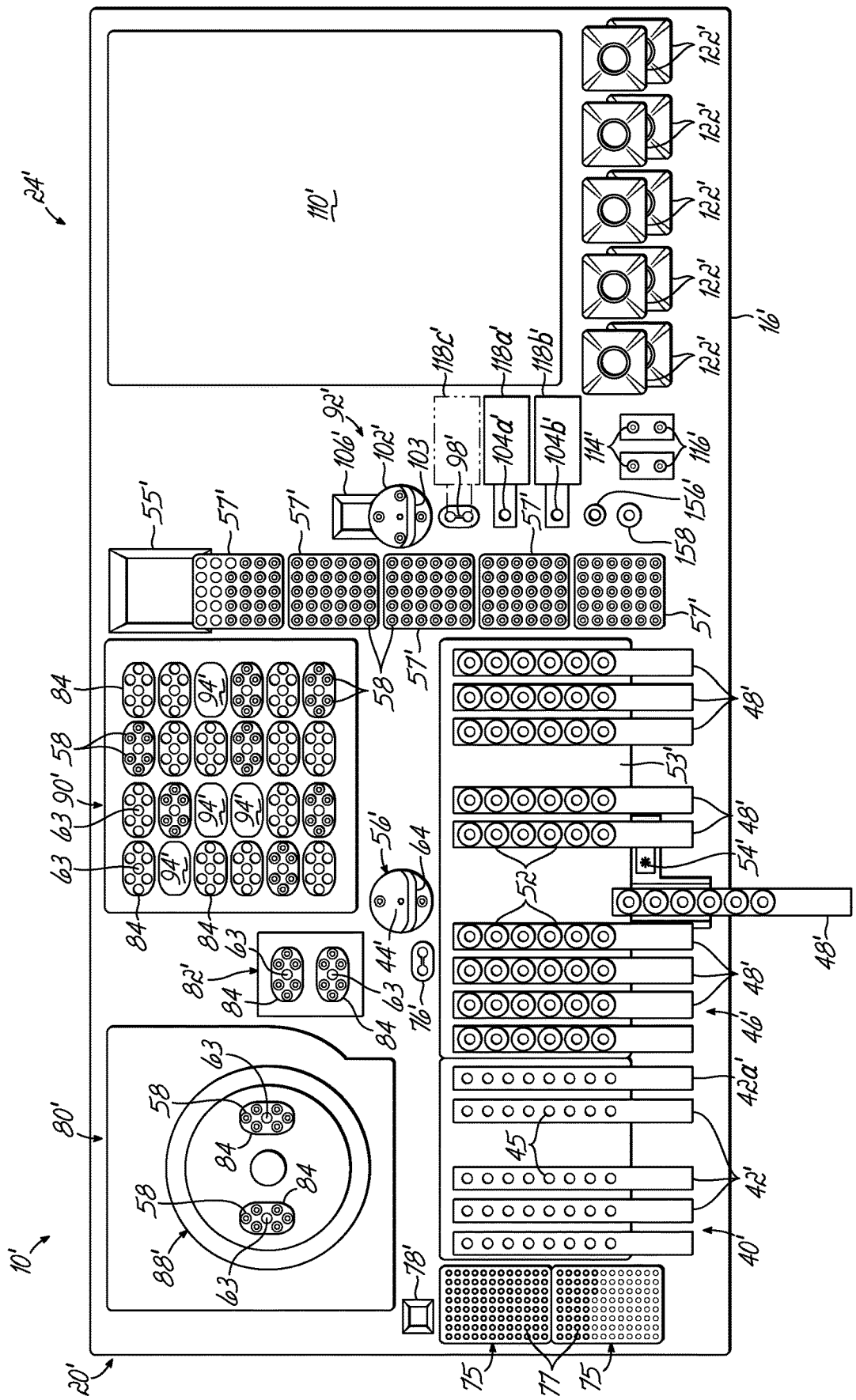
FIG. 3B is a top view of the automated sample preparation and analysis system of FIG. 1B and according to one embodiment of the present invention.
Figure 3C:
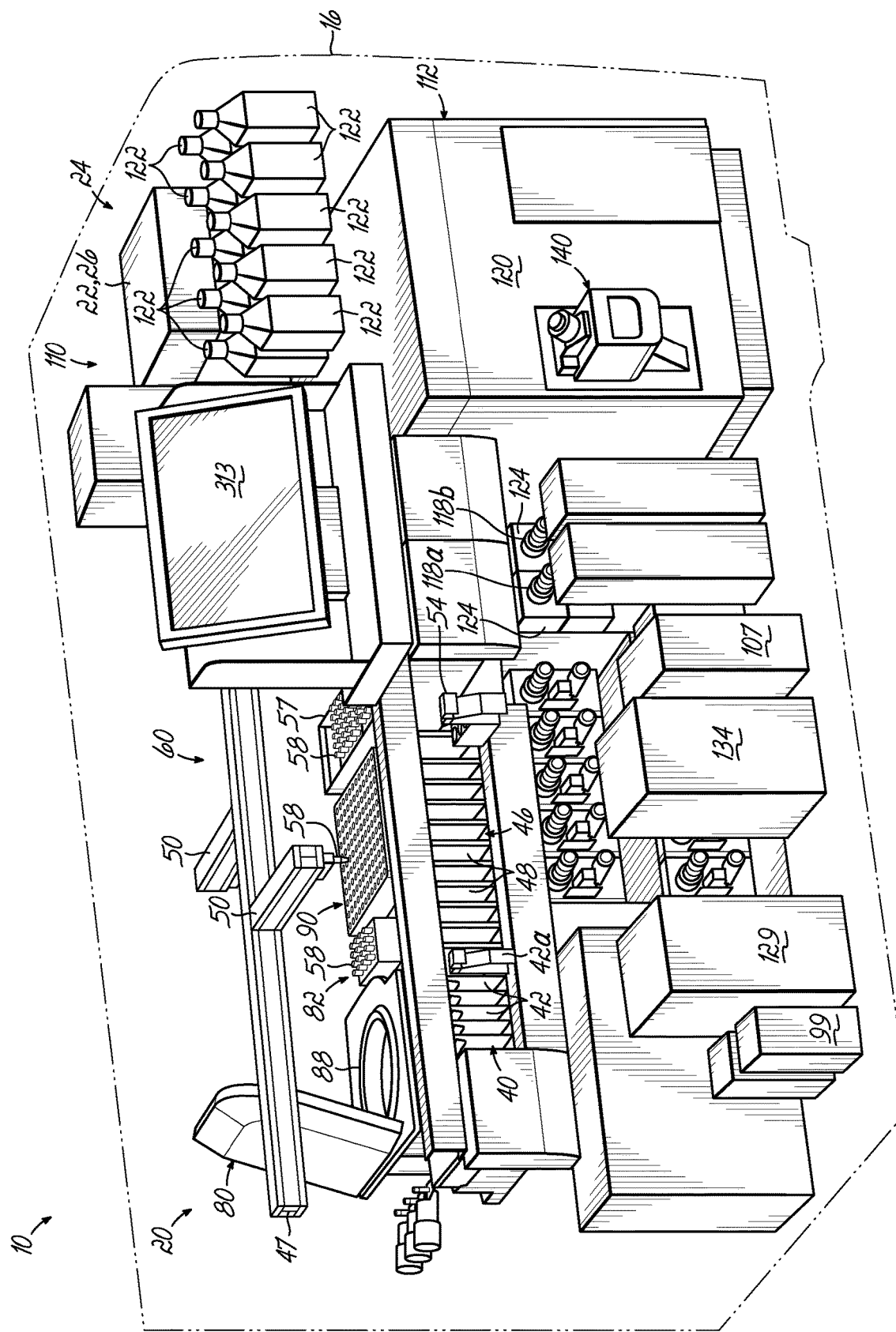
FIG. 3C is a side elevational view of the automated sample preparation and analysis system of FIG. 1A with the front cover removed.
Figure 3D:
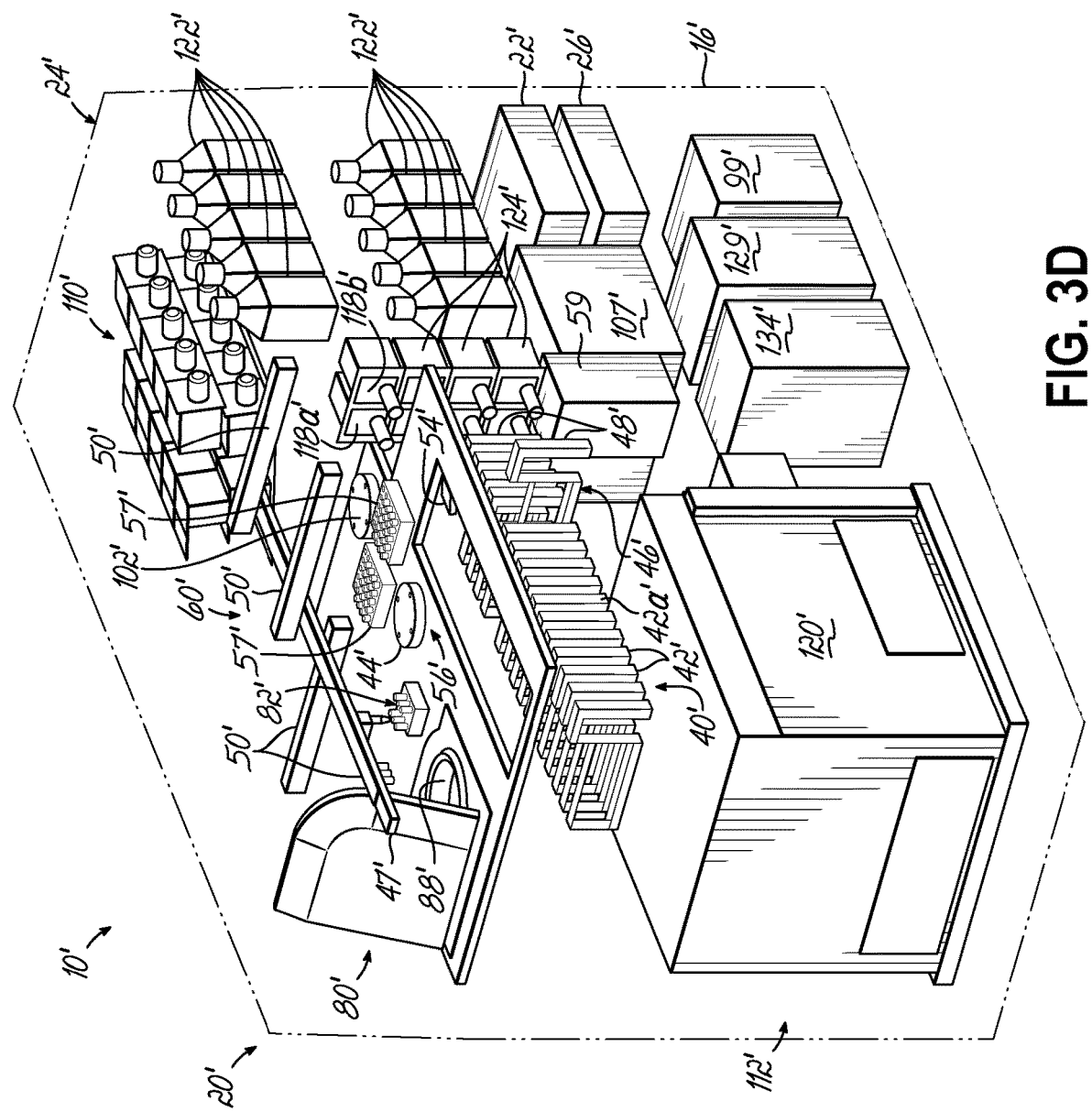
FIG. 3D is a side elevational view of the automated sample preparation and analysis system of FIG. 1B with the front cover removed.
Figure 4A:
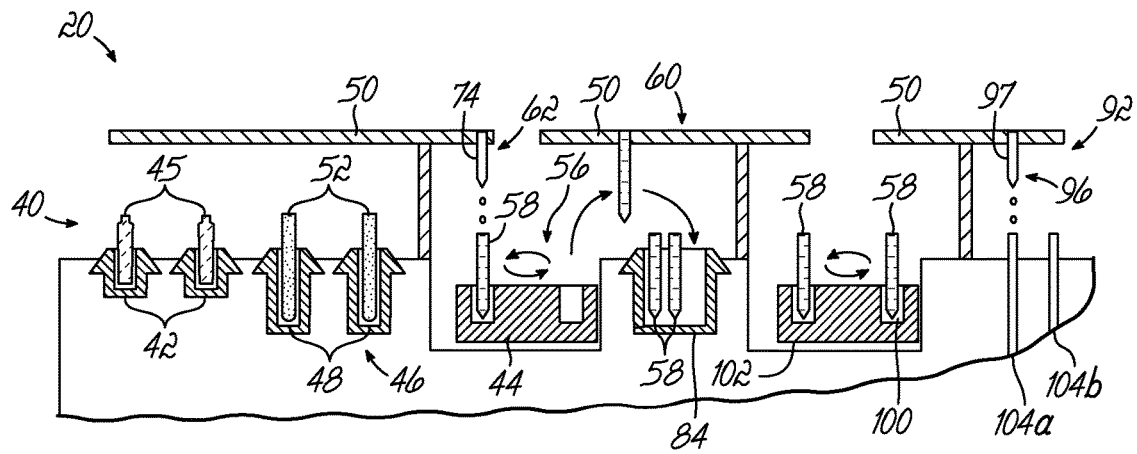
FIG. 4A is a schematic view of a sample preparation station and a transport assembly of the automated sample preparation and analysis system of FIG. 1A in accordance with one embodiment of the present invention.

In the illustrated embodiment, the sampling station 56 includes a rotatable table 44 that rotates each vessel 58 between at least two positions. In one position, the vessel 58 may be received from the transport assembly 60. In another position, the vessel 58 is positioned to receive a portion of the specimen 23 (FIG. 2) via a sample pipette assembly 62 (FIG. 4A). The rotatable table 44 may include a vessel cap opening and closing device 64 (FIG. 3B) for opening and closing the hinged lid 71 (FIG. 6A) of the vessel 58 as the vessel 58 is transported between the first and second positions. Accordingly, the hinged lid 71 (FIG. 6A) may be in the closed position (FIG. 6A) when the vessel 58 is delivered to the first position of the sampling station 56. Rotation of the rotatable table 44 moves the vessel 58 to the second position and causes the guide rod 72 (FIG. 6A) to engage the opening and closing device 64, thereby opening the hinged lid 71 (FIG. 6B). One such rotatable table with opening and closing device is described in aforementioned U.S. Provisional Application No. 61/408,059, entitled "A Reaction Vessel and Apparatus and Method of Opening and Closing a Reaction Vessel," filed on Oct. 29, 2010, and International Application No. PCT/FI2011/050950, entitled "A Reaction Vessel and Apparatus and Method for Opening and Closing a Reaction Vessel," filed on even date herewith, and the disclosures of which are incorporated herein by reference in their entireties.

The sample pipette assembly 62 (FIG. 4A) may include a pipette shaft 74 (FIG. 4A) that is movable, for example via a robotic device, in one or more of the x-y-z directions and between two or more of the specimen dock 40, the reagent station 46, and the sampling station 56. The pipette shaft 74 (FIG. 4A) may be constructed with a single tip construction that is washed between aspirations at a pipette wash station 76 or, alternatively, may be adapted to receive a disposable tip (not shown) that is then ejected before acquiring a new disposable tip to aspirate a new sample. In the former embodiment, after a sample is dispensed to the vessel 58, the single tip is washed, one or more times, by an appropriate solvent solution, such as by multiple aspirations and dispensing of the solvent. In the latter embodiment, the sample preparation station 20 may include a tip storage station 75 for storage and supplying disposable tips from one or more disposable tip racks 77. After the sample is dispensed to the vessel 58 in this embodiment, the disposable tip is ejected from the pipette shaft into a disposable tip waste chute 78, which is coupled to a larger waste storage container (107).

The sample pipette assembly 62 (FIG. 4A) may aspirate an aliquot of the specimen 23 (FIG. 2) from the specimen container 45 from within the specimen dock 40 and dispense the aliquot of the specimen 23 (FIG. 2) into the vessel 58 within the sampling station 56. Additionally, or alternatively, the sample pipette assembly 62 (FIG. 4A) may aspirate an aliquot of a desired reagent from one of the reagent containers 52 within the reagent station 46 and dispense the aliquot of the desired reagent into the vessel 58 within the sampling station 56, which may or may not previously include the sample, i.e., the aliquot of the specimen 23 (FIG. 2).

In some embodiments, it may be necessary to mix the specimen 23 (FIG. 2) prior to aspirating. For example, blood specimens may partition over time, i.e., separation of blood cells (erythrocytes, leukocytes, etc.) from the plasma. Some drugs are distributed unequally between the blood cells and the plasma (for example, with 40-50% in erythrocytes, 10-20% in leukocytes, and 30-40% in the plasma). These distributions may be dependent on temperature, hematocrit, and metabolite concentration. Thus, in order to properly measure the particular drug, or other analyte, concentration, a proper sampling of the whole blood must be acquired. One method of mixing the specimen may occur by aspirating and dispensing the specimen 23 (FIG. 2) a number of times (for example, 13 times) with the sample pipette assembly 62 (FIG. 4A). The number of aspirations may depend on at least the volume of the specimen container 45, the aspiration volume, and the dispensing "speed." One method of mixing the specimen 23 (FIG. 2) using aspiration and dispensing is described in detail in U.S. Provisional Application No. 61/552,472, entitled "Method for Treating a Sample," filed on even date therewith, and the disclosure of which is incorporated herein by reference in its entirety.

In other embodiments, the pipette shaft 74 (FIG. 4A) may shake (move rapidly in at least one dimension) or the sample may be first directed to mixing station (not shown) that is separate from the sampling station 56 to gently mix the specimen 23 (FIG. 2) prior to sampling.

According to still another embodiment, the sample is selected from a culture plate using a commercially-available colony picker instrument, for example, the PICKOLO (Tecan Group, Ltd., Männedorf, Switzerland) or the QPIX (Genetix, now part of Molecular Devices, San Jose, Calif.). The colony picker is capable of collecting an aliquot of the specimen 23 (FIG. 2) from a colony, optionally, a pre-selected or pre-designated colony, on a culture plate and depositing the sample into the vessel 58. The colony-containing vessel may then be mixed, as described above, to lyse the cells and denature the proteins in order to stabilize the sample for later microbial analysis.

Following receipt of the aliquot(s) of the specimen 23 (FIG. 2) and/or reagent (which will now be referred to hereinafter for convenience as the "sample") the hinged lid 71 (FIG. 6A) is closed via a separate robotic component or the opening and closing device 64. Closing the hinged lid 71 prevents loss of the sample through evaporation. Moreover, because one or more of the liquids dispensed into the vessel 58 may be volatile, sealing of the vessel 58 may be used to prevent evaporation of the one or more volatile liquids and preserve the intended concentration of the sample.

The sample within the vessel 58 is transferred via the transport assembly 60 from the sampling station 56 to a secondary processing station 80. The secondary processing station 80 includes, for example, one or more of a mixing station 82, an incubation station (not shown), and a matrix interference removal station (illustrated as a centrifuge 88). According to one embodiment, each of the mixing station 82 and the matrix interference removal station is capable of accepting either vessels 58 or a vessel rack 84 such that two or more vessels 58 may be processed simultaneously. However, the use of the vessel racks 84 is not required.

The mixing station 82, if included in the secondary processing station 80, may include a shaker, a vortex mixer, or another apparatus capable of accelerating the mixing of the sample within the vessel 58. As shown, the mixing station 82 may be configured to accommodate sixteen vessels 58 (FIG. 3A) or twelve individual vessels 58 via two vessel racks 84 (FIG. 3B).

The incubation station, if included, may also be incorporated in either of an on-line or off-line configuration. The incubation station is configured to heat a sample, with or without additional reagents, at an elevated temperature (by way of example, at a specified temperature ranging from about 27° C. to about 70° C., including, particularly, 37° C., 50° C., or 70° C.) for a predetermined duration of time and based on a selected assay. For example, the incubation temperature and duration for a particular sample type and/or selected assay type may be determined by incubating a panel of the same sample and assay types at a range of temperatures and/or a range of times. Following incubation, each sample in the panel is analyzed with a control standard and the digestion efficiency of the incubation is calculated. The temperature and time producing the optimal digestion efficiency may then be selected as a preset or previously determined incubation temperature and time for that sample and assay type.

The matrix interference removal station, if included within the secondary processing station 80, may be incorporated in either of an on-line or off-line configuration (e.g., the on-line configuration being a configuration in which the sample moves between one or more stations of the sample preparation station 20 through fluidic connections without being contained in a vessel 58, the off-line configuration being a configuration in which the sample is transported within a vessel 58 between stations of the sample preparation station 20). In embodiments that include an on-line matrix interference removal station, the analyte-containing prepared sample may flow directly from the matrix interference removal station to the next station, such as through tubing. This second station may include, for example, a second matrix interference removal station (not shown). In embodiments that include an off-line matrix interference removal station, the analyte-containing prepared sample is collected from the matrix interference removal station and placed into a vessel 58 if not already contained in a vessel 58.

The matrix interference removal station is operable to separate one or more of residual proteins, phospholipids, salts, metabolites, carbohydrates, nucleic acids, and/or other substances that may otherwise interfere with subsequent processing or analysis of the desired analytes and prior to transferring the now prepared sample to the sample analysis station 24. In some embodiments, the matrix interference removal station separates contaminants from the analyte-containing prepared sample, or more simply, the "prepared sample" (for example, by separating precipitated solids from a resulting supernatant liquid, wherein the supernatant liquid forms the prepared sample). The matrix interference removal station may include, for example, one or more of a phase separation station (not shown), a centrifuge (illustrated as reference number 88 in FIG. 3A and reference number 88' in FIG. 3B), a sonicator (not shown), a heating station (not shown), a flash freeze station (not shown), an affinity purification station (not shown), or a filtration station (not shown). Each embodiment of the matrix interference removal station may be configured to accommodate one or more vessels 58 or one or more vessel racks 84, or the contents of one or more vessels 58, as appropriate.

One of ordinary skill in the art will readily appreciate that incorporation of the centrifuge 88 into the housing 16 with the analytical instrumentation of the system 10 may cause undesirable interference with those analytical instruments. In this integral configuration example, the ability of the analytical instruments to perform with a particular reliability may be compromised. This may be due to, at least in part, the high rotational speed required to draw down the precipitating solids from the supernatant liquid. Therefore, it may be necessary for embodiments of the system 10 including an integrated centrifuge 88 to further include features that reduce transmission of vibrations thereof to other components of the system 10. Moreover, because of the desire to reduce the overall footprint of the system 10, the overall size of the centrifuge 88 may be reduced and/or configured to be a standalone centrifuge 88 that is not integral with other components of the system 10, but yet accessible by the transport assembly 60.

The matrix interference removal station may include an affinity extraction or purification station, for example, an immunoaffinity extraction or purification system. An exemplary immunoaffinity system may use a Mass Spectrometry Immunoassay ("MSIA") antibody enriched substrate. One suitable, commercially-available MSIA substrate includes those from Intrinsic Bioprobes Inc. (Tempe, Ariz.) and that are described in U.S. Pat. No. 6,783,672, the disclosure of which is incorporated herein by reference in its entirety. More specifically, MSIA substrates may include monolith substrates formed of glass, crystal, or metal having attached antibodies with a specific affinity for the analyte of interest. MSIA substrates may be developed with antibodies specific to the analyte to be extracted. Exemplary analytes include, but are not limited to, small molecules, small molecule variants, proteins, protein fragments, and protein variants. During analyte extraction, the sample is aspirated into the MSIA pipette tip or passed through the MSIA column so that the analyte of interest forms an affinity association with the attached antibody. Following association of the analyte with the antibody, the remaining matrix portion of the sample is dispensed from the MSIA tip or column. The analyte of interest is subsequently eluted from the antibodies into an appropriate media that is configured to release the analyte from the antibody for further analysis. One exemplary MSIA method is described in greater detail in U.S. Pat. No. 6,974,704, the disclosure of which is incorporated herein by reference in its entirety.

Though not specifically shown, the matrix interference removal station may, in yet other embodiments, include additional techniques known in the art of chemical separation, such as liquid-liquid extraction, solid phase supported liquid extraction, random access media column extraction, monolithic column extraction, dialysis extraction, dispersive solid phase extraction, solid phase micro-extraction, immunoaffinity extraction, and size exclusion using membrane filters with gravity, vacuum, or centrifugation. Many of these techniques may be practiced off-line or on-line, as appropriate, if fluid connections are created between subsequent steps of the method. Additionally, many of these techniques may be practiced in a variety of formats including, for example, using a column or cartridge format, using a pipette tip format, using a magnetic bead format, or using a plate or chip format.

In still yet another embodiment, the matrix interference removal station may include two or more matrix interference removal methods in series. According to this embodiment, the first matrix interference removal station, for example a phase separation station, removes precipitated proteins while the second matrix interference removal station, for example a solid phase extraction station, removes additional residual proteins, phospholipids, and salts from the sample prior to analysis. Additional examples of combinations of matrix interference removal techniques include, but are not limited to, solid phase extraction followed by liquid-liquid extraction, phase separation followed by size exclusion affinity liquid chromatography, solid phase extraction followed by size exclusion affinity liquid chromatography, and immunoaffinity extraction prior to or following any of the aforementioned methods.

Embodiments of the system 10 that include a filtration station may in turn include a vacuum and/or positive pressure filtration system (not shown) for passing the sample through a filter membrane (not shown) for collecting and/or removing precipitated proteins or other solid particles from the sample. The vacuum and/or positive pressure system may, or may not, include a filter (for example, a speedvac), to dry down the sample in order to remove a liquid, for example a solvent, from the sample. Alternatively, the filtration station may include a High Performance Liquid Chromatography ("HPLC") system (not shown) or an Ultra-High Performance Liquid Chromatography ("UHPLC") system containing at least one LC column having suitable stationary and mobile phases to remove matrix interference. In some embodiments, the filtration station may in actuality include two or more LC columns arranged on-line and in series (often referred to as two-dimensional LC or multi-dimensional LC). Examples of suitable LC columns include a size exclusion chromatography, high turbulence chromatography, a reversed-phase chromatography, ion-exchange chromatography, bio-affinity chromatography, or other as known in the art.

Embodiments of the system 10 that include a phase separation component may include an on- or off-line solid phase extraction station (not shown) having a vacuum and/or positive pressure source (not shown) to assist in moving the sample through a solid phase extraction matrix. The solid phase extraction matrix, in turn, may include one or more suitable porous stationary phase material layers. According to one embodiment, the solid phase extraction matrix (not shown) further includes one or more filters arranged on one or both sides of the porous stationary phase material. The solid phase extraction matrix may be arranged, for example, within a column, cartridge, a pipette tip, or in a plate or chip format.

After the sample has passed through the secondary processing station 80, the prepared sample is transported via the transport assembly 60 to an analysis staging station 90. The analysis staging station 90 includes two or more vessel positions 94 (FIG. 3A) or two or more vessel rack positions 94' (FIG. 3B) for accepting vessels 58 or vessel racks 84, respectively. In the particular illustrative examples, the analysis staging stations 90, 90' accommodate about one hundred thirty-two vessels 58 (FIG. 3A) or twenty-four vessel racks 84 (FIG. 3B) that are, in turn, capable of accepting up to about six vessels 58 each, for a total of one hundred forty-four vessels 58. Each vessel position 94 may be stationary within the analysis staging station 90 such that once an individual vessel 84 is placed within a vessel position 94 of the analysis staging station 90, its position does not change but for transfer by the transport assembly 60.

While not specifically shown, the analysis staging station 90 may include a cooling system to maintain the temperature of the analysis staging station 90 at a constant controlled temperature, for example, a temperature of about 4° C. to about 10° C. In this way, and along with the hinged lid 71 (FIG. 6A) described previously, the rate of degradation or evaporation of the prepared sample is further reduced while the prepared sample is awaiting analysis.

Alternatively, the analysis staging station 90 may include a heating system, or an incubation station, as described above, to maintain the temperature of the analysis staging station 90 at a constant controlled temperature for incubation, for example, a temperature ranging from about 23° C. to about 70° C. Some specimen types, particularly microbiological specimens, may require extended incubation of the otherwise prepared sample prior to analysis. Following completion of the incubation time designated for the specific sample, the prepared and incubated sample may be selected for analysis according to the analysis selection criteria described in detail below.

When a particular prepared sample is selected for analysis (the details of the selection criteria being described in detail below), the vessel 58 containing the prepared sample is transferred via the transport assembly 60 from the analysis staging station 90 to an injector station 92. The injector station 92 may include an injector pipette assembly 96 (FIG. 4A) to transfer an aliquot of the prepared sample from the vessel 58 to the sample analysis station 24. The injector pipette assembly 96 (FIG. 4A) includes a pipette shaft 97 (FIG. 4A) that may be constructed in a manner that is similar to the sample pipette assembly 62 (FIG. 4A) that was described in detail above.

According to that embodiment, and as shown in FIGS. 3A-3D and FIG. 4A, a wash station 98 having a solvent supply 99 fluidically coupled thereto is provided to wash the pipette shaft 97 between aspiration-dispensing as necessary. In another embodiment, not particularly shown herein, the pipette shaft 97 may be shaped to receive a disposable tip, which may be provided in addition to or in alternative to the wash station 98.

The injector station 92 may include a rotatable table 102 having a structure that is similar to the sampling station 56 and may include a vessel cap opening and closing device 103 for opening and closing the hinged lid 71 (FIG. 6A) of the vessel 58 as it is transported to a ready position 100. Following aspiration of an aliquot of the prepared sample by the injector pipette assembly 96, the vessel 58 may be rotated away from the ready position 100, thereby closing the hinged lid 71 (FIG. 6A), and preparing the vessel 58 for receipt by the transport assembly 60 for transport and release to a storage facility (not shown) or a waste chute 106 leading to the vessel waste storage 107. Disposable pipette tips may also be ejected from the pipette shaft 97 into the waste chute 106.

As described in detail above, a sample of a specimen 23 (FIG. 2) is prepared at the sample preparation station 20 before that prepared sample is moved to the sample analysis station 24. As such, at least some of the movable portions of the sample preparation station 20, including the sampling station 56, the transport assembly 60, the rotatable tables 44, 102, the injector station 92, and the injector pipette assembly 96, acting individually or in concert, may comprise a transport mechanism to transport the prepared sample from the sample preparation system 12 to the sample analysis system 14. One having ordinary skill in the art will appreciate that alternative embodiments of a transport mechanism to transport a prepared sample from a sample preparation system 12 to a sample analysis system 14 may be used without departing from the scope of embodiments of the invention. In the exemplary embodiment, the transport mechanism may comprise the injector pipette assembly 96, which removes an aliquot of the prepared sample for dispensing to the sample analysis station 24.

Turning now to the details of the sample analysis station 24, and in particular to FIGS. 3A-3D and 4B, one embodiment of the sample analysis station 24 may be an LCMS system having a liquid chromatography station 110 and a mass spectrometer station 112. The liquid chromatography station 110 (referred to hereinafter as "LC station" 110) may include one, two, or more injection ports 104a, 104b for accepting the aliquot of the prepared sample from the injector pipette assembly 96 for analysis. The injection ports 104a, 104b may be connected on-line to one or more chromatography columns (e.g., a preparatory column 114 and an analytical column 116) for separation of the prepared sample into analytes of interest eluting at one or more elution times and a plurality of ancillary or waste eluents. As shown in the illustrative embodiments, the LC station 110 includes two separation channels, i.e., LC channels 118a, 118b (a third LC channel 118c shown in phantom). Each LC channel 118a, 118b, 118c includes one preparatory column 114 and one analytical column 116, arranged in series. The preparatory column 114, according to some embodiments, may be a size exclusion affinity liquid chromatography column used for, in essence, matrix interference removal. The analytical column 116 may be a reversed-phase LC column for analyte isolation. Exemplary embodiments include a Cyclone P 0.5×50 mm TURBOFLOW size exclusion affinity liquid chromatography column (Thermo Fisher Scientific, Inc., Waltham, Mass.), described in detail in U.S. Pat. Nos. 5,772,874; 5,919,368; and 6,149,816, the disclosures of which are all of which are hereby incorporated herein by reference in their entireties, and a Hypersil GOLD PFP 2.1×50 mm, 1.9µ UHPLC analytical column (Thermo Fisher Scientific, Inc., Waltham, Mass.). The columns, according to additional embodiments, may be capillary columns (having an internal diameter of approximately 300 µm), nano columns (having an internal diameter ranging from about 74 µm to about 100 µm), available in packed tip formats, standard packed formats, and biphasic columns for two-dimensional work, for example.

Briefly stated, the TURBOFLOW turbulent flow liquid chromatography apparatus includes a chromatography column that is formed as a substantially uniformly distributed multiplicity of rigid, solid, porous particles ("stationary phase") having substantially uniform mean cross-section dimensions and a plurality of pores within each particle. The particles are selected from a range of various sizes and shapes and are held together in a column by pressure, sintering, or the like so that interstitial channels having a total interstitial volume of not less than some designated percentage of the total volume of the column. The surfaces of the particles, including the inner surfaces of the pores in the particles, are chromatographically active, as by being coated with chromatographic stationary phase layers. In operation, the turbulent flow of the mobile phase through the TURBOFLOW column causes larger molecules to elute more rapidly than smaller molecules, the latter of which filter through the pores of the particles comprising the stationary phase. Further differentiation in elution times of various molecules is based, at least in part, in the molecules affinity to the coating of the particles. By adjusting the mobile phase (e.g., the pH, relative concentration of aqueous and organic solvents, and so forth) the affinity of one or more molecules is altered and the various component molecules isolated or separated.

In other embodiments, the preparatory column 114 may be a conventional size exclusion column or any other liquid chromatography column that may be utilized as a matrix interference removal device.

Each of the two LC channels 118a, 118b is associated upstream with a respective injector port 104a, 104b and associated downstream with a single mass spectrometer 120 of the mass spectrometer station 112 in a manner that enables multiplexing or staggered sample introduction into the mass spectrometer 120 as described in detail below.

The selection of the appropriate preparatory and analytical columns 114, 116 may be based, at least in part, on the ability of an LC channel 118a, 118b to provide a range of retention times for analytes of interest versus the eluent. Conventionally, the preparatory and analytical columns 114, 116 are matched for a particular analyte from a particular type of sample; however, the matching of columns 114, 116 may vary from one assay type to another. More specifically, each desired analyte will have a ratio of concentration distribution between two immiscible solvents (e.g., octanol and water a solvent from supply 129) at equilibrium, which is referred to as the partition coefficient. Said another way, the partition coefficient is a measure of a desired analyte's hydrophilicity ("water loving") or hydrophobicity ("water fearing"). Often the partition coefficient is reported as the logarithm of the partition coefficient, referred simply as "log P." It would be readily appreciated that because log P is logarithmic in nature, each unit represents a difference in hydrophobicity by factor of 10. Thus, two analytes having similar log P values may have similar hydrophobicities (i.e., chemistry) and may be easily separated by the same mobile and stationary phases; two analytes having different log P values tend to result in vastly different retention characteristics on the same LC system and may require quite different mobile and/or stationary phases to achieve a desired chromatographic separation. As a consequence, analytes are conventionally grouped together according to similar log P values and run in batch modes using the same mobile phase and mass spectrometer settings.

In a conventional system, when a new prepared sample is to undergo testing in accordance with an assay type that is different from the assay type for which the system is presently configured, one or more of the columns must be exchanged. Exchanging a column requires a user to assemble a compression fitting and ferrule onto the end of a fluid-carrying length of tubing. The compression fitting and tubing is inserted into a column end fitting of the column and tightened with two properly sized wrenches. While the user must ensure that the junction is not under tightened (leading to a leak), great care must also be taken to not over tighten the joint (leading to galling, breakage, or tube collapse). Further, repeated exchange of columns may lead to material fatigue and increased likelihood of galling, breakage, or tube collapse.

Alternatively, one or more universal sets of columns may be used where the universal set of columns has an ability to process and isolate a variety of analytes of interest, including and up to the number of assay types processed by the system 10. In this way, the assay menu including a plurality of analytes may require only one or a few select universal sets of columns, thus greatly simplifying the user interface and the user interaction with the system 10. While the universal sets may be described as a preparatory column with an analytical column 114, 116, it will be understood that the sets may comprise any number of columns. Embodiments of such universal sets of columns are described in U.S. Provisional Patent Application No. 61/408,266, entitled "LC-MS Configuration for Purification and Detection of Analytes Having a Broad Range of Hydrophobicities," naming inventors Herman, DeWitte, Jardine, and Argot, filed on Oct. 29, 2010, and International Application No. PCT/US11/58430, entitled "LC-MS Configuration for Purification and Detection of Analytes Having a Broad Range of Hydrophobicities," filed on even date herewith, the disclosures of which are incorporated herein by reference in their entireties.

Briefly, each universal column isolates, or purifies, a broad range of desired analytes based on, for example, the relative hydrophobicities of the analytes using one set of LC columns and one set of mobile phase buffers per set. Isolation may be further dependent on mobile phase flow rate, relative ratios of one mobile phase buffer to another or others, temperature, and so forth. Instead of manually changing columns and mobile phases as described above, the universal method allows LCMS purification and analysis of a broad range of analytes, having a broad range of log P values, to be accomplished using one set of LC columns and one set of mobile phase buffers by selecting LC system parameters (e.g., flow rate, ratios of one buffer to another, temperature, and the like) and MS system parameters (e.g., ionization voltage, desolvation temperature, and the like) that are particular to a range of log P values or different classes of analytes.

It will be understood that the universal set of columns need not be limited to single set of columns, but may instead include two or more sets that are specifically directed to a given range of log P values, i.e., class of analytes. Then, and in accordance with the methods described in greater detail below, the two or more LC channels 118a, 118b may be multiplexed to greatly enhance the efficiency of the system 10. Each of the two or more LC channels 118a, 118b may be assigned to a particular universal set of columns for a particular class of analytes. Further, two or more of the LC channels 118a, 118b may be associated with similar or overlapping ranges of log P values and thus either of the channels may be appropriate used to elute certain analytes.

Figure 7A:
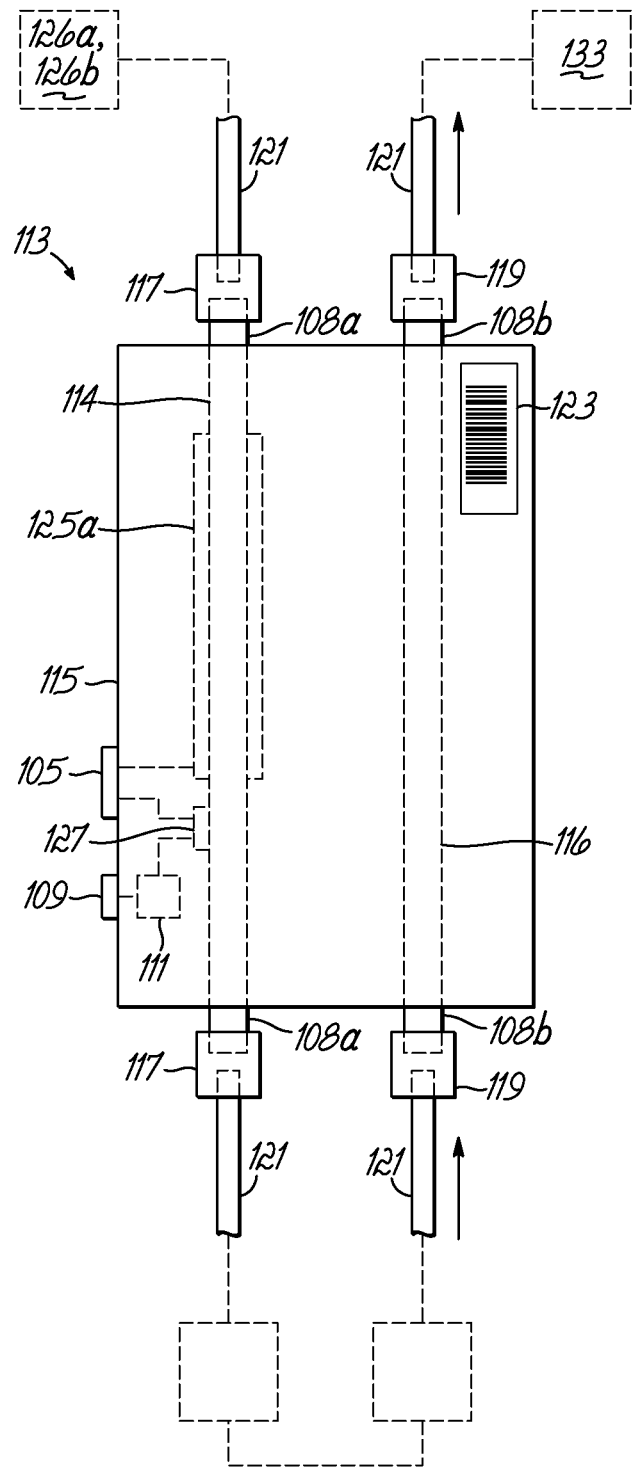
FIG. 7A is a side elevational view of a dual-column chromatography cartridge in accordance with one embodiment of the present invention.

Indeed, in yet other embodiments, the set of universal columns may be packaged within a unitary cartridge, or housing, for ease of exchanging columns as necessary, and as provided in greater detail in International Application No. PCT/US2011/58229, and U.S. Provisional Application No. 61/408,044, both entitled "Modular Multiple-Column Chromatography Cartridge," naming inventor Brann, filed on Oct. 28, 2011, and Oct. 29, 2010, respectively, the disclosure of which are incorporated herein by reference in their entireties. One such dual-column chromatography cartridge 113 is shown in FIG. 7A according to a longitudinal arrangement, with an alternate arrangement shown in FIG. 7C according to a lateral arrangement. The cartridge 113 includes a housing 115 having two chromatography columns—a first column 114 and a second column 116—at least partially contained therein. Preferably, but not necessarily, the columns 114, 116 are affixed to the housing 115. The two columns 114, 116 in each cartridge 113 may be matched for purposes of conducting chromatographic separations of a specific analyte (or analytes). For instance, the first column 114 may comprise a cleanup column such as the TURBOFLOW, described above, or an HPLC column while the second column 116 may comprise an analytical column.

The first column 114 comprises two column end fittings 108a with one such end fitting 108a at each end of the column 114. Likewise, the second column 116 comprises an end fitting 108b at each end of the column 116. As is known, column end fittings 108a, 108b are attachment points for fluidic connections to external tubing 121. Accordingly, one or more connectors 117, 119 are employed in order to connect the two end fittings 108a of the first column 114 to fluid tubing 121 as well as to connect the two end fittings 108b of the second column 116 to fluid tubing 121. The tubing 121 may fluidically couple one or both ends of the first column 114 to at least one valve (two valves 126a, 126b are shown) so as to direct flow in either direction through the first column 114, depending on whether the column 114 is being loaded or flushed. The tubing 121 is also fluidically coupled to the second column 116 with for providing fluid to the second column from the second valve 126b and outputting eluting analytes to another valve 133. It would be readily appreciated that the tubing 121 may be coupled to the column ends of the second column 116 in an opposite sense to that shown in FIG. 7A such that fluid flow through the second column 116 would be in the opposite direction to that shown.

In some embodiments, the cartridge 113 may include a passive indicator 123 capable of being read by a barcode reader (not shown) or other apparatus of the system 10 (FIG. 1A). The combination of a passive indicator 123 and a reader may enable system software to be able to automatically verify that the columns 114, 116 within a selected and inserted cartridge 113 are appropriate for an analysis protocol currently being conducted by the system 10 (FIG. 10).

The cartridge 113 may further, or alternatively, include various electronic control, sensing, data storage or logic components together with associated external electronic connectors. For example, the cartridge 113 may include one or more heaters 125a in intimate contact with one or more of the contained columns (though only association with the first column 114 is shown) so as to control temperature during a chromatographic procedure. The heater 125a may be used, for instance, to increase temperature so as to release a sample fraction previously retained or concentrated on a stationary phase within the first column 114 such that the sample fraction may be transferred to the second column 116. The heater 125a may comprise any of a several heating devices such as a coiled resistance wire or commercially-available heating tape, for example. In that regard, the cartridge 113 may include one or more temperature sensors 127. Such sensors 127, if present, may work in conjunction with any on-board heaters 125a as part of a temperature control loop to control the temperature of the one or more columns 114, 116. The control logic may be implemented in software of a controller, generally, the sample preparation controller 22 (FIG. 2), specifically, or, alternatively, may be implemented in firmware of an on-board circuitry module 111 which may comprise electronic memory or controller logic. In addition, or alternative, the circuitry module 111 may be used to actively record computer-readable data or other information pertaining to the module, including module history information, wherein such information is downloadable by or transferrable to external apparatus (such as the sample preparation controller 22 of FIG. 2) through a standard interface 109, such as a USB port. Sill other electrical or electronic connectors 105 may be employed to provide power to the heater 125a, to read the sensor(s) 127, etc.

Figure 7B:
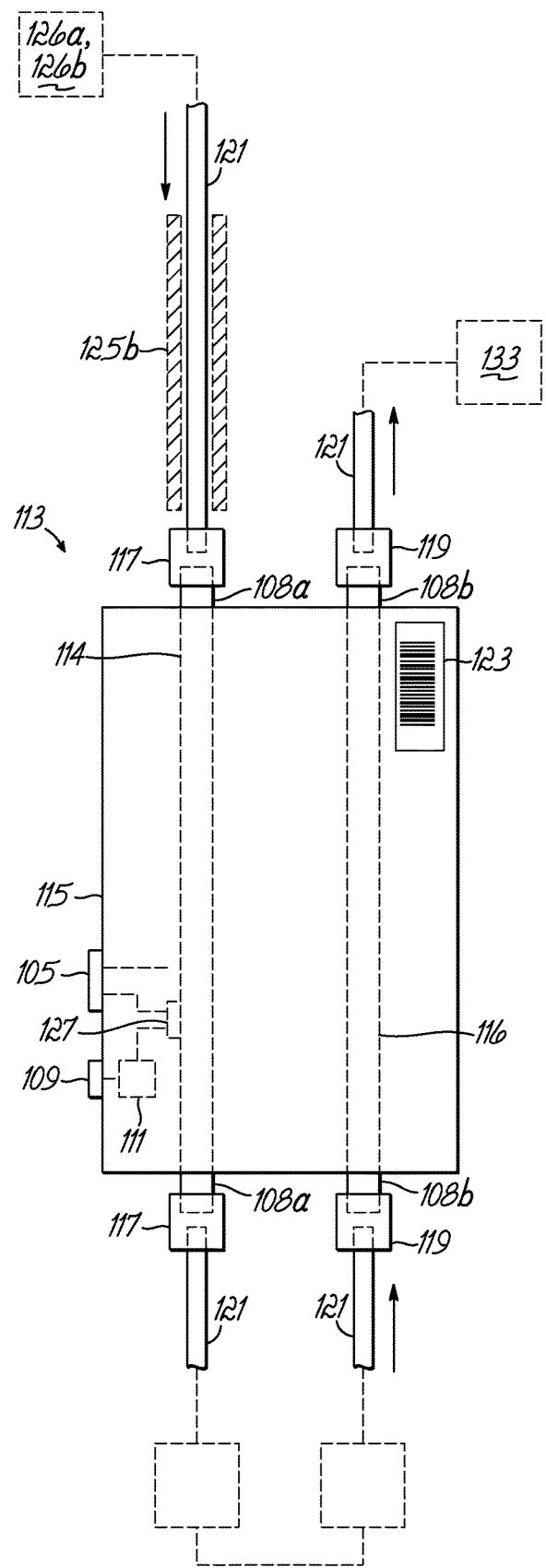
FIG. 7B is a side elevational view of a dual-column chromatography cartridge in accordance with another embodiment of the present invention.
Figure 7C:
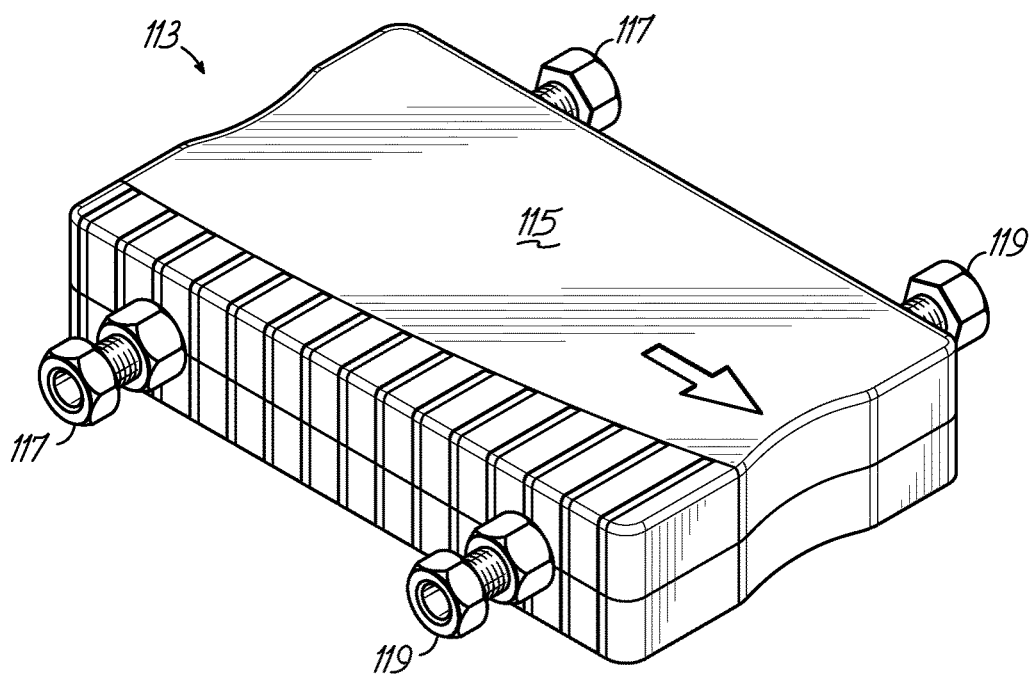
FIG. 7C is a perspective view of a top portion of a dual-column chromatography cartridge in accordance with one embodiment of the present invention.

Depending upon the rate of fluid flow, the configuration illustrated in FIG. 7A may not allow sufficient time for the fluid within the one or more columns 114, 116 to achieve the desired temperature. Therefore, a second heater 125*b* may additionally, or alternatively, included as shown in FIG. 7B. The second heater 125*b* is configured such that the fluid is in contact with a heated length of the tubing 121 for a sufficient time so as to achieve the desired temperature within the first column 114. The second heater 125*b* may comprise any of a several heating devices described above.

Figure 7D:
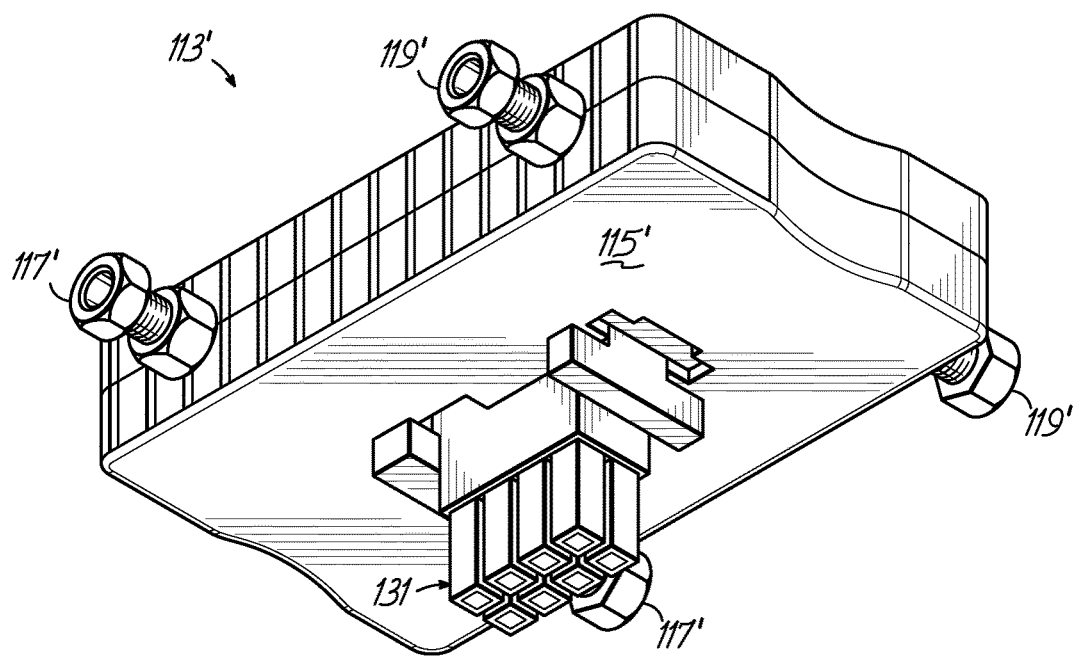
FIG. 7D is a perspective view of a bottom portion of a dual-column chromatography column in accordance with another embodiment of the present invention.

FIG. 7D illustrates a perspective view of a cartridge 113' in accordance with another embodiment of the present invention. In many situations, it may be desirable to fabricate a cartridge 113' so as to allow the user to simply, with one motion, insert the cartridge 113' into a holder or cradle 1118 (FIG. 8) such that electrical connections to the cartridge 113' are made at the same time that correct cartridge positioning is achieved. Accordingly, the cartridge 113' may comprise a single electrical connector port 131 that replaces and provides the functionality of both the standard interface port 109 and the separate electrical connector 105 shown in FIGS. 7A and 7B. The connector port 131 is shown on the underside of the cartridge 113', in this example, since it may be advantageous for the user to insert the cartridge 113' by applying a downwardly-directed force into a cradle 1118, such as the one described in greater detail below in reference to FIG. 8. The single downward motion will then both align the cartridge 113' and cause the connector port 131 to make contact with a mating connector in, for instance, a base plate 1222. Other connector port and insertion configurations are also possible and are not limited to the specific illustrative embodiments shown herein.

Figure 8:
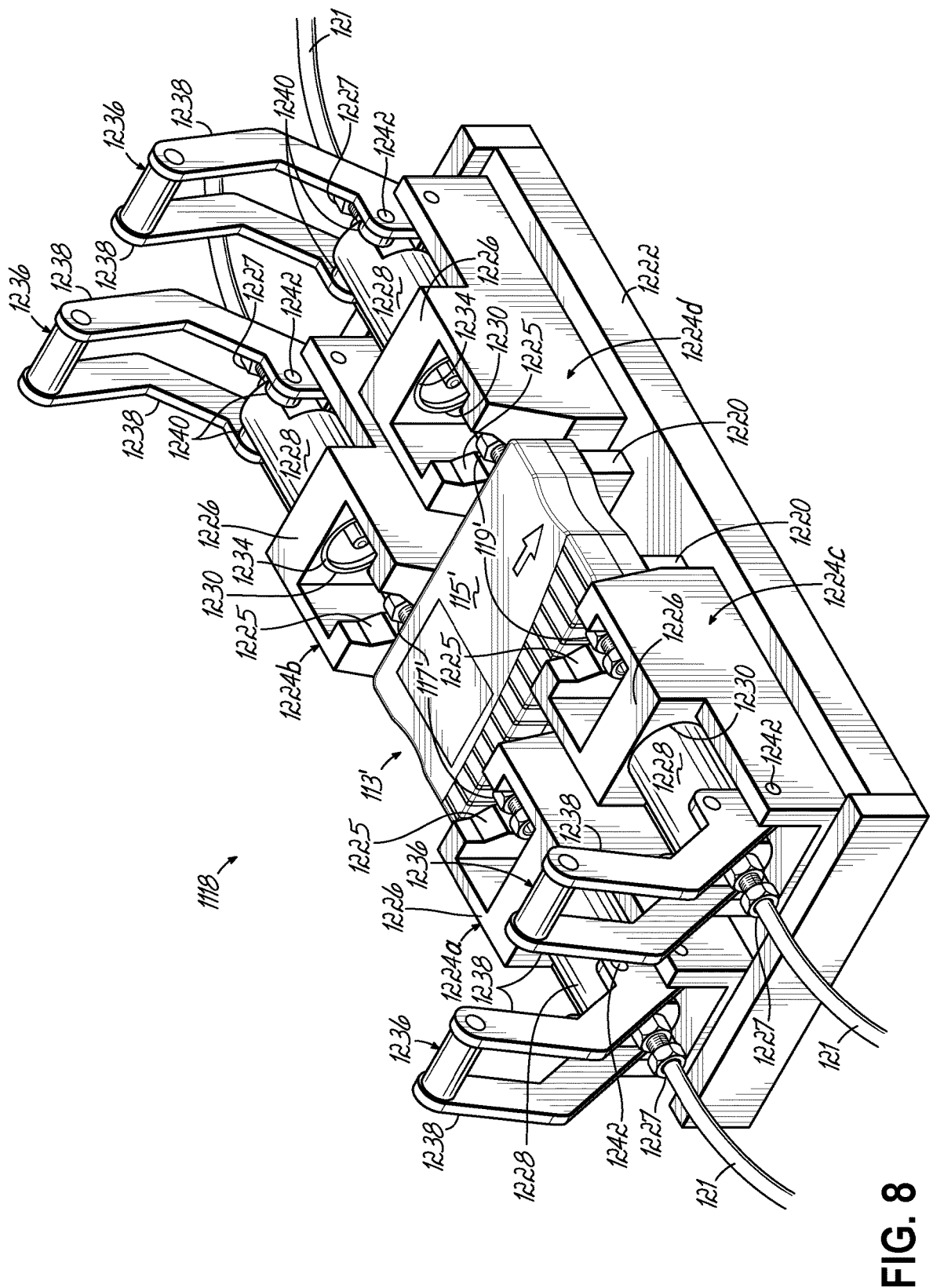
FIG. 8 is a perspective view of a cradle configured to receive one or more dual-column chromatography cartridges in accordance with one embodiment of the present invention.

FIG. 8 illustrates a cartridge 113' mounted on cartridge support members 1220, which are mounted on the base plate 1222. A plurality of connector apparatii 1224*a*, 1224*b*, 1224*c*, 1224*d* are also mounted on the base plate 1222. Grooves 1225 in each of first and second connector apparatii 1224*a*, 1224*b* connect the inlet and outlet connectors 117' of the first column 114 (FIG. 7A) of the cartridge 113' to associate the fluid tubing 121 via an end fitting 1227; similar grooves 1225 in each of third and fourth connector apparatii 1224*c* and 1224*d* provide similar functions with respect to the second column 116 (FIG. 7A) of the cartridge 113'. In this example, electronic or other electrical connections to the cartridge 113' may be facilitated by a connector (not shown) mounted to the base plate 1222 and positioned beneath the cartridge 113'.

Each connector apparatus 1224*a*, 1224*b*, 1224*c*, 1224*d* further comprises a body 1226 and a piston 1228. The body 1226 includes an open bore 1230. The piston 1228 is capable of being slidably inserted at least partially into the bore 1230 of the body 1226 and is also capable of being at least partially retracted from the bore 1230. Preferably, a portion of the bore 1230 comprises a shape that mates with the piston 1228 such that the piston 1228 is capable of being slidably inserted into the bore 1230. A bushing or other bearing 1234 may be provided within the portion of the bore 1230 that receives the piston 1228 so as to provide a smooth sliding surface for the reciprocating movement of the piston 1228. The reciprocating movement of the piston 1228 within the body 1226 may be controlled manually by a user by means of a pushing and latching mechanism 1236 (hereafter "locking mechanism" 1236). As shown, the locking mechanism 1236 may comprise a hand operated lever 1238 and a coupling bar 1240 such that the coupling bar 1240 is mechanically engaged to the lever 1238 by means of a first pivot pin 1242 about which an end of the coupling bar 1240 is free to rotate. A second pivot pin (not shown) similarly provides mechanical engagement between the opposite end of the coupling bar 1240 and the piston 1228 so that rotational motion of the lever 1238 is converted into translational motion of the piston 1228. With sufficient translational motion, the piston 1228 engages and forms fluid communication with the outlet connectors 117, 118.

Figure 4B:
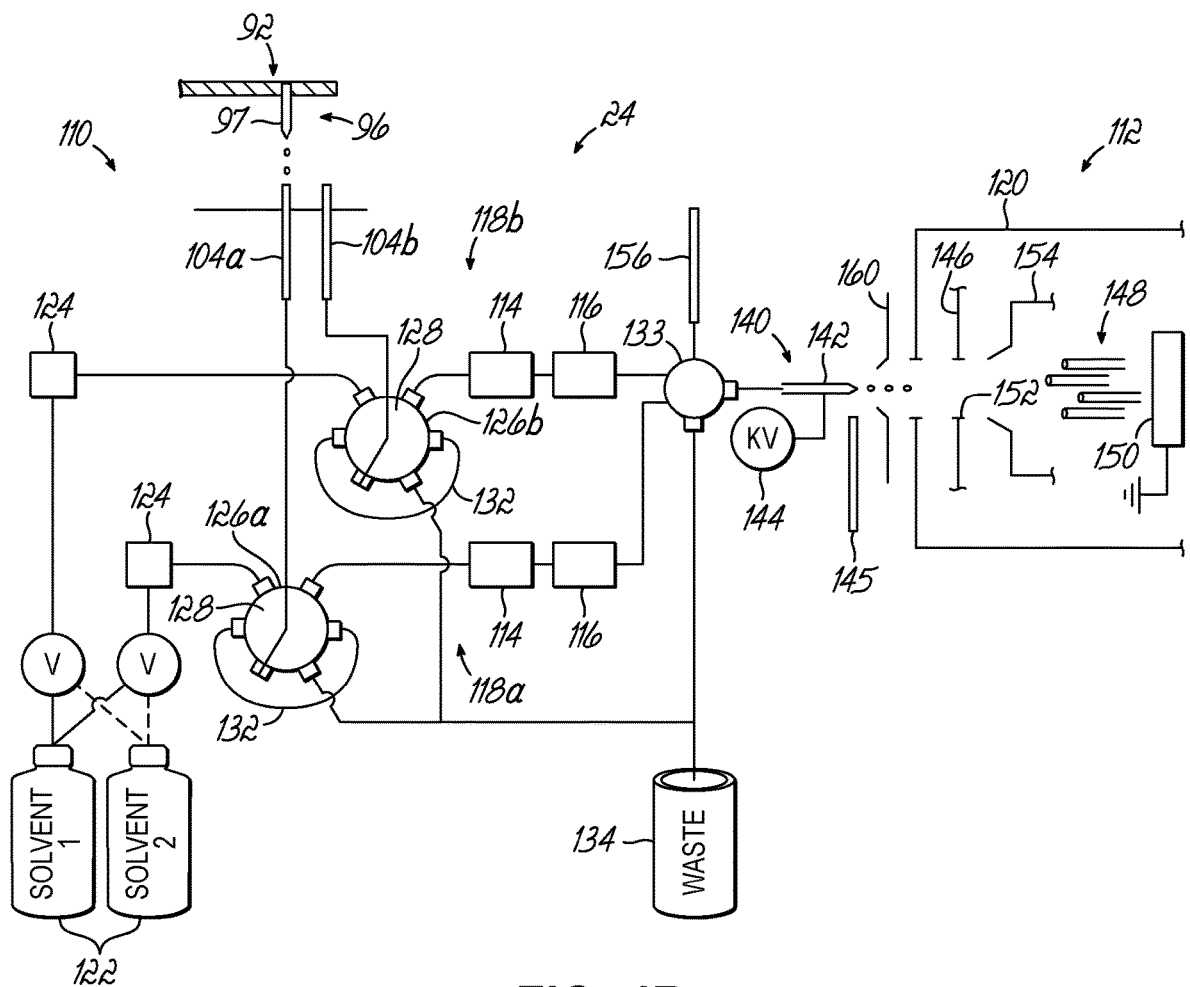
FIG. 4B is a schematic view of a sample preparation station and a sample analysis station of the automated sample preparation and analysis system of FIG. 1A in accordance with one embodiment of the present invention.

While FIGS. 4B and 7A-7B are illustrative of embodiments of liquid chromatography plumbing, one of ordinary skill in the art will readily appreciate that additional plumbing arrangements may be used. For example, the preparatory column 114 and the analytical column 116 need not be fluidically coupled in series. Instead, more complex plumbing arrangements may be used where the LC channels 118*a*, 118*b* are not isolated, one or more columns 114, 116 may be by-passed as necessary, and so forth. Exemplary plumbing arrangements are further described in C. Chassaing and Robins, S., "Turbulent Flow Chromatography: an Evolving Solution for Bioanalysis." *CHROMAT. TODAY* 2009; 9:20-24; L. Du, et al. "High Turbulence Liquid Chromatography Online Extraction and Tandem Mass Spectrometry for the Simultaneous Determination of Suberoylanilide Hydroxamic Acid and its Two Metabolites in Human Serum." *RAPID COMM. MASS SPECT.* 2005; 19:1779-1787; and T. Edge, "Chapter 4: Turbulent Flow Chromatography in Bioanalysis." In: I. D. Wilson, ed. *HANDBOOK OF ANALYTICAL SEPARATIONS*. Elsevier Science B.V. 2003; Vol 4:91-128; each reference is incorporated herein by reference in its entirety.

Referring still to FIG. 4B, each LC channel 118*a*, 118*b* may be further associated with at least one pump 124 and at least one valve 126*a*, 126*b* to control the flow of the mobile phases and the prepared sample through the sample analysis station 24.

While any one of a number of various pumps, including, for example, reciprocating, dual piston, or peristaltic pumps, these conventional pumps require multiple strokes per sample injection. By contrast, syringe pumps may be considered to be preferred to inject the prepared sample and the mobile phases from a mobile phase container 122 into and through the columns 114, 116 and interconnected tubing lines because of the reduced volume of mobile phase and reduced dead volume required for each analysis and the reduced wear on the LC station 110 overall. With each stroke of the piston of a conventional pump, a slight pressure differential may be created within the LC channel 118*a*, 118*b* over the time of the injection. Further, since different solvents or mobile phases may have different compressibilities, the pressure may vary over longer-time periods when mobile phase composition is varied, such as in gradient elution. Discontinuous or varying pressure may influence the rate at which some components elute. Thus, it would be advantageous to have a pump configured to provide a single shot stroke per sample injection to yield a more controlled sample flow, constant pressure over the injection time, smaller dead volume, and more consistent pressure across multiple samples and assays.

One such suitable pump 124 according to one embodiment of the present invention is briefly described below, is shown in to FIGS. 9A-9E, and is described in greater detail in U.S. Provisional Application No. 61/552,955, entitled "Syringe Pump," filed on even date herewith, and the disclosure of which is incorporated herein by reference in its entirety.

Figure 9A:
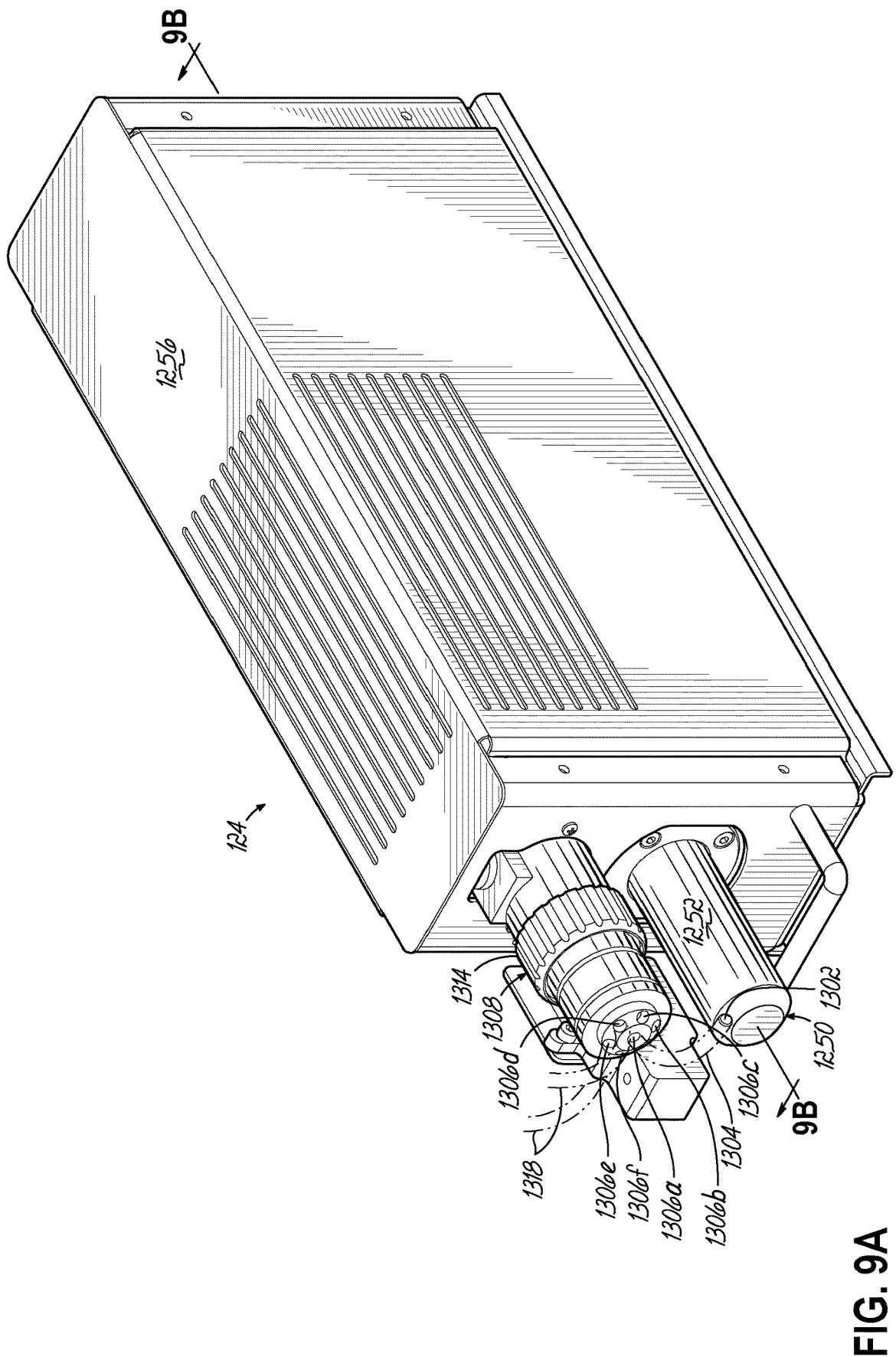
FIG. 9A is a perspective view of a pump for a dual-column liquid chromatography of an automated sample preparation and analysis system in accordance with one embodiment of the present invention.
Figure 9B:
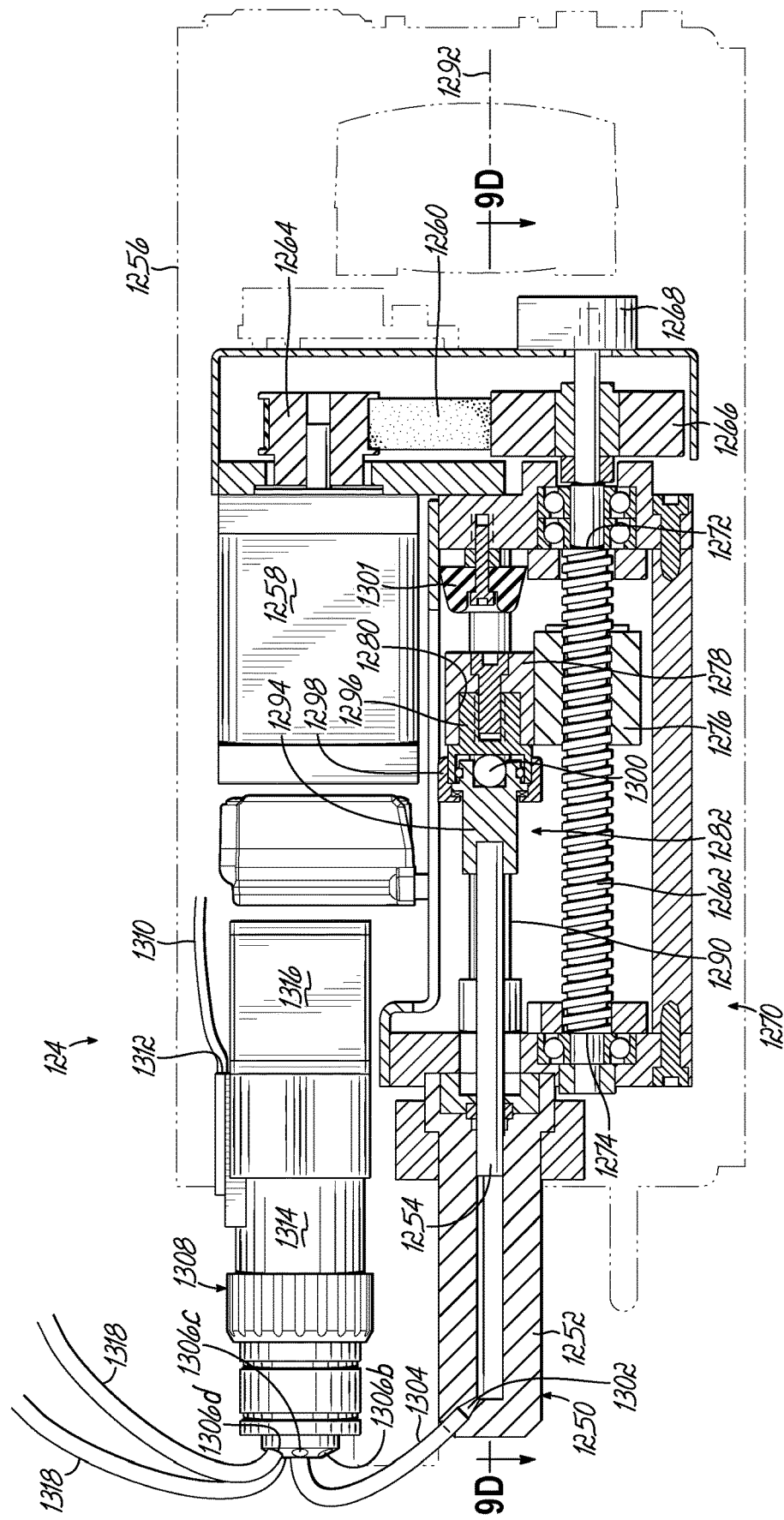
FIG. 9B is a cross-sectional view taken along line 9B-9B in FIG. 9A, with a piston of the pump retracted.

Referring to FIGS. 9A and 9B, the pump 124 includes a piston pump 1250 having a barrel 1252 and a piston 1254 in slidable relation with the barrel 1252 and coupled to a housing 1256. The piston 1254 is driven by a motor 1258, such as a stepper motor, via a drive belt 1260 and a lead screw 1262. More specifically, the motor 1258 drives a first pulley 1264, which is mechanically-coupled to a second pulley 1266 by the drive belt 1260. Rotation of the drive belt 1260 may be monitored, if desired, by a rotation sensor 1268. Suitable materials from which the piston 1254 may be fabricated are, for example, various ceramics, including zirconia and synthetic sapphire.

The lead screw 1262 is operably coupled to the second pulley 1266 such that rotation of the second pulley 1266 rotates the lead screw 1262. To maintain stability of the lead screw 1262 relative to the piston 1254, the lead screw 1262 may be rotatably coupled to a piston chamber 1270 at each end 1272, 1274 of the lead screw 1262 and which is, in turn, coupled within the housing 1256. The lead screw 1262, between the points at which the lead screw 1262 is coupled to the piston chamber 1270, receives a threaded flange nut 1276 such that rotation of the lead screw 1262 is configured to cause a linear movement of the threaded flange nut 1276 along the lead screw 1262 and between the first and second ends 1272, 1274.

An alignment plate 1278 is operably coupled to the threaded flange nut 1276 for transferring the linear movement of the flange nut 1276 to the piston 1254. The alignment plate 1278 may include three bores: a first bore 1280 is operably coupled to the piston 1254 via a flexible joint 1282, which is described in greater detail below, and each of second and third through bores 1284, 1286 receives a respective guide pin 1288, 1290. The guide pins 1288, 1290 are secured to the piston chamber 1270 and provide structural stability and reciprocating-direction guidance (indicated by axis 1292) to the piston 1254.

The flexible joint 1282 coupling the piston 1254 to the alignment plate 1278 allows for some movement of the piston 1254 relative to the barrel 1252. In this way, the piston 1254 may self-correct its position and/or angular alignment with respect to the barrel 1252 during operation of the pump 124, reducing the amount of wear on the seal formed between the piston 1254 and the barrel 1252, and providing for both a more efficient stroke and a more continuous output flow. In the illustrative embodiment of the flexible joint 1282, an adaptor end 1294 of the piston 1254 is coupled to an insert 1296, which is operably secured within the first bore 1280 of the alignment plate 1278, for example, by a threaded nut 1298.

A semi-compliant ball, compressible, bearing 1300 is positioned between the adaptor end 1294 and the insert 1296. In a rest state, the ball bearing 1300 is fully expanded and the adaptor end 1294 is biased away from the insert 1296. However, atypical movement the piston 1254 during operation of the pump 124, for example, jamming the piston 1254 such that the piston 1254 is resisted from moving into the barrel 1252, creates a force on the piston 1254. The force compresses the ball bearing 1300 between the adaptor end 1294 and the insert 1296, which reduces the stress placed onto the seal. A bumper 1301 may also be provided for buffering the force created when the piston 1254 is excessively drawn in the rearward direction.

By selecting the features of the lead screw 1262, the threaded nut 1298, and the motor 1258, the pump 124 may be configured to provide sufficient stroke volume such that a single stroke of the piston 1254 displaces a sufficient volume of fluid to complete a single LC injection in accordance with the selected assay or to elute an entire sample from the LC column 114, 116 in accordance with a chromatography system fluid flow rate and working flow pressure. The flow rate may need to be variable within a range from about 0 mL per minute to about 3 mL per minute. The working fluid pressure may vary between systems and experiments. The working fluid pressure may vary between systems and experiments. In some situations, the maximum working fluid pressure may be about 100 bars. In other systems, the maximum working fluid pressure may be about 200 bars, about 400 bars, about 600 bars, about 800 bars, about 100 bars, or about 1500 bars. By configuring the features, such as the torque, of the pump 124 accordingly, the pump 124 may be designated to operate at a certain maximum pressure. Generally, conventional pumps that are designed to operate at higher fluid pressures may also operate at lower pressures. For example, by configuring the features of the instant pump 124 accordingly—a force of approximately 900 pounds applied to a 7 mm diameter piston 1254—a pressure of about 1000 bar (about 15000 pounds per square inch) would correlate to a volume displacement of about 3 mL. Generally, the piston diameter may range from about 4 mm to about 10 mm.

Other suitable configurations may include, for example, a motor 1258 having a working load capacity of about 900 pounds and a thread pitch of the lead screw 1262 ranging from about 2 mm to about 20 mm, wherein the pitch is measured as an amount of linear travel per 360-degrees of rotation of the lead screw 1262. Suitable stepper motors include, for example, those that are commercially-available from ElectroCraft, inc. (Dover, N.H.) and their equivalents. Furthermore, air bubbles formed within one or more of the fluid lines may be passed during a single stroke and eliminates the need for otherwise clearing the fluid lines.

Figure 9C:
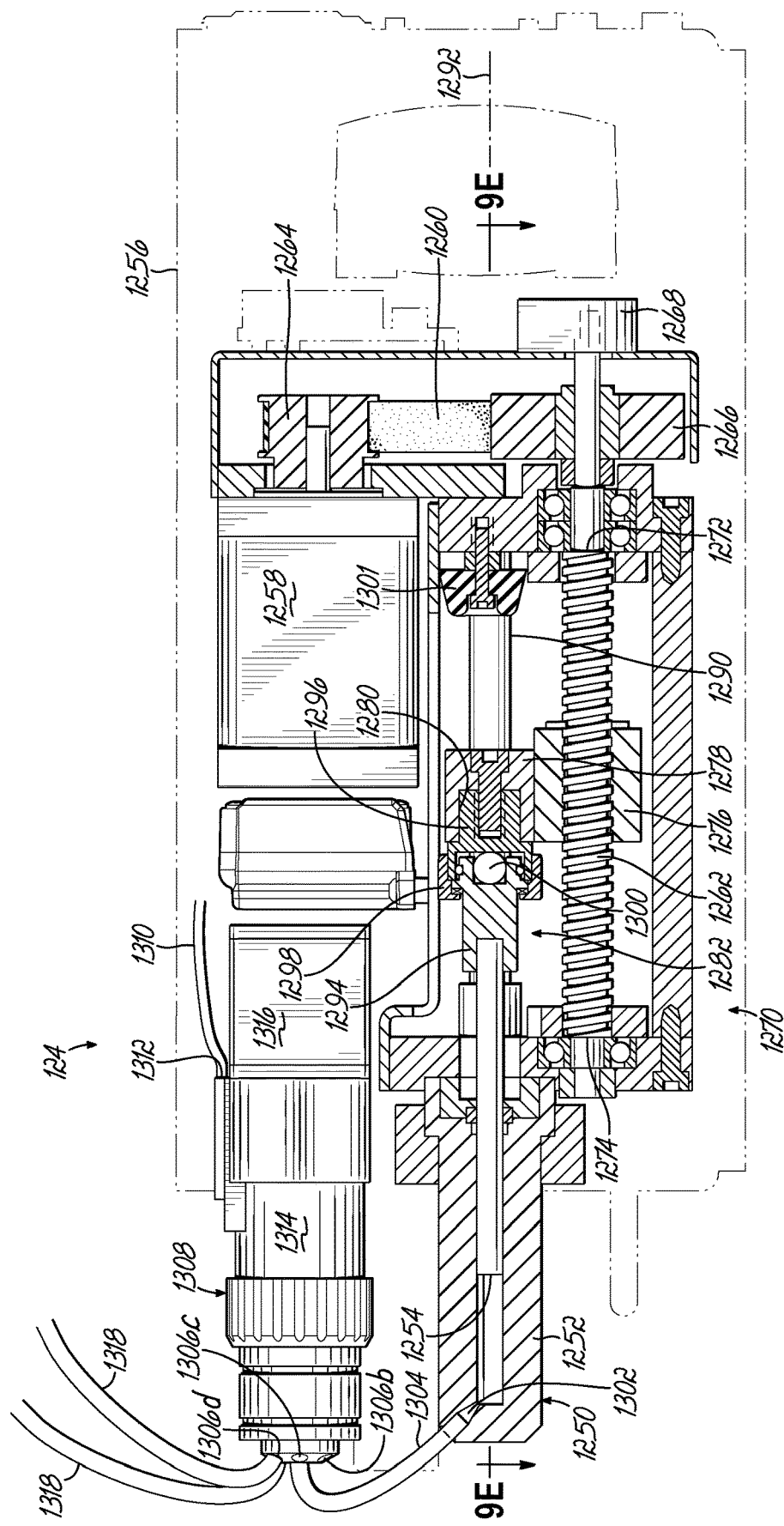
FIG. 9C is a cross-sectional view taken along line 9B-9B in FIG. 9A, with the piston of the pump extended.
Figure 9D:
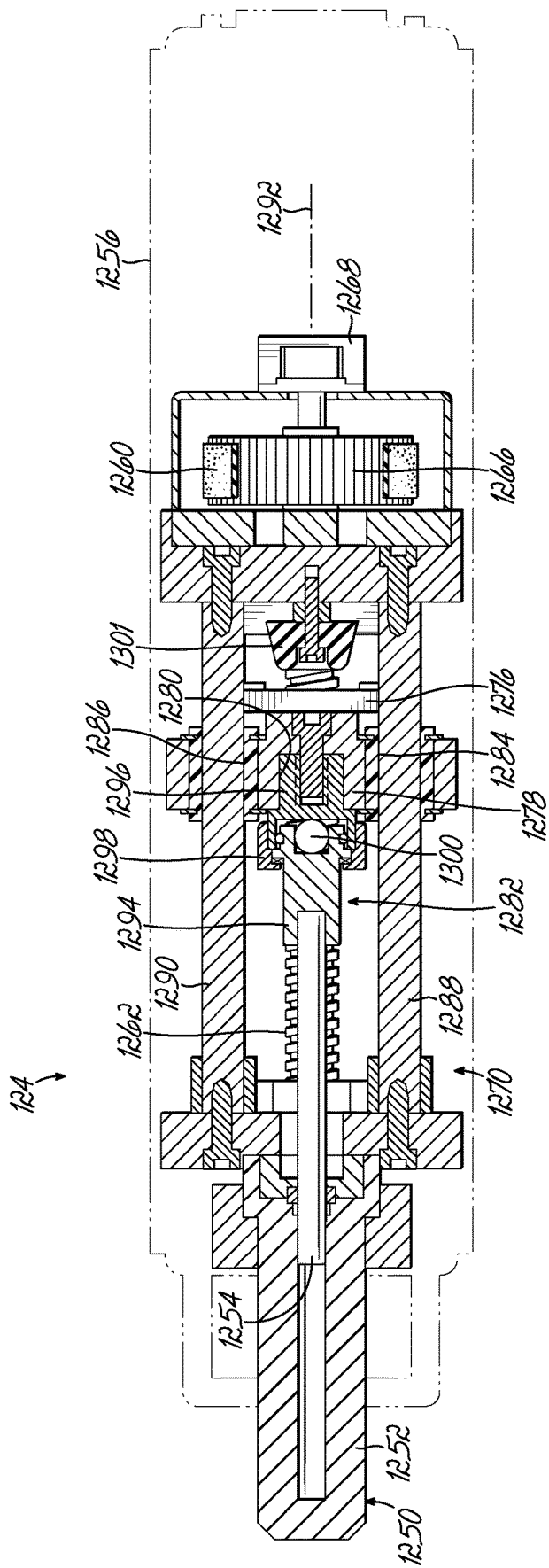
FIG. 9D is a cross-sectional view taken along line 9D-9D in FIG. 9B.
Figure 9E:
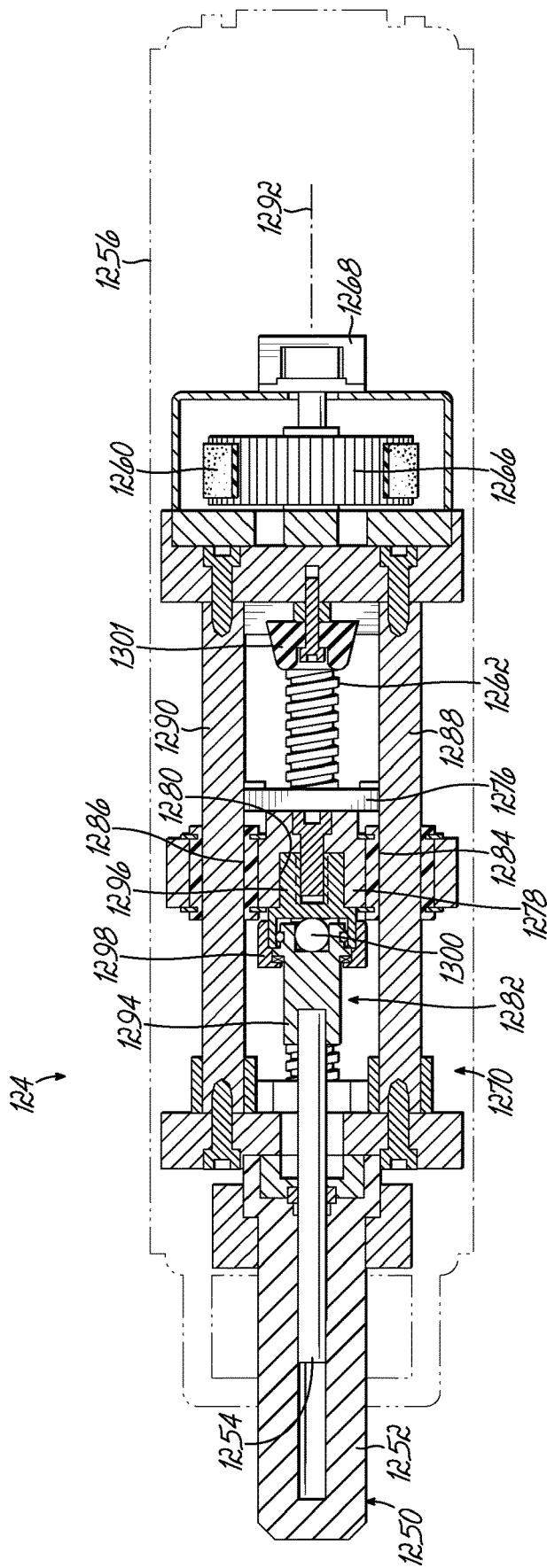
FIG. 9E is a cross-sectional view taken along line 9E-9E in FIG. 9C.

In that regard, one method of using the pump 124 in accordance with one embodiment of the present invention is described with reference to FIGS. 9B and 9C. More specifically, in FIG. 9B, the piston 1254 is in a fully retracted position and the barrel 1252 is filled with a volume of fluid, generally a solvent or a mobile phase. The motor 1258 is then operated so as to cause the threaded flange nut 1276 and the alignment plate 1278, and thus the piston 1254, to advance further into the barrel 1252, as shown in FIG. 9C. As a result, at least a portion of the volume of the fluid is ejected from outlet 1302 of the barrel 1252 and enters a fluid conduit 1304 connecting the outlet 1302 with a first port 1306*a* of a rotary valve 1308. The rotary valve 1308 may be a multi-port injection valve that is known and used by those of ordinary skill in the art of liquid chromatography, and may include, for example, the commercially-available RHEODYNE TITANHT, 6-position, 7-port rotary valve (Rheodyne, LLC, Rohnert Park, Calif.). Accordingly, the rotary valve 1308 may include any number of auxiliary ports, though four of five auxiliary ports 1306*b*, 1306*c*, 1306*d*, 1306*e* are shown in the specific illustrative embodiment. A sixth port 1306*f* is directed to an exit port 1312, which is coupled to a multi-port valve 126*a*, 126*b* (FIG. 4B) (described in greater detail below) via a fluid conduit 1310.

An internal channel (not shown) within the rotary body 1314 is configured to creates fluid communication between the first port 1306*a* and one of the auxiliary ports 1306*b*, 1306*c*, 1306*d*, 1306*e* or the exit port 1312 via the sixth port (not shown). In that regard, the rotary body 1314, a motor 1316 (generally, a stepper motor) is operably coupled to the rotary body 1314 and configured to rotate the rotary body 1314 and to align the internal channel with a select one of the ports 1306*b*, 1306*c*, 1306*d*, 1306*e*.

In the ejection mode, that is, when the piston 1254 advances to eject the fluid, the internal channel is rotated so as to fluidically couple the first port 1306*a* to the sixth port 1306*f*. The fluid thus exits the pump 1308 and enters the multi-port valve 126*a*, 126*b* (FIG. 4B).

At the end of the stroke, as shown in FIG. 9C, the piston 1254 is then retracted to the position shown in FIG. 9B. Prior to retraction, the internal channel of the rotary body 1314 is rotated such that the first port 1306a is fluidically coupled to one of the auxiliary ports 1306b, 1306c, 1306d, 1306e. Each of these auxiliary ports 1306b, 1306c, 1306d, 1306e includes a fluid conduit 1318, which lead to a respective solvent or mobile phase container 122 (FIG. 3A) or possibly to a sample source or sample loop. While not necessary, each mobile phase container 122 (FIG. 3A) may contain a different mobile phase for conducting a different one of the assays. In any event, the internal channel is aligned to the select one of the auxiliary ports 1306b, 1306c, 1306d, 1306e such that the barrel 1252 is refilled with the appropriate mobile phase or sample.

Once the internal channel is so configured, the barrel 1252 is filled with the appropriate mobile phase by operating the motor 1258 so as to retract the piston 1254 and to the position shown in FIG. 9B. Retraction of the piston 1254 draws mobile phase liquid from the aligned auxiliary port 1306b, 1306c, 1306d, 1306e, through the internal channel, through the outlet 1302, and into the barrel 1252. The rotary body 1314 is then rotated and prepared for ejection of the mobile phase or sample.

It would be readily understood that when the mobile phase is change, that is from a first mobile phase for a first selected assay, to a second mobile phase for a second selected assay, then multiple strokes of the piston 1254 may be necessary to sufficiently fill the barrel 1252 with the appropriate mobile phase. In that regard, fluid ejected from the barrel 1252 during a flushing process may be directed to the waste container 134 (FIG. 3C) for disposal.

Figure 9F:
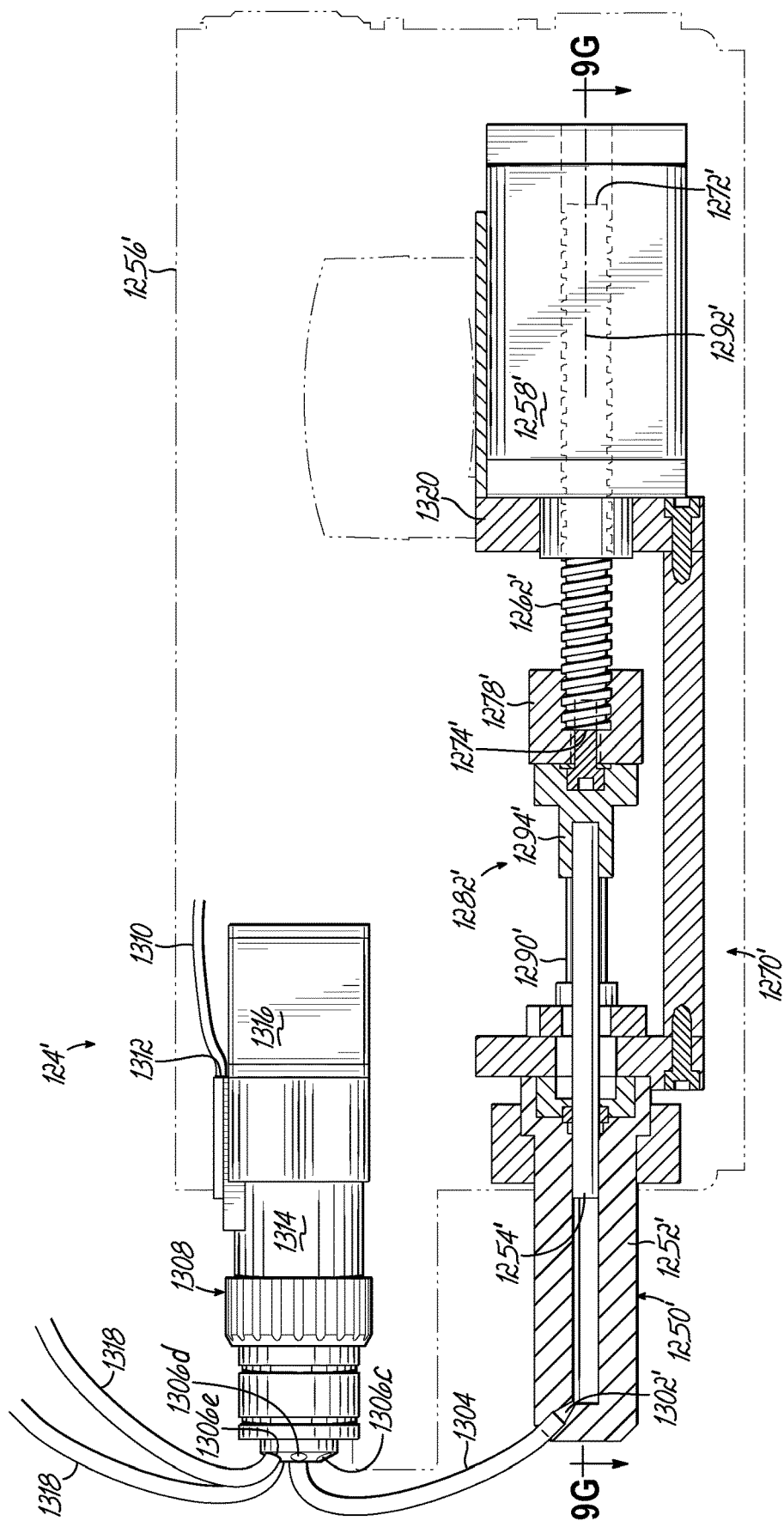
FIG. 9F is a cross-sectional view of a portion of a pump in accordance with another embodiment of the present invention.
Figure 9G:
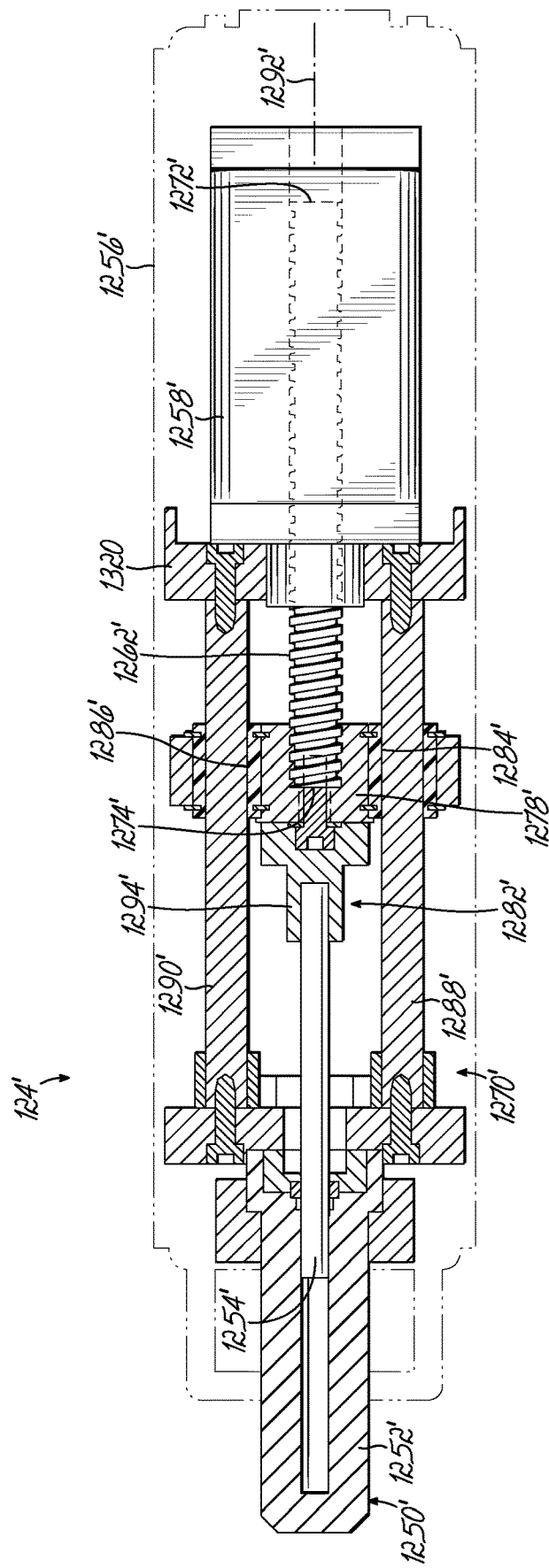
FIG. 9G is a cross-sectional view taken along line 9G-9G in FIG. 9F.

Another embodiment of a pump 124' suitable for use within the present system 10 (FIG. 1) is shown and described with reference to FIGS. 9F-9G, and where similar numbers with primes refer to similar features. Specifically, in FIG. 9F, the lead screw 1262' is positioned in-line with the piston 1254' and not vertically offset as was shown in FIG. 9B. Additionally, the motor 1258' is operably coupled to the lead screw 1262' and positioned in-line with both the lead screw 1262' and the piston 1254'.

At least one guide pin (two guide pins 1288', 1289' are shown) flanks the axis 1292' defined by piston 1254' and is coupled to the piston 1254' by an alignment plate 1278'. As was described in detail above, the alignment plate 1278' with the guide pins 1288', 1289' are configured to maintain a horizontal alignment of the piston 1254' during a stroke.

In operation, the lead screw 1262' extends through, and is threadably connected with a stationary plate 1320 proximate the first end 1272' of the lead screw 1262' while the piston 1254' is structurally secured to the second end 1274' of the lead screw 1262'. Operation of the motor 1258' causes rotation of the lead screw 1262' with respect to the stationary plate 1320. Because the stationary plate 1320 is secured within the housing 1256', rotation of the lead screw 1262' causes a linear movement of the same, which drives the piston 1254' with respect to the barrel 1252'. The mobile phase may be loaded and ejected in the pump 124' in a manner that is similar to the method described above with respect to the pump 124 (FIG. 9A).

Figure 10A:
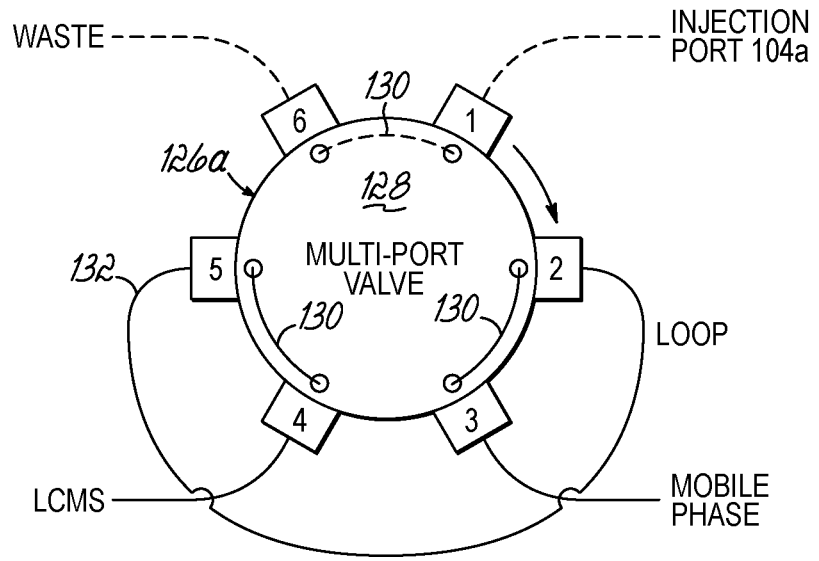
FIG. 10A is a schematic illustration of a multi-port valve having a fill-in loop, shown in an "in-line" position, and according to one embodiment of the present invention.

The volume of fluid displaced during a single stroke of the piston 1254 is directed to one valve 126a, 126b for driving the sample injections. In that regard, and turning now to FIGS. 10A and 10B, the details of the valves 126a, 126b are shown and described in greater detail. The valves 126a, 126b are injection valves having six ports (illustrated as "1" through "6") each fluidically coupled to one injection port 104a, 104b one or more of the mobile phase supplies 122 (FIG. 3A), a waste container 134 (FIG. 3A), the columns 114, 116 (FIG. 7A), and a fluid loop 132 connecting Port-2 to Port-5. Each valve 126a, 126b further includes a rotatable center 128 having three internal channels 130 for coupling two adjacent ports, as shown. The valves 126a, 126b have two configurations: "in line" and "fill in loop." FIG. 10A illustrates the "in-line" position where the mobile phase from at least one of the mobile phase supplies 122 (FIG. 3A) is directed via the pump 124 (FIG. 9A) and the fluid line into Port-3. The rotatable center 128 is such that the mobile phase moves through one internal channel 130 to Port-2 where the mobile phase fills, or pressurizes, the loop 132 and enters Port-5. The mobile phase then moves through another internal channel 130 to Port-4 and is directed to the columns 114, 116 (FIG. 7A). Meanwhile, the appropriate injection port 104a, 104b is fluidically coupled to Port-1 and, via an internal channel 130, to the waste container 134 (FIG. 3A) via Port-6.

Figure 10B:
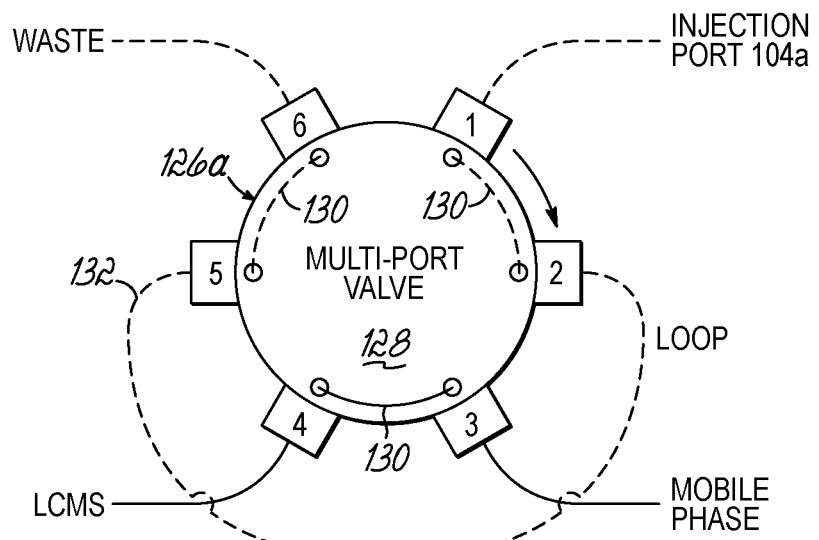
FIG. 10B is a schematic illustration of the multi-port valve of FIG. 10A, shown in a "fill in loop" position.

Rotation of the rotatable center 128 places the valve 126a into a "fill in loop" position, which is illustrated in FIG. 10B. As shown, the mobile phase now moves through an internal channel 130 to Port-4 and out to the columns 114, 116 (FIG. 7A). The prepared sample, on the other hand, enters the valve 126a via Port-1 and is directed by an internal channel 130 out to loop 132 so as to fill loop 132. The sample moves out of loop 132 at Port-5 and is directed, via another internal channel 130, to the Port-6 and then to waste container 134 (FIG. 3A). Once a sufficient volume of the prepared sample has been introduced, for example, three-times the volume of the loop 132, the rotatable center 128 is again rotated to transition the valve 126a, 126b to the "in-line" position of FIG. 10A. Accordingly, the prepared sample remaining within the injection port 104a, 104b is directed to the waste container 134 (FIG. 3A) while the mobile phase enters the loop 132, thereby displacing the prepared sample from the loop 132 and into the columns 114, 116 (FIG. 7A). Continued flow of the mobile phase flushes all of the prepared sample from the loop 132 and into the columns 114, 116 (FIG. 7A).

While not specifically shown, it will be appreciated that the appropriate injection port 104a, 104b may then receive a flush solvent (e.g., from a solvent container, not shown) to flush the injection port 104a, 104b, the fluid line, the appropriate internal channels 130, and the loop 132 in preparation for receiving the next prepared sample and reducing the likelihood of cross contamination.

It would be readily appreciated, and indeed is explained in greater detail below, that the rotation of the rotatable center 128 of the valves 126a, 126b may be controlled by logic and timed in accordance with a scheduler.

Turning again to FIGS. 3A, 3B, and 4B, the sample analysis station 24 includes a separate injection port 156 that is associated with the valve 133 and therefore by-passes the LC channels 118a, 118b. The injection port 156 may be used for injecting a calibration standard or a control standard (illustrated throughout as "QC") for performing a calibration or control analysis respectively as appropriate. In some embodiments, a calibration solution supply 158 (FIG. 3B) may be provided near the injection port 156 for ease of access when a calibration standard is necessary. For clarity of discussion of the mass spectrometer 120 hereafter, only the prepared sample injections will be discussed. Yet it will be understood that a sample calibration standard or control standard injected via the injection port 156 would be analyzed in a similar manner.

The injected, prepared sample moves through the columns 114, 116 in a known manner such that at least one of the analytes of interest will elute off the columns 114, 116 at a retention time that differs from the retention time of other analytes of interest and/or the matrix components, i.e., eluents. The eluents and analytes from both of the first and second LC channels 118a, 118b are directed into the valve 133 where the eluents are directed into the waste container 134 while the analytes are directed to an ionization source 140 of the mass spectrometer station 112. Alternative methods of sample introduction may include, but are not limited to, on-line methods (such as, flow injection analysis, direct infusion, and injection loops) and off-line methods (such as, solid phase extraction, blood spot surface coatings, matrix-assisted laser desorption/ionization ("MALDI") plate coatings, or coatings on general surfaces), may also be used to introduce the sample to the mass spectrometer 120.

As shown in FIG. 4B, an atmospheric pressure ionization (either electrospray ionization ("ESI") or atmospheric pressure chemical ionization ("APCI")) device (referred to generally herein as "nebulizing ionizer") is used for ionizing the analytes received by the ionization source 140. In that regard, the nebulizing ionizer includes a capillary, probe, or needle (referred hereinafter as "needle" 142) having a solvent conduit therein (not shown) and surrounded by a gas conduit therein (not shown). An outlet of the gas conduit is positioned about 0.1 mm to about 0.2 mm proximally to an outlet of the solvent conduit. In ESI operation a voltage generator 144 is electrically coupled to the needle 142 and is operable to create a high voltage difference between the needle 142 and the counter-electrode that is either at the mass spectrometer 120.

In use, a solvent is supplied to the solvent conduit at a rate ranging from about 400 µL/min to about 2000 µL/min; however, one of ordinary skill in the art will readily appreciate that the solvent supply varies with the particular ionization source 140 selected. The particular solvent used is dependent on the chemical nature of the analyte in study, and the methodology for selection of an appropriate solvent is well known to those of ordinary skill in the art. A gas, typically an inert gas, such as $N_2$, is supplied to the gas conduit at pressures ranging from about 0 bar to about 7 bar. The voltage generator 144 is activated and provides a voltage potential, typically ranging from about −5 kV to about 5 kV, to the solvent within the needle 142.

The solvent traverses the solvent conduit to the solvent conduit outlet. There, the charged solvent is impacted by the surrounding high-pressure gas leaving the gas conduit outlet. This high-pressure gas, together with formation of a Taylor cone (not shown) at the needle tip under the influence of the electric field, causes the flow of the charged solvent to be nebulized into a spray of charged, nebulized solvent which may contain one or more analytes of interest eluted from the columns 114, 116 (FIG. 7A).

In APCI operation, the voltage generator 144 is electrically-coupled to a corona discharge electrode 145 positioned distal to the outlets, instead of to the needle 142. The high voltage applied to the corona discharge electrode 145, if present, is operable to ignite a plasma which aids in the ionization of the nebulized solvent; however other ionization methods may be used and are generally known in the art. The plasma causes the ionization of the solvent and analytes(s), and a portion of the charged solvent/analyte(s) will enter into the mass spectrometer 120 as gas phase ions of the analytes ("gas phase ions"). A ion source that is switchable between ESI and APCI modes is described in U.S. Provisional Application No. 61/408,034, entitled "Combined Ion Source for Electrospray and Atmospheric Pressure Chemical Ionization," naming inventors Hardman, Dunyach, Atherton, and Belford, filed on Oct. 29, 2010, and U.S. application Ser. No. 13/280,069, filed on even date here with, the disclosure of which are incorporated herein by reference in their entireties.

It would be readily appreciated that other ionization techniques are known and may be implemented as necessary or desired. For instance, ionization sources 140 suitable for ionization of liquid samples may include, for example, heated electrospray ionization ("HESI"), nanospray ionization ("NSI"), thermospray, sonic spray, atmospheric pressure photoionization ("APPI"), laser diode thermal desorption ("LDTD"), atmospheric sampling glow discharge ionization source ("ASGDI"), paperspray ionization techniques capable of extracting a specimen from a dried blood-spot, and inductively-coupled plasma ("ICP"). Ionization sources 140 that are suitable for ionization of gas samples may include, for example, chemical ionization ("CI"), electron impact ("EI"), resonance enhanced multi-photon ionization ("REMPI"), resonance multi-photon detachment ("RMPD"), glow discharge, and spark ionization. Furthermore, the ionization sources 140 for gas samples may be adapted for use with liquid samples. Ionization sources 140 that are suitable for desorbtion and ionization of a sample from a surface include, for example, MALDI, surface-assisted laser desorption/ionization ("SALDI"), surface-enhanced laser desorption/ionization ("SELDI"), desorption electrospray ionization ("DESI"), direct analysis in real time ("DART"), discontinuous atmospheric pressure interface ("DAPI"), laser diode thermal desorption ("LDTD"), and field desorption. This listing of possible ionization sources 140 is not exhaustive and may include other ionization sources and/or permutations as would be readily understood by those of ordinary skill in the art of mass spectroscopy and analytical chemistry.

A skimmer 160, positioned distal to the corona discharge electrode 145, acts in conjunction with an auxiliary gas (not shown, but directed between the outlets and the skimmer 160) to contain and/or focus the gas phase ions into a vacuum chamber of the mass spectrometer 120. The auxiliary gas may be supplied at rates that range generally from about 0 L/min to about 15 L/min.

Referring still to FIG. 4B, the illustrative example of the mass spectrometer 120 includes an interface 146 with the ionization source 140, a mass filter 148, and an ion detector 150. The regions containing the mass filter 148 and the ion detector 150 are maintained under vacuum. This interface 146 includes an orifice 152 of a skimmer cone 154 that provides an opening into a higher vacuum chamber containing the mass filter 148 while maintaining vacuum pressures.

In the illustrated example, the mass filter 148 is shown to be a conventional quadrupole; however, those skilled in the art will understand the determination by which the appropriate mass filter modality for a given assay is selected. In fact, other mass spectrometer embodiments may include, for example, a single quadrupole modalities, time-of-flight ("TOF") or exactive modalities, ion trap ("OT") modalities, hybrid modalities, such as Q-TOF, TOF-TOF, Q-Exactive, LTQ-orbitrap, and LTQ-FT, or a mass spectrometer modified for proton transfer.

Single quadrupoles offer the benefits of small size, simple operation, and low cost; however, single quadrupoles lack analyte specificity and high back-ground noise levels, which lead to poor detection limits. TOF and Exactive modalities provide the benefits of greater selectivity of the gas phase ions for identification of analytes and may lead to the possibilities of archiving data for later review and identification of unknown analytes. However, as compared to quadrupole modalities, TOF and Exactive modalities are larger, more expensive, and require higher vacuums without gaining much decrease in the background noise levels.

Hybrid modalities, as compared with quadrupoles, TOF, and Exactive modalities, provide greater specificity for parent/fragment gas phase ion pairs with confirmation by accurate mass measurements, and, as to the TOF and Exactive modalities, the hybrid mass spectrometers may be operated in a manner that is similar to the TOF and Exactive modalities. However, hybrid modalities are much larger, more temperature sensitive, require a higher vacuum, are more expensive, and require higher power than quadrupole, TOF, and Exactive modalities.

Ion trap modalities allow the consideration and summation of multiple fragments for analyte quantification, which is particularly advantageous for vitamin D and testosterone-type assays, and increased mass specificity. However, these modalities tend to much more expensive, require higher vacuum and power, and are larger than the other available modalities.

Still other modalities are available, and may include, for example, ion cyclotron resonance ("ICR") or magnetic sector-based analyzers. While these modalities offer high resolution and specificity, each is also very expensive. Furthermore, other detectors/analyzers may be used with, or in place of the mass spectrometer. For example, these detectors may include, for example, electrochemical devices, nuclear magnetic resonance ("NMR"), absorbance, fluorescence, refractive index, pH, and/or conductivity.

In the illustrated quadrupole mass filter modality, an ion current is directed through four parallel electrodes comprising the mass filter 148, wherein the four parallel electrodes are comprised of two pairs of electrodes. A radiofrequency field and a DC voltage potential are applied to each of opposing pairs of electrodes by appropriate power supplies such that the two pairs are 180 degrees out of phase in RF voltage and differ in polarity of DC voltage potentials. Only those ions within the ion current having a first mass-to-charge ratio, m1/z1, will continue through the parallel electrodes to the ion detector 150. Said another way, the m1/z1 ions will be equally attracted to and deflected by the two pairs of electrodes while the mean free path induced by the radiofrequency field onto the m1/z1 ions does not exceed the distance between the electrodes. Thus, the m1/z1 ion will balance the radiofrequency and DC voltage forces from the parallel electrodes and traverse the parallel electrodes to impact the ion detector 150.

The m1/z1 ions that reach the ion detector 150, which may be in one embodiment, an electron multiplier ("EM") having a plurality of dynodes. In some embodiments, the EM may be replaced by a photomultiplier tube ("PMT") so as to detect photons produced by secondary electrons impinging on an optional phosphorescent screen (not shown). Each m1/z1 ion entering the EM strikes a first dynode and produces secondary electrons, which strike a third dynode to produce more secondary electrons, and so forth. The cascade of secondary electrons is finally captured by the multiplier collector, typically an anode, and measured as a current (I) induced by a total number (n) of secondary electrons over a measured detection time (t) and in accordance with n/t=I/e, wherein e is the elemental charge. In other embodiments, the ion detector 150 may include a phosphorescent screen where the m1/z1 ions collide with an electrode plate to produce secondary electrons that are directed to the phosphorescent screen. The secondary electrons incident on the phosphorescent screen produce photons that are detected by a PMT.

Analysis by way of a quadrupole mass filter 148 continues with altering the operational conditions of the mass filter 148 such that ions having a second mass-to-charge ratio, m2/z2, will traverse the mass filter 148 and impact the ion detector 150 in the manner similar to what was just described for m1/z1 ions. A spectrum may then be generated relating the ion flux, total ion current ("TIC"), or normalized relative abundances with respect to m/z of the ions detected.

In some embodiments, the resolution of the MS technique may be enhanced by employing "tandem mass spectrometry" or "MS/MS" for example via use of a triple quadrupole mass spectrometer. In those embodiments using a triple quadrupole, such as, for example, the mass-spectrometer described in greater detail in U.S. Pat. No. 6,987,261, entitled "Controlling Ion Populations in a Mass Analyzer," assigned to Thermo Finnigan, LLC, naming inventors Horning, Malek, Syka, and Wieghaus, and the disclosure of which is incorporated herein by reference in its entirety, three quadrupole stations are aligned in series. According to one embodiment in accordance with this technique, a first quadrupole station is operated to generate a first ion (also referred to as a parent ion or a precursor ion by those skilled in the art) having a particular m/z. In this way, the first quadrupole station may be used as a high pass filter to eliminate interfering substances, which is particularly useful in complex samples, such as samples prepared from biological or patient specimens. Suitable first quadrupole stations may include an ion trap or other mass filter modalities as described previously.

The first ion may then pass to a second quadrupole station, such as a fragmentation chamber, in which the first ions are fragmented into one or more second ions (also known as product ions or fragment ions). Accordingly, the second quadrupole station may be a collision cell wherein the incoming first ions collide with, and are fragmented by, neutral gas molecules (e.g., Ar). This process is called Collision Activated Dissociation ("CAD"). In other embodiments where fragmentation is not necessary, the second quadrupole station may be a second ion trap or mass filter.

The second ions then enter a third quadrupole station, often a mass filter or ion trap, where the second ions corresponding to the analyte of interest are separated from ions of no immediate diagnostic interest.

Each of the quadrupole stations may be operated in triple quadrupole in one of several modes, including: a scan mode (scan or transmission of select m/z ions), pass mode (wide range of m/z ions permitted to pass), a fragmenting mode (collision of ions with an inert gas causing fragmentation), or a set mode (ions of a single m/z ions value transmitted). Selection of any one of these modes permits various operational parameters for analysis of the prepared sample in accordance with the predetermined assay.

Figure 11:
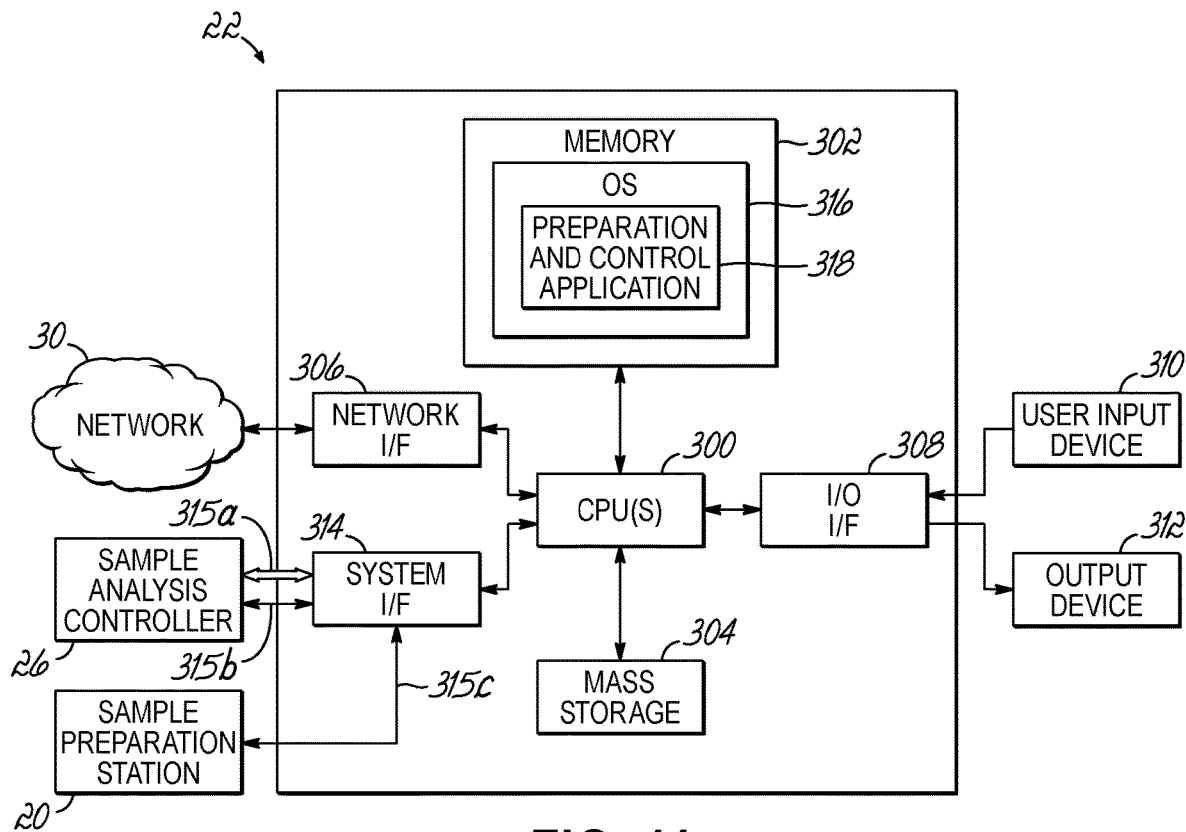
FIG. 11 is a diagrammatic view of a hardware and software environment for a sample preparation controller and in accordance with one embodiment of the present invention.

Turning now to the hardware and software environments of the system 10, FIG. 11 is a diagrammatic illustration of a hardware and software environment for the sample preparation controller 22 consistent with embodiments of the present invention. In specific embodiments, the sample preparation controller 22 is a computer, computing system, computing device, server, disk array, or programmable device such as a multi-user computer, a single-user computer, a handheld computing device, a networked device (including a computer in a cluster configuration), a mobile telecommunications device, a video game console (or other gaming system), etc. As such, the sample preparation controller 22 is referred to hereinafter as "prep controller" 22.

The prep controller 22 includes at least one central processing unit ("CPU") 300 coupled to a memory 302. Each CPU 300 is typically implemented in hardware using circuit logic disposed on one or more physical integrated circuit devices or chips. Each CPU 300 may be one or more microprocessors, micro-controllers, field programmable gate arrays, or ASICs, while memory 302 may include random access memory ("RAM"), dynamic random access memory ("DRAM"), static random access memory ("SRAM"), flash memory, and/or another digital storage medium, and also typically implemented using circuit logic disposed on one or more physical integrated circuit devices, or chips. As such, the memory 302 may be considered to include memory storage physically located elsewhere in the prep controller 22, e.g., any cache memory in the at least one CPU 300, as well as any storage capacity used as a virtual memory, e.g., as stored on a mass storage device 304 or as stored on the LIS 28 (FIG. 2) coupled to prep controller 22 through at least one network interface 306 (illustrated as, and hereinafter, "network I/F" 306) by way of the at least one network 30. It will be appreciated that the at least one network 30 may include at least one private communications network (e.g., such as an intranet) and/or at least one public communications network (e.g., such as the Internet).

The prep controller 22 is coupled to at least one peripheral device through an input/output device interface 308 (illustrated as, and hereinafter, "I/O I/F" 308). In particular, the prep controller 22 receives data from a user through at least one user input device 310 (including, for example, a keyboard, mouse, a microphone, and/or other user interface) and/or outputs data to the user through at least one output device 312 (including, for example, a display, speakers, a printer, and/or another output device). Moreover, in some embodiments, the I/O I/F 308 communicates with a device that is operative as a user input device 310 and output device 312 in combination, such as a touch screen display 313 (FIG. 1).

In addition to the network I/F 306 and the I/O I/F 308, the prep controller 22 may include a system interface 314 (illustrated as "system I/F" 314). The system I/F 314 is connected to at least one communication link to the sample analysis controller 26 as well as at least one communication link to the sample preparation station 20. In particular, the system I/F 314 provides both a high level data interface link, as indicated at arrow 315*a* (e.g., a TCP/IP link) or other common link, and a low level data interface link, as indicated at arrow 315*b* (e.g., a CAN BUS, a uni-directional contact closure communication link, or a bi-directional I/O level communication link) to the sample analysis controller 26. The system I/F 314 also provides a low level data interface link (e.g., a contact closure, CAN BUS, or other I/O level link, as indicated at arrow 315*c*) to the sample preparation station 20 for control by the prep controller 22. As such, the prep controller 22 is configured to provide commands and other instructional data to the sample analysis controller 26 and receive results information via the TCP/IP link 315*a*. Moreover, the prep controller 22 is configured to provide low level data commands to control the sample analysis station 24 (FIG. 2) and receive status information to track the operation of the sample analysis station 24 (FIG. 2) or control the sample analysis station 24 (FIG. 2) via the I/O level link 315*b*.

The prep controller 22 is typically under the control of an operating system 316 (illustrated as "OS" 316) resident in the memory 302 and executes or otherwise relies upon various computer software applications, sequences of operations, components, programs, files, objects, modules, etc., consistent with embodiments of the invention. In specific embodiments, the prep controller 22 executes or otherwise relies on at least one preparation control application 318 (referred to hereinafter as "control application" 318) to manage the operation of the sample preparation station 20 and monitor the sample analysis station 24 (FIG. 2), as well as process the results provided by the sample analysis station 24 (FIG. 2).

Figure 12:
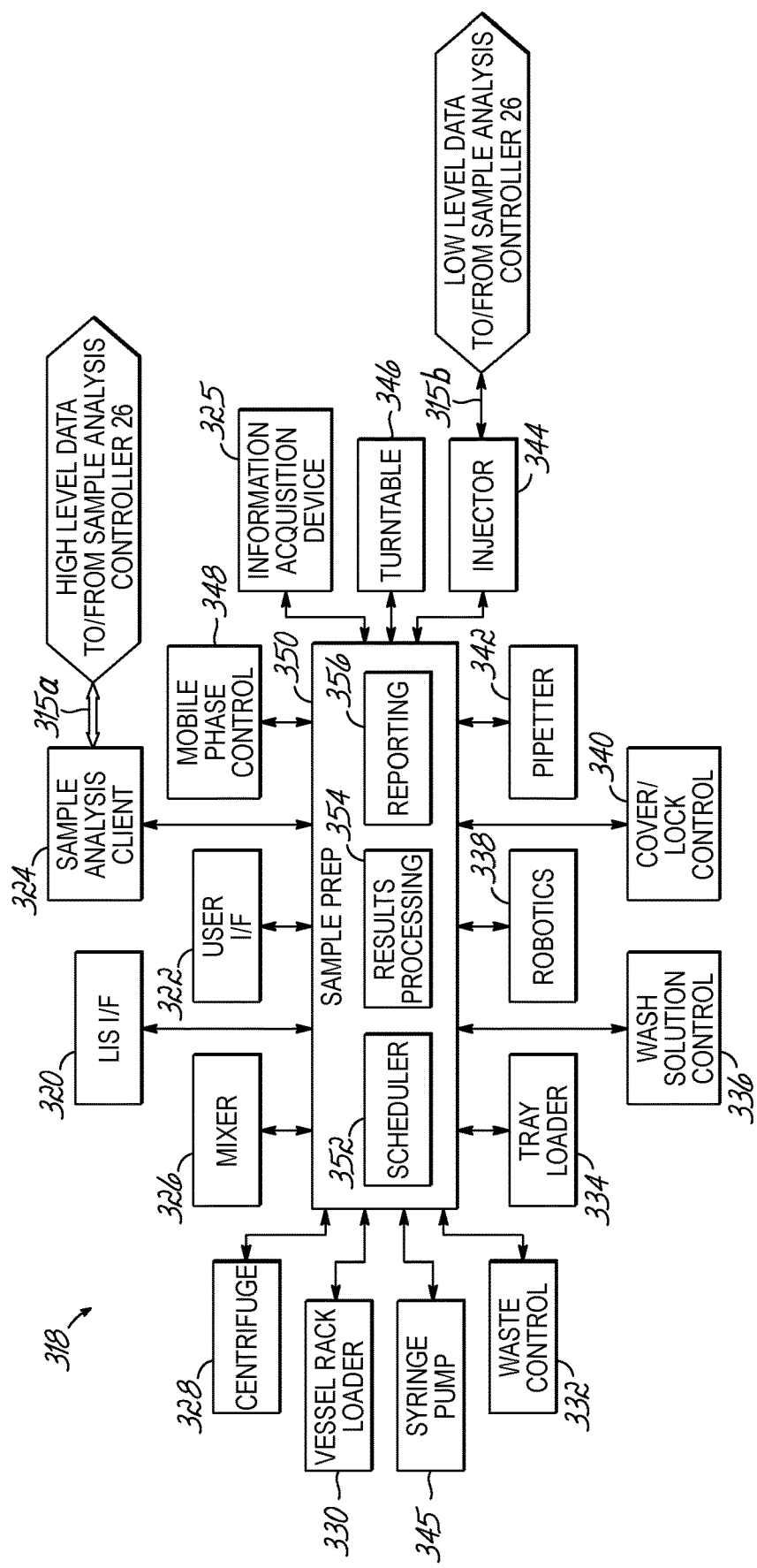
FIG. 12 is a diagrammatic view of a plurality of modules for a sample preparation controller and in accordance with one embodiment of the present invention.

FIG. 12 is a diagrammatic illustration of a plurality of applications, sequences of operations, components, programs, files, objects, modules, etc. (each of which is referred to hereinafter as a "module" for simplicity), that may be included in the control application 318 of FIG. 11. Specifically, the control application 318 may include one or more of each of the following modules: a LIS interface module 320 (illustrated as "LIS I/F" 320); a user interface module 322 (illustrated as "user I/F" 322); a sample analysis station client module 324; an information acquisition device module 325; a mixer module 326; a centrifuge module 328; an optional vessel rack loader module 330 (such as for the system 10' of FIG. 3B); a waste control module 332; a tray loader module 334; a wash solution control module 336; a robotics module 338; a cover/lock control module 340; a pipetter module 342; an injector module 344; a syringe pump module 345; a turntable module 346; a mobile phase control module 348; and a sample preparation module 350. The sample preparation module 350, in turn, may include a scheduler module 352, a results processing module 354, and a reporting module 356.

With respect to the individual modules, the LIS I/F module 320 is configured to control communications between the prep application 318 and the LIS 28 (FIG. 2), while the user interface module 322 is configured to provide human perceptible outputs to a user (not shown) (e.g., such as audibly and/or visually perceptible sounds and/or images with the output device 312) (FIG. 11). The sample analysis station client 324, on the other hand, is configured to send data (such as commands and other instructional data) and receive data (such as results) respectively to and from the sample analysis controller 26 (FIG. 2) via the high level data link 315*a*. The information acquisition device module 325 is configured to control the operation of the information acquisition device 54 (FIG. 3A). The mixer modules 326 and the centrifuge module 328 are configured to control at least a portion of the secondary processing station 80 (FIG. 3A), including one or more respective mixing stations 82 (FIG. 3A) and/or centrifuges 88 (FIG. 3A). The vessel loader module 330, if present, is configured to control the transport assembly 60 (FIG. 3A) to load vessels 58 (FIG. 3B) from the storage station 59 (FIG. 3D) or another portion of the secondary processing station 80 (FIG. 3A).

The sample preparation station 20 (FIG. 2) often produces waste as a result of the preparation of the samples. Such waste may include a portion of a sample that was not analyzed by the sample analysis station 24 (FIG. 2), waste produced by cleaning the sample pipette assembly 62 (FIG. 4A), cleaning the injector pipette assembly 96 (FIG. 3A), clearing the sample preparation station 20 (FIG. 2) of the vessels 58 (FIG. 3A) that are no longer necessary, and/or clearing the sample preparation station 20 (FIG. 2) of samples that are no longer necessary. As such, the control application 318 includes the waste control module 332 which operates to clear the sample preparation station 20 (FIG. 2) of that waste. The tray loader module 334 is configured to control the transport assembly 60 (FIG. 3A) to load at least one vessel 58 of the vessel rack 84 (FIG. 3B), if used, to the injector station 92 (FIG. 3A), while the wash solution control module 336 monitors the amount of wash solution from the flush solvent container (not shown) and controls the dispensing of that wash solution. The robotics module 338, on the other hand, controls the movement of the transport assembly 60 (FIG. 3A) generally (including any grippers used to transport vessels 58 (FIG. 3A) and/or vessel racks 84 (FIG. 3B), if used, within the system 10 (FIG. 1)), while the cover/lock control module 340 ensures that one or more covers 357*a*, 357*b* (FIG. 1) of the system 10 (FIG. 1) are closed and locked while the system 10 (FIG. 1) operates to prepare the samples. The turntable module 346 controls the sampling station 56 (FIG. 3A) and the rotatable tables 44, 102 (FIG. 3A) of the system 10 (FIG. 1), while the mobile phase control module 348 is configured to monitor the level of mobile phases within the mobile phase supplies 122 (FIG. 3A) to determine if any volume thereof is low. In one embodiment, the system 10 (FIG. 1) may include sensors (not shown) that are configured to indicate the level of the mobile phases and communicate that information via the low-level data link 315*b* received by the injector module 344, while in an alternative embodiment the system 10 (FIG. 1) is configured to determine how much of any particular mobile phase remains by calculating the amount of mobile phase used during testing.

With respect to the remaining modules, the pipetter module 342 controls the operation of the sample pipette assembly 62 (FIG. 4A), while the injector module 344 controls the injector pipette assembly 96 (FIG. 4A) for injecting the prepared sample into the appropriate injector port 104*a*, 104*b* (FIG. 3A). Moreover, the injector module 344 is configured to receive status and/or other low-level data from the sample analysis station 24 (FIG. 2), and provide commands and/or other low-level data to the sample analysis station 24 (FIG. 2) though the system I/F 314 (FIG. 11). For example, the injector module 344 may be configured to receive status information about individual components of the sample analysis station 24 (FIG. 2), including whether a particular injector port 104*a*, 104*b* (FIG. 3A), the valves 126*a*, 126*b* (FIG. 3A), and/or the mass spectrometer 120 (FIG. 3A) is available or ready. The control application 318 may in turn utilize that data to control the operation of the sample analysis station 24 (FIG. 2) via commands sent through the sample analysis station client module 324. A syringe pump module 345 is configured to receive instructions for, operate, and/or report the status of the pump 124 (FIG. 9A). For example, the syringe pump module 345 may control a stroke volume, a stroke rate, report whether the pump 124 (FIG. 9A) is available, report whether the pump 124 (FIG. 9A) is operating properly, etc. Although not illustrated, one or more of modules 326-248 may be configured to communicate with their respective components through the low level data interface link 315*c* (FIG. 11).

The sample preparation module 350 is configured to monitor and supervise the operation of modules 320-348. In addition, the sample preparation module 350 is configured to schedule samples for preparation and analysis by the sample preparation station 20 (FIG. 2) and the sample analysis station 24 (FIG. 2), respectively, with the scheduler module 352. The scheduler module 352 is configured to determine an order in which to process specimens. For example, each specimen 23 (FIG. 2) received by the system 10 (FIG. 1) is associated with data used to determine a target time to result and/or target time to prepare that specimen 23 (FIG. 2). The scheduler module 352, in turn, determines when each specimen 23 (FIG. 2) should be prepared and/or analyzed based upon the specimen type, whether the specimen 23 (FIG. 2) is a priority specimen, the type of assay to perform, and the time for completion associated with that specimen 23 (FIG. 2), as well as corresponding data associated with other samples and/or specimens 23 (FIG. 2) in the system 10 (FIG. 1). Thus, a second specimen with a short time for completion may be processed prior to a first specimen with a longer time for completion and received prior to that second specimen. The scheduler module 352 thus provides the ability to dynamically adjust the order in which samples are prepared and analyzed by the system 10 (FIG. 1).

The sample preparation module 350 may further include a results processing module 354. The results processing module 354 is configured to analyze results from the sample analysis station 24 (FIG. 2) and determine if those results are consistent with calibration and/or control data. The results processing module 354 may also be configured to format results for storage by the LIS 28 (FIG. 2). The reporting module 356, in turn, is configured to provide reports about operation of the system 10 (FIG. 1), such as event reports and alarm reports.

Figure 13:
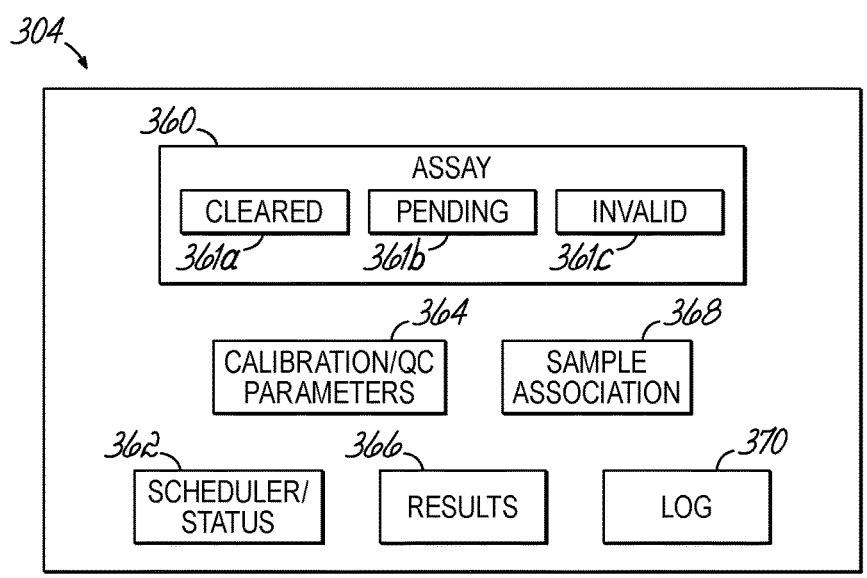
FIG. 13 is a diagrammatic view of the data structure included in the mass storage device of a sample preparation controller in accordance with one embodiment of the present invention.

FIG. 13 is a diagrammatic illustration of a plurality of data structures that may be included in the mass storage device 304 of the prep controller 22 (FIG. 2). Specifically, FIG. 13 illustrates that the mass storage device 304 may include an assay data structure 360, a scheduler/status data structure 362, a calibration/control parameters data structure 364 (illustrated as "CALIBRATION/QC PARAMETERS" 364), a results data structure 366, a sample association data structure 368, and a log data structure 370. The assay data structure 360 may be a database configured to store information about each type of assay, and in particular reagents or solvents that may be used to prepare a specimen 23 (FIG. 2) for analysis, operations to prepare the specimen in accordance with a particular assay, and/or information required by the sample analysis station 24 (FIG. 2) to perform the analysis. Moreover, the assay data structure 360 may store data about the types of assays that the system 10 (FIG. 1) may run.

Specifically, the system 10 (FIG. 1) may be configured to monitor whether there is enough reagent for the particular type of assay and prevent that type of assay from being run when there is not enough reagent. Moreover, the system 10 (FIG. 1) may be configured to determine which types of assays are associated with calibration data such that data associated with that type of assay may be determined. As such, the assay data structure 360 includes a cleared assay list 361*a* indicating types of assays for which the system 10 (FIG. 1) has sufficient reagents and that are associated with a valid calibration, as well as a pending assay list 361*b* indicating types of assays for which the system 10 (FIG. 1) has sufficient reagents but is associated with a calibration that is currently pending.

The system 10 (FIG. 1) will perform an assay in the cleared assay list 361*a* but refrain from performing an assay that is in the pending assay list 361*b* until a calibration curve for that assay has been generated. The assay data structure 360 also includes an invalid assay list 361*c* indicating types of assays for which the system 10 (FIG. 1) does not have sufficient reagents, or types of assays that are not associated with a calibration or that are associated with an invalid calibration. The system 10 (FIG. 1) will not prepare a sample in accordance with an assay in the invalid assay list 361*c* until such time as that assay is moved to the cleared assay list 361*a*.

With respect to the remaining data structures, the scheduler/status data structure 362 may store data used by the prep controller 22 (FIG. 2) to determine the order in which to prepare specimens, data used by the prep controller 22 (FIG. 2) to determine the order in which to perform sample preparations, and/or data indicating the status of each specimen 23 (FIG. 2), sample, or prepared sample in the system 10 (FIG. 1), and/or the testing to be performed by the system 10 (FIG. 1) for a particular sample. That data may be provided to the user for the user to view data about the specimens 23 (FIG. 2), prepared samples, and/or tests to be performed by the system 10 (FIG. 2). The calibration/control parameters data structure 364 stores data about calibrations and/or control results of the sample analysis station 24 (FIG. 2), while the results data structure 366 may store the results of tests performed by the sample analysis station 24 (FIG. 2). The sample association data structure 368 is configured to associate a specimen 23 (FIG. 2) with a particular result or set of results. The log data structure 370 may store a log of operational data about the system 10 (FIG. 1), including events and/or alarms detected thereby.

Figure 14:
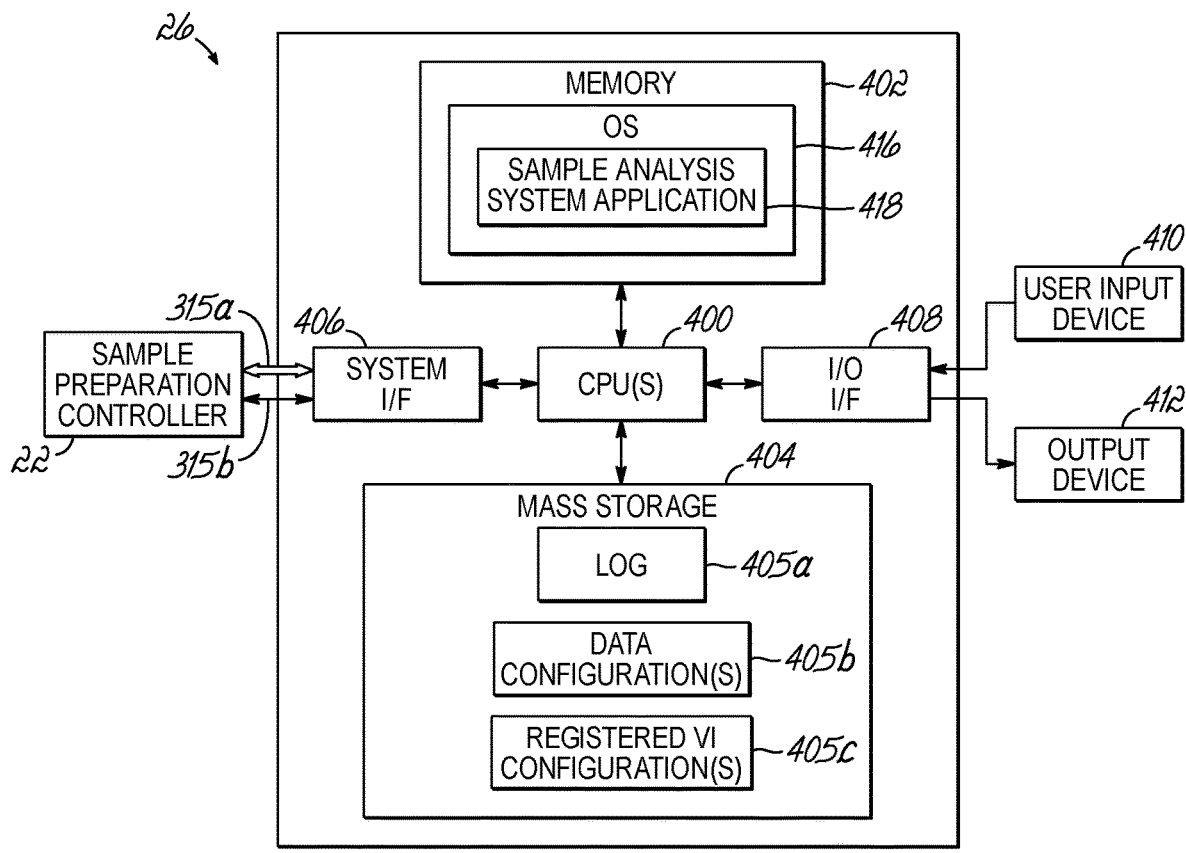
FIG. 14 is a diagrammatic view of a hardware and software environment for a sample analysis controller and in accordance with one embodiment of the present invention.

FIG. 14 is a diagrammatic illustration of a hardware and software environment for the sample analysis controller 26 consistent with embodiments of the present invention. In specific embodiments, and similarly to the prep controller 22 (FIG. 2), the sample analysis controller 26 is a computer, computing system, computing device, server, disk array, or programmable device such as a multi-user computer, a single-user computer, a handheld computing device, a networked device (including a computer in a cluster configuration), a mobile telecommunications device, a video game console (or other gaming system), etc.

The sample analysis controller 26 includes at least one CPU 400 coupled to a memory 402. Each CPU 400 is typically implemented in hardware using circuit logic disposed on one or more physical integrated circuit devices or chips. Each CPU 400 may be one or more microprocessors, micro-controllers, field programmable gate arrays, or ASICs, while memory 402 may include RAM, DRAM, SRAM, flash memory, and/or another digital storage medium, and also typically implemented using circuit logic disposed on one or more physical integrated circuit devices, or chips. As such, memory 402 may be considered to include memory storage physically located elsewhere in the sample analysis controller 26, e.g., any cache memory in the at least one CPU 400, as well as any storage capacity used as a virtual memory, e.g., as stored on a mass storage device 404, which may contain a log data structure 405*a* to store data associated with the sample analysis controller 26 and/or sample analysis station 24 (FIG. 2), and a configuration data structure 405*b* which may store information used to generate a methodology of how the sample analysis station 24 (FIG. 2) will prepare the sample. In one embodiment, the configuration data structure 405*b* stores configuration data in the XML format. The configuration data structure 405*b* may also indicate each of the assays that are performable by the sample analysis station 24 (FIG. 2). As such, the configuration data structure 405*b* may be accessed by the prep controller 22 or the sample analysis controller 26 in response to a query from the prep controller 22 as to which assays may potentially be performed. A registered virtual interface configuration data structure 405*c* (illustrated as "registered VI configuration(s)" 405*c*) stores information about the configuration of virtual interfaces (FIG. 15) utilized by the sample analysis controller 26.

The sample analysis controller 26 is coupled to the prep controller 22 through at least one system interface 406 (illustrated as "system I/F" 406). As such, the system I/F 406 may include appropriate circuitry to communicate across the high level data link 315*a* and the low level data link 315*b*. The sample analysis controller 26 is coupled to at least one peripheral device through an input/output device interface 408 (illustrated as, and hereinafter, "I/O I/F" 408). In particular, the sample analysis controller 26 receives data from a user through at least one user input device 410 (including, for example, a keyboard, mouse, a microphone, and/or other user interface) and/or outputs data to the user through at least one output device 412 (including, for example, a display, speakers, a printer, and/or another output device). Moreover, in some embodiments, the I/O I/F 408 communicates with a device that is operative as a user input device 410 and output device 412 in combination, such as the touch screen display 313 (FIG. 1). In specific embodiments, the sample analysis controller 26 is generally configured to provide data to the prep controller 22 and not otherwise be accessible through the user input device 410 or provide information through the output device 412. However, in certain circumstances, such as during debugging, maintenance, and/or administrative functions, it may be desirable for users to be able to access the sample analysis controller 26 through the user input device 410 and for the sample analysis controller 26 to provide human perceptible output through the output device 412.

The sample analysis controller 26 is typically under the control of an OS 416 resident in the memory 402 and executes or otherwise relies upon various computer software applications, sequences of operations, components, programs, files, objects, modules, etc., consistent with embodiments of the invention. In specific embodiments, the sample analysis controller 26 executes or otherwise relies on at least one sample analysis application 418 (referred to hereinafter as "sample analysis application" 418) to receive commands from the prep controller 22, operate the sample analysis station 24 (FIG. 2), and provide results back to the prep controller 22.

FIG. 15 is a diagrammatic illustration of a plurality of applications, sequences of operations, components, programs, files, objects, modules, etc. (each of which is referred to hereinafter as a "module" for simplicity), that may be included in the sample analysis application 418 of FIG. 14. The sample analysis application 418 includes a sample analysis station service module 420 that is configured to communicate via the high level data link 315*a* with the sample analysis station client module 324 (FIG. 12) of the control application 318 (FIG. 12). The sample analysis station service module 420 functions as the primary point of communication between the control application 318 (FIG. 12) and the sample analysis application 418. As such, the sample analysis station service module 420 may receive instructional data, including an indication of the assay type to perform, what analytes to detect with the assay type, the amount of prepared sample necessary in accordance with the assay, and a globally unique identification designator ("GUID") of the prepared sample. Results for an analyzed sample will include the GUID of the specimen 23 (FIG. 2) for the system 10 (FIG. 1) to associate specimens 23 (FIG. 2) and their results. The sample analysis station service module 420 is configured to analyze that instructional data and use that data to look up, with a data manager 422, how to operate the sample analysis station 24 (FIG. 2) to prepare the same in accordance with the assay. The sample analysis station service module 420, in turn, is configured to provide the results back to the sample analysis station client module 324 (FIG. 12).

The sample analysis application 418 also includes an acquisition service 424 that operates to multiplex the operation of the sample analysis station 24 (FIG. 2) and pass commands to the components of the sample analysis station 24 (FIG. 2). In particular, the acquisition service 424 may be configured to operate in a modular manner with respect to a plurality of different sample analysis stations 24 (FIG. 2), and as such communicate with components of the sample analysis station 24 (FIG. 2) through various virtual interfaces, each virtual interface being specific to one or more of those components. For example, and as described above, the sample analysis station 24 (FIG. 2) may include the mass spectrometer 120 that in turn includes pumps 124, and valves 126a, 126b. As such, the acquisition service 424 communicates with a multiplexing virtual interface 426 (illustrated as, and referred to hereinafter, as a "MUX VI" 426) that translates modular data from the acquisition service 424 into data that is appropriate for the injector pipette assembly 96, the pumps 124, and the valves 126a, 126b. The acquisition service 424 similarly communicates with a mass spectrometer virtual interface 428 (illustrated as, and referred to hereinafter, as "MS VI" 428) that translates modular data from the acquisition service 424 into data that is appropriate to operate the mass spectrometer 120. The MUX VI 426 and MS VI 428 also operate to translate data from the respective injector pipette assembly 96, the pumps 124, the valves 126a, 126b, or the mass spectrometer 120 to data that may be understood by the acquisition service 424, if necessary.

In particular, the MUX VI 426 translates modular commands to operate the injector pipette assembly 96, the pumps 124, or the valves 126a, 126b from the acquisition service 424 into commands that are appropriate for the firmware 430 of the injector pipette assembly 96 of the sample preparation station 20 (which may be physically located at the sample analysis station 24, both shown in FIG. 2) as well as the firmware 430 of the pumps 124 and the valves 126a, 126b of the sample analysis station 24 (FIG. 2). Correspondingly, the MUX VI 426 translates data specific to the injector pipette assembly 96 and the pumps 124 and/or the valves 126a, 126b (e.g., status data) into data that may be understood by the acquisition service 424, if necessary. Similarly to the MUX VI 426, the MS VI 428 translates modular commands to operate the mass spectrometer 120 from the acquisition service 424 into commands that are appropriate for the firmware 432 of the components of the mass spectrometer 120, and also translates data from the mass spectrometer 120 (e.g., result data) into data that may be understood by the acquisition service 424, if necessary.

As illustrated in FIG. 15, the MUX VI 426 is also configured to provide information to the injector module 344 (FIG. 12) of the control application 318 (FIG. 12) via the low level link 315b through the system interface 406 (FIG. 14). This low level link 315b may carry status data from the components of the sample analysis station 24 (FIG. 2), such as the status of the injector pipette assembly 96 or a component thereof, as well as the status of the one or more valves 126a, 126b and the status of an analysis of a prepared sample. Thus, the control application 318 (FIG. 12) may know the status of the sample analysis station 24 (FIG. 2) and may control at least some of the operations thereof.

The sample preparation controller 22 (FIG. 2) is configured to provide a user interface of the system 10 (FIG. 1) to a user, such as the touch screen display 313 (FIG. 1). The user interface may allow the user to input data, such as data associated with particular specimens, as well as view data about the system 10 (FIG. 1), including status information and results of an analysis. In some embodiments, the system 10 (FIG. 1) does not require user input, but instead may automatically determine which assay to run by querying the LIS 28 (FIG. 2). Accordingly, the user interface may be used for displaying system status and system diagnostics to a passive user.

Figure 16A:
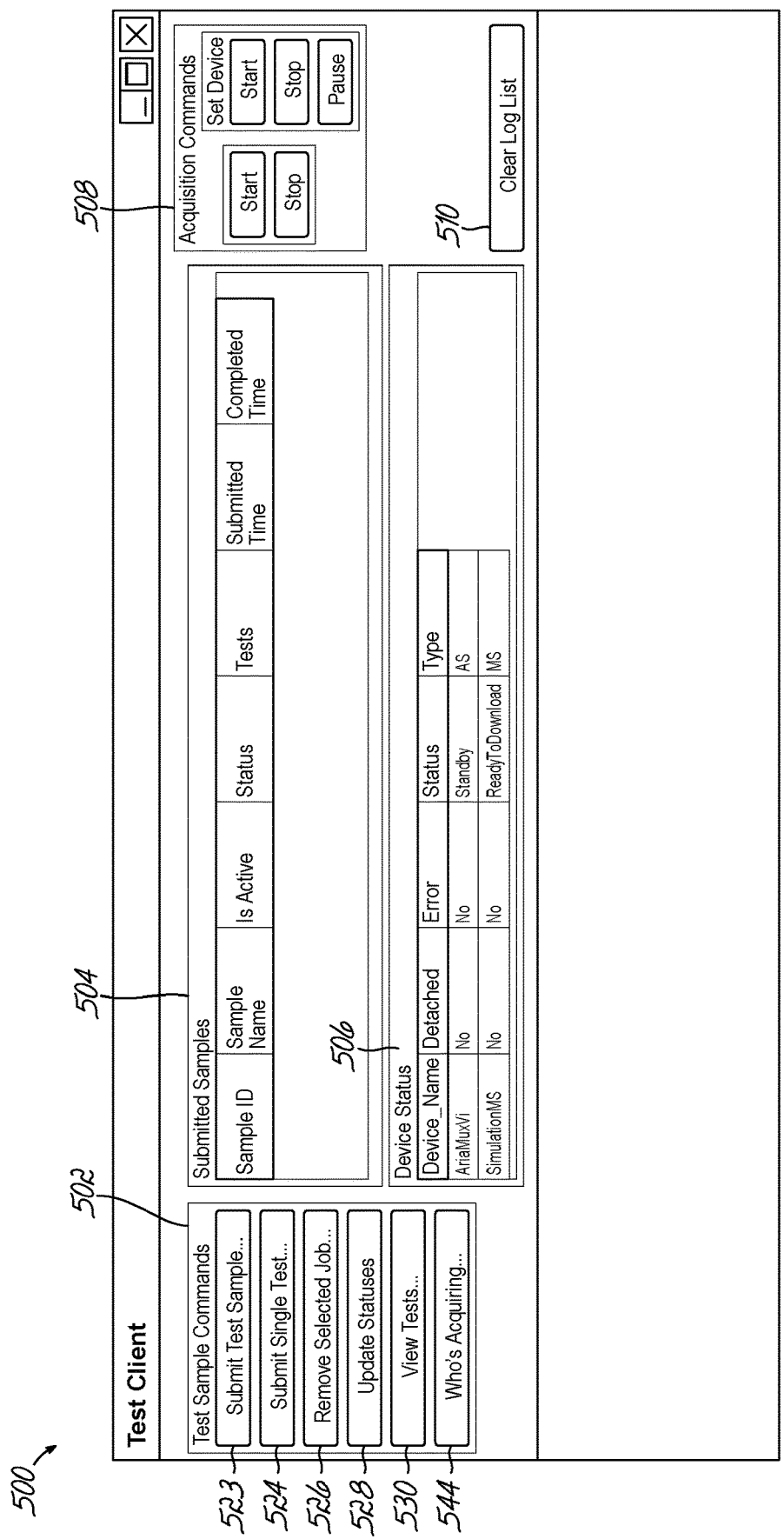

FIGS. 16A-16G illustrate screenshots that may be provided by the sample preparation controller 22 (FIG. 2) consistent with embodiments of the present invention. In particular, FIG. 16A illustrates a start screen 500 that may be presented to a user, for example a laboratory technician, to enter information about a specimen. The start screen 500 includes a test sample commands section 502 for the user to interact with the system 10 (FIG. 1); a submitted samples section 504 for displaying a list that includes the ID, name, status, assay type, and schedule for specimens 23 (FIG. 2) loaded into the system 10 (FIG. 1); a device status section 506 that provides information regarding the sample preparation station 20 (FIG. 2) and the sample analysis station 24 (FIG. 2), such as errors, statuses, and identification information thereof; and an acquisition commands section 508 for initiating, starting, or pausing the system 10 (FIG. 1). The user may also clear a log by selecting a clear log button 510.

In the test sample commands section 502, the user may select a submit test sample user interface component 523 to enter information regarding a particular specimen 23 (FIG. 2) and to start an analysis thereof. In response to selection of the submit test sample user interface component 523, the sample preparation controller 22 (FIG. 2) provides a setup single test sample component 512, illustrated in FIG. 16B. The setup single test sample component 512 allows the user to input particular information through user interfaces (e.g., each user interface being a text box, a selection box, a check box, or some other appropriate human perceptible user interface), such as a sample name in a sample name user interface 514, the type of assay to perform in an assay type user interface 516, the time for the result of a sample analysis to be provided in a time to result user interface 517, whether the specimen is a priority specimen through a priority user interface 518, a dilution factor in a dilution factor user interface 519, a volume of the sample in a volume user interface 520 (entered in mL), and an indication of the person who submitted the specimen 23 (FIG. 2) in a submitter user interface 522 (e.g., the name of the laboratory technician). The user may then select an "OK" or "Cancel" button as appropriate and return to the start screen 500.

If more than one test is ordered by a prescribing physician for a particular specimen 23 (FIG. 2), the user may select a submit single test user interface 524 to enter information for an additional test in a manner similar to that described in connection with FIG. 16B. The user may also remove a particular job (i.e., test or sample) by selecting the appropriate specimen 23 (FIG. 2) or test within the submitted samples section 504 and then selecting a remove selected job user interface 526. Selecting an update statuses user interface 528 that allows the user to retrieve current information on the status of each test of the specimen 23 (FIG. 2) that is presently under analysis.

Figure 16C:
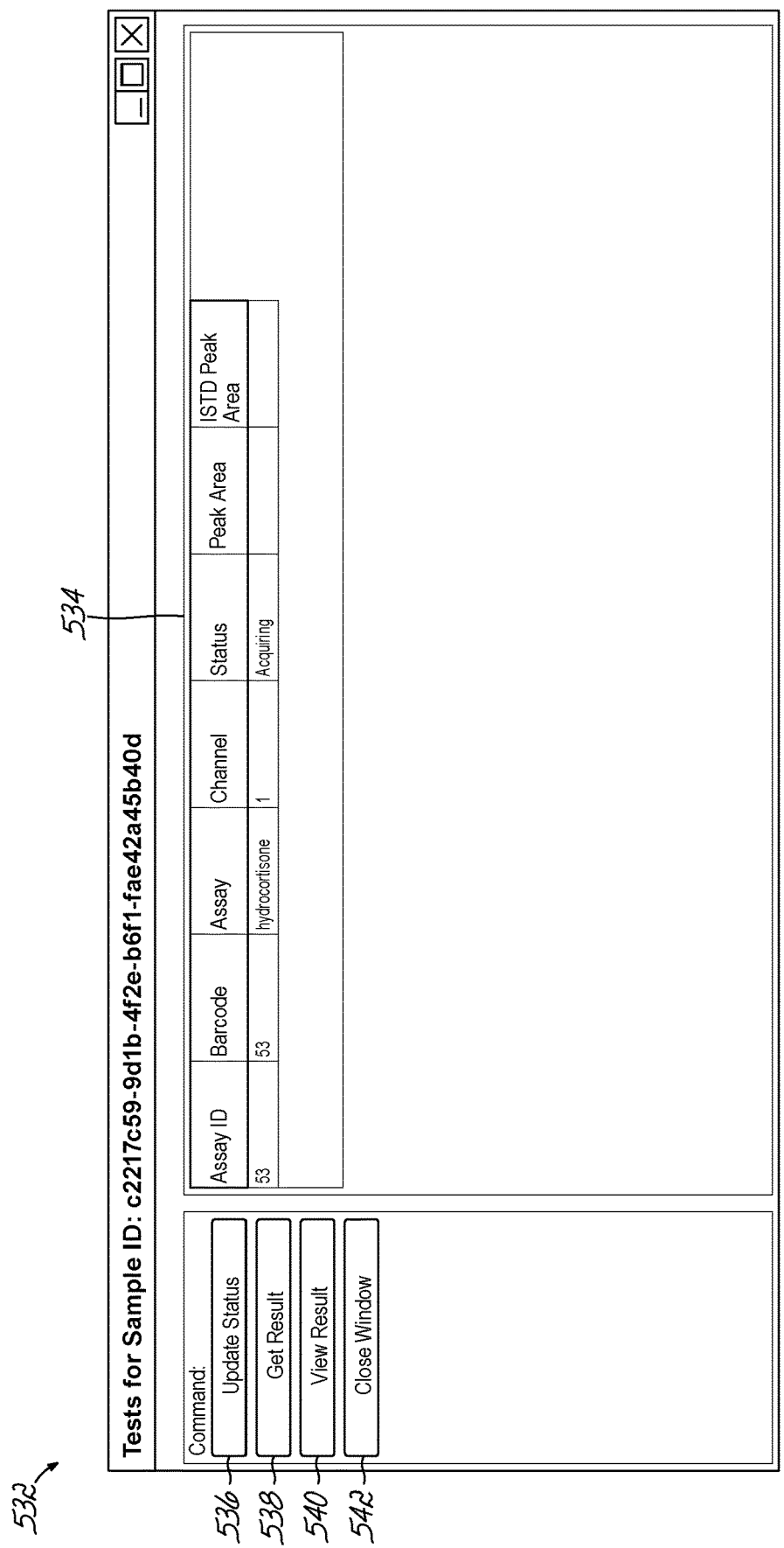

The user may also select a desired appropriate specimen 23 (FIG. 2) or test within the submitted samples section 504 and then select a view tests section 530 to open a test for sample window 532, illustrated in FIG. 16C, to display the status and results for a selected specimen 23 (FIG. 2) or test. As shown, the test information component 534 provides various information about the prepared sample under analysis in a list and includes an indication of an assay ID used for the prepared sample, barcode for the prepared sample, assay selected for the prepared sample, the LC channel 118a, 118*b* (FIG. 4B) scheduled to receive that prepared sample, and the status of that prepared sample. Information regarding result data from the analysis of that prepared sample may also be displayed, such as a peak area (i.e., "AA") and an internal standard ("ISTD") peak area. As illustrated in FIG. 16C, results for a hydrocortisone assay of vessel number fifty-three are being acquired. The user may select an update status user interface 536, get result user interface 538, view result user interface 540, or close window user interface 542, as appropriate. Selection of the close window user interface 542 returns the user to the start screen 500 (FIG. 16A).

Returning again to FIG. 16A, the user may also select a "Who's Acquiring" user interface 544 to have the system 10 (FIG. 1A) identify the specimen 23 (FIG. 2) and/or assay for the specimen 23 (FIG. 2) from the submitted samples section 504 that is being acquired.

Once the analysis of the prepared sample has completed such that the data related thereto has been gathered (e.g., the acquisition is "complete"), the status of the particular sample associated with that data indicated in the submitted samples section 504 is updated to "Complete." The user may then select the particular sample and select a view tests user interface 530 to review the results.

Figure 16D:
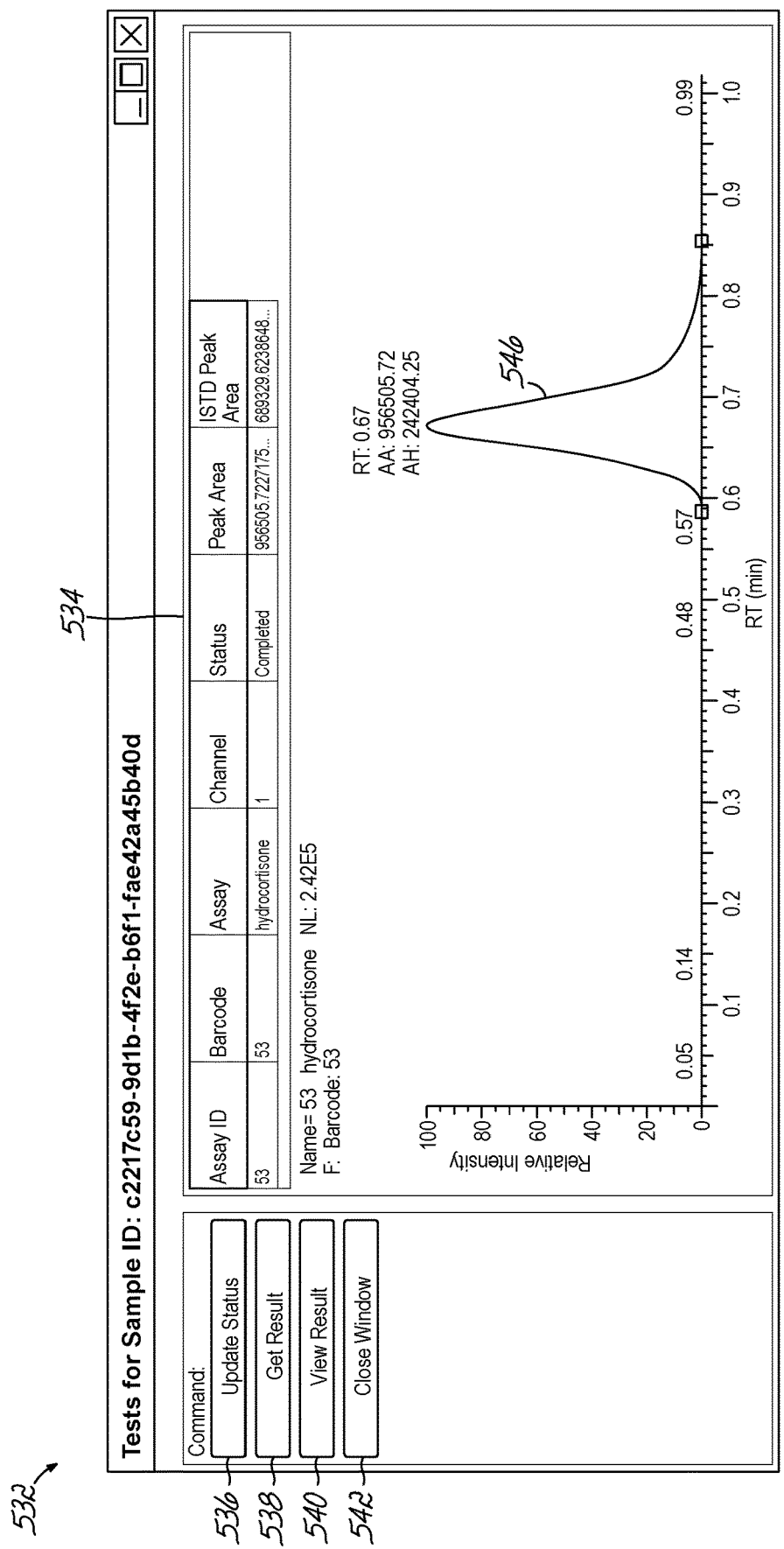

FIG. 16D illustrates a test for sample window 532 that is provided once an analysis has completed. Accordingly, the status under the information block has been updated to "Completed" and the calculated values for the hydrocortisone assay are provided, as appropriate, under peak area and ISTD peak area. A chromatogram 546 is also displayed, specifically shown herein as illustrating the hydrocortisone results.

Figure 16E:
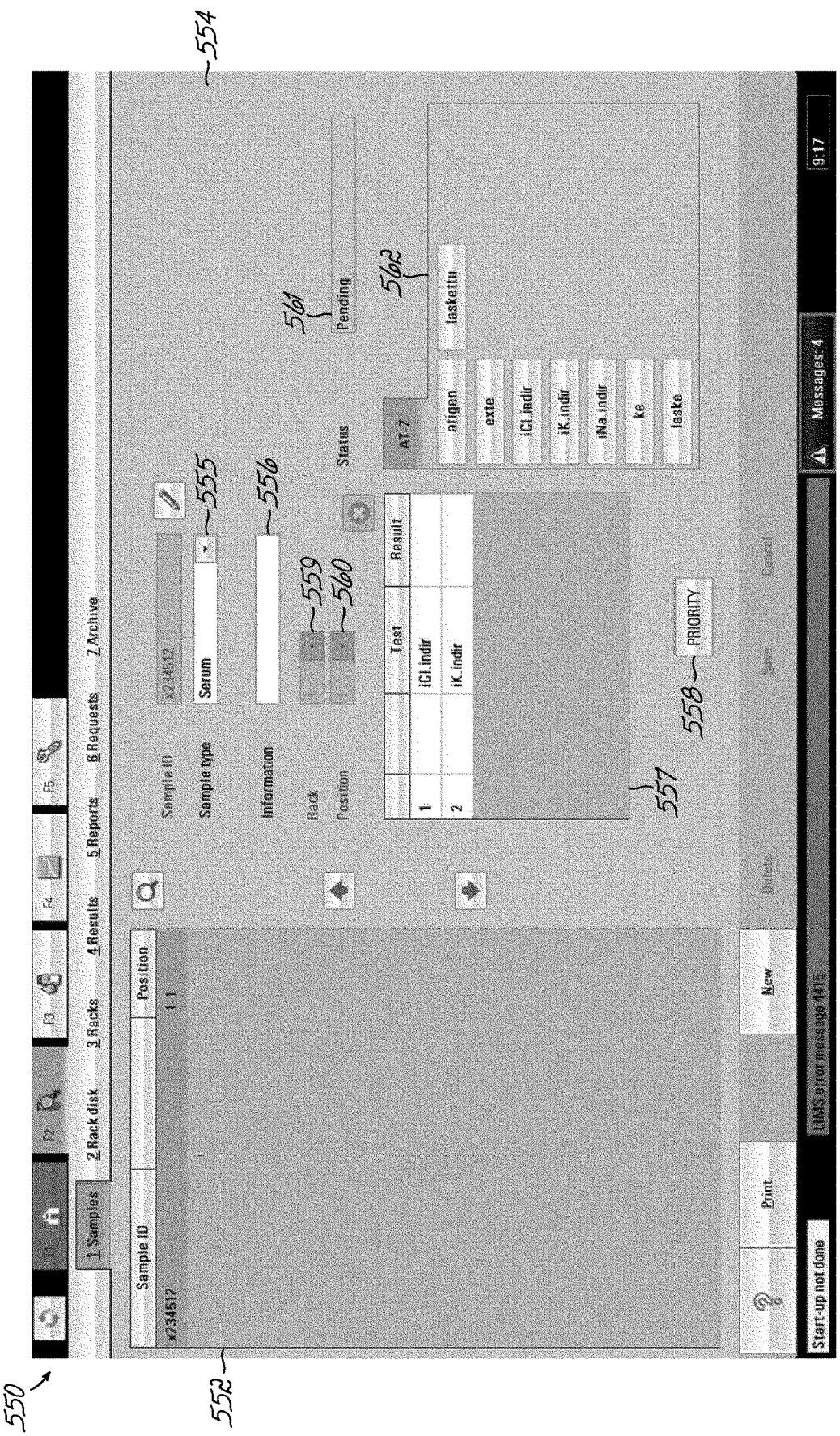
Figure 16F:
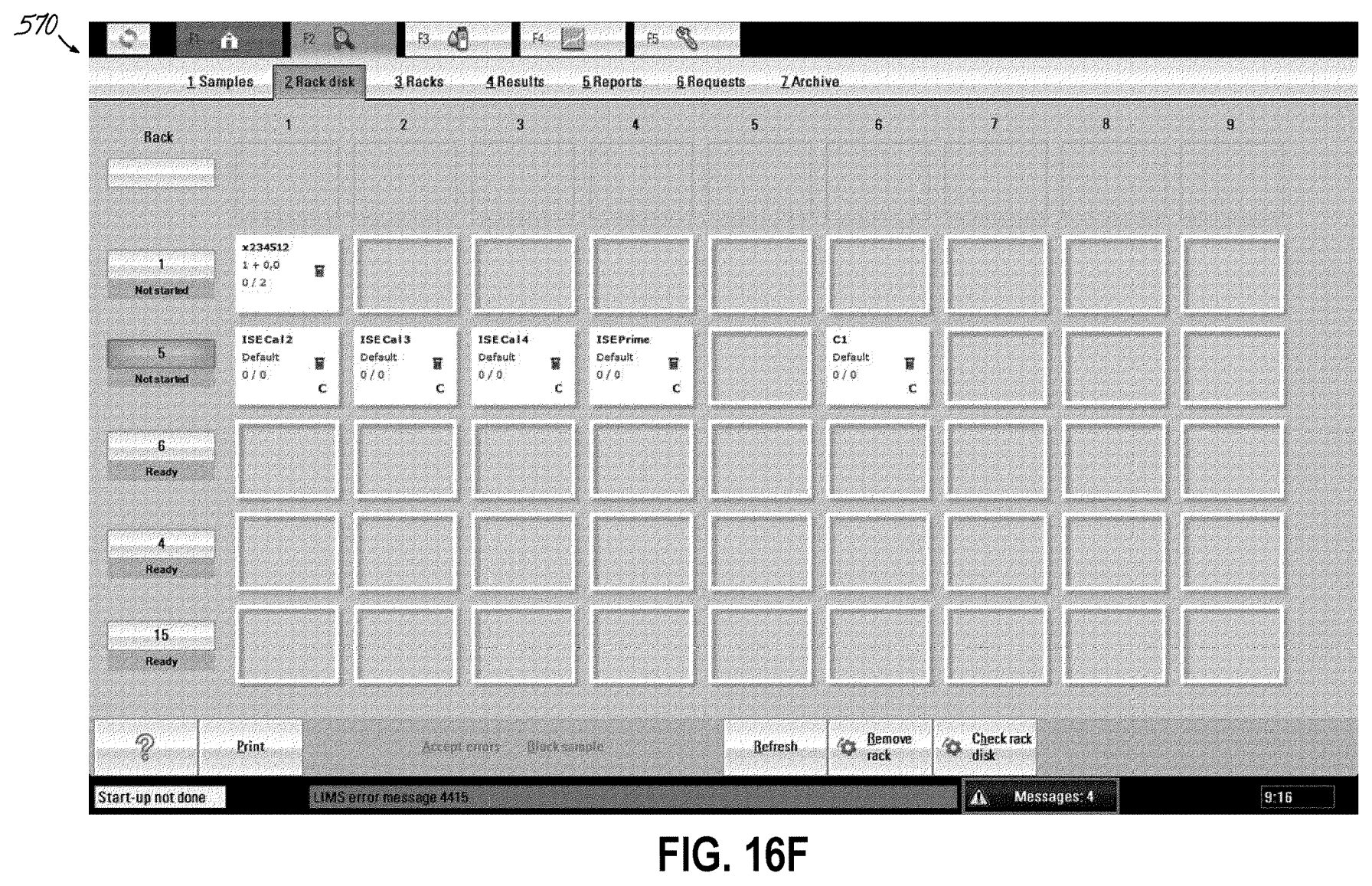
Figure 16G:
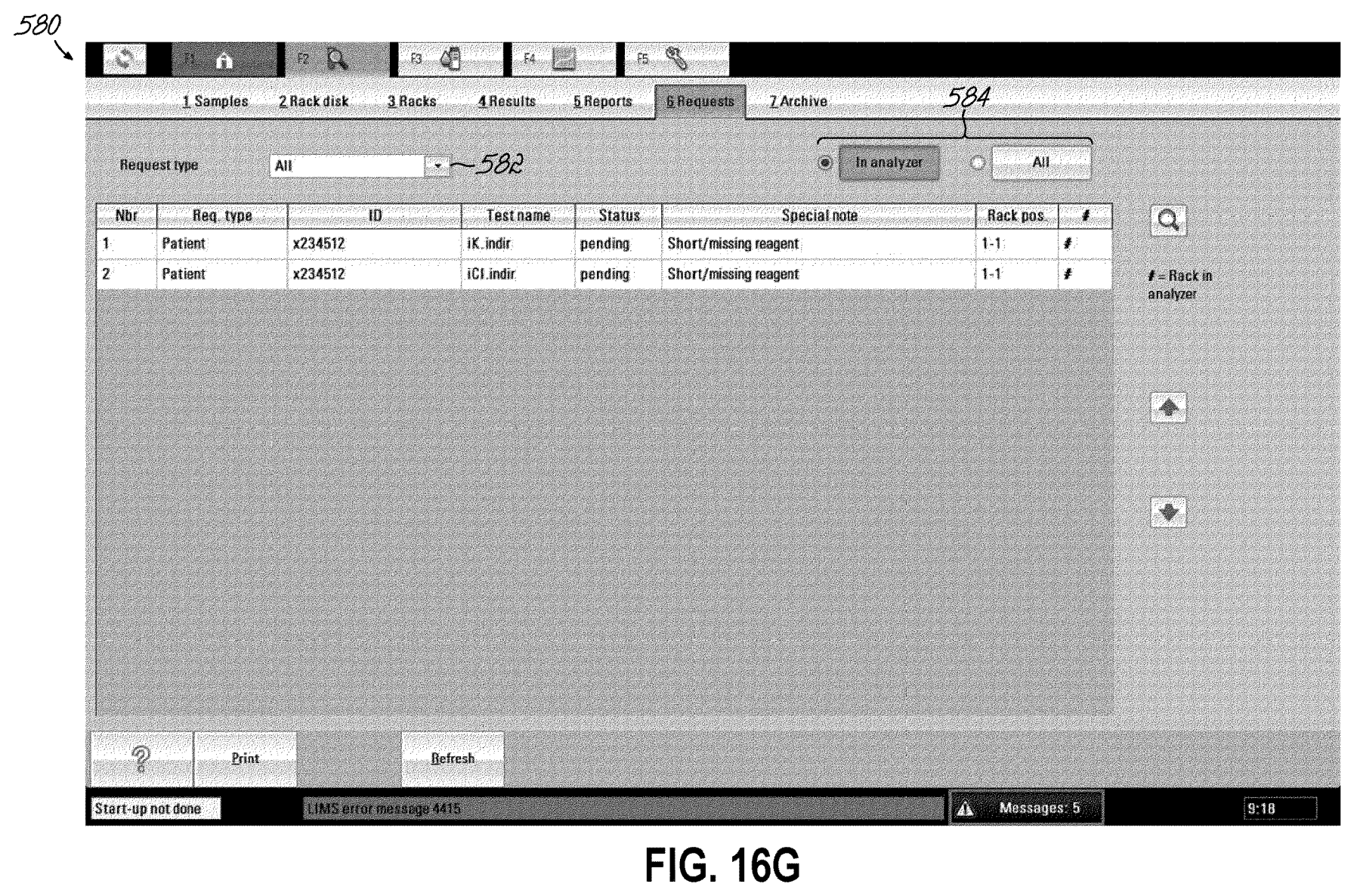

FIGS. 16E-16G illustrate a plurality of additional screens that may be provided by the system 10 (FIG. 1) consistent with embodiments of the present invention. Specifically, one or more of the screens illustrated in FIGS. 16E-16G may be provided in addition to, or instead of, one or more of the screens illustrated in FIGS. 16A-16D. In particular, FIG. 16E illustrates a specimen information screen 550 that may be provided by the system 10 (FIG. 1) consistent with embodiments of the present invention. The specimen information screen 550 provides a specimen section 552 that indicates information associated with a specimen 23 (FIG. 2) in the system 10 (FIG. 1), and in particular lists its location within the system 10 (FIG. 1) and/or in a vessel 58 (FIG. 2) and/or a particular vessel rack 84 (FIG. 3B), if used. The specimen section 552 also provides a list of each specimen 23 (FIG. 2) in the system 10 (FIG. 1). As such, a particular specimen 23 (FIG. 2) in the list can be selected and the information associated therewith viewed in a specimen data section 554. The specimen data section 554 indicates information associated with a selected specimen 23 (FIG. 2) as well as allows the user to input data about that particular specimen 23 (FIG. 2). In particular, the user may specify the type of specimen in a specimen type control 555, information associated with the specimen 23 (FIG. 2) (e.g., such as a Time to Return results or a Time to Prepare the specimen 23) in a information control 556, as well as view the tests for the specimen 23 (FIG. 2) and any results in a specimen test status control 557. Moreover, the user may designate a selected specimen as a priority specimen by selecting a "Priority" button 558.

As illustrated in FIG. 16E, the specimen information screen 550 may also includes a position indicator 560 and, optionally, a rack indicator 559 indicating the position and rack, respectively, of the specimen 23 (FIG. 2) in the vessel 58 (FIG. 3A) or vessel rack 84 (FIG. 3B). The specimen information screen 550 further includes a status indicator 561 to indicate the status of the specimen 23 (FIG. 2) or prepared sample thereof. In one embodiment, the specimen information screen 550 further includes a specimen interaction section 562 that may include a plurality of buttons for the user to specify data associated with the specimen 23 (FIG. 2), including the particular type of tests to perform on the specimen 23 (FIG. 2).

FIG. 16F illustrates a specimen location screen 570 that graphically illustrates the locations of specimens 23 (FIG. 2) within the system 10 (FIG. 1) and, optionally, in respective vessels 58 (FIG. 3A) or vessel racks 84 (FIG. 3B) loaded into the system 10 (FIG. 1) consistent with embodiments of the present invention. As illustrated in FIG. 16F, each vessel 58 (FIG. 3A) or vessel rack 84 (FIG. 3B) is illustrated in a particular row and, if appropriate, each specimen 23 (FIG. 2) of that vessel 58 (FIG. 3A) or vessel rack 84 (FIG. 3B) is illustrated in a corresponding column along with some information about that specimen 23 (FIG. 2). As such, the specimen location screen 570 may provide the user with a more easily understood graphical illustration of the location of any particular specimen 23 (FIG. 2) of the system 10 (FIG. 1) than the specimen section 552 of FIG. 16E. As an example, the sole sample listed in the specimen section 552 of FIG. 16E is illustrated in FIG. 16F at the first vessel rack 84 (FIG. 3B) in the first position thereof. Additional control samples are illustrated in the fifth vessel rack 84 (FIG. 3B) in corresponding positions. Information corresponding to the sample is also illustrated in the specimen location screen 570, including the ID of the specimen 23 (FIG. 2) (i.e., x234512), as well as the number of assays that have been performed on prepared samples of the specimen 23 (FIG. 2) in relation to the total number of assays to perform on prepared samples of the specimen 23 (FIG. 2) (i.e., the indication of "0/2," with zero being the number of assays that have been performed on prepared samples of the specimen 23 (FIG. 2) and two being the total number of assays to perform on prepared samples of the specimen 23 (FIG. 2)).

FIG. 16G illustrates a test status screen 580 that illustrates the status of each test to be performed by the system 10 (FIG. 1) consistent with embodiments of the present invention. Users can sort the tests by assay type with a test type control 582, as well as sort the tests by those that have specimens 23 (FIG. 2) that are currently loaded in the system 10 (FIG. 1), generally, or in a vessel 58 (FIG. 3A), on vessel racks 84 (FIG. 3B) in the system 10 (FIG. 1) with a vessel rack control 584. In any event, the test status screen 580 indicates the request type of each test (e.g., as illustrated, "Patient" requests), the ID of the specimen 23 (FIG. 2) for each test, and the assay type for the test. The test status screen 580 further illustrates the status of each test and any notes associated with the tests, as well as the rack position of the specimen 23 (FIG. 2) for each test and whether the vessel 58 (FIG. 3A) or the vessel rack 84 (FIG. 3B) with the specimen 23 (FIG. 2) of the test is loaded into the system 10 (FIG. 1).

A person having ordinary skill in the art will recognize that the environments illustrated in FIGS. 1-16G are not intended to limit the scope of embodiments of the present invention. In particular, system 10, the sample preparation station 20, sample preparation controller 22, the sample analysis station 24, and/or the sample analysis controller 26 may have alternative configurations consistent with alternative embodiments of the invention. For example, the sample preparation station 20 and the sample analysis station 24 may not be provided in a single housing but may instead be physically spaced from each and connected through at least one data communication link (e.g., such as links 315*a*, 315*b*, 315*c* and/or a link through network 30) as well as through at least one transport mechanism (e.g., to provide prepared samples from the sample preparation station 20 to the sample analysis station 24). Also for example, the sample preparation station 20 and the sample analysis station 24 may be integrated with each other within a single housing, yet retain their respective and distinct functions.

Moreover, the system 10, the sample preparation station 20, the sample preparation controller 22, the sample analysis station 24, and/or the sample analysis controller 26 may include fewer or additional components consistent with alternative embodiments of the present invention. Indeed, a person having skill in the art will recognize that other alternative hardware and/or software environments may be used without departing from the scope of the present invention. For example, the control application 318 and/or the sample analysis application 418 may be configured with fewer or additional modules, while the memory 304 may be configured with fewer or additional data structures. Additionally, a person having ordinary skill in the art will appreciate that the sample preparation controller 22 and/or sample analysis controller 26 may include more or fewer applications disposed therein. As such, other alternative hardware and software environments may be used without departing from the scope of the present invention.

Still further, a person having ordinary skill in the art will recognize that the screenshots illustrated in FIGS. 16A-16G are not intended to limit the scope of embodiments of the present invention. In particular, the screens illustrated by the screenshots of FIGS. 16A-16G may include more or fewer sections, user interfaces, or human perceptible components consistent with embodiments of the present invention.

The routines executed to implement the embodiments of the present invention, whether implemented as part of an operating system or a specific application, component, program, object, module or sequence of instructions executed by one or more computing systems or controllers will be referred to herein as a "sequence of operations," a "program product," or, more simply, "program code." The program code typically comprises one or more instructions that are resident at various times in various memory and storage devices in a computing system or controller, and that, when read and executed by one or more processors of the computing system or controller, cause that computing system or controller to perform the steps necessary to execute steps, elements, and/or blocks embodying the various aspects of the present invention.

While the present invention has and hereinafter will be described in the context of fully functioning computing systems and controllers, those skilled in the art will appreciate that the various embodiments of the present invention are capable of being distributed as a program product in a variety of forms, and that the invention applies equally regardless of the particular type of computer readable signal bearing media used to actually carry out the distribution. Examples of computer readable signal bearing media include but are not limited to physical and tangible recordable type media such as volatile and nonvolatile memory devices, floppy and other removable disks, hard disk drives, optical disks (e.g., CD-ROM's, DVD's, etc.), among others.

In addition, various program code described hereinafter may be identified based upon the application or software component within which it is implemented in a specific embodiment of the present invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the present invention is not limited to the specific organization and allocation of program functionality described herein.

Figure 17:
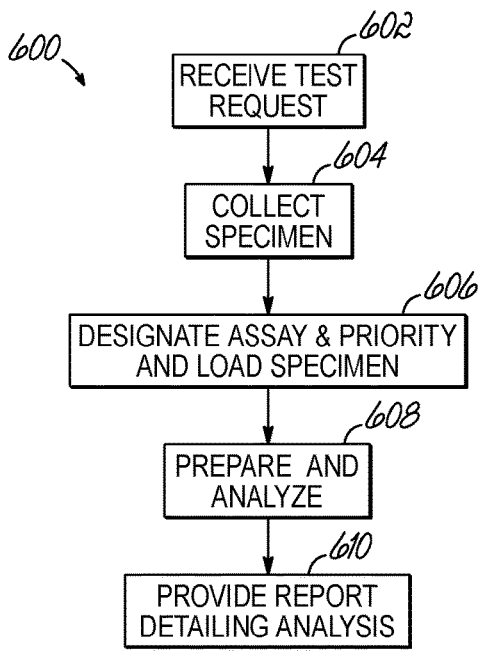
FIG. 17 is a flowchart illustrating a sequence of the operations for collecting, preparing, and analyzing a prepare sample in accordance with one embodiment of the present invention.

Consistent with embodiments of the present invention, an automated preparation and analysis system may be used to automatically prepare a specimen for a selected test in accordance with a predetermined assay. FIG. 17 is a flowchart 600 illustrating a sequence of operations that generally describes the operational flow for collecting a specimen, preparing a sample of that specimen, and analyzing a prepared sample of that specimen consistent with embodiments of the present invention. Initially a test request, order, or procedure prescription is received, such as from a prescribing physician or a laboratory technician, and input by a user into a hospital or laboratory system (block 602). A user, for example, may be a medical transcriptionist, phlebotomist, or laboratory technician that inputs the test request into a LIS system. The test request is transmitted as appropriate to an individual who collects the appropriate specimen (block 604) in a manner that is well known. For example, blood samples may be collected into septum covered test tube via a syringe port while environmental samples may be collected using a swab and deposited into a collection vessel including transport media.

Once the specimen is in an appropriate specimen container, such as a vessel that may be used by the automated preparation and analysis system, a user may designate an assay for preparation and analysis of the specimen, a priority and/or a desired time to return a result of the analysis for the specimen, and load the specimen (block 606). Then, in accordance with the procedures set forth in greater detail below, the system samples the specimen and generates a prepared sample that is subsequently analyzed (e.g., the analytes of the prepared sample are quantified) in accordance with one or more assays (block 608). Once the analysis is complete, the system prepares results and provides them in a report in an appropriate human perceptible form for the user, such as the prescribing physician or laboratory technician (block 610).

The automated sample preparation and analysis system is configured to automatically prepare specimens with a sample preparation station for analysis by a sample analysis station. The sample analysis station, in turn, is configured to analyze the prepared sample generated from the specimen and output data relating to an analysis of the analytes of the prepared sample. The sample preparation station is under control of a sample preparation controller while the sample analysis station is under the control of a sample analysis controller.

Figure 18:
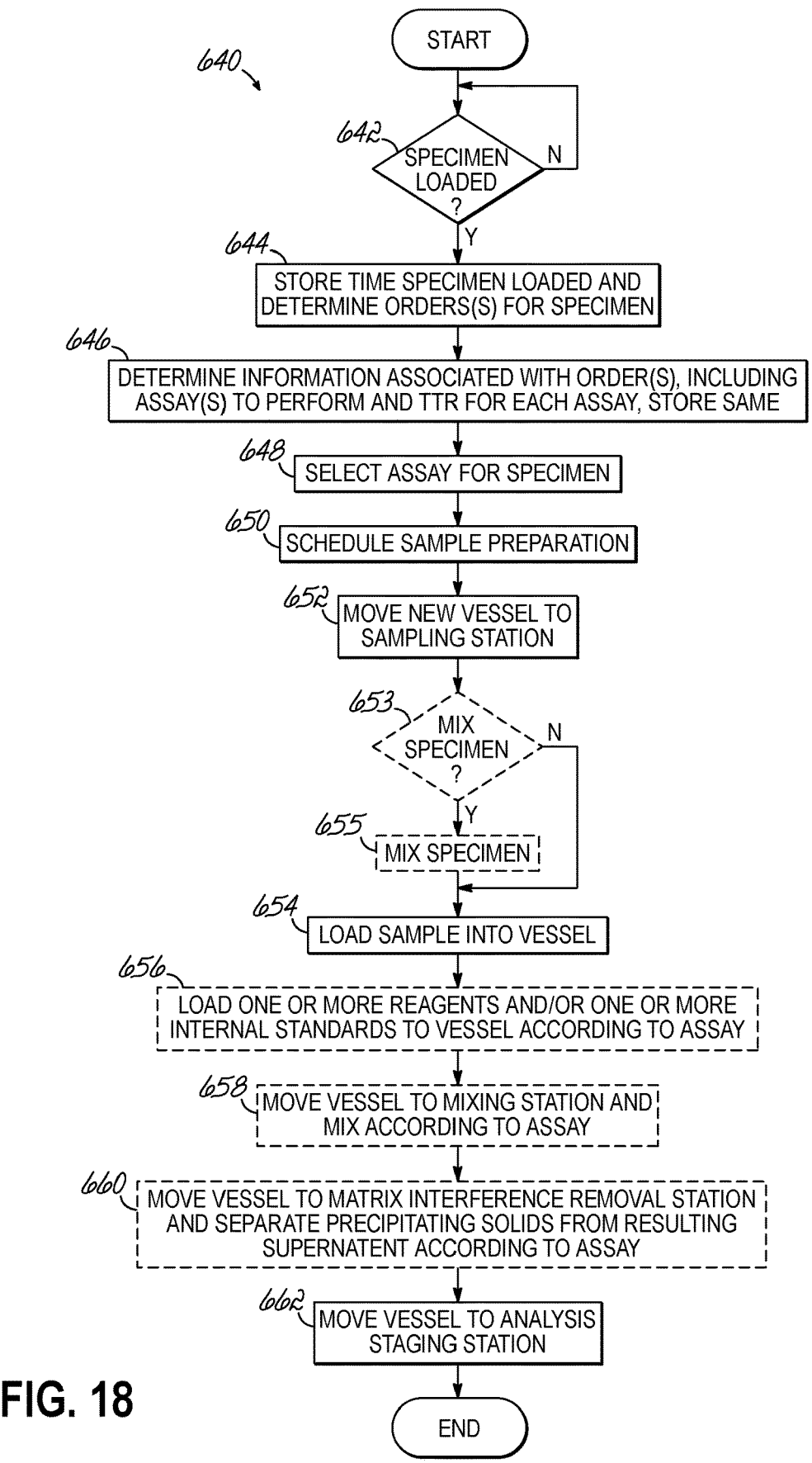
FIG. 18 is a flowchart illustrating a sequence of operations for preparing a sample in accordance with one embodiment of the present invention.

FIG. 18 is a flowchart 640 illustrating a sequence of operations for the sample preparation controller to operate the sample preparation station to prepare a sample consistent with embodiments of the present invention. Initially, the sample preparation controller determines whether a specimen has been loaded to the system (block 642). When a specimen has not been loaded ("No" branch of decision block 642), the sequence of operations returns back to block 642. When a specimen has been loaded ("Yes" branch of decision block 642) the sample preparation controller determines at least one order, i.e., a test, for the sample (block 644) and determines information associated with the at least one order, including at least one assay type to perform as well as a Target Time to Result (hereinafter referred to, and illustrated as, "TTR") and optionally a Target Time to Prepare the Sample (hereinafter referred to, and illustrated as "TTP"), for each assay (block 646). In particular, the sample preparation controller may determine the order for testing the sample and the information associated with that order via a user input device of the sample preparation controller or by associating an indication of assay included within a barcode or RFID antenna on the vessel with information stored at the sample preparation controller stored across a network, such on a LIS.

When an assay type and its respective TTR have been determined, the sample preparation controller is configured to select the assay from a plurality of unique assays to be performed on the specimen (block 648), including the methodologies for preparing and analyzing the sample. For example, the assay may specify the types of reagents to add to the sample, whether mixing, centrifuging, and/or incubation of the sample are required, and an indication of the type of analysis to perform on the prepared sample.

After selecting the assay for each assay type ordered for the specimen (block 648), the sample preparation controller schedules the sample preparation (block 650). After sample preparation is scheduled (block 650), the sample preparation controller controls the sample preparation station to move a new vessel to a sampling station (block 652). The sample preparation controller may then determine whether the particular specimen to be loaded should be mixed (block 653). If the specimen is of the type that separation may inherently occur over time, for example, the separation of red blood cells from the plasma in a blood specimen, then mixing may be necessary to ensure a proper sampling of the specimen is loaded for testing. If mixing is necessary, or desired ("Yes" branch of decision block 653), then the specimen is mixed (block 655). Mixing may occur in any manner that is generally known, including aspirating/dispensing multiple times with the sample pipette assembly, stirring the specimen with the pipette shaft of the sample pipette assembly, use of a stir bar, use of a vortex mixer, or any other known method. With mixing complete, or if the determination was that mixing was not necessary ("No" branch of decision block 653), then at least a portion of the specimen (i.e., a sample of the specimen) is aspirated and loaded into the vessel (block 654). The sample preparation controller may then control the sample preparation station to prepare the sample for analysis, such as by LCMS.

For example, in conventional mass spectrometry of samples for analysis of the presence and quantitation of a small molecule analyte, samples are prepared by combining them with one or more reagents or solvents in a vessel, mixing the contents of the vessel, then separating contaminants from a supernatant containing one or more analytes of interest. The assay may define one or more reagents to mix with the sample, if any, at one or more time points in the assay, and when and whether to mix and/or use the matrix interference removal station with that sample. As such, the sample preparation controller may optionally load one or more reagents and/or one or more internal standards (i.e., a known quantity of an analyte for quantitative comparative analysis) to the vessel according to the assay (e.g., the assay associated with the sample in the vessel) (block 656), optionally move the vessel to the mixing station and mix the contents of that vessel according to the assay (block 658), and optionally move the vessel to the matrix interference removal station to separate precipitating solids from resulting supernatant liquid according to the assay (block 660). After the sample preparation steps, the sample preparation controller moves the vessel to an analysis staging station (block 662). At the analysis staging station, the prepared sample waits for selection and injection into the sample analysis station.

In conventional mass spectrometry analysis of samples for the presence and quantization of a protein or peptide analyte, the samples may be prepared by combining the sample with one or more reagents or proteases in a vessel, mixing the contents of the vessel, and then isolating one or more proteins or peptides of interest. The assay may define one or more reagents or proteases to mix with the sample, if any, at one or more time points in the assay, and when and whether to mixed and/or incubate the sample. As such, the sample preparation controller may optionally load one or more reagents, proteases, and/or one or more internal standards (i.e., a known quantity of a labeled analyte for quantitative comparative analysis) to the vessel according to the assay (e.g., the assay associated with the sample in the vessel), optionally move the vessel to the mixing station and mix the contents of that vessel according to the assay, and optionally move the vessel to the incubator according to the assay. After the sample preparation steps, the sample preparation controller moves the vessel to an analysis staging station. At the analysis staging station, the prepare sample waits for selection and injection into the sample analysis station.

Figure 19:
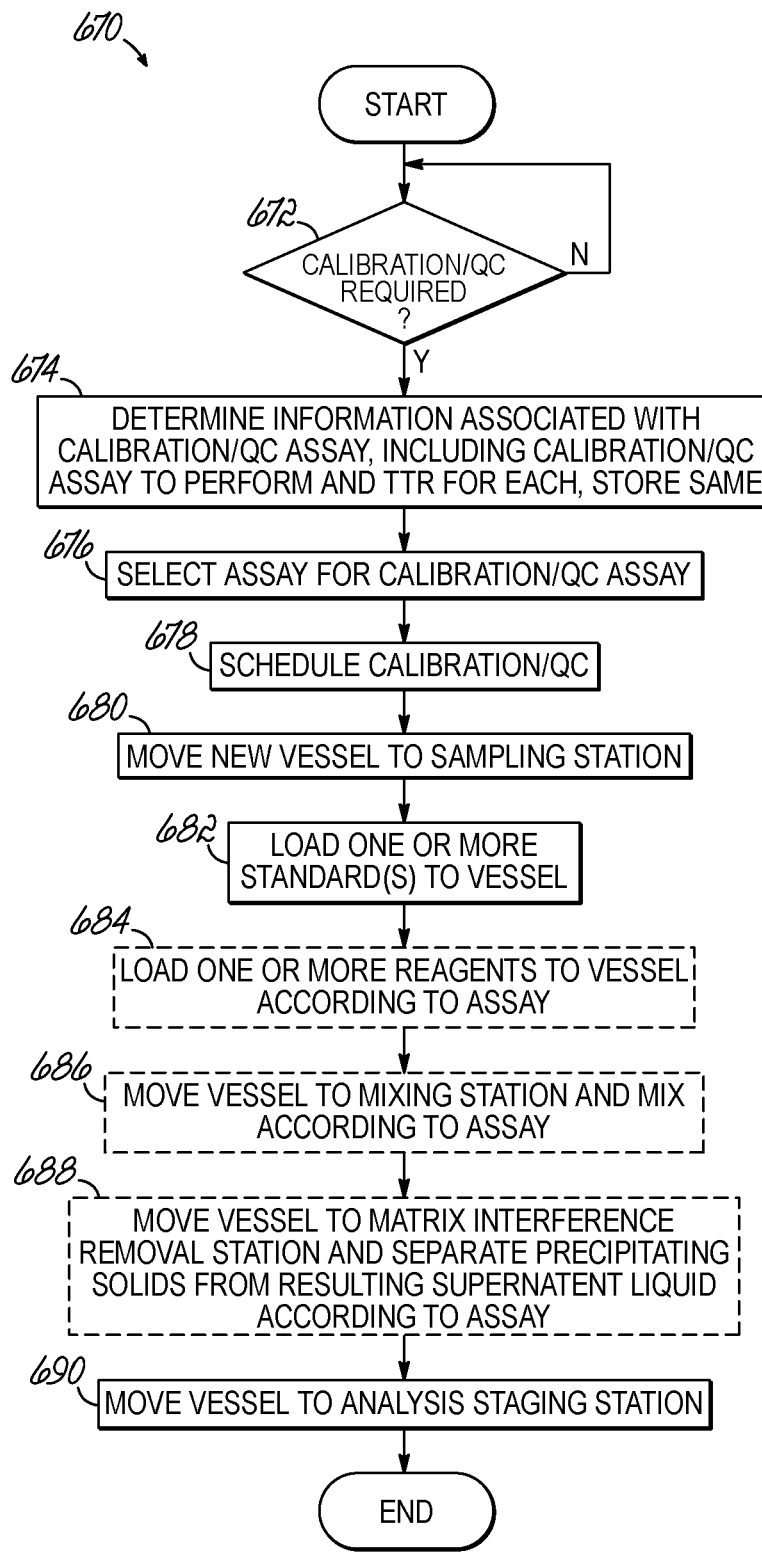
FIG. 19 is a flowchart illustrating a sequence of operations for preparing a calibration and/or control standard in accordance with one embodiment of the present invention.

FIG. 19 is a flowchart 670 illustrating a sequence of operations for the sample preparation controller to operate the sample preparation station to prepare a calibration and/or control standard consistent with embodiments of the present invention. The sample preparation controller initially determines whether a calibration and/or control test is required (block 672). When a calibration or control is not required (e.g., a calibration and/or control has not been automatically or manually added to the system) ("No" branch of decision block 672) the sequence of operations returns to block 672. However, when a calibration or control is required ("Yes" branch of decision block 672) the sample prep controller is configured to determine and select the appropriate assay for the calibration or control (blocks 674, 676) from a plurality of unique assays. The vessel containing the calibration or control standard may include a barcode and/or RFID antenna that is read by an information acquisition device to indicate the appropriate assay to be selected.

After selecting the assay for the calibration or control (block 676), the sample preparation controller schedules the calibration or control (block 678). The sample preparation controller then controls the sample preparation station to move a new vessel to the sampling station (block 680) and load at least one internal standard (i.e., a known quantity of control standard for control analysis or a known quantity of a calibration standard for a calibration) to the vessel (block 682). The sample preparation controller may optionally load one or more reagents or solvents to the vessel according to the assay for preparing the calibration or control standard (block 684), optionally move the vessel to the mixing station and mix the contents of that vessel according to the assay (block 686), and optionally move the vessel to the matrix interference removal station to separate precipitating solids from resulting supernatant liquid according to the assay (block 688). After the preparation steps, the sample preparation controller moves the vessel to an analysis staging station (block 690). At the analysis staging station, the prepared calibration or control vessel waits for selection and injection to the sample analysis station.

During operation, the automated sample preparation and analysis system is configured to prepare a plurality of samples and prioritize the preparation of those samples according to a Target Time to Result ("TTR"). This allows the system to dynamically change its operation to prepare and analyze a later received sample before an earlier received sample. The TTR may be specified by a user or automatically set by the system when there is no user specified time. For example, certain specimen types, such as blood or saliva, may degrade relatively quickly, while alternative specimen types, such as urine, degrade relatively slowly.

As such, the system may automatically assign a specimen type TTR to specimen types that degrade relatively quickly (e.g., the specimen type TTR being a value that ensures that samples from particular specimen types are processed before they may degrade to a point where they are unusable) and assign a system TTR to specimen types that degrade relatively slowly (e.g., the system TTR being a time before which the samples from other specimen types should be processed by the system). Additionally, or alternatively, the system may determine that a particular specimen is a priority specimen without a user specified TTR. As such, the system may assign an adjusted specimen type TTR (e.g., if the specimen type is of the type that degrades relatively quickly), an adjusted system TTR (e.g., if the specimen type is of the type that does not degrade relatively quickly), or a predetermined priority TTR to the assays for the priority specimens. In specific embodiments, the adjusted specimen type TTR may be half the normal specimen type TTR, the adjusted system TTR may be half the normal system TTR, and the priority TTR may be specified by a user or manufacturer of the system.

Figure 20:
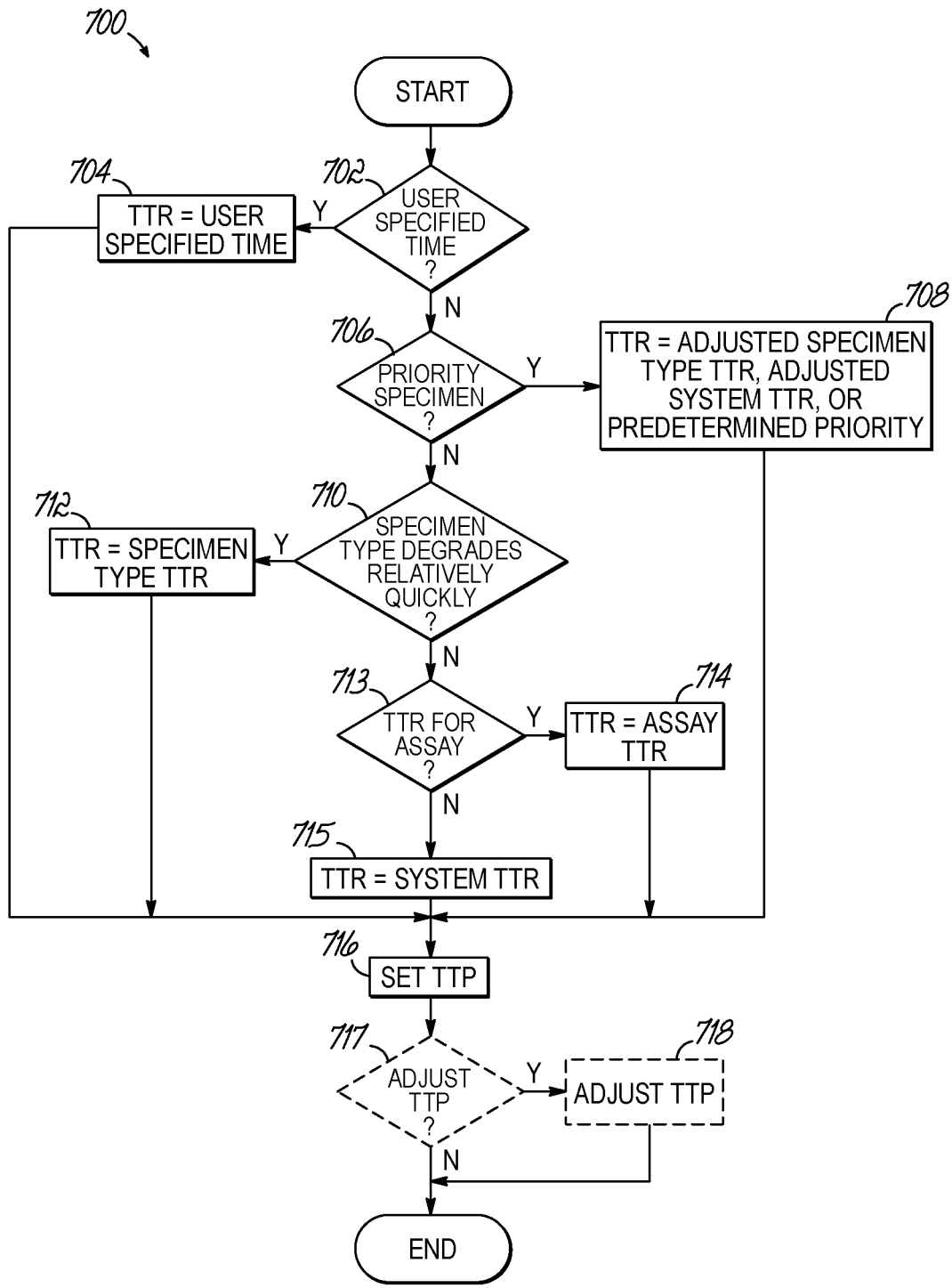
FIG. 20 is a flowchart illustrating a sequence of operations for preparing a specimen with an appropriate time to result in accordance with one embodiment of the present invention.

FIG. 20 is a flowchart 700 illustrating a sequence of operations for the sample preparation controller to associate the preparation of a specimen with an appropriate TTR consistent with embodiments of the invention. Specifically, the sample preparation controller determines if a user has specified a time for the completion of the test, i.e., the preparation and analysis of a sample in accordance with a predetermined assay (block 702). When the user has specified a time for the completion of the test ("Yes" branch of decision block 702), the sample preparation controller sets the TTR to that user specified time (block 704) and the sequence of operations may end. When the user has not specified a time for the completion of the test ("No" branch of decision block 702), the sample preparation controller determines whether the specimen is a priority specimen (block 706). When the specimen is a priority specimen ("Yes" branch of decision block 706) the sample preparation controller sets the TTR to an adjusted specimen type TTR, an adjusted system TTR, or a predetermined priority TTR, whichever is shortest (block 708), and the sequence of operations may end. When the specimen is not a priority specimen ("No" branch of decision block 706) the sample preparation controller determines whether the specimen is of the type that degrades relatively quickly (block 710). When the specimen is of the type that degrades relatively quickly ("Yes" branch of decision block 710), the sample preparation controller sets the TTR to a specimen type TTR that corresponds to the specimen type of the sample (block 712) and the sequence of operations may end. When the specimen is not of the type that degrades relatively quickly ("No" branch of decision block 710), the sample preparation controller determines whether the assay associated with the specimen has a predetermined TTR (block 713). When the assay associated with the specimen has a predetermined TTR ("Yes" branch of decision block 713), the sample preparation controller sets the TTR to the TTR for the assay (block 714). However, when the assay associated with the specimen does not have a predetermined TTR ("No" branch of decision block 713), the sample preparation controller sets the TTR to the system TTR (block 715).

In some embodiments, it may be beneficial to set a Target Time to Prepare ("TTP"), such as when a number of tests are in queue and the prepared sample would be considered to be more stable than a specimen awaiting preparation. Accordingly, the sample preparation controller may specify a TTP for each specimen which indicates a target time for the preparation of that specimen. The TTP, however, may be subsequently adjusted. For example, and as explained above, some specimens may be of the type that degrade relatively quickly. For those specimens, it may be advantageous to prepare them more quickly. As such, and in an optional step, the sample preparation controller sets a TTP for the specimen (block 716) and determines whether to adjust the TTP in accordance with the specimen type and/or another designation by the user (block 717). When the TTP requires no adjustment ("No" branch of decision block 717), the sequence of operations may end. If an adjustment in TTP is required ("Yes" branch of decision block 717), the adjustment is made in accordance with a predetermined mathematical formula (block 718) and the sequence of operations may end.

A scheduler of the sample preparation controller may be configured to determine the order in which to prepare samples within the sample preparation station, as well as reserve the components thereof accordingly for the system to prepare samples for subsequent analysis within the TTR.

Figure 21:
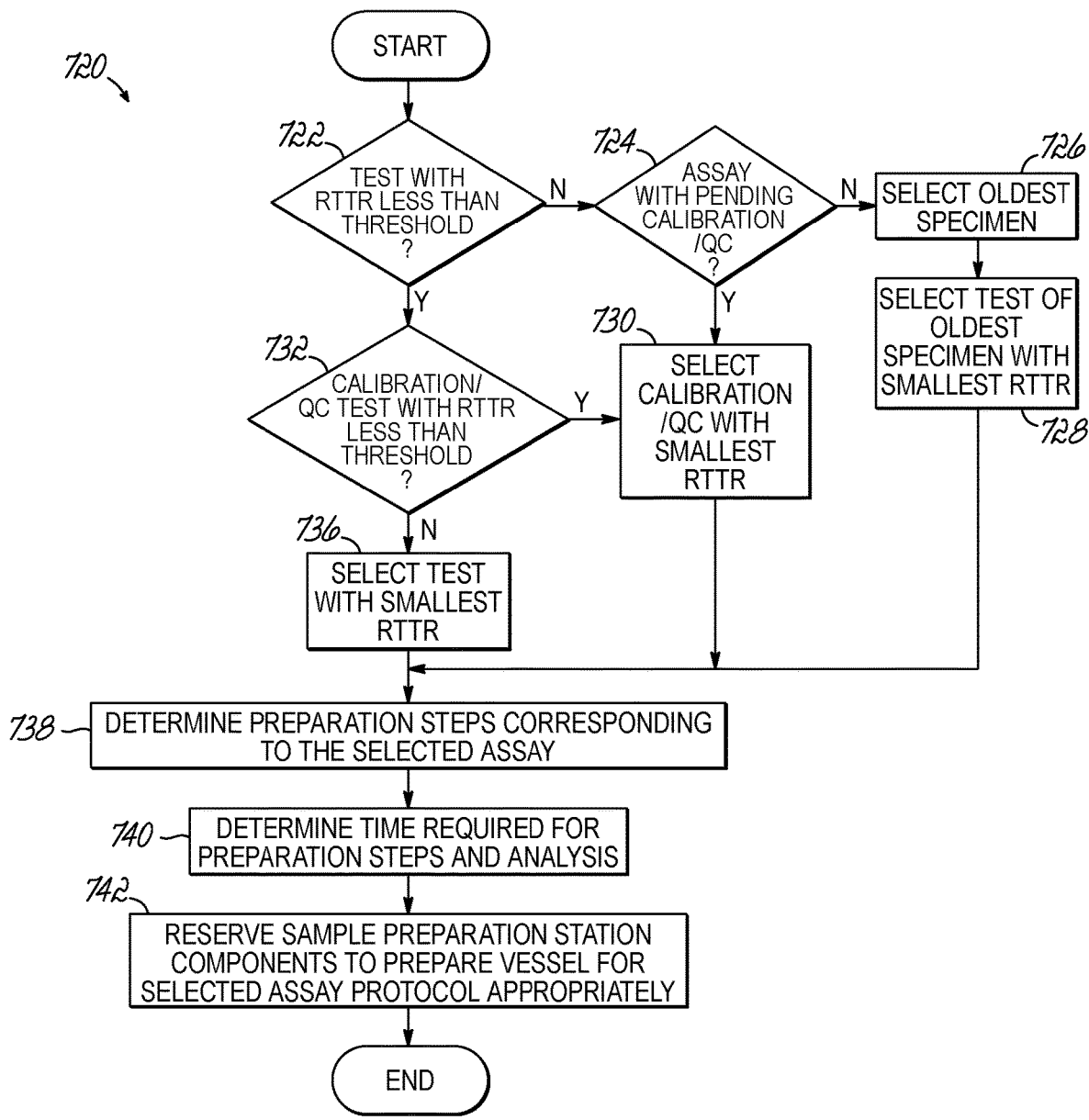
FIG. 21 is a flowchart illustrating a sequence of operations for a scheduler to determine the steps of preparing a sample according to one embodiment of the present invention.

FIG. 21 is a flowchart 720 illustrating a sequence of operations for the scheduler to determine the steps to prepare a sample according to a predetermined assay and correspondingly schedule the components of the sample preparation station consistent with embodiments of the present invention. The scheduler initially determines if there are any tests (sample preparation and analysis) that have a Remaining Target Time to Result (hereinafter referred to, and illustrated as, "RTTR") less than a predetermined threshold (e.g., which may be a time much larger than that typically required to prepare and analyze a sample, and which may be about an hour) (block 722). When the scheduler determines that there are no tests with an RTTR less than the predetermined threshold ("No" branch of decision block 722), the scheduler determines whether there is a calibration or control standard that needs to be prepared for a calibration or control of the system, i.e., whether there is an assay with a pending calibration or control (block 724). If there is no calibration or control standard that needs to be prepared ("No" branch of decision block 724) the scheduler selects the oldest specimen in the system (e.g., the specimen that was loaded earliest) (block 726) and selects the test for that oldest specimen with the smallest RTTR (block 728).

Returning to block 724, when there is an assay with a pending calibration or control requiring calibration standards or control standards to be tested (prepared and analyzed) ("Yes" branch of decision block 724), the scheduler selects the calibration or control test with the smallest RTTR (block 730). Returning to block 722, when there is a test with an RTTR less than the predetermined threshold ("Yes" branch of decision block 722), the scheduler determines whether there is a calibration or control test request with an RTTR less than the predetermined threshold (block 732).

When there is a calibration or control test with an RTTR less than the predetermined threshold ("Yes" branch of decision block 732), the scheduler selects the calibration or control test with the smallest RTTR (block 730). However, when there is no calibration or control test with an RTTR less than the predetermined threshold ("No" branch of decision block 732), the scheduler selects the test (for a specimen) with the smallest RTTR (block 736).

In response to selecting the test of the oldest specimen with the smallest RTTR (block 728), selecting the calibration or control test with the smallest RTTR (block 730), or selecting the test with the smallest RTTR (block 736), the scheduler determines the preparation steps and methodologies corresponding to the selected assay (block 738), determines an estimated time required for the test, i.e., the preparation and analysis steps (e.g., with such a determination taking into account previously determined estimations for the time required to prepare and/or analyze previous samples) (block 740), and reserves sample preparation station components to prepare the sample within the vessel in accordance with the assay and as appropriate with respect to the RTTR (block 742), if able. In this manner, the scheduler may prepare samples from the specimens or vessels for calibration or control tests appropriately and with respect to their RTTR for analysis within the RTTR.

The sample preparation controller is configured to routinely check whether a particular assay may be performed by the system. For example, a particular assay cannot be performed when there is no valid calibration data for that assay or when there is not enough of a particular consumable (e.g., a reagent, solutions, internal standard, and so forth) required to complete a test in accordance with that assay. For example, the system may be configured to perform categories of assays, such as therapeutic drug monitoring assays (detection of immunosuppressants such as tacrolimus, everolimus, sirolimus, and cyclosporin A or chemotherapeutics such as methotrexate, busulfan, 5-fluorouracil, and docetaxel), endocrinological assays (detection of 25OH vitamin D2, 25OH vitamin D3, testosterone, cortisol, hydrocortisone, cortisone, progesterone, hydroxyprogesterone, predisone, and androstenedione), and pain management or drugs-of-abuse assays (detection of phencyclidine, benzoylecgonine, cocaine, delta9-THC, 11-norDelta, 9-THC-COOH, amphetamine, methamphetamine, MDMA, opiates/opiods, hydromorphone, norhydrocodone, norcodeine, morphine, hydrocodone, codeine, noroxycodone, oxymorphone, dihydrocodeine, oxycodone, 6-MAM, tapentadol, norfentanyl, fentanyl, tramadol, methadone, and metoprolol). It would be appreciated that this listing of possible analytes is not all-inclusive but rather additional analytes, such as proteins and other large molecules, obtained from patient samples or environmental samples, may also be analyzed with selection of proper separation and analytical techniques known to those of ordinary skill in the art. Each category of assay, in turn, may include individual types of assays that are specific to a particular therapeutic drug, hormone, or drug-of-abuse, and so forth and thus require specific consumables and/or parameters for preparation and/or analysis thereof.

Figure 22:
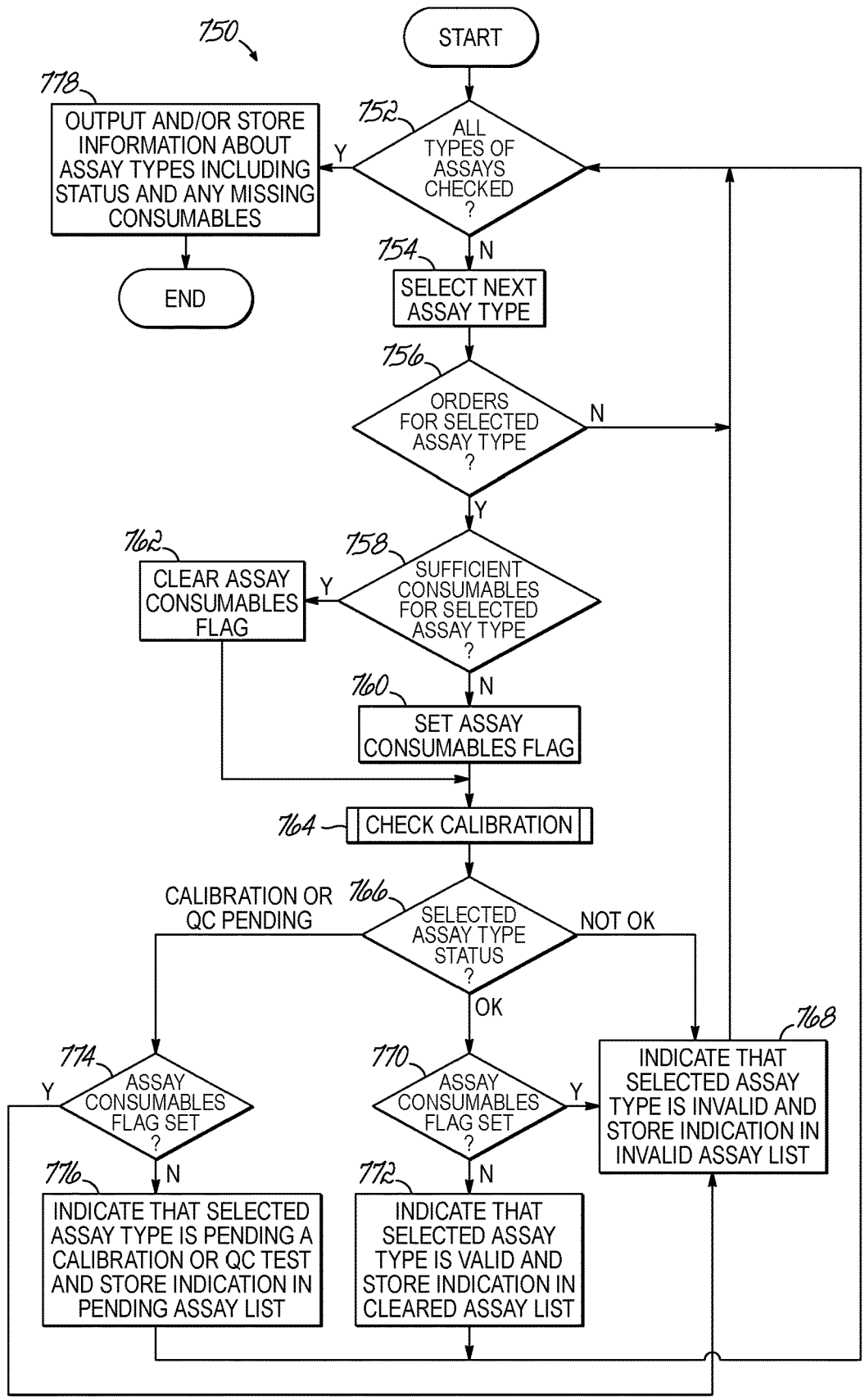
FIG. 22 is a flowchart illustrating a sequence of operations for determining whether a particular assay may be performed and according to one embodiment of the present invention.

FIG. 22 is a flowchart 750 illustrating a sequence of operations for the sample preparation controller to determine whether a particular assay may be performed by the system consistent with embodiments of the present invention. For example, the sample preparation controller may determine, upon initialization, what types of assays can be performed by inquiring for that information from the sample analysis controller. The sample preparation controller, in turn, determines whether those types of assays may be performed. Thus, the sample preparation controller determines whether all types of assays that may be performed by the system have been checked (block 752). When all types of assays have not been checked ("No" branch of decision block 752) the sample preparation controller may select the next assay type (block 754) and determine whether there are any orders for that selected assay type (block 756). When there are no orders for the selected assay type ("No" branch of decision block 756), the sequence of operations may return to block 752. However, when there are orders for the selected assay type ("Yes" branch of decision block 756), the sample preparation controller determines whether there are sufficient consumables for testing a sample in accordance with the selected assay type (block 758).

The system may include one or more reagents, solvents, or internal standards for testing one or more samples in accordance with one or more assays. The sample preparation controller, in turn, tracks the levels of each reagent, solvent, and internal standard and/or the use of each reagent, solvent, and/or internal standard to determine when such reagents, solvents, or internal standards are low and/or depleted. As such, when the volume of at least one reagent, solvent, and/or internal standard for use in accordance with the selected assay type is insufficient (e.g., is low or has a volume that is not enough to use to fully test a sample associated with that selected assay protocol) ("No" branch of decision block 758), the sample preparation controller sets an assay consumables flag (block 760). However, when the volume of each reagent, solvent, and/or internal standard associated with of the selected assay type is sufficient ("Yes" branch of decision block 758) the sample preparation controller clears the assay consumables flag (block 762).

In response to setting the assay consumables flag (block 760) or clearing the assay consumables flag (block 762), the sample preparation controller performs a calibration checking subroutine (block 764) to determine whether the selected assay type is associated with valid calibration data. After the calibration checking subroutine (block 764) the sample preparation controller determines the status of the selected assay type (e.g., whether it is time for a calibration assay for the selected assay type or whether the results of a check of the selected assay type indicate that the present calibration is no longer valid) (block 766). When the status of the selected assay type is not OK (e.g., the selected assay type is not associated with valid calibration data and there is a calibration or control test pending for that selected assay type) ("NOT OK" branch of decision block 766), the sample preparation controller indicates that the selected assay type is invalid and stores an indication of such in an invalid assay list (block 768). However, when the status of the selected assay type is OK (e.g., the selected assay type is associated with valid calibration data and there is no calibration or control test pending for that selected assay type) ("OK" branch of decision block 766), the sample preparation controller determines whether the assay consumables flag is set (block 770).

When the assay consumable flag is set (e.g., indicating that the volume of at least one reagent, solvent, and/or internal standard for use in accordance with the selected assay type is insufficient) ("Yes" branch of decision block 770), the sequence of operations proceeds to block 768. However, when the assay consumable flag is not set (e.g., indicating that the volume of each reagent, solvent, and/or internal standard for use in accordance with the selected assay type is sufficient) ("No" branch of decision block 770), the sample preparation controller indicates that the selected assay type is cleared to be run by the system (e.g., valid) and stores an indication of such in a valid assay list (block 772). Returning to block 766, when the status of the selected assay type indicates that a calibration or control test is pending ("CALIBRATION OR QC PENDING" branch of decision block 766), the sample preparation controller determines whether the assay consumables flag is set (block 774). When the assay consumables flag is not set ("No" branch of decision block 774), the sample preparation controller indicates that the selected assay type is pending a calibration or control test and stores and indication of such in a pending assay list (block 776) and the sequence of operations may return to block 752. Otherwise, if a consumables flag is set ("Yes" branch of decision block 774), then the sequence of operations goes to block 768.

In response to block 768, block 772, or block 776, or in response to determining that the assay consumable flag is not set for a selected assay type whose status is that a calibration or control test is pending ("No" branch of decision block 774), the sequence of operations returns to block 752. Referring to block 752, when all types of assays have been checked ("Yes" branch of decision block 752), the sample preparation controller outputs and/or stores information about each assay type, including their statuses and whether there are any missing or low consumables (block 778), after which the sequence of operations may end.

Figure 23:
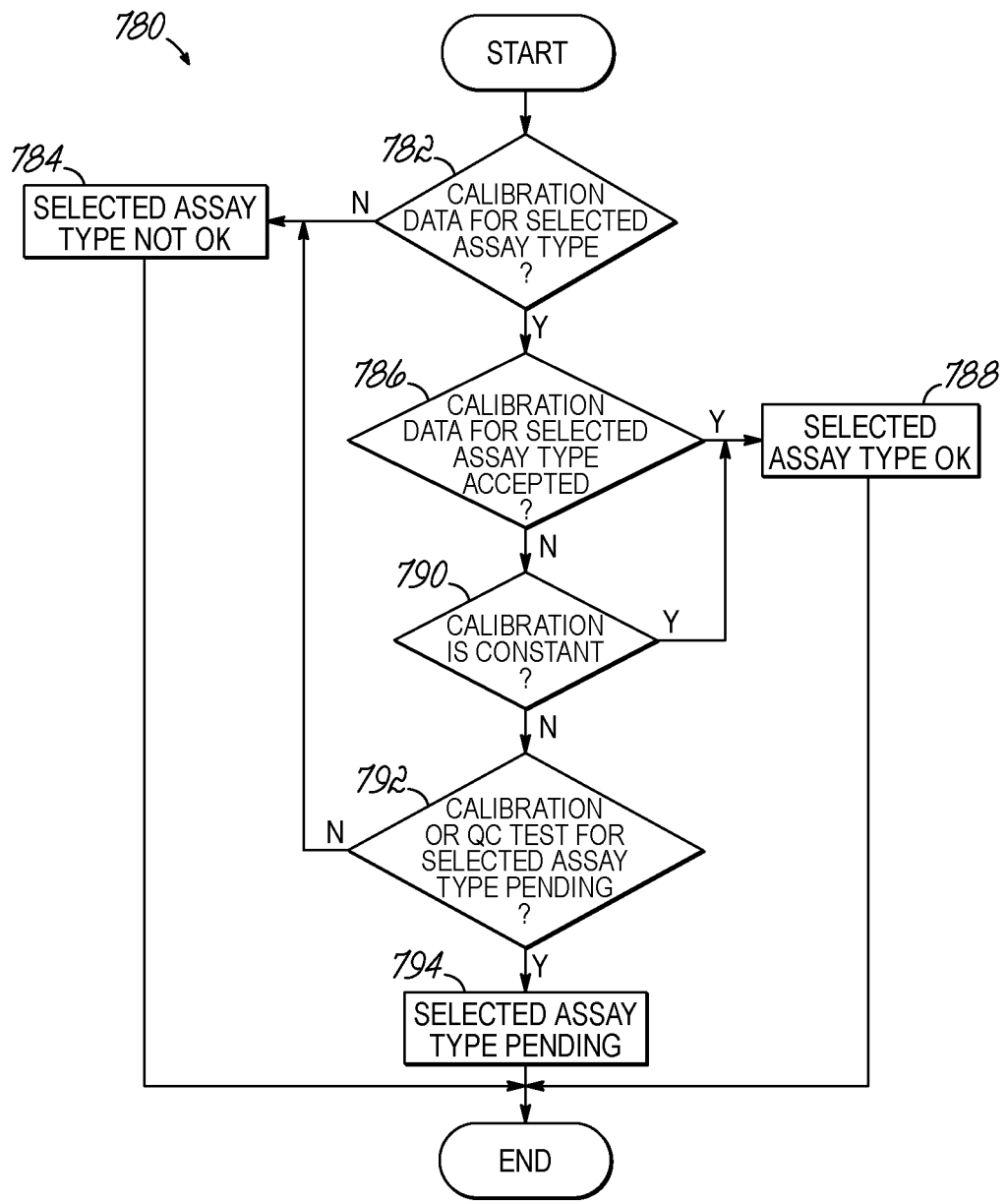
FIG. 23 is a flowchart illustrating a sequence of operations for performing a calibration check in accordance with one embodiment of the present invention.

FIG. 23 is a flowchart 780 illustrating a sequence of operations for the sample preparation controller to perform a calibration checking subroutine consistent with embodiments of the present invention. Initially, the sample preparation controller determines whether there is calibration data for the selected assay type (block 782). When there is no calibration data for the selected assay type ("No" branch of decision block 782), the status of the selected assay type is set to "NOT OK" (block 784) and the sequence of operations may end. However, when there is calibration data for the selected assay type ("Yes" branch of decision block 782), the sample preparation controller determines whether the calibration data for the selected assay type has been accepted by the user as an appropriate mathematical model for relative quantification of the selected assay type with one or more known control samples (block 786). When the user has accepted the calibration data ("Yes" branch of decision block 786), the status of the selected assay type is set to "OK" (block 788) and the sequence of operations may end.

However, when the user has not accepted the calibration data ("No" branch of decision block 786), the sample preparation controller determines whether the user has entered calibration coefficients such that actual calibration assays for the selected sample type are not necessary (e.g., whether the calibration is "constant") (block 790). When the calibration is constant ("Yes" branch of decision block 790), the sequence of operations may proceed to block 788. However, when the calibration is not constant ("No" branch of decision block 790), the sample preparation controller determines whether there is a calibration or control test for the selected assay type pending (block 792). When there is not a calibration or control test for the selected assay type pending ("No" branch of decision block 792), the sequence of operations may proceed to block 784. However, when there is a calibration or control test for the selected assay type pending ("Yes" branch of decision block 792), the status of the selected assay type is set to "PENDING" (block 794) and the sequence of operations may end.

During operation, the sample preparation controller is configured to select a particular assay to perform based on information generated by the scheduler. However, factors may arise that force the sample preparation controller to deviate from a previous schedule, including the scheduling of calibration tests, the scheduling or need for QC tests, and/or priority tests that have been input after, but performed before, the particular test.

The sample preparation controller is thus configured to determine whether a test can be performed in accordance with a particular assay when that assay is selected to be performed.

Figure 24:
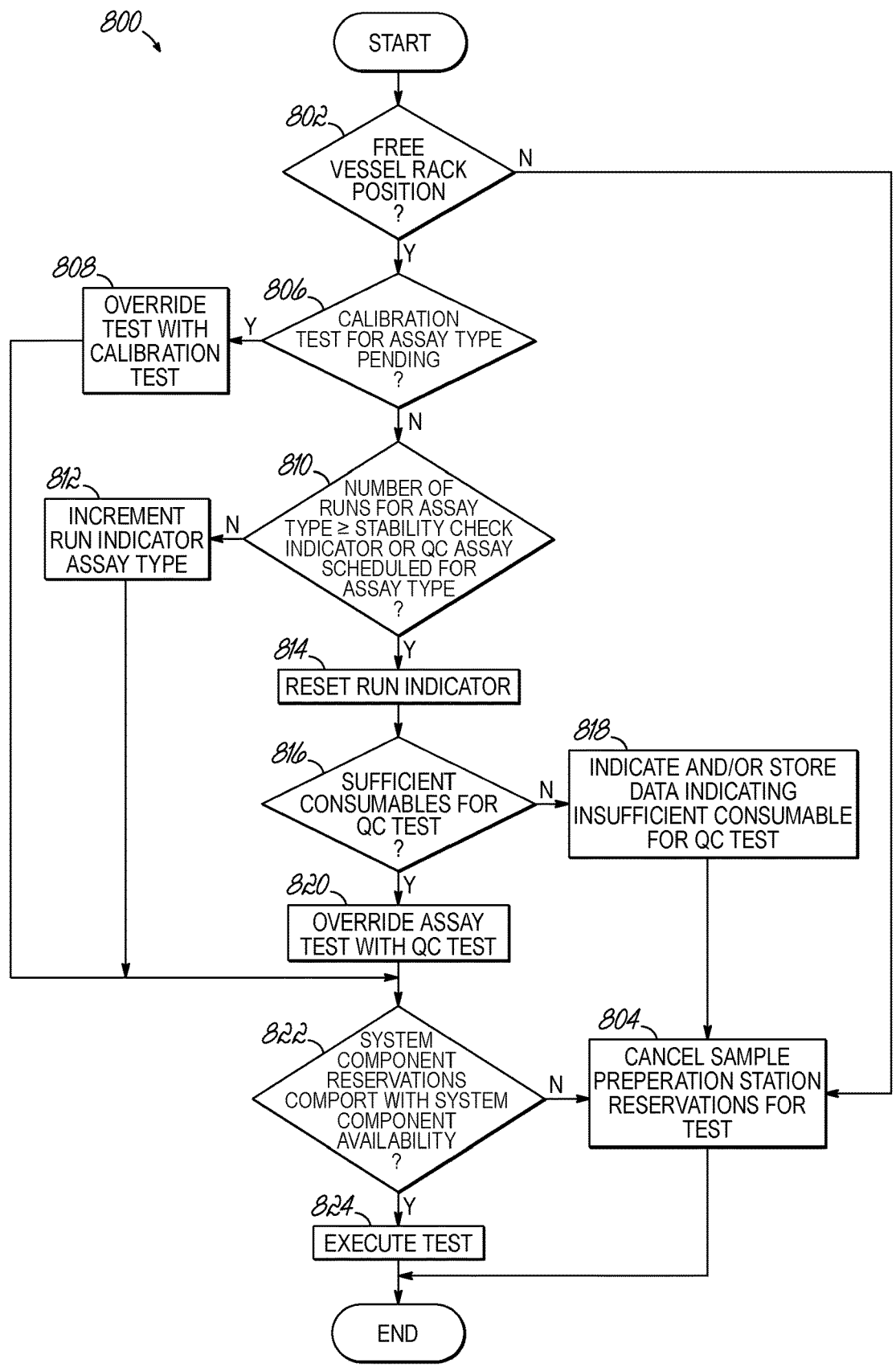
FIG. 24 is a flowchart illustrating a sequence of operations for performing or overriding a particular test according to one embodiment of the present invention.

FIG. 24 is a flowchart 800 illustrating a sequence of operations for the sample preparation controller to perform or override a particular test consistent with embodiments of the invention. The sample preparation controller initially determines whether there is a free vessel position to receive a vessel (e.g., such as a vessel that will contain the sample and/or consumables appropriate for the test) (block 802). When there is no free vessel position ("No branch of decision block 802), the sample preparation controller may cancel the sample preparation station component reservations for the test (block 804) and the sequence of operations may end. However, when there is a free vessel position ("Yes" branch of decision block 802), the sample preparation controller determines whether a calibration test is pending for the assay type (block 806).

When a calibration test is pending for the assay type ("Yes" branch of decision block 806), the sample preparation controller may override the sample test ("test") with a calibration test for the assay type (block 808). When there is no calibration test pending for the assay type ("No" branch of decision block 806), the sample preparation controller determines whether the number of runs for the assay type are greater than or equal to a stability check indicator, or whether there is a control test scheduled for the assay type (block 810).

A control test may be periodically performed for a check of the validity of the current calibration data for the assay type. In one particular embodiment, the control test may be performed about every twenty runs of its respective assay type, or after a defined run time, or "QC time." As such, the sample preparation controller may increment a run indicator each time a test is completed in accordance with a particular assay type to track the number of runs of the particular assay type. Alternatively, a user may manually schedule a control test. Thus, when the run indicator for the assay type is not greater than or equal to the stability check indictor, or when the user has not manually scheduled a control test for the assay type ("No" branch of decision block 810), the sample preparation controller increments the run indicator for the assay type (block 812).

However, when the run indicator for the assay type is greater than or equal to the stability check indicator, a defined control time has expired, or when the user has manually scheduled a control test for the assay type ("Yes" branch of decision block 810), the sample preparation controller clears the run indicator (block 814) and determines whether the volumes of the reagents, solvents, and/or internal standards used by a control test associated with the pending assay is sufficient (block 816). When the volume of at least one reagent, solvent, and/or internal standard used by the control test associated with the pending assay is insufficient ("No" branch of decision block 816), the sample preparation controller indicates and/or stores data indicating that there is at least one insufficient consumable for the control test associated with the pending assay (block 818) and proceeds to block 804. However, when the volume of each reagent, solvent, and/or internal standard for the control test is sufficient for that assay ("Yes" branch of decision block 816), the sample preparation controller may override the test with a control test for the assay type (block 820).

In response to overriding the test with the calibration test (block 808), incrementing the run indicator for the assay type (block 812), or overriding the test with the control test (block 820), the sample preparation controller determines whether the sample preparation station component reservations for the test, calibration test, or control test comport with the availability of those components (e.g., whether the preparation for the sample may still be performed by the components of the sample preparation station with respect to previous reservations therefor) (block 822). When the sample preparation station component reservations no longer comport with the availability of those components ("No" branch of decision block 822), the sequence of operations proceeds to block 804. However, when the sample preparation station component reservations still comport with the availability of those components ("Yes" branch of decision block 822) the sample preparation controller performs the sample preparation (e.g., whether it is the original test for the sample, the test for the calibration standard that overrode that original test, or the control standard that overrode that original test) (block 824).

The sample preparation controller is configured to monitor the components of the sample preparation station to effectively prepare the sample in the system. For example, when the sample preparation station includes a centrifuge and mixer, the sample preparation controller is configured to monitor the operation and loading of those components to maximize the number of vessels processed thereby. More specifically, the sample preparation controller may be configured to monitor which vessels require processing by a mixer, which vessels require processing by a centrifuge, and control the loading and operation of the mixer and centrifuge to operate on those vessels appropriately.

Figure 25:
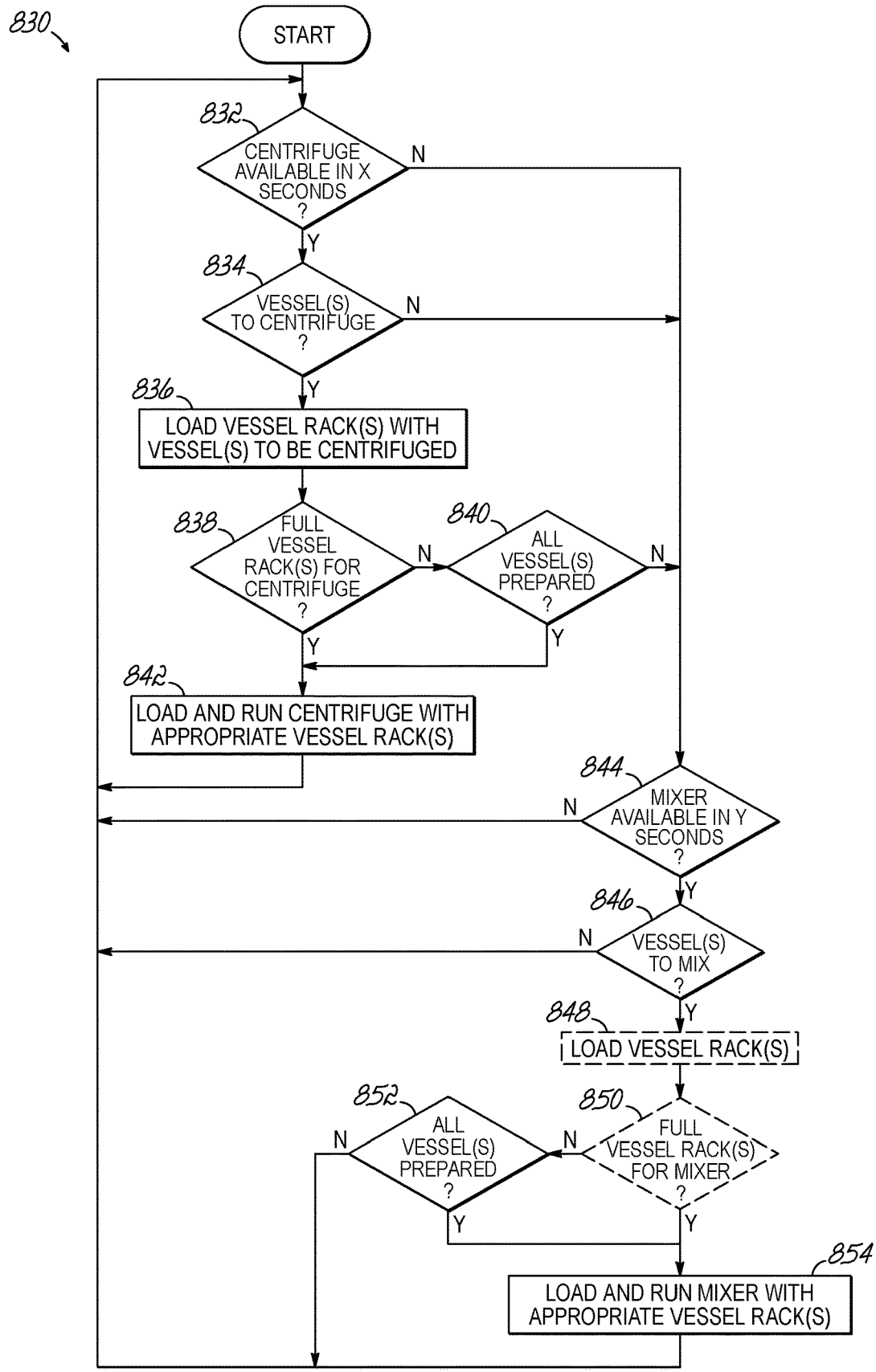
FIG. 25 is a flowchart illustrating a sequence of operations for a centrifuge and a mixer according to one embodiment of the present invention.

FIG. 25 is a flowchart 830 illustrating a sequence of operations for the sample preparation controller to monitor the operation of the centrifuge and the mixer consistent with embodiments of the present invention. The sample preparation controller may determine whether the centrifuge is available within a predetermined number of seconds, which, for example, may be about sixty seconds (block 832). When the centrifuge is available within the predetermined number of seconds ("Yes" branch of decision block 832), the sample preparation controller determines whether there are vessels associated with a test having an assay that calls for the next preparation step for those vessels to be performed with a centrifuge (e.g., vessels to be centrifuged, such as vessels that have already been processed by the mixer) (block 834). When there are vessels to be centrifuged ("Yes" branch of decision block 834), the sample preparation controller may optionally operate the sample preparation station to load at least one vessel rack with the vessels to be centrifuged (block 836) and determines whether there are full vessel racks for processing with the centrifuge (block 838). When there are not full vessel racks for processing with the centrifuge ("No" branch of decision block 838), the sample preparation controller determines whether all vessels have been prepared (block 840).

Otherwise, if vessel racks are not used, then when there are vessels to be centrifuged ("Yes" branch of decision block 834), then the sample preparation controller operates the sample preparation station to load two or more vessels into the centrifuge. When there are not sufficient vessels to fill the available positions in the centrifuge ("No" branch of decision block 838), the sample preparation controller determines whether all vessels have been prepared (block 840).

In any event, when there are sufficient vessels to fill the available positions in the centrifuge ("Yes" branch of decision block 838) and/or when all vessels have been prepared ("Yes" branch of decision block 840), the sample preparation controller loads the centrifuge with the appropriate vessels and centrifuges the vessels (block 842).

When the centrifuge is not available within the predetermined number of seconds ("No" branch of decision block 832), when there are no vessels associated with a test having an assay that calls for the next preparation step for those vessels to be performed with a centrifuge ("No" branch of decision block 834), or when all vessels have not been prepared ("No" branch of decision block 840), the sample preparation controller determines whether the mixer is available within a predetermined number of seconds, which, for example, may also be about sixty seconds (block 844). When the mixer is not available within the predetermined number of seconds ("No" branch of decision block 844), the sequence of operations may return to block 832. However, when the mixer is available within the predetermined number of seconds ("Yes" branch of decision block 844), the sample preparation controller determines whether there are vessels associated with a test associated with an assay that calls for the next preparation step for those vessels to be performed with a mixer (e.g., vessels to be mixed) (block 846).

When there are no vessels to be mixed ("No" branch of decision block 846), the sequence of operations may return to block 832. However, when there are vessels to be mixed ("Yes" branch of decision block 846), the sample preparation controller may optionally load the vessel racks, if used, (block 848) and determines whether there are sufficient vessels for processing with the mixer (block 850). When there are not sufficient vessels for processing with the mixer ("No" branch of decision block 850), the sample preparation controller determines whether all vessels have been prepared (block 852). Thus, when there are sufficient vessels for processing with the mixer ("Yes" branch of decision block 850) or when all vessels have been prepared ("Yes" branch of decision block 852), the sample preparation controller loads the mixer with the appropriate number of vessels and operates on the vessels to mix the contents thereof (block 854). However, when all vessels have not been prepared ("No" branch of decision block 852), the sequence of operations may return to block 832.

In some embodiments, the sample preparation controller may be configured to determine to load vessels to the centrifuge or mixer, without regard to whether all the centrifuge positions are filled with vessels or whether all vessels have been prepared. As such, the sample preparation controller may analyze the RTTRs of the tests associated with each vessel to determine whether the smallest RTTR is less than a centrifuging threshold to determine whether to load and run the centrifuge and/or whether the smallest RTTR is less than a mixing threshold to determine whether to load and run the mixer. As such, if there is a sample associated with a small RTTR, such as a priority sample, the centrifuge and/or the mixer may not be loaded to full capacity despite there being one or more specimens, samples, and/or vessels that still require processing. The sample preparation controller may be configured to determine availability and schedule vessels for sample preparation components other than or in addition to the exemplary centrifuge and mixer, for example, a matrix interference removal station or an incubator.

Figure 26A:
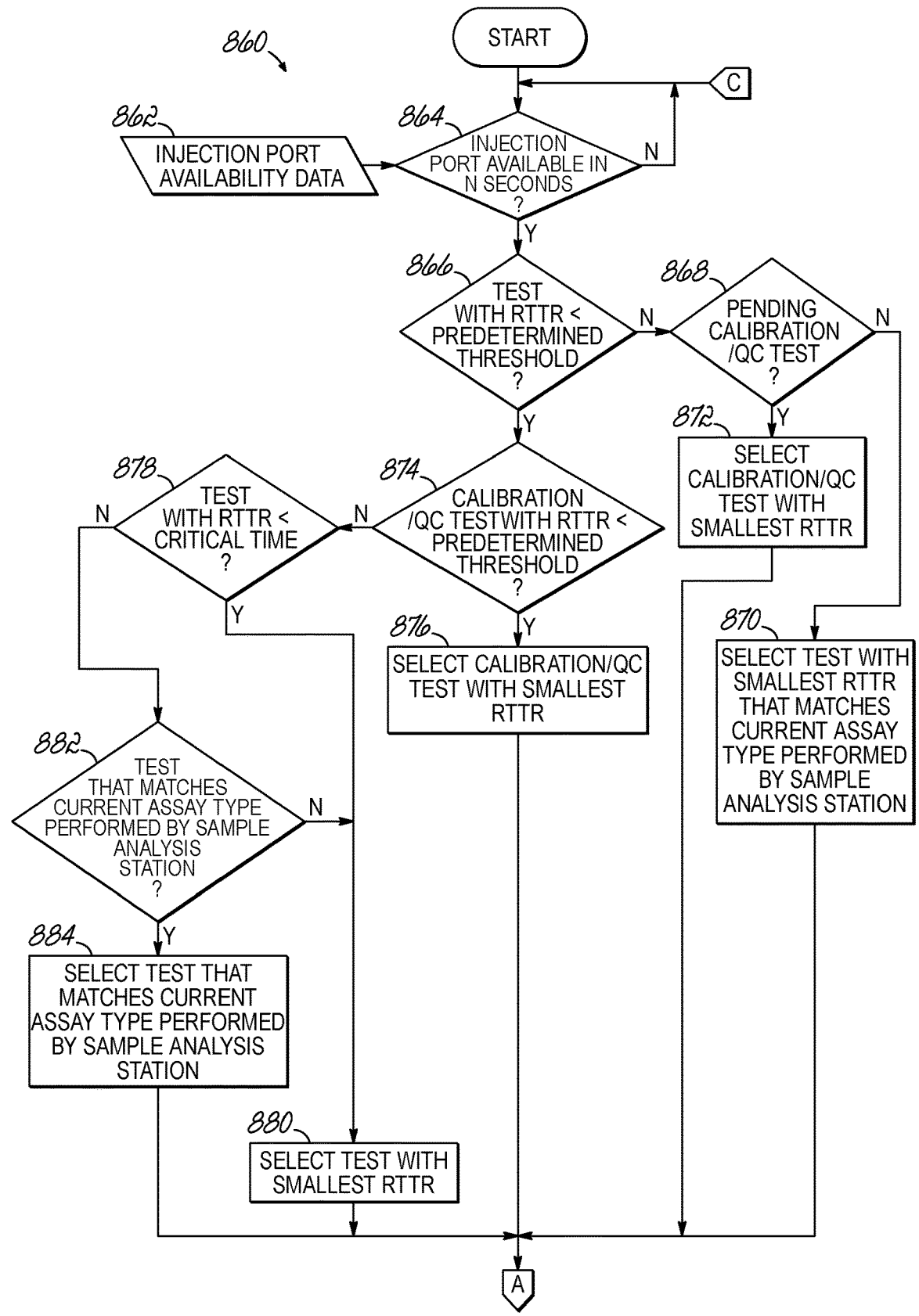
FIGS. 26A-26C are a flowchart illustrating a sequence of operations for injecting a prepared sample into an analysis station and in accordance with one embodiment of the present invention.
Figure 26B:
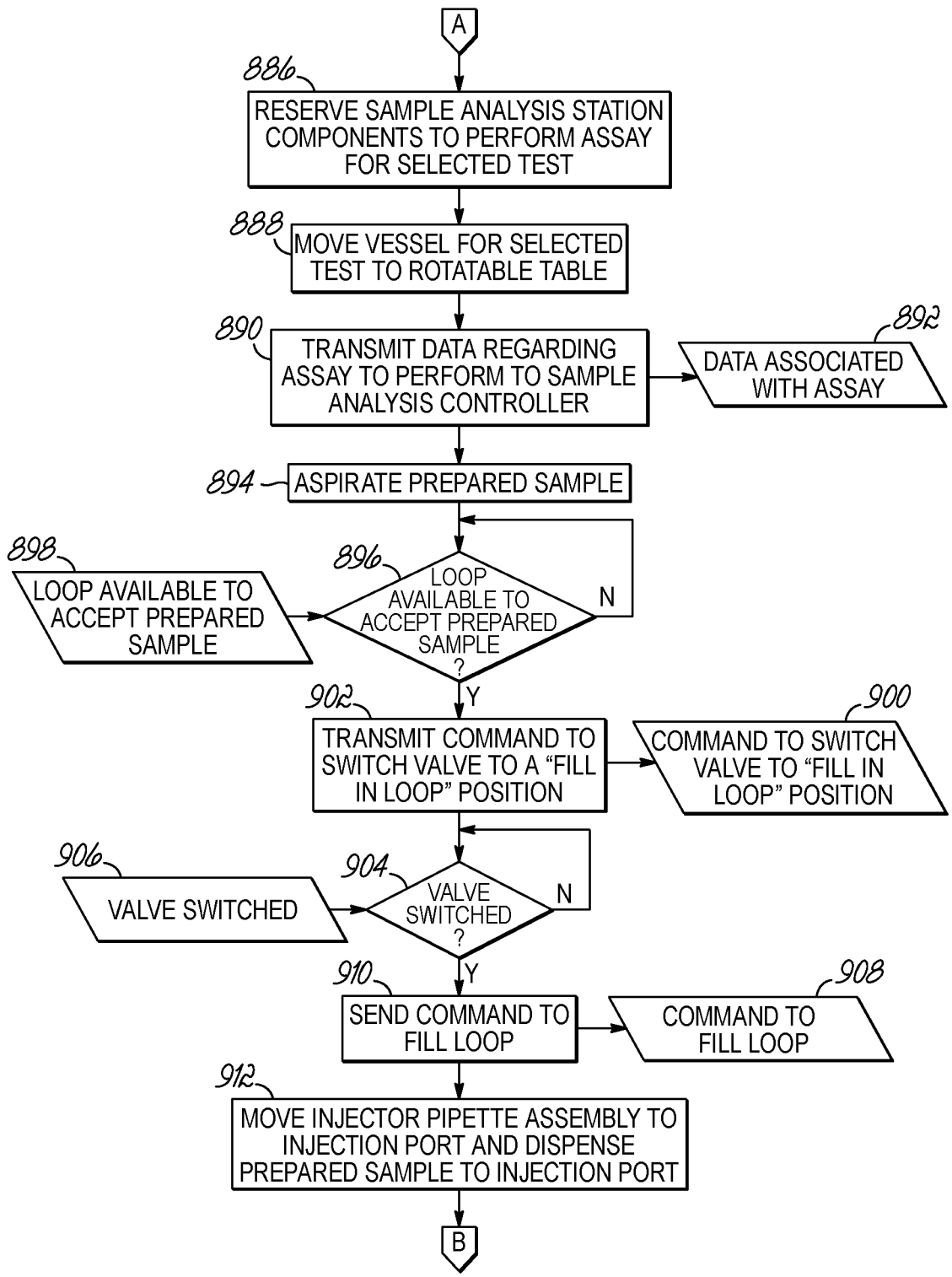
Figure 26C:
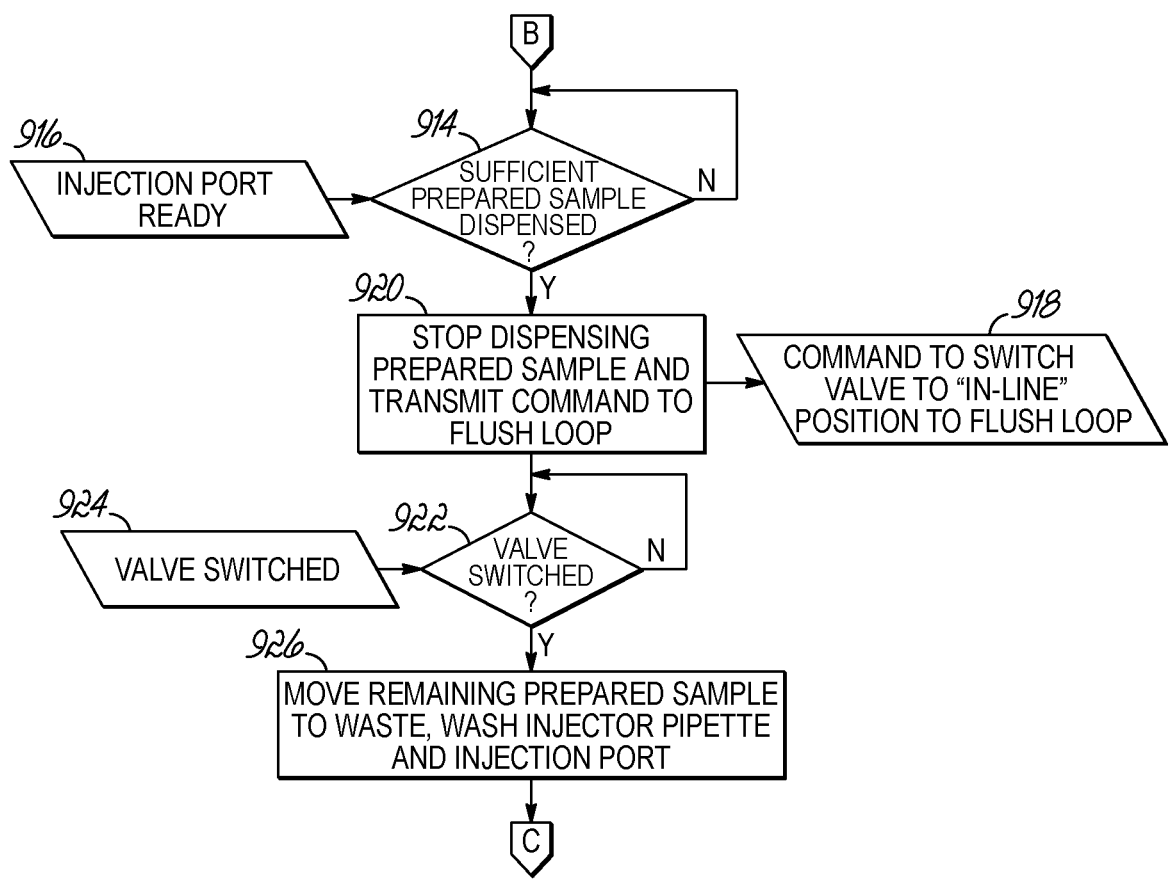

FIGS. 26A-26C are a flowchart 860 illustrating a sequence of operations for the sample preparation controller to control the sample preparation station and sample analysis station to load a prepared sample, fill a sample loop of an injection valve, and perform housekeeping operations on the vessel, the injection port, and the injection valve consistent with embodiments of the present invention. In particular, the flowchart 860 is performed with respect to tests that are associated with prepared samples. The sample preparation controller begins by determining, based on port availability data sent to the sample preparation controller from the sample analysis controller via a high level data interface link (i.e., a TCP/IP link) (block 862), whether a port is available in N seconds (e.g., which may correspond to the time required to move a vessel to the rotatable table, then aspirate and dispense the prepared sample in that vessel to an injection port) (block 864). When the injection port is not available in N seconds ("No" branch of decision block 864) the sequence of operations may return to block 864. However, when the injection port is available in N seconds ("Yes" branch of decision block 864), the sample preparation controller determines whether there are any tests with an RTTR less than a predetermined threshold (block 866). When there is no test with an RTTR less than the predetermine threshold ("No" branch of decision block 866), the sample preparation controller determines whether there is a pending calibration or control test (block 868). When there is not a pending calibration or control test ("No" branch of decision block 868), the sample preparation controller selects the test with the smallest RTTR that matches the current assay type being performed by the sample analysis station (block 870). When there is a pending calibration or control test ("Yes" branch of decision block 868), the sample preparation controller selects the calibration or control test with the smallest RTTR (block 872).

Returning to block 866, when there is a test with an RTTR less than the predetermined threshold ("Yes" branch of decision block 866), the sample preparation controller determines whether there is a calibration or control test with an RTTR less than the predetermined threshold (block 874). When there is a calibration or control test with an RTTR less than the predetermined threshold ("Yes" branch of decision block 874), the sample preparation controller selects the calibration or control test with the smallest RTTR (block 876). However, when there is no calibration or control test with an RTTR less than the predetermined threshold ("No" branch of decision block 874), the sample preparation controller determines whether there is a test with an RTTR less than a critical time (e.g., which may correspond to a typical time required for switching the chemistries associated with the LC columns, such as one or more stationary or mobile phases) (block 878).

When there is a test with an RTTR less than the critical time ("Yes" branch of decision block 878), the sample preparation controller selects the test with the smallest RTTR (block 880). When there is no test with an RTTR less than the critical time ("No" branch of decision block 878), the sample preparation controller determines whether there is a test that matches the current assay type that is being performed by the sample analysis station (block 882). When there is no test that matches the current assay type that is being performed by the sample analysis station ("No" branch of decision block 882), the sequence of operations proceeds to block 880.

However, when there is a test that matches the current assay type that is being performed by the sample analysis station ("Yes" branch of decision block 882), the sample controller selects the test that matches the current assay type that is being performed by the sample analysis station and that has the smallest RTTR (block 884). In response to selecting the test (blocks 870, 872, 876, 880, or 884), the sample preparation station reserves the sample analysis station components to perform the test in accordance with the assay (block 886) and moves the vessel for the selected test to the rotatable table (block 888). The sample preparation controller than transmits data associated with the selected assay to the sample analysis controller (block 890). Such data is sent from the sample preparation controller to the sample analysis controller via the high level data interface link (block 892) and may include an indication of the test to perform, what analytes to detect with the assay type, the amount of prepared sample for the test, and a GUID of the sample.

Once data associated with the test has been transmitted to the sample analysis controller (block 890), the sample controller operates the injector pipette assembly to aspirate the prepared sample from the vessel associated with that test (e.g., the vessel in the rotatable table) (block 894) and determines whether the loop intended for the prepared sample is available to accept the prepared sample (block 896) based on data from the sample analysis controller transmitted via the low level data link indicating same (block 898). When the sample preparation controller determines that the loop intended for the prepared sample is not available ("No" branch of decision block 896) the sequence of operations may return to block 896. However, when the sample preparation controller determines that the loop intended for the prepared sample is available ("Yes" branch of decision block 896), the sample preparation controller transmits a command (block 900) to the sample analysis controller via the low level data link to switch the valve intended for the prepared sample to a "fill in loop" position (e.g., such as that illustrated in FIG. 10B) (block 902).

The sample preparation controller may also determine whether the valve has been switched (block 904) based on data from the sample analysis controller transmitted via the low level data link indicating the same (block 906). When the sample preparation controller determines that the valve has not been switched ("No" branch of decision block 904) the sequence of operations may return to block 904. When the sample preparation controller determines that the valve has been switched ("Yes" branch of decision block 904) the sample preparation controller transmits a command (block 908) to the sample analysis controller via the low level data link to fill the loop (block 910) and moves the injector pipette assembly with the prepared sample to the injector port intended for the prepared sample and dispenses the prepared sample to that injector port (block 912).

While dispensing the sample to the injection port, the sample preparation controller determines whether sufficient prepared sample has been dispensed (e.g., which may be a volume of prepared sample having three times the volume of the loop to sufficiently flush the loop with the prepared sample) (block 914) based on data from the sample analysis controller transmitted via the low level data link indicating same (e.g., that the injection port is "ready") (block 916). When there has not been sufficient prepared sample dispensed ("No" branch of decision block 914), the sample preparation controller operates the injector pipette assembly to dispense more prepared sample to the injection port and returns to block 914. However, when there has been sufficient prepared sample dispensed ("Yes" branch of decision block 914), the sample preparation controller stops the injector pipette assembly from dispensing the prepared sample and transmits a command (block 918) to switch the valve to the "in-line" position to flush the loop transmitted via the low level data link (block 920). The sample preparation controller then determines whether the valve has been switched (block 922) based on data from the sample analysis controller transmitted via the low level data link indicating the same (block 924). When the valve has not been switched ("No" branch of decision block 922), the sequence of operations may return to block 922. However, when the valve has been switched ("Yes" branch of decision block 922), the sample preparation controller moves the remaining prepared sample to waste, washes the injector pipette assembly and the injection port (including fluid lines and internal channels of the valve, as appropriate) (block 926), and proceeds back to block 864.

Figure 27A:
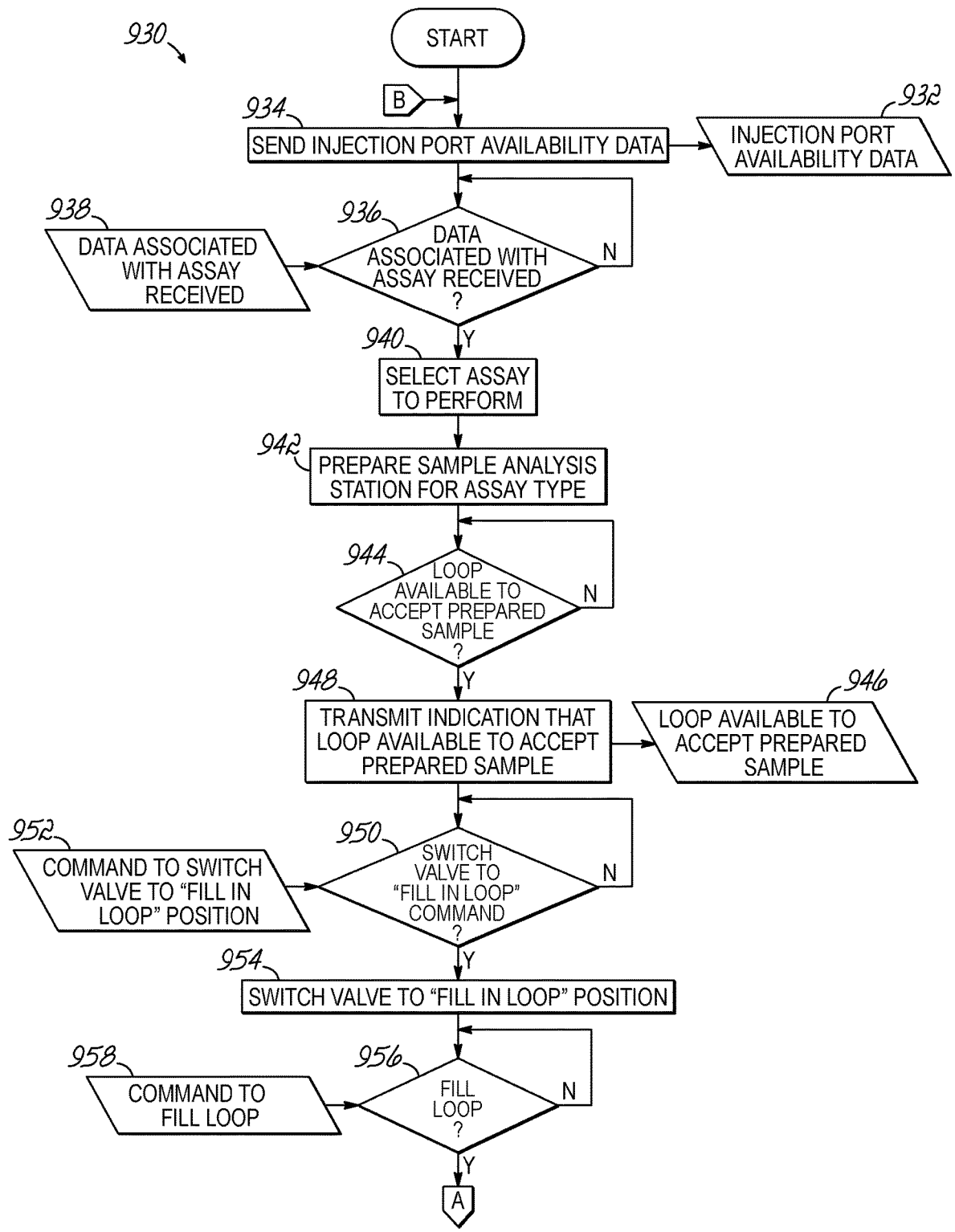
FIG. 27A-27B are a flowchart illustrating a sequence of operations for determining and performing an assay type according to one embodiment of the present invention.
Figure 27B:
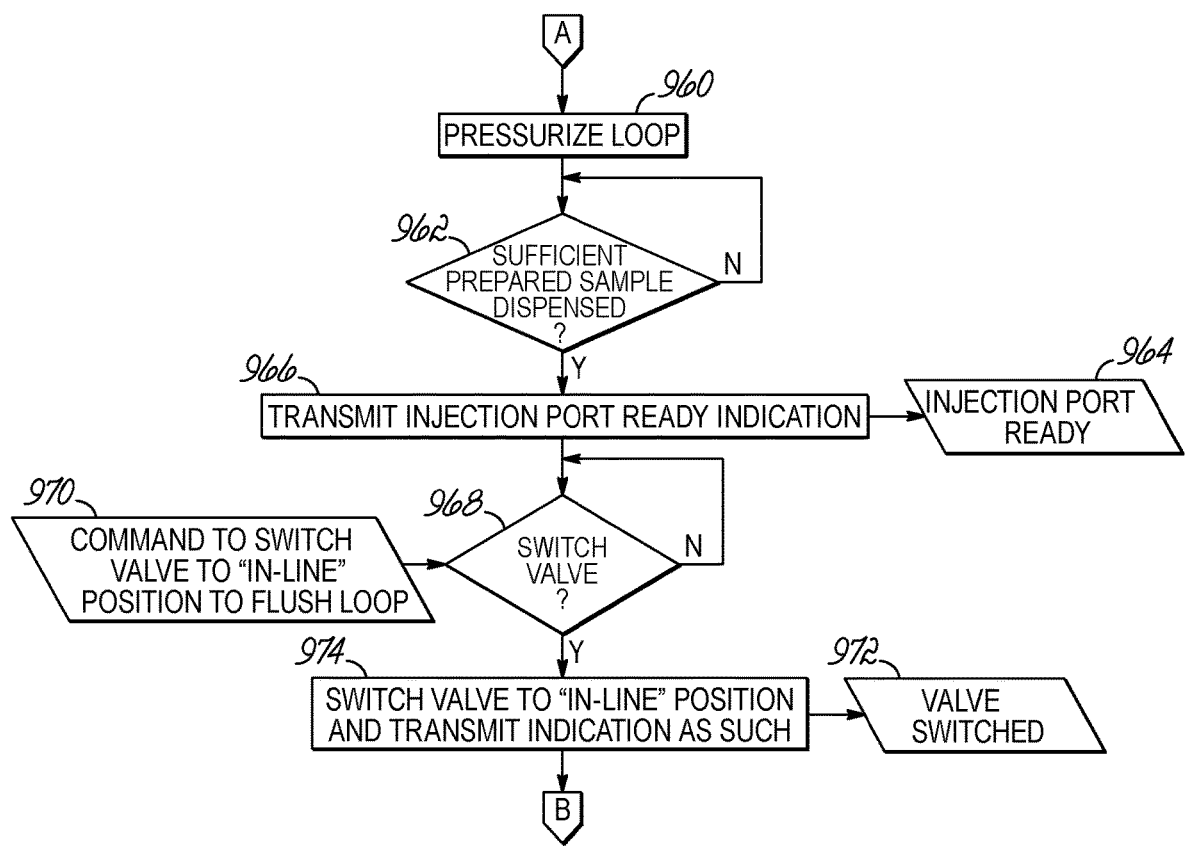

FIGS. 27A-27B are a flowchart 930 illustrating a sequence of operations for the sample analysis controller to determine an assay type to perform and operate the sample analysis station to switch a valve to a "fill in loop" position, then switch the valve to an "in-line" position consistent with embodiments of the present invention. Specifically, the sample analysis controller transmits injection port availability data (block 932) indicating the availability of at least one injection port of at least one respective LC channel of the LC station via the high level data interface link (block 934). In one embodiment, the sample analysis controller transmits the injection port availability data for an injection port when that respective injection port will be available in N seconds. In an alternative embodiment, the sample analysis controller periodically batch transmits injection port availability data for all the injection ports of the LC station such that the sample preparation controller separately tracks the availability of those injection ports. In a further alternative embodiment, the sample analysis controller continuously updates injection port availability data for all the injection ports of the LC station. In any event, the sample analysis controller determines whether it has received data associated with the assay (block 936) based on data transmitted by the sample preparation controller to the sample analysis controller over the high level data interface link (block 938). When the sample analysis controller has not received data associated with the assay ("No" branch of decision block 936), the sequence of operations may return to block 936. However, when the sample analysis controller has received data associated with the assay ("Yes" branch of decision block 936), the sample analysis controller may determine, from that data, the assay type to perform and the methodology to use to perform the test, including but not limited to the analytes of interest to analyze (block 940).

After determining the assay type to perform and the methodology therefor (block 940), the sample analysis controller prepares the sample analysis station for that assay type (block 942). For example, the preparation of the sample analysis station for the assay type may include determining which of the LC channels of the LC station will receive the next prepared sample and determining operational parameters of the LC columns and/or the mass spectrometer. These operational parameters, in turn, may include determining the mobile phase buffer solution flow rate, the composition of the mobile phase buffer solution, the ratio of an aqueous mobile phase buffer solution to a non-aqueous mobile phase buffer solution, a gradient for varying the ratios of the aqueous and non-aqueous mobile phase buffer solutions, an ionization voltage, a desolvation temperature, a lens amplitude, a collision gas temperature, and a collision gas pressure, to name a few. The sample analysis controller also determines whether the loop of the valve that is to accept the prepared sample associated with the test is available to accept a prepared sample (block 944). When the loop of the valve is not available to accept the prepared sample ("No" branch of decision block 944), the sequence of operations may return to block 944.

However, when the loop of the valve is available to accept the prepared sample ("Yes" branch of decision block 944), the sample analysis controller transmits an indication (block 946) that the loop is available to accept the prepared sample via the low level data link (block 948) and the sample analysis controller determines whether to switch the valve to the "fill in loop" position (block 950) based on a command to switch the valve to the "fill in loop" position transmitted via the low level data link (block 952). When the sample analysis controller determines not to switch the valve to the "fill in loop" position ("No" branch of decision block 950) the sequence of operations may return to block 950. However, when the sample analysis controller determines to switch the valve to the "fill in loop" position ("Yes" branch of decision block 950) the sample analysis controller switches the valve to the "fill in loop" position (block 954) and determines whether to pressurize the loop (block 956) based on a command to fill the loop transmitted via the low level data link (block 958). When the sample analysis controller determines not to fill the loop ("No" branch of decision block 956), the sequence of operations may return to block 956. However, when the sample analysis controller determines to fill the loop ("Yes" branch of decision block 956), the sample analysis controller fills the loop (block 960) with the prepared sample.

After filling the loop (block 960), the sample analysis controller determines whether there has been sufficient prepared sample dispensed to the injection port (block 962). When there has not been sufficient prepared sample dispensed to the injection port ("No" branch of decision block 962), the sequence of operations may return to block 962. However, when there has been sufficient prepared sample dispensed to the injection port ("Yes" branch of decision block 962), the sample analysis controller transmits an indication (block 964) that the injector port is ready via the low level data link (block 966) and determines whether to switch the valve to the "in-line" position (block 968) based on a command transmitted from the sample preparation controller via the low level data link (block 970). When the sample analysis controller determines that the valve should not be switched ("No" branch of decision block 968) the sequence of operations may return to block 968. However, when the sample analysis controller determines that the valve should be switched ("Yes" branch of decision block 968), the sample analysis controller switches the valve to the "in-line" position, thereby pressurizing the loop, and transmits an indication (block 972) as such via the low level data link (block 974).

Various modules of the sample analysis application of the sample analysis controller are configured to operate in a modular fashion. For example, the sample analysis station service module and the acquisition service module are configured to share data therebetween to operate the sample analysis station.

Figure 28:
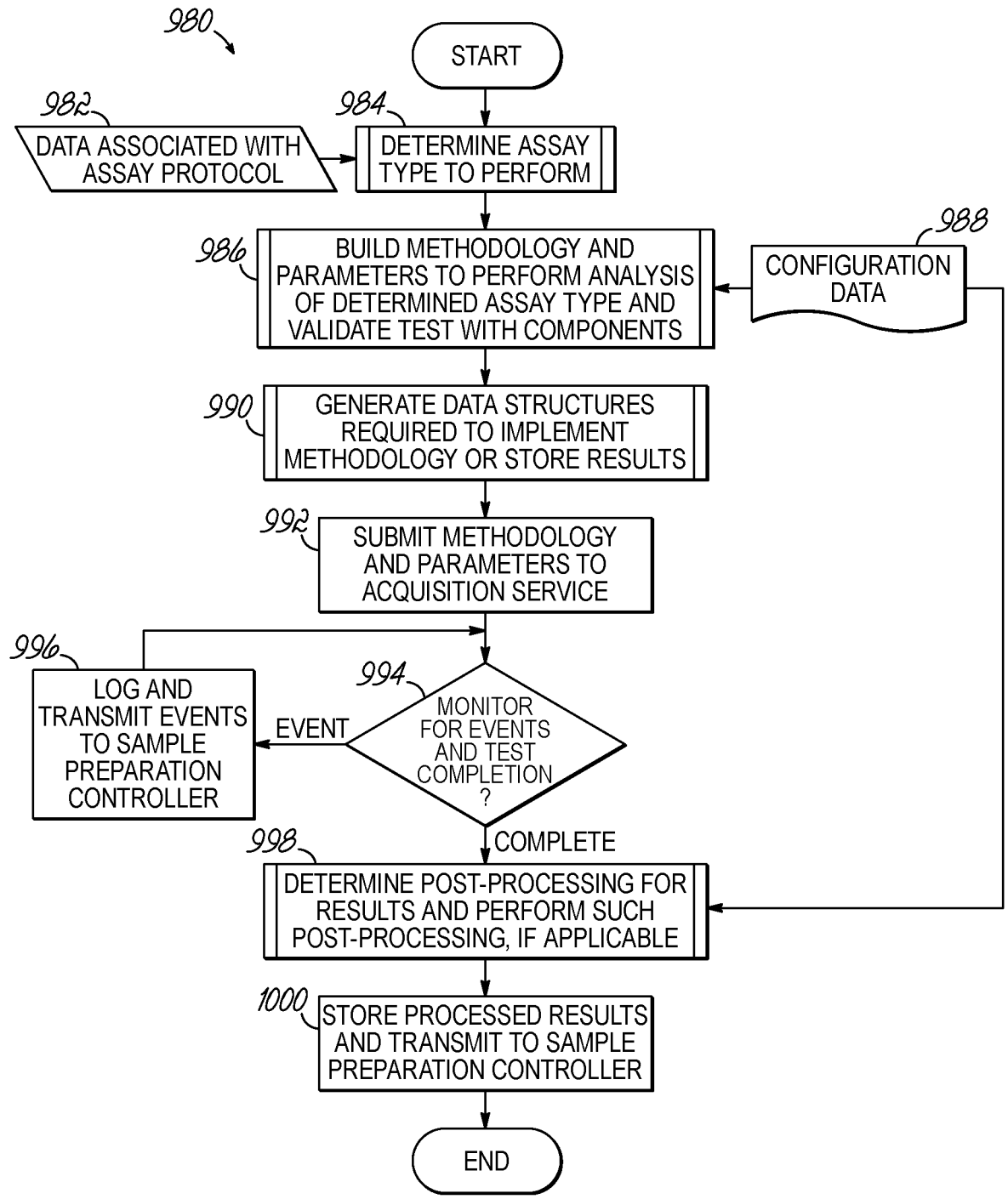
FIG. 28 is a flowchart illustrating a sequence of operations for building a methodology for performing a sample analysis according to one embodiment of the present invention.

FIG. 28 is a flowchart 980 illustrating a sequence of operations for a sample analysis station service module and/or data manager of a sample analysis controller to build a methodology for the analysis and dispatch that test for performance by the sample analysis station consistent with embodiments of the present invention. In particular, the sample analysis station service module is configured to receive data associated with the test that may include an indication of the assay type to perform, what analytes to detect, the amount of prepared sample for the test, and a GUID of the sample (block 982). In turn, the data manager may analyze that received data and determine an assay type to perform from that received data (block 984).

Once the data manager has determined the assay type (block 984) it builds the methodology and parameters for the sample analysis station to perform the analysis of the determined assay (block 986) based on data associated with that assay type in a configuration data structure file (e.g., an XML configuration data file) (block 988). Moreover, when building the methodology, the data manager may validate that the components of the sample analysis station are capable of performing the test (block 986). Validation of the components may include determining whether the components of the sample analysis station are able to perform their individual portions of the methodology for the test as well as reserving the components of the sample analysis station to perform their portions of the methodology for the test.

To store results of the test, the data manager also generates data structures required to implement the methodology for the test or required to store results (block 990). For example, the data manager may create data files and/or data folders that are used to store the results. In any event, the sample analysis station service module submits the methodology for the assay type and any parameters to the acquisition service module for that acquisition service module to operate the sample analysis station and perform the test (block 992). After submitting the methodology for the test (block 992), the sample analysis station service module and/or data manager monitor for indications of events and an indication that the analysis has completed (block 994). When the sample analysis station service module or data manager determines that an event has occurred (e.g., such as errors or status changes) ("Event" branch of decision block 994), the sample analysis station service module or data manager logs that event and transmits that event to the sample preparation controller for that sample preparation controller to notify a user (block 996).

However, when the sample analysis station service module or data manager determines that the test is complete ("Complete" branch of decision block 994), the sample analysis station service module determines whether any post-processing of the raw results data is required and performs that post-processing, if applicable (block 998). The determination of whether post-processing is required and what post-processing to perform, if any, is determined based on the configuration data structure file (block 988). For example, the raw result data may include total ion count ("TIC") measured at the ion detector of the mass spectrometer. This TIC may include measurements of the ion counts for one or more analytes, some of which may be of no diagnostic interest for the current test. As such, the sample analysis station service module may post-process the raw result data by filtering the ion data for one or more analytes from the total ion data. In turn, the sample analysis station service module stores and transmits results data to the sample preparation controller (block 1000).

As described in detail above, the acquisition service of the sample analysis application is configured to interface with the components of the sample analysis station through various virtual interfaces. The acquisition service and virtual interfaces, in turn, follow the methodology for the assay determined from the sample analysis station service module or data manager.

Figure 29:
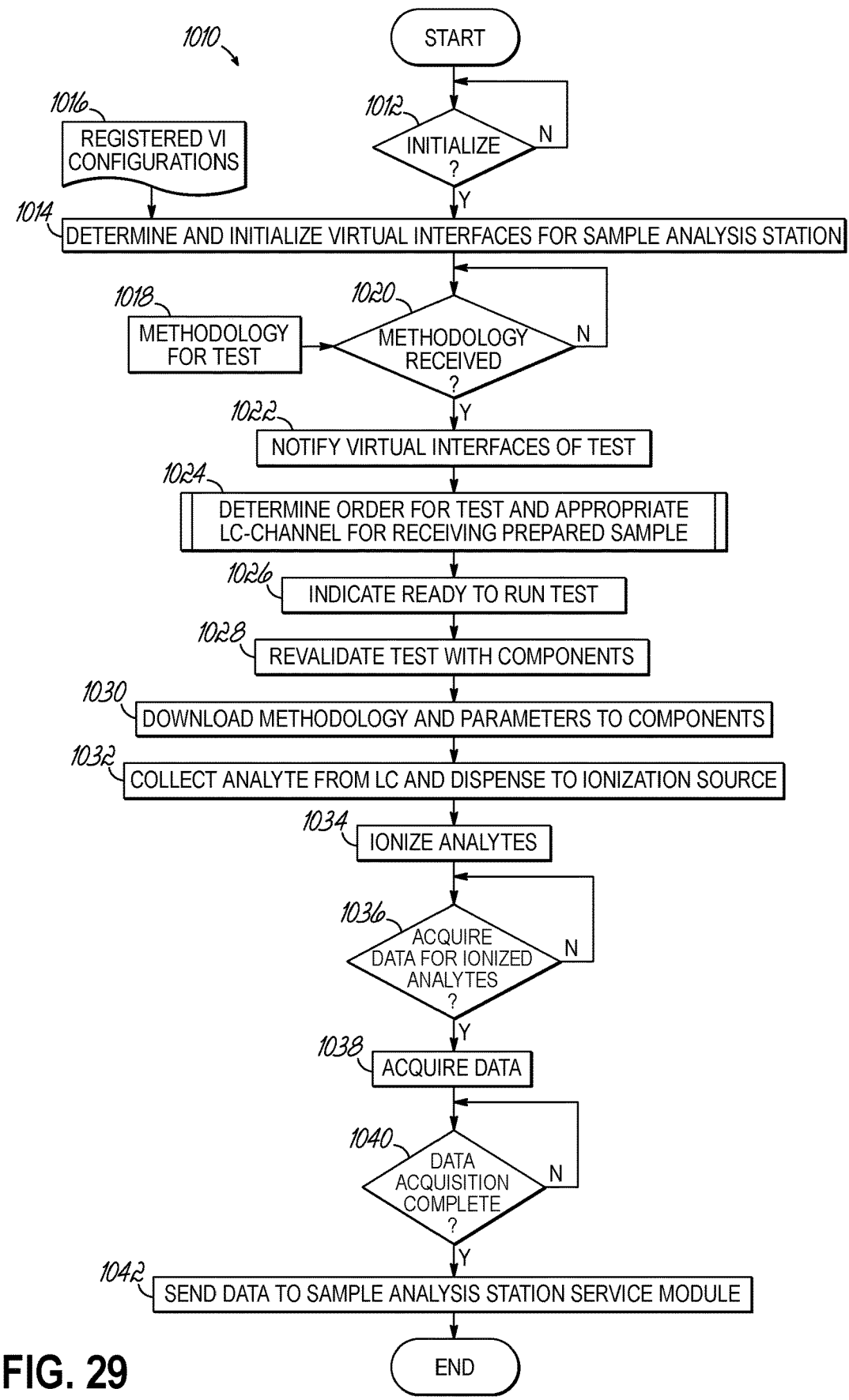
FIG. 29 is a flowchart illustrating a sequence of operations to collect data for an appropriate analyte according to one embodiment of the present invention.

FIG. 29 is a flowchart 1010 illustrating a sequence of operations for the acquisition service and the virtual interfaces to implement the test and collect data for the appropriate analyte consistent with embodiments of the present invention. Upon initialization ("Yes" branch of decision block 1012), the acquisition service determines what virtual interfaces are configured for the sample analysis station and initializes those virtual interfaces (block 1014). The acquisition service determines which virtual interfaces are configured for the sample analysis station based on a registered virtual interface configurations data file (block 1016). The acquisition service also determines whether a methodology for the test (block 1018) has been received from the sample analysis station service module and/or the data manager (block 1020). When a methodology has not been received ("No" branch of decision block 1020), the sequence of operations may return to block 1020. When a methodology has been received ("Yes" branch of decision block 1020), the acquisition service notifies virtual interfaces of the test (block 1022). In turn, the MUX VI determines the order in which the tests are to be performed by the sample analysis station (e.g., when the sample analysis station is capable of performing multiple tests in a serial or multiplexed fashion) and determines the appropriate LC-channel to receive the prepared sample (block 1024).

In response to the virtual interfaces indicating that they are ready to run the test, and in particular to the MUX VI indicating that it is ready to run the test (block 1026), the acquisition service revalidates the test with the components of the sample analysis station (e.g., that the components of the sample analysis station are able to perform their individual portions of the assay as well as that the reservations of the components are still valid) (block 1028) and downloads the methodology for the assay, as well as any operational parameters, to the components of the sample analysis station (block 1030). In particular, this may include collecting one or more analytes from the LC and dispensing the analytes to the ionization source (block 1032), then ionizing the analytes (block 1034). The acquisition service then determines whether to acquire data for the ionized analytes (block 1036).

In particular, the actual window of interest to monitor for eluted analytes of interest may be only a portion of the total time required for the test. As such, the acquisition service may be configured to monitor for selected analytes during an appropriate retention time window. Thus, when the acquisition service determines that it is at the appropriate retention time window in which to collect data for one or more analytes of interest ("Yes" branch of decision block 1036), the acquisition service acquires the data and stores it in the files and/or folders that were previously set up by the sample analysis station service module and/or the data manager (block 1038). When the acquisition service determines that it is not at the appropriate retention time window ("No" branch of decision block 1036), the sequence of operations may return to block 1036. In any event, when data acquisition is not complete (e.g., the retention time window for one or more analytes of interest has not passed) ("No" branch of decision block 1040), the acquisition service continues to acquire data and the sequence of operations may return to block 1038. Thus, when data acquisition is complete (e.g., the retention time window is over or has passed) ("Yes" branch of decision block 1040), the acquisition service sends the acquired data to the sample analysis station service module (block 1042) and the sequence of operations may end. According to another embodiment, the acquisition service may monitor for eluted analytes, including but not limited to specific analytes of interest, during the entire sample elution time.

Figure 30:
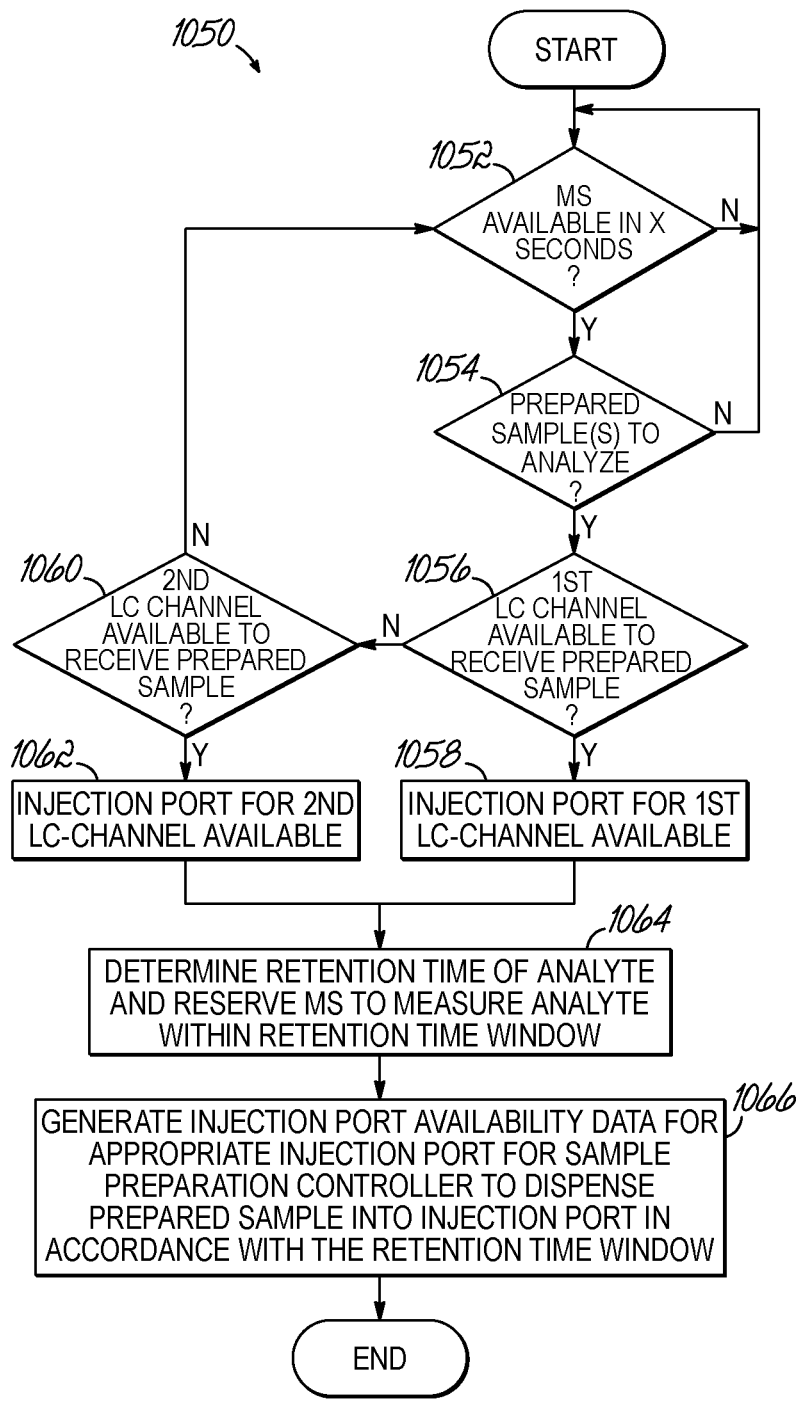
FIG. 30 is a flowchart illustrating a sequence of operations to monitor a status of the sample analysis station according to one embodiment of the present invention.

FIG. 30 is a flowchart 1050 illustrating a sequence of operations for the sample preparation controller to maintain and monitor the operation of the sample analysis station consistent with embodiments of the present invention. The sample preparation controller may determine whether the mass spectrometer is available within a predetermined number of minutes for receiving a prepared sample from the injector pipette assembly, which, for example, may be a range from about two minutes to about six minutes (block 1052). When the mass spectrometer is available within the predetermined number of minutes, ("Yes" branch of decision block 1052), the sample preparation controller determines whether there is a prepared sample ready for analysis (block 1054). If a prepared sample is ready for analysis ("Yes" branch of decision block 1054), then the sample preparation controller will continue in a manner to determine how to inject the prepared sample into the sample analysis station. Otherwise, if there is no prepared sample ready to undergo analysis within the sample analysis station ("No" branch of decision block 1054) or the mass spectrometer is not available ("No" branch of decision block 1052), then the sequence returns to block 1052.

In some embodiments of the invention, the automated sample preparation and analysis system is configured to analyze a plurality of prepared samples in a multiplexed fashion. According to at least one of those embodiments, and after the sample preparation controller has determined that a prepared sample is ready for analysis, the MUX VI may determine whether the first LC channel is available to receive the prepared sample (block 1056), which may consider factors such as whether the first LC channel has eluted all of an earlier prepared sample, whether the appropriate columns are in-place within the LC channel and ready to accept the prepared sample in accordance with the test, whether the appropriate mobile phase is in use in accordance the test, and whether the flow rate of the mobile phase through the first LC channel is appropriate in accordance with the test. If the determination results in the first LC channel being available ("Yes" branch of decision block 1056), then the first LC channel injection port is available (block 1058). However, if the determination results in the first LC channel not being available ("No" branch of decision block 1056), then the MUX VI will determine whether the second LC channel is available to receive the prepared sample (block 1060), which may consider factors that are similar to those that were described with reference to the decision of the first LC channel availability. If the second LC channel is available ("Yes" branch of decision block 1060), then the second LC channel injection port is available (block 1062). When the second LC channel is not available ("No" branch of decision block 1060), the sequence of operation returns the determination of mass spectrometer availability (block 1052). In any event, when the MUX VI determines whether a particular LC channel is available it may send an indication of such to the sample preparation controller through the sample analysis station service module. In some embodiments, the MUX VI determines the availability of LC channels proactively (e.g., for a particular time in the future) and provides the sample preparation controller with injection port availability data corresponding to the future availability of injection ports that corresponds to the future availability of respective LC channels.

With the appropriate LC channel availability determined, the sample preparation controller determines the retention times of the one or more analytes within the prepared sample under consideration and uses this determination to reserve the mass spectrometer for a time correlating the retention time of the analytes in order to measure the analyte eluted at the appropriate retention time window (block 1064). The sample preparation controller will then generate injection port availability data for the appropriate injection port for the injector pipette assembly to dispense an aliquot of the prepared sample into the appropriate injection port in accordance with the retention time window (block 1066).

After the aliquot of the prepared sample is injected into the appropriate injection port, the aliquot will traverse the multi-port valve, loop, and columns as was described in greater detail above. The analytes eluted from the columns are then provided to the mass spectrometer for analyte quantification. Once the analyte(s) of interest is/are detected and measured by the ion detector of the mass spectrometer, the sample preparation controller will determine how to process and report the measured data.

Figure 31:
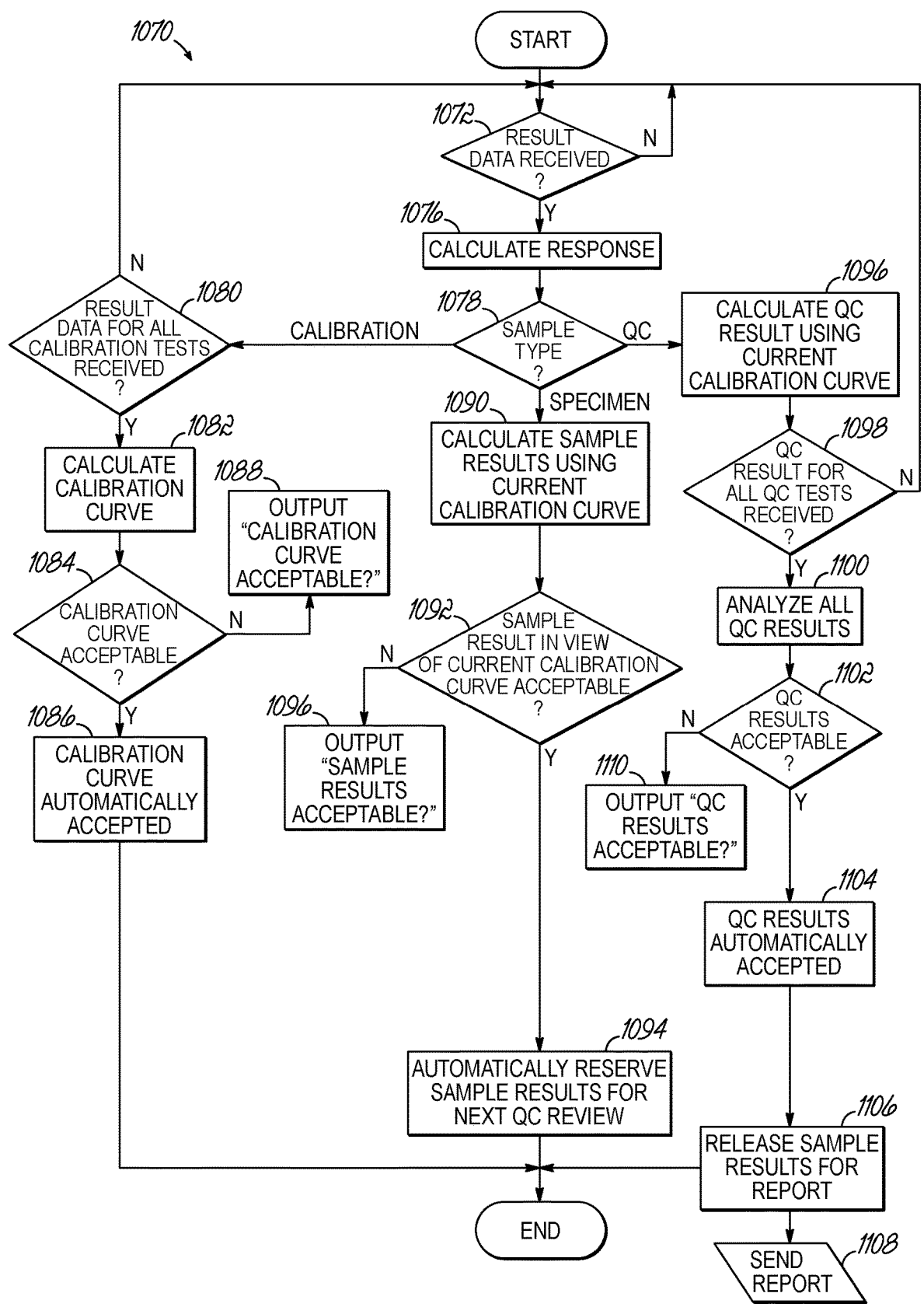
FIG. 31 is a flowchart illustrating a sequence of operations for processing and reporting various sample types according to one embodiment of the present invention.

FIG. 31 is a flowchart 1070 illustrating a sequence of operations for the processing and reporting various sample types consistent with embodiments of the present invention. The sample preparation controller may determine whether the measured result data has been received (block 1072). If the result data has been input into the sample preparation controller ("Yes" branch of decision block 1072), then the sample preparation controller will calculate a response (block 1076); if no result data is received ("No" branch of decision block 1072), then the sequence of events returns to block 1072.

After the response is calculated (block 1076), the sample preparation controller determines the type of sample that is being analyzed (block 1078). If the sample was a known standard for generating a calibration curve ("Calibration" branch of decision block 1078), then the sample preparation controller will determine whether all result data for all calibration tests has been received, i.e., whether all concentrations/dilutions of the known calibration standard have been analyzed by the mass spectrometer (block 1080). When all calibration tests have been analyzed and the results received ("Yes" branch of decision block 1080), the sample preparation controller will calculate the calibration curve (block 1082). Calculation of the calibration curve is in accordance with a mathematical model, which for example, may include any degree of polynomial, exponential, logarithmic, natural log, or other type of curve, where the calibration curve is fit to the result data. When there is less than a required number of result data points for one or more calibration standards ("No" branch of decision block 1080), the sample preparation controller returns to block 1072.

Once the calibration curve has been calculated, the sample preparation controller will make a determination as to whether the calibration curve is acceptable (block 1084). The criteria for determining whether a calibration curve is acceptable may be based on any known statistical model, where the degree of fit between the calibration curve, as compared with the result data, is quantified. One exemplary manner of analysis includes a statistical regression where the calibration curve must "fit" the result data within a designated standard deviation. If the fit of the calibration curve to the result data is acceptable ("Yes" branch of decision block 1084), then the calibration curve is automatically accepted (block 1086). If the calibration curve is not acceptable ("No" branch of decision block 1084), then the sample preparation controller will output "Calibration Curve Acceptable?" (block 1088) for the user to make a manual determination on the calibration curve.

Returning again to the determination of the sample type (block 1078), if the determination is that the sample is a specimen ("Specimen" branch of decision block 1078), then the sample preparation controller will calculate the sample results using the current calibration curve (block 1090). The current calibration curve may be any calibration curve that has been previously automatically or manually accepted and subsequently used without error or invalidation. In some embodiments, the calculation of sample results includes the evaluation of the sample results against the calibration curve and the extrapolation of the analyte concentration, as is known in the art.

The sample preparation controller then makes a determination of whether the calculated sample result is acceptable in view of the current calibration curve (block 1092). In practice, this may include an evaluation as to whether the sample results fall within the bounds of the calibration curve, i.e., the minimum and maximum extreme concentrations of the calibration standards analyzed in calculating the current calibration curve. If the analyte response for the sample falls just beyond the bounds of the current calibration curve (for example, within a predetermined percentage or duration), then a new sample from the specimen may be acquired and prepared in accordance with the assay but at a new dilution factor and the present analyte response discarded. If the analyte response falls outside of the predetermined percentage or deviation, then a new calibration test may be triggered and the present analyte response discarded. If no analyte response results or a response from an internal standard falls outside a predetermined bound, then an error may be indicated and the present analyte response discarded. If the calculated sample result is acceptable ("Yes" branch of decision block 1092), then the sample preparation controller will automatically reserve the sample results for the next control review (block 1094). In this way, the performance and/or operation of the system may be assessed. If the system were to fail a subsequent control analysis, then the accuracy and/or the precision of the sample results calculated and deemed acceptable (blocks 1090 and 1092, respectively) may be called into question. If the calculated sample result is not acceptable ("No" branch of decision block 1092), then the sample preparation controller will output "Sample Result Acceptable?" (block 1096) for the user to make a manual determination.

Once again returning to the determination of the sample type (block 1078), if the determination returns that the sample is a known standard sample for performing a control test ("QC" branch of decision block 1078), then the sample preparation controller will calculate the control results using the current calibration curve (block 1096). This calculation may be performed in a manner that is similar to the method described above with reference to the specimen (see block 1090). The sample preparation controller will then determine whether all control results for all control tests has been received, i.e., whether all concentrations/dilutions of the known control standards have been analyzed by the mass spectrometer (block 1098). When all control tests have been received ("Yes" branch of decision block 1098), the sample preparation controller will analyze all control results (block 1100). If not all control tests are received ("No" branch of decision block 1098), then the sequence returns to block 1072.

After analysis of the control results (block 1100), the sample preparation controller will determine whether the control results are acceptable (block 1102). The criteria used for this determination may vary and one of ordinary skill in the art will readily appreciate the particular statistical analysis that will best make the determination. According to one embodiment, the sample preparation controller may make the determination on the Westgard Rules (J O Westgard, et al. "A multi-rule Shewhart chart for quality control in clinical chemistry." *Clin. Chem*. 1981; 27:493-550.), which uses a combination of criteria, referred to a control rules, for determining whether an analytical system is "in-control" or "out-of-control." The rules may include: (1) review result data when a single control measurement exceeds the mean±3σ (where 3σ is the third standard deviation); (2) reject all data when a single control measurement exceeds the mean±2σ; (3) reject all data when a run of two consecutive control measurements exceed the mean±2σ; (4) reject all data when a first control measurement within a group exceeds the mean±2σ and a second control measurement within the group exceeds the mean±2σ in the opposite direction as the first control measurement; and (5) reject all data when first, second, third, and fourth control measurements (in succession) are on the same side of the mean±1σ. Other rules are known and may be included as appropriate.

If the control results are acceptable ("Yes" branch of decision block 1102), then the sample preparation controller will automatically accept the control results (block 1104) and release the sample results for reporting (block 1106). The sample report is then sent by the sample preparation controller (1108). Further, if further analysis of the sample is not required, the vessel may be discarded. If the control results are not acceptable ("No" branch of decision block 1102), then the sample preparation controller will output "control Results Acceptable?" (block 1110) for the user to make a manual determination.

In certain assay embodiments, for example for testing microbiological samples, two or more sample analysis methods may be performed on a single specimen. For example, a first sample analysis method may be performed to obtain a full identification of the analyte or set of analytes in the sample, acquiring data over the entire sample elution time window. Following analysis of the full identification data, the sample analysis controller may return a result indicating the identification of the analyte or microorganism (based upon a set of analytes) in the sample. The resulting identification may result in a request for a second sample analysis method, for example, to perform antibiotic susceptibility testing ("AST") on the identified sample, for example, by incubating one or more aliquots of the sample in the presence of one or more antibiotics. In the case of AST testing, the second sample analysis method may acquire data only over a specified retention time window specific to the identified sample.

Figure 32:
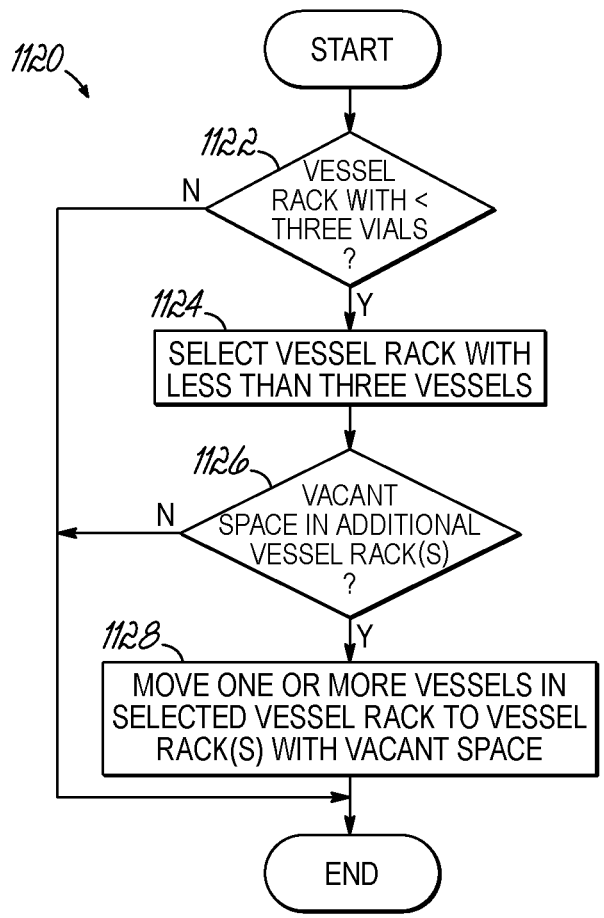
FIG. 32 is a flowchart illustrating a sequence of operations to consolidate vessels in vessels racks according to one embodiment of the present invention.

The sample preparation controller, in addition to normal functions to operate the sample preparation station and coordinate with the sample analysis controller to perform a test, is configured to perform housekeeping routines to consolidate vessel racks and clear the sample preparation station of samples that are no longer necessary. In particular, FIG. 32 is a flowchart 1120 for the sample preparation controller to consolidate vessels in vessel racks, if used, and consistent with embodiments of the present invention utilizing vessel racks. In particular, the sample preparation station determines whether any vessel rack in the sample preparation station has less than three vessels (block 1122). When there is no vessel rack in the sample preparation station with less than three vessels ("No" branch of decision block 1122), the sequence of operations may end. Otherwise, when there is a vessel rack in the sample preparation station with less than three vessels ("Yes" branch of decision block 1122), the sample preparation station selects that vessel rack with less than three vessels (block 1124) and determines whether there is vacant space (e.g., a place for an additional vessel) in any other vessel racks in the sample preparation station (block 1126). When there is vacant space in one or more vessel racks ("Yes" branch of decision block 1126), one or more vessels are moved from the selected vessel rack to the one or more vessel racks with vacant space (block 1128). When there is no vacant space in one or more vessel racks ("No" branch of decision block 1126), or in response to moving vessels from a selected vessel rack to one or more vessel racks with vacant space (block 1128), the sequence of operations may end.

Figure 33:
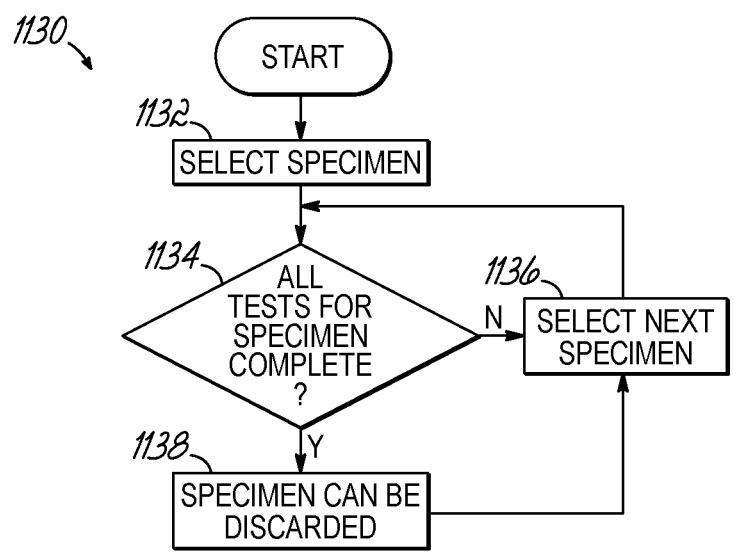
FIG. 33 is a flowchart illustrating a sequence of operations to determine whether to discard specimens according to one embodiment of the present invention.

FIG. 33 is a flowchart 1130 for the sample preparation controller to determine whether specimens may be discarded from the sample preparation station consistent with embodiments of the present invention. The sample preparation station may initially select a specimen to analyze for housekeeping (block 1132) and determine whether all test for that specimen have been completed (block 1134). When all tests for the specimen have not completed ("No" branch of decision block 1134), the sample preparation controller selects the next specimen to analyze for housekeeping (block 1136) and the sequence of operations proceeds back to block 1132. However, when all tests for the specimen have been completed ("Yes" branch of decision block 1134), the sample preparation controller indicates, or stores an indication, that the specimen may be discarded (block 1138) and the sequence of operations proceeds back to block 1136. In some embodiments, a user may remove specimens that may be discarded, while in alternative embodiments the sample preparation station may be configured to move such specimens to the waste receptacle.

Figure 34A:
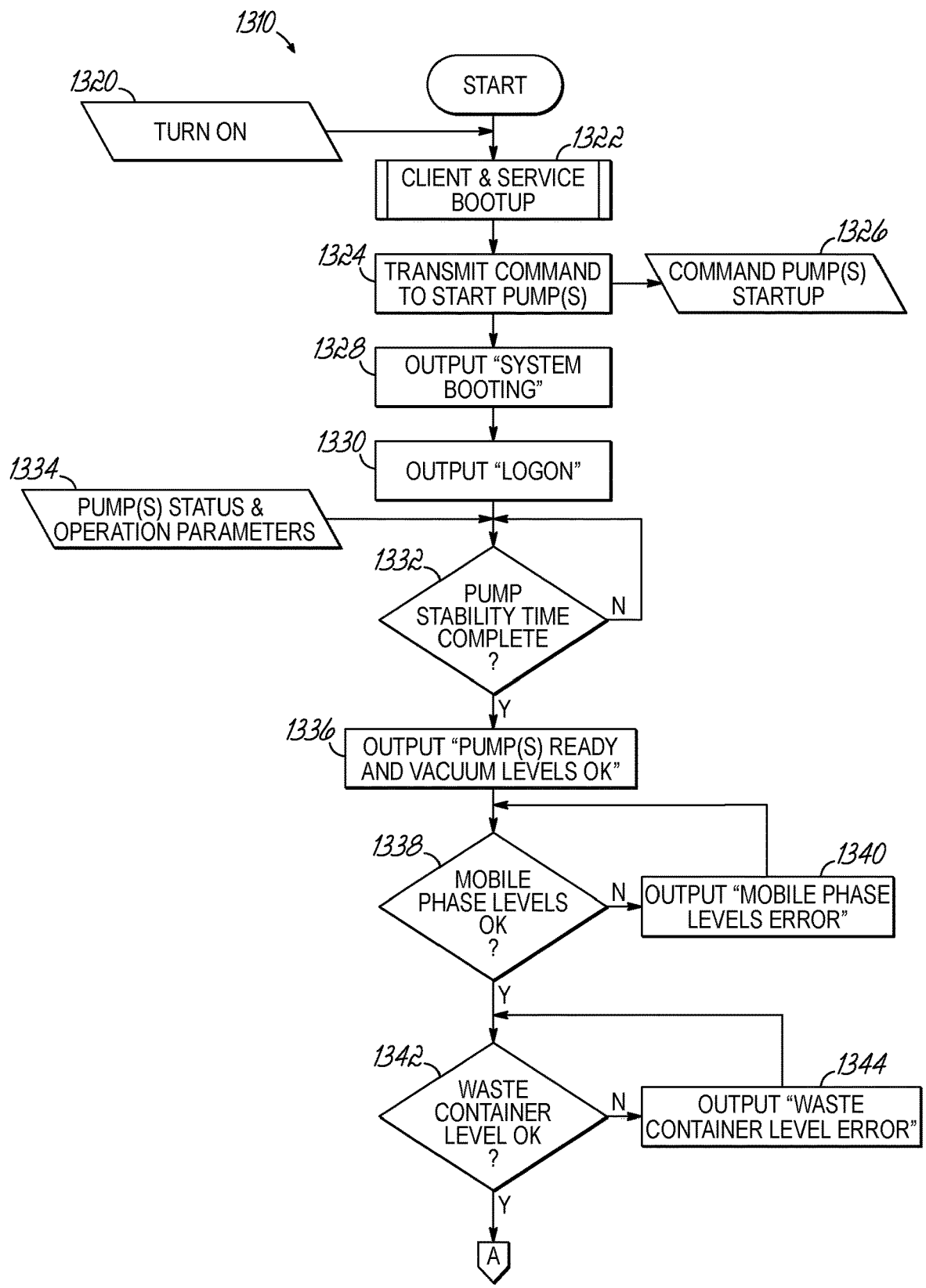
FIGS. 34A-34B are a flowchart illustrating a sequence of operations to booting an automated sample preparation and analysis system in accordance with one embodiment of the present invention.
Figure 34B:
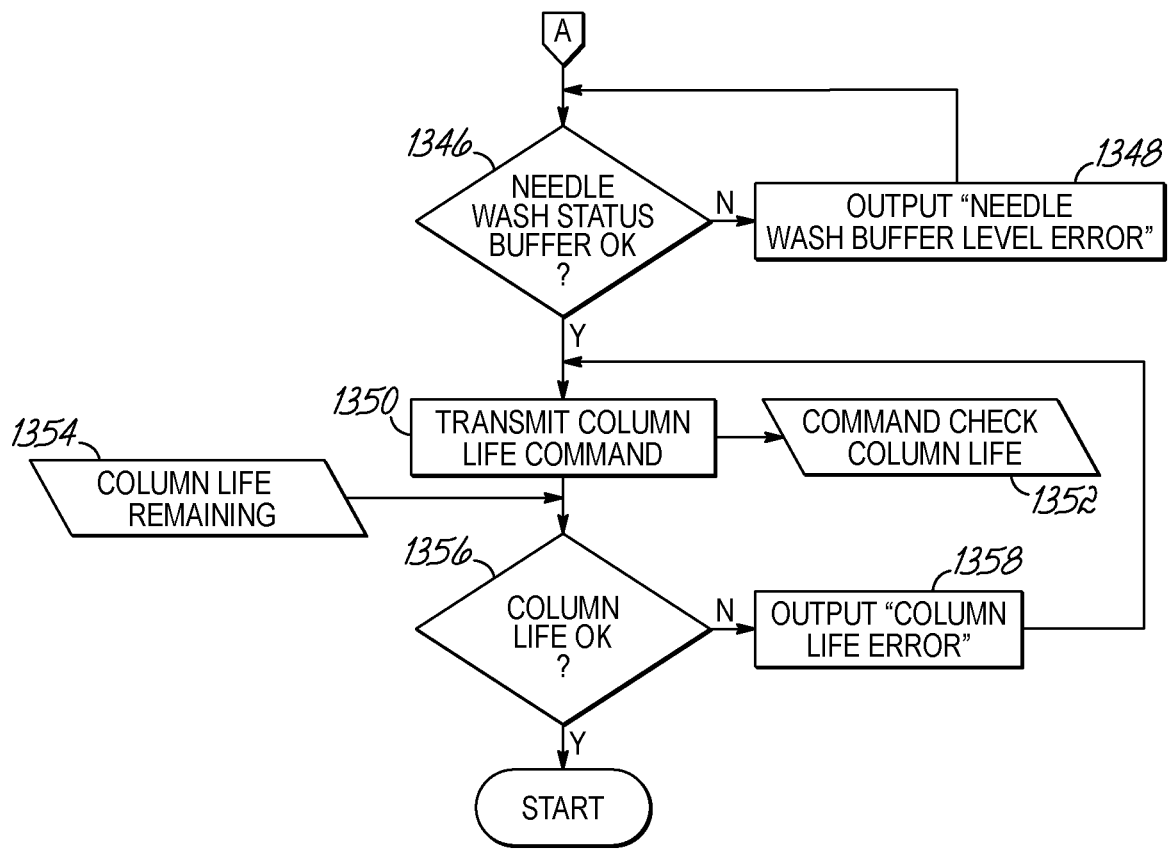

FIGS. 34A-34B are a flowchart 1310 for a method of booting up the system consistent with embodiments of the present invention. The system receives a command from the user to turn on (block 1320), which causes the client and the service to initiate a booting sequence (block 1322). Once the sample preparation controller is sufficiently booted, the sample preparation controller transmits a command (block 1326) to start the pumps (block 1324), which may include starting a turbo pump (i.e., a pump that is internal to the mass spectrometer) and a roughing pump (i.e., a pump that is external to the mass spectrometer). A status update may be output indicating that the system is booting (block 1328). If a secured system is used, the sample prep controller may output a logon command from an authorized user (block 1330).

During the method of booting up, the sample preparation controller monitors the vacuum pressures and functionality of the pumps over a period of time and reports a status of the same (block 1334). While the time period may vary, generally a period ranging from about 4 hours to about 8 hours is appropriate. If the pump stability time is not complete ("No" branch of decision block 1332), then the sample prep controller continues to monitor the received pump status and operation parameters (block 1332). Otherwise ("Yes" branch of decision block 1332), the method continues and an output may be displayed indicating that the pumps are ready (block 1336).

The sample prep controller may then proceed to monitor the status of one or more fluid levels within the system. In that regard, the sample prep controller may query as to whether the mobile phase levels are ok (block 1338). If the mobile phase levels are low or not available ("No" branch of decision block 1338), then a mobile phase level error output (block 1340) is provided. The error may include specific instructions as to which mobile phase levels are low, other errors, as appropriate, and/or solutions to the error. If the mobile phase levels are ok ("Yes" branch of decision block 1338), then the method continues by checking the waste container level (block 1342). If the waste container is absent or full (i.e., beyond a threshold volume) ("No" branch of decision block 1342), then a waste container level error output (block 1344) is provided. Again, the error may provide a suitable solution to the user. If the waste container levels are ok ("Yes" branch of decision block 1342), then the method may continue by checking the needle wash buffer level (block 1346). If the needle wash buffer levels are low or not available ("No" branch of decision block 1346), then a needle wash level error output (block 1348) is provided and, optionally, include one or more instructions and/or solutions. If the needle wash levels are ok ("Yes" branch of decision block 1346), then the sequence of operations continues.

The sample preparation controller may then transmit a command (block 1352) to check the column life remaining for a particular loaded column cartridge (block 1350). Column life may be determined by one or more factors, including, for example, a number of samples run, a total time of use, a total volume injected, and so forth. Based on one or more of these factors, a column life remaining is provided (block 1354) and, if the column life is below a predetermined threshold ("Yes" branch of decision block 1356), then the sequence may end. Otherwise, a column life error output (block 1358) may be output and the method may return to block 1350 and the output may include information such as which cartridge to replace.

Figure 35A:
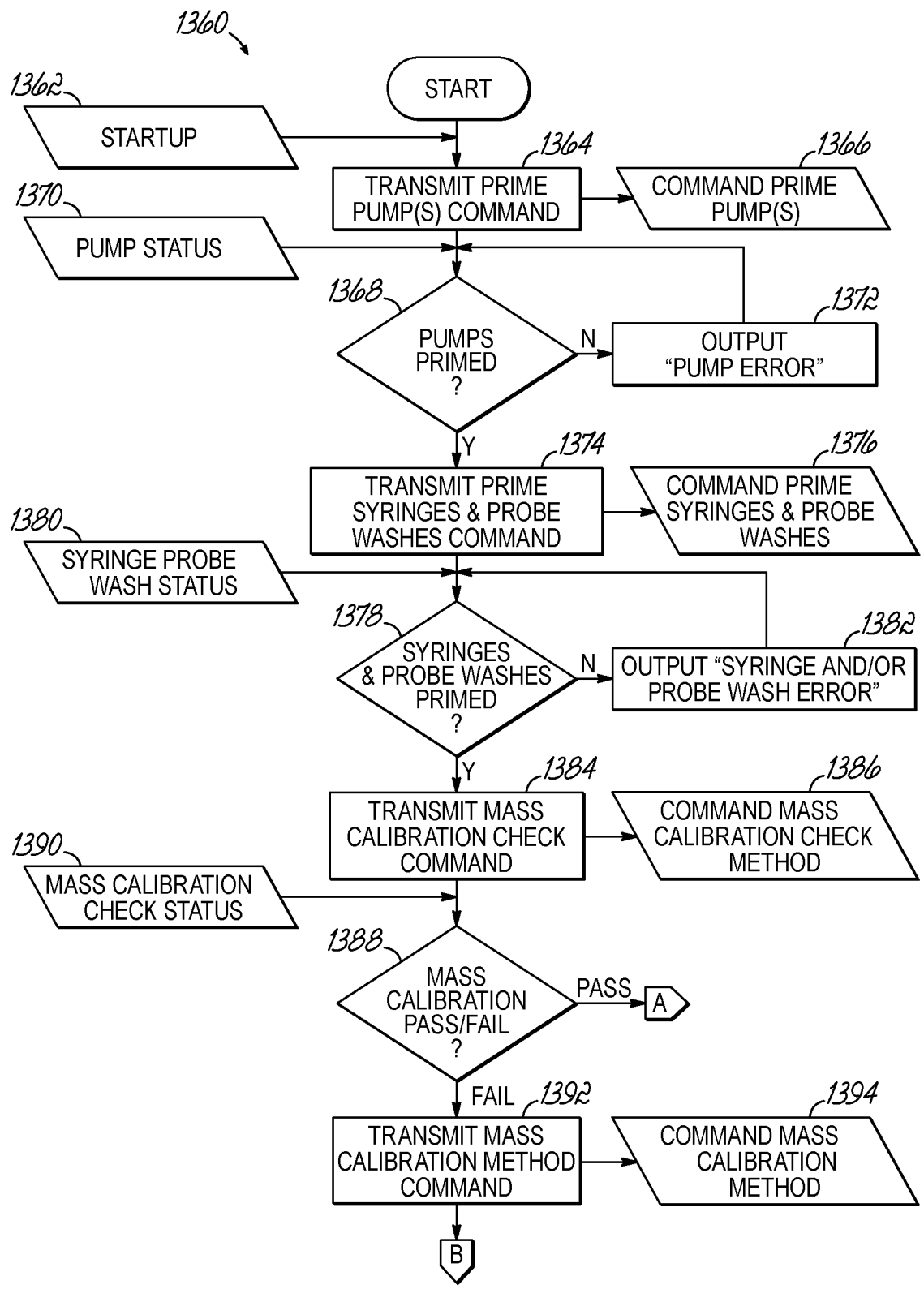
FIGS. 35A-35B are a flowchart illustrating a sequence of operations for starting and entering an idle state of an automated sample preparation and analysis system in accordance with one embodiment of the present invention.
Figure 35B:
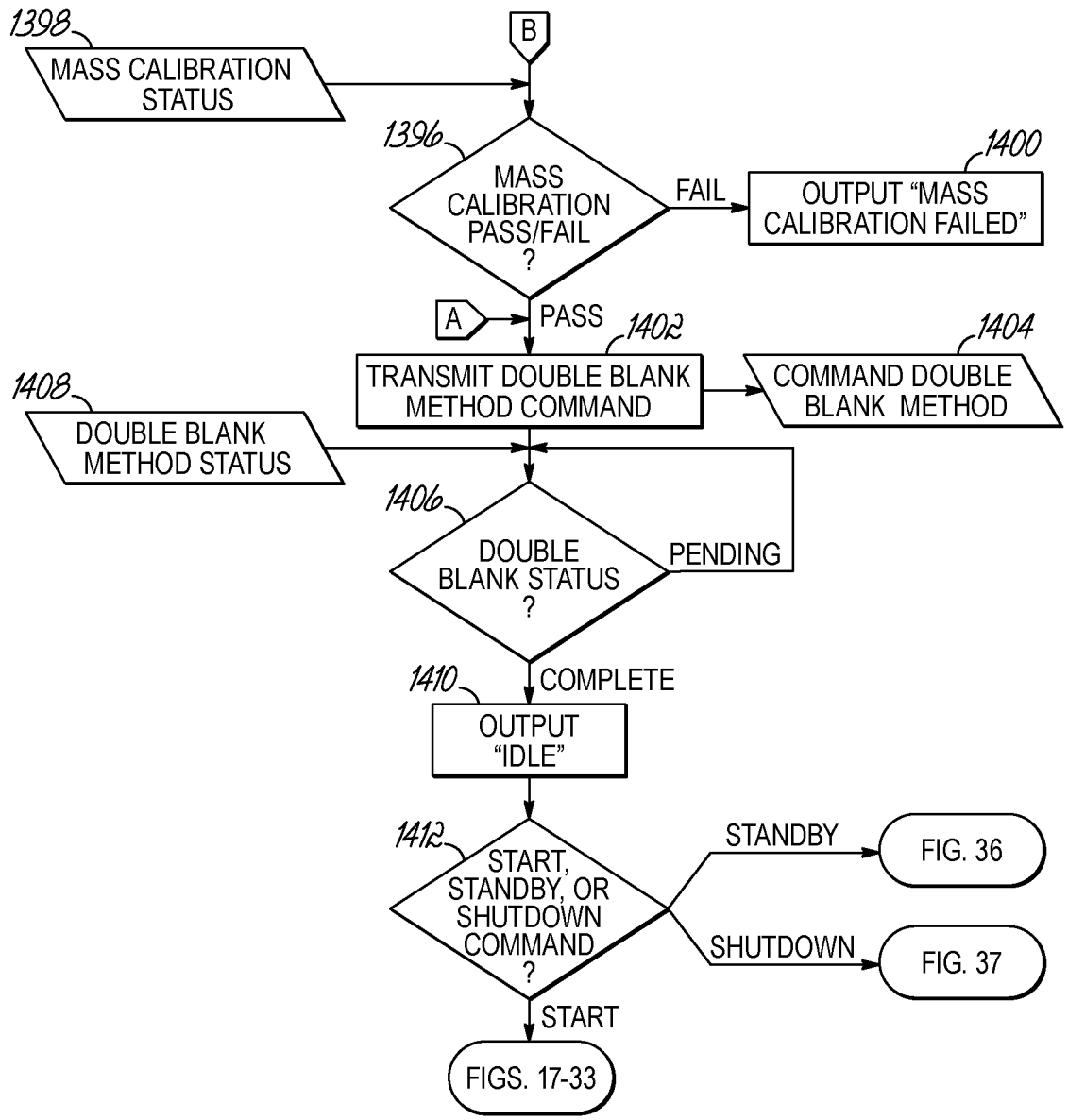

FIGS. 35A-35B are a flowchart 1360 for a method of starting the system and entering an idle state in preparation for receiving a specimen consistent with embodiments of the present invention. In that regard, a startup command is received (block 1362). The sample prep controller then transmits a command (block 1366) to prime the pumps (block 1364) and monitors the status thereof. If the pumps are not primed ("No" branch of decision block 1368) as indicated by a received pump status (block 1370), then a pump error (block 1372) is provided and the system continues to monitor the status. Otherwise ("Yes" branch of decision block 1368), the method continues and the sample preparation controller may transmit a command (block 1376) to prime the syringes and the probe wash (block 1374). If the syringe and/or the probe wash are not primed ("No" branch of decision block 1378) as indicated by a received syringe and probe wash status (block 1380), then a syringe and probe wash error (block 1382) is provided and the system continues to monitor the status. If the syringe and probe wash are primed ("Yes" branch of decision block 1378), then the method may continue.

The sample prep controller may then transmit a command (block 1386) to perform a method for checking the calibration of the mass spectrometer (block 1384). In that regard, a mass spectrometer calibration solution is injected and analyzed in accordance with a selected assay. The calibration solution may include a number of known analytes, at known concentrations, and that are suitable for comparison with the current calibration curve. The results of the analysis are then compared against the known values for determining whether the current calibration remains valid. If the analysis indicates that the calibration has passed ("Pass" branch of decision block 1388) as determined from a returned status of the calibration check (block 1390), then the method continues and the system may enter an idle state, which is described in greater detail below. If the analysis indicates that the calibration has failed ("Fail" branch of decision block 1388), then the sample preparation controller may transmit a command (block 1394) for performing a mass spectrometer calibration method (block 1392). The calibration method includes injecting a number of solutions, each containing a varying amount of one or more analytes, for generating a calibration curve in manner that is discussed in greater detail below. If the mass spectrometer calibration passes ("Pass" branch of decision block 1396) as indicated by the status received (block 1398), then the system may enter an idle state; however, if the calibration fails ("Fail" branch of decision block 1396), then a mass spectrometer calibration error is output (block 1400).

To enter the idle state, the sample preparation controller transmits a command (block 1404) to run a double blank method for all channels that are presently in use (block 1402). In that regard, a blank injection (also referred to as a "fake" injection) is made and the analyzed and then repeated. Once the second blank injection has been analyzed and the double blank method is complete ("Complete" branch of decision block 1406) as determined from a received double blank status (block 1408), then the system returns to block 1406 may alert the user of the idle state status and output an idle indication (block 1410). If the double blank method is not complete ("Pending" branch of decision block 1406), then the system waits until the determination is "Yes."

With the system in the idle state, the sample prep controller may continue to transmit commands (block 1404) for double blank methods (block 1402) until a start, standby, or shutdown command is received. In that regard, the standby method is described with reference to FIG. 36 ("Standby" branch of decision block 1412), the shutdown method is described with reference to FIG. 37 ("Shutdown" branch of decision block 1412), and the start method may include any one of the methods as provided in FIGS. 17-33 ("Start" branch of decision block 1412).

Figure 36:
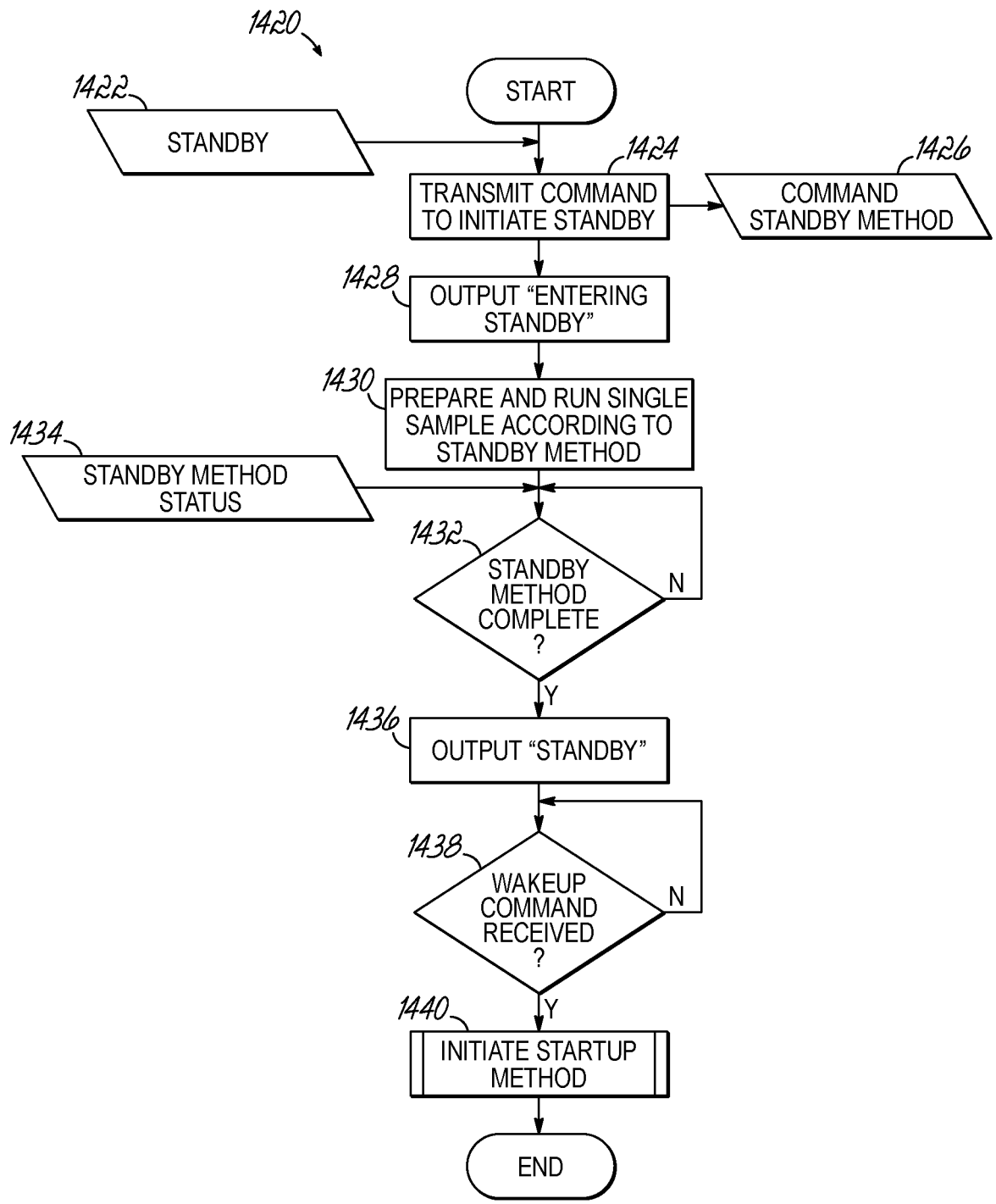
FIG. 36 is a flowchart illustrating a sequence of initiating a standby state for an automated sample preparation and analysis system in accordance with one embodiment of the present invention.

FIG. 36 is a flowchart 1420 illustrating a method of entering a standby state consistent with embodiments of the present invention. The system may receive a command to enter a standby state (block 1422), which causes the sample preparation controller to transmit a command (block 1426) to initiate a standby method (block 1424). The system may then indicate that it is entering the standby mode (block 1428) and then prepares and analyzes a single sample according to a standby assay procedure (block 1430). If the standby method is determined to be incomplete ("No" branch of decision block 1432) from the received standby method status (block 1434), then the system continues to wait and monitor the standby method. If the standby method is completed ("Yes" branch of decision block 1432), then a standby output is provided (block 1436) and remains until a wake up command is received (block 1438). So long as no wake up command is received ("No" branch of decision block 1438), then the system remains in standby. If a wake up command is received ("Yes" branch of decision block 1438), such as loading a specimen or the user indicating the system should start or shutdown, then the method may initiate the start up method 1440, as was described in the flowchart 1360 of FIG. 35. In standby, the pumps may not be operating, the column heaters may be off; the gas pressure may be off, the capillary temperature of the mass spectrometer may be decreased to about 200° C., and/or the reagent cooling may remain on.

Figure 37:
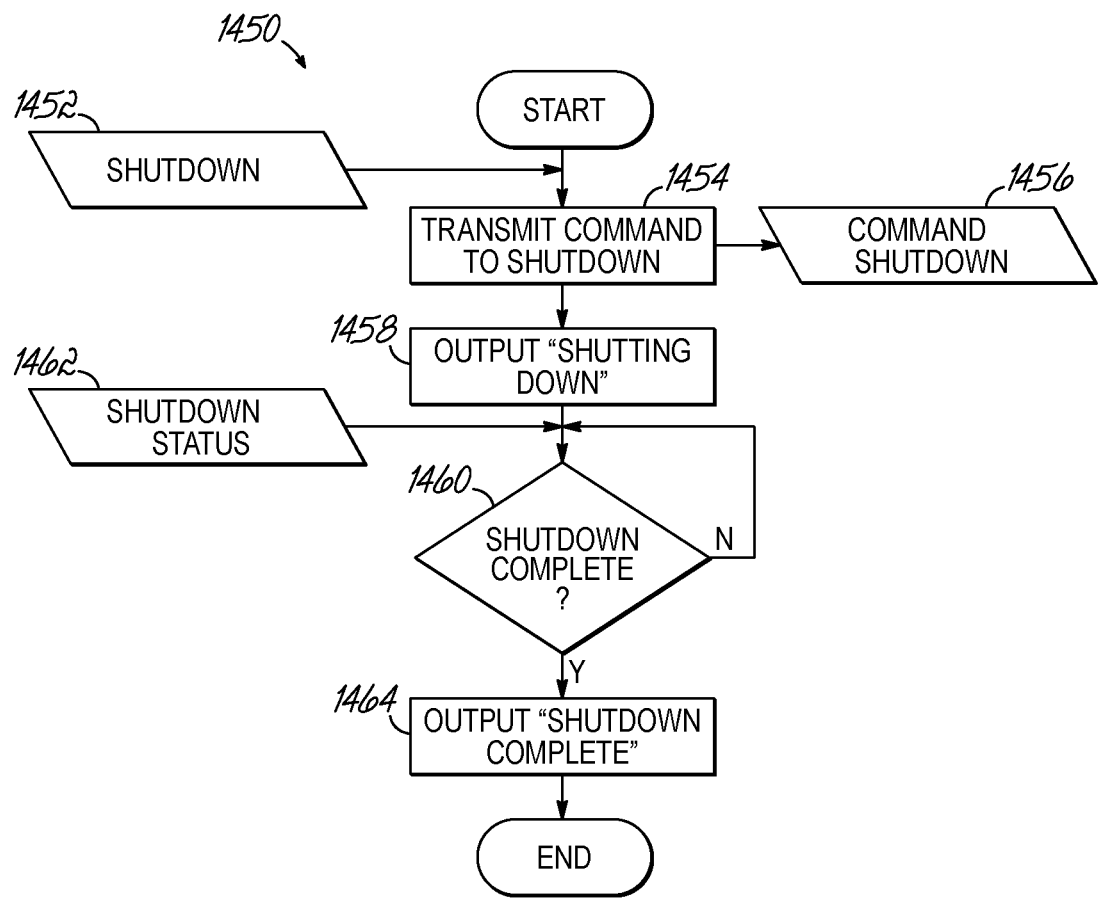
FIG. 37 is a flowchart illustrating a sequence of shutting down an automated sample preparation and analysis system in accordance with one embodiment of the present invention.

FIG. 37 is a flowchart 1450 illustrating a method of shutting down the system consistent with embodiments of the present invention. The system receives a shutdown command (block 1452), transmits a command (block 1456) to initiate a shutdown procedure (block 1454), and may output a shutting down indication (block 1458). This may include terminating the operation of the pumps and stopping all fluid flows while maintaining heating and cooling in those portions of the system as appropriate. When the shutdown procedure is complete ("Yes" branch of block 1460) as determined by a received shutdown status (block 1462), then the system may indicate that shutdown is complete (block 1464). Otherwise, the system continues to monitor the shutdown status ("No" branch of decision block 1460).

Figure 38:
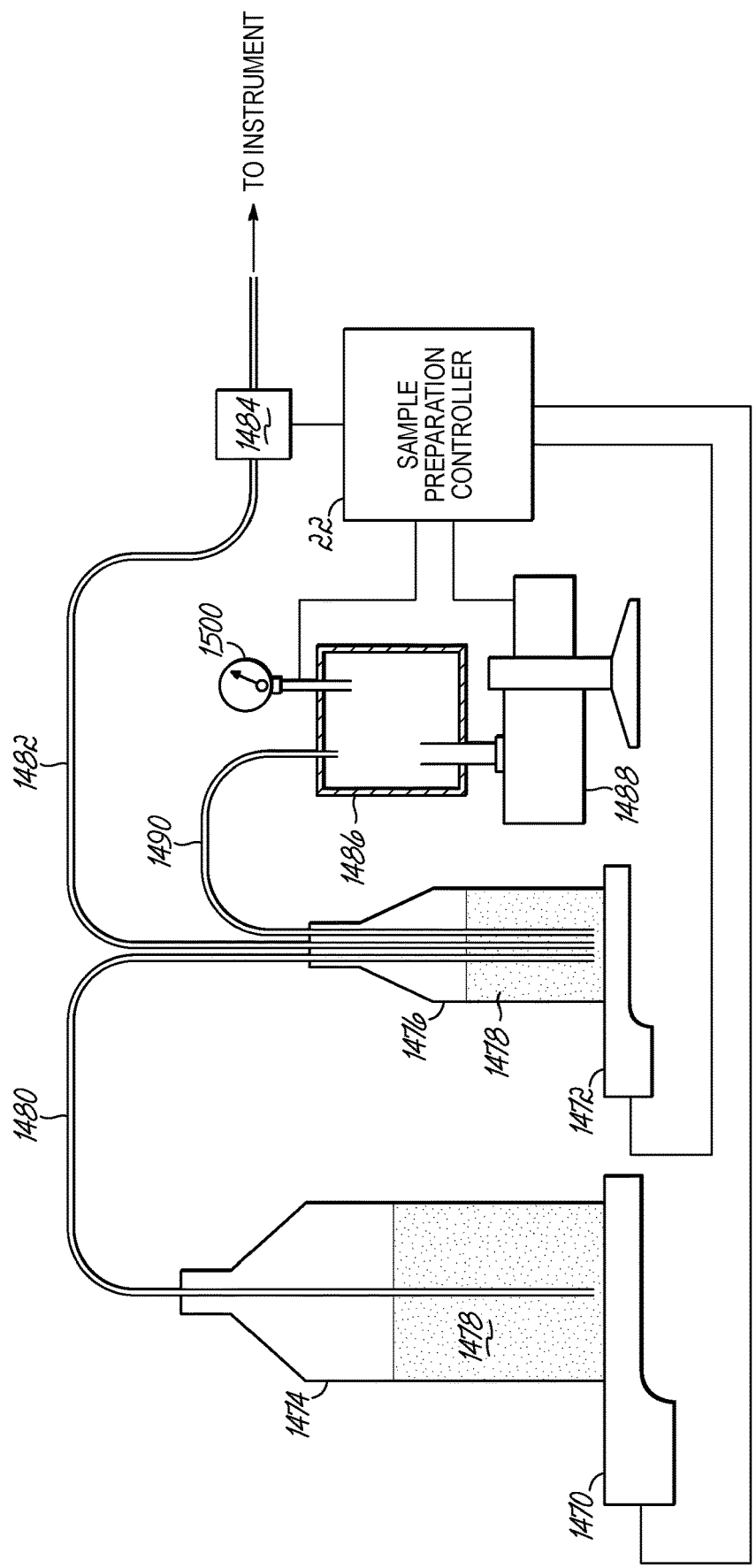
FIG. 38 is a fluid system for managing one or more fluid levels within an automated sample preparation and analysis system in accordance with one embodiment of the present invention.

FIG. 38 illustrates a fluid system for managing one or more fluid levels within the system 10 (FIG. 1A) and in accordance with one embodiment of the present invention. In that regard, two load cells 1470, 1472 may be operably coupled to the sample preparation controller 22 or another controller as appropriate. Each load cell 1470, 1472 is associated with a fluid container 1474, 1476 containing the same fluid 1478 therein. As shown, a first fluid container 1474 may be larger volume as compared to the second fluid container 1476 such that the first fluid container 1474 is a fluid supply and the second fluid container 1476 is an auxiliary fluid supply. While not required, the second fluid container 1476 may be configured to contain a smaller volume of the fluid 1478 as compared to the first container 1474 so as to be stored with the system 10 (FIG. 1A) under the cover 16 (FIG. 1A) and yet coupled to an external and accessible source. A first fluid line 1480 extends between the first fluid container 1474 and the second fluid container 1476, and a second fluid line 1482 extends between the second fluid container 1476 and is fluidically coupled to the system 10 (FIG. 1A) via a solenoid valve 1484. The fluid 1478 of the second fluid container 1476 is under partial vacuum as the second fluid container 1476 is coupled to a vacuum chamber 1486 and a vacuum pump 1488 via a separate vacuum line 1490.

In use, as the fluid 1478 is removed from the second fluid container 1476 during the preparation and/or analysis of one or more samples in accordance with one or more assays, the weight of the second fluid container 1476 with the fluid 1478 decreases, as determined by the second load cell 1472 at the sample preparation controller 22. When the weight of the second fluid container 1476 with the fluid 1478 falls below a first threshold value (e.g., an indirect measure of a minimum fluid volume), then the vacuum pump 1488 is activated to draw a vacuum on the vacuum chamber 1486. Because the vacuum chamber 1486 is coupled to the sealed second fluid container 1476, the vacuum pump 1488 also draws a vacuum on the second fluid container 1476. With sufficient vacuum pressure generated within the second fluid container 1476, the fluid 1478 may be withdrawn from the first fluid container 1474, through the first fluid line 1480, and into the second fluid container 1476. The fluid 1478 will continue to transfer the fluid 1478 from the first fluid container 1474 to the second fluid container 1476 until the weight of the second fluid container 1476 with the fluid 1478 therein reaches a second threshold value (e.g., an indirect measure of a maximum fluid volume). At that time, the sample preparation controller 22 sends a command to the vacuum pump 1488 to terminate operation, the vacuum within the vacuum chamber 1486 decreases, and the fluid transfer stops.

Although not shown, one having ordinary skill in the art will appreciate that the sample preparation controller may further control the sample preparation station to discard vessels of prepared samples that have been analyzed. As such, the sample preparation controller may first determine whether the prepared samples in such vessels have been analyzed, and whether an analysis of that prepared sample should be re-performed. When re-performance of an analysis is unnecessary, the vessel with the prepared sample may be discarded to a waste receptacle. Otherwise, the vessel may be kept in the sample preparation station.

Example 1

Figure 39A:
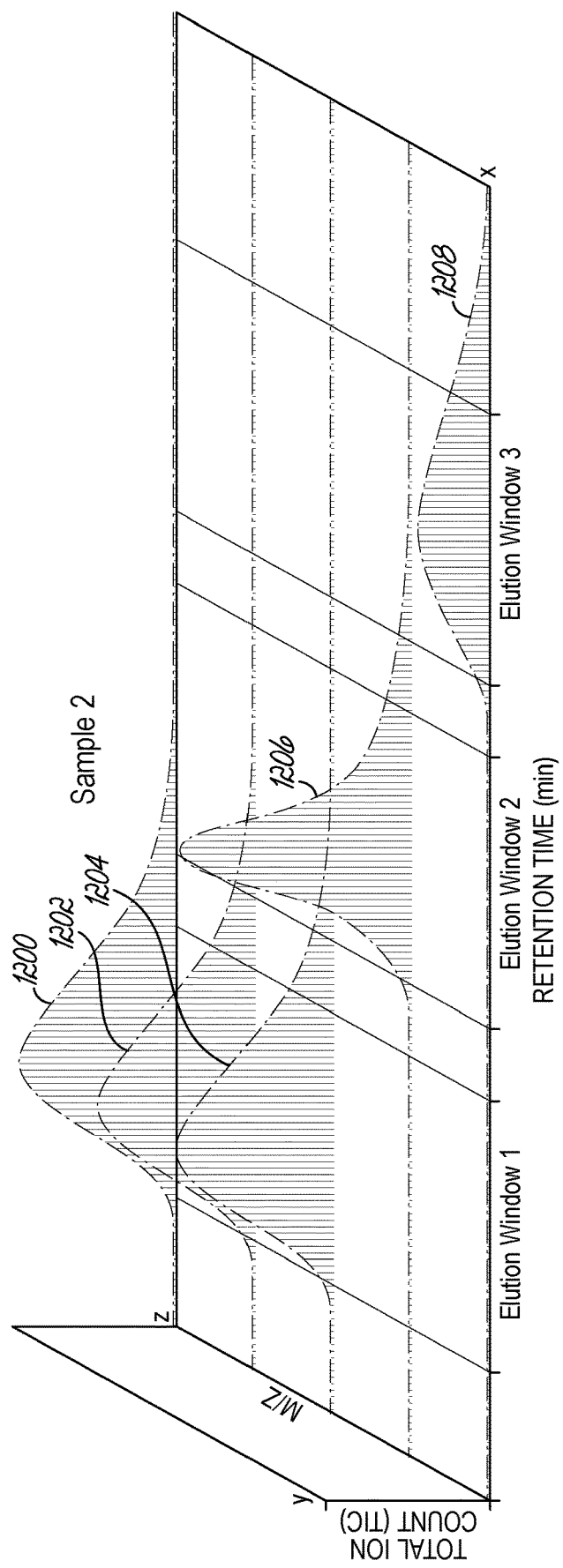
FIG. 39A is an exemplary chromatograph for a second sample prepared and analyzed with an automated sample preparation and analysis system and in accordance with an embodiment of the present invention.

Turning now to FIG. 39A, five chromatograms 1200, 1202, 1204, 1206, 1208 corresponding to each of five analytes contained within a second sample are schematically shown as would be detected on a LC-MS system. A chromatogram is a graphical representation of the time dependent total ion count ("TIC") for each analyte of interest measured at the ion detector 150 (FIG. 4B). Accordingly, the chromatogram includes retention time along the x-axis, TIC along the y-axis, and m/z along the z-axis. In the particular example, the first, second, and third chromatograms 1200, 1202, 1204 correspond to first, second, and third analytes that elute substantially simultaneously off of the columns 114, 116 (FIG. 7A) during a first elution window. The fourth and fifth chromatograms 1206, 1208 correspond to fourth and fifth analytes, respectively, which elute at later times (second and third elution windows, respectively).

The LC-MS system is capable of scanning at a rate that ranges from 2000 amu/sec to about 5000 amu/sec, or said another way, at about 10 SRM/sec to about 50 SRM/sec, where SRM represents an observed "selected reaction monitoring," transition. Accordingly, and for purposes of example only, a two second elution window during which the chromatographic peak containing the analytes of interest is delivered by the LC to the mass spectrometer 120 (FIG. 4B) could be scanned 20 to 50 times during the elution window. This replication of measurements improves the signal-to-noise ratio and may result in greater sensitivity for low concentration analytes. However, this replication of measurements also requires large data storage capabilities. In order to reduce the amount of information saved and transmitted from the sample analysis controller 26 (FIG. 2) to the sample preparation controller 22 (FIG. 2) the replicated TIC data measured by the ion detector 150 (FIG. 4B) may be sampled, filtered, or otherwise compressed into raw data for transmission from the sample analysis controller 26 (FIG. 2) to the sample preparation controller 22 (FIG. 2). For example, sampling of the chromatogram for each analyte may include saving an m/z value every 30 milliseconds. In addition to this sampled data, the raw data for each chromatogram may include the m/z value, an integral of the chromatogram, and the maximum TIC. This raw data, along with a sample/test identifier and the elution window are sent to the sample preparation controller 22 (FIG. 2) for further post processing.

The raw data, as shown in FIG. 39B, may be in a tabular format or any other human perceivable format or, alternatively and/or additionally the raw data may be formatted for electrical transmission to the sample preparation controller 22 (FIG. 2) for additional post processing.

The raw data may then be evaluated against an appropriate calibration curve for the corresponding analyte. The calibration curve may be constructed in a known manner. Briefly, this includes the preparation and analysis of two or more samples containing a known but varying amount of the analyte. The response of the ion detector 150 (FIG. 4B) is then recorded for the known samples and plotted against concentration. For simplicity, detection and reporting on the internal standard is not shown. A mathematical model is fit to the known sample data. Exemplary calibration curves are shown in FIGS. 39C-39E as follows: FIG. 39C illustrates a linear response with concentration of analyte 1; FIG. 39D illustrates a negative exponential response with concentration of analyte 2; and FIG. 39E illustrates a positive exponential response with concentration of analyte 3. One of ordinary skill in the art would readily appreciate that a wide range of mathematical models may be used to correlate the analyte response with concentration and the manner by which the model may be determined, for example, a least squares fit regression.

With the mathematical model of the calibration curve determined, the raw data for the prepared sample, i.e., an unknown sample, is evaluated in view of the calibration curve. Accordingly, the raw data representing the response of the appropriate analyte of the prepared sample is plotted against the calibration curve. The resultant concentration of the analyte within the prepared sample may be extrapolated from the calibration curve. Finally, and from the dilution factors associated with the test, the concentration of the analyte in the original specimen may be determined from the prepared sample in accordance with:

$$C1V1=C2V2$$

wherein, C1 is the concentration of the analyte within the prepared sample, V1 is the volume of the prepared sample, V2 is the volume of the specimen, and C2 is the determinable concentration of the analyte in the specimen.

It will further be appreciated that if the response of the analyte of the prepare sample falls outside of the range of concentrations tested for a particular calibration curve, then the calibration curve may be invalid and inappropriate for evaluation of the prepared sample.

Example 2

FIG. 40 illustrates TIC for all m/z values measured, in toto, at the ion detector 150 (FIG. 4B) of the mass spectrometer 120 (FIG. 4B) for a plurality of prepared samples, ad infinitum, where the prepared samples undergo a multiplexing protocol and are scheduled as described in detail previously. The peaks represent one or more gas phase ions corresponding to one or more analytes eluting off of the columns 114, 116 (FIG. 7A). In this way, and as clearly demonstrated in this figure, the resources of the mass spectrometer 120 (FIG. 4B) are maximized as compared to conventional methodologies where one sample must completely elute from a column 114, 116 (FIG. 7A) and be analyzed before a second sample may be injected into the column 114, 116 (FIG. 7A) for analysis.

As also shown in FIG. 40, each time a new sample is injected into the columns 114, 116 (FIG. 7A), a signal may be generated to indicate a zeroing of the retention time window and the start of a new analysis. The signal may be generated when the valve 126a, 126b (FIG. 4B) is switched from the "fill in loop" position to the "in-line" position.

Further, and as is clearly demonstrated in the figure, the analytes contained within any one particular sample may not necessarily be the same in type or in quantity as analytes contained in any one of the other samples.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of applicants' invention.

What is claimed is:

1. An automated sample preparation and analysis system, comprising:
 a sample preparation system configured to prepare a plurality of samples of one or more specimens in accordance with one or more assays selected from a database containing a plurality of assays;
 a sample analysis system comprising a liquid chromatography system and mass spectrometer, the sample analysis system configured to analyze the plurality of prepared samples in accordance with the one or more selected assays; and
a controller configured to determine, based on either user input or one or more specimen types, a respective target time to result for each of the plurality of samples and to dynamically adjust the order of the plurality of samples for preparation by the sample preparation system dependent on the respective target time to result and/or one or more a respective target time to prepare for each of the plurality of samples and further configured to dynamically adjust the order of the plurality of prepared samples for analysis by the sample analysis system based on the respective target time to result for each of the plurality of samples:
 wherein the controller further determines whether the mass spectrometer is available for receiving a prepared sample within a predetermined amount of time less than or equal to about 6 minutes.

2. The automated sample preparation and analysis system of claim 1, wherein the controller is configured to control the operation of the sample preparation system.

3. The automated sample preparation and analysis system of claim 1, wherein the order for the preparation of the plurality of samples is dependent on a remaining target time to result for a sample.

4. The automated sample preparation and analysis system of claim 1, wherein the target time to result and/or the target time to prepare one or more of the plurality of samples is specified by a user via a user input device.

5. The automated sample preparation and analysis system of claim 1, wherein the target time to result and/or the target time to prepare one or more of the plurality of samples is automatically determined by the controller based on relative degradation rates of respective specimen types.

6. An automated sample preparation and analysis system, comprising:
 a sample analysis system of the type that includes a mass spectrometer, the sample analysis system configured to analyze a plurality of samples according to respective assays selected from a database containing a plurality of assays; and a sample preparation system including a controller configured to adjust the order of the samples for analysis by the sample analysis system;
 wherein the order in which the plurality of samples are analyzed is dependent on at least one of a user specified target time to result for a sample, an automatically assigned target time to result for a sample, or a remaining target time to result for a sample; and
 wherein the controller further determines whether the mass spectrometer is available for receiving a prepared sample from the sample preparation system within a predetermined amount of time less than or equal to about 6 minutes.

* * * * *